United States Patent
Deng et al.

(10) Patent No.: US 9,902,735 B2
(45) Date of Patent: Feb. 27, 2018

(54) HETEROARYL SUBSTITUTED COMPOUNDS AS RORγ INHIBITORS

(71) Applicant: GlaxoSmithKline Intellectual Property Developement Limited, Middlesex (GB)

(72) Inventors: Jing Deng, Shanghai (CN); Hui Lei, Shanghai (CN); Xin Ma, Shanghai (CN); Xichen Lin, Shanghai (CN)

(73) Assignee: GLAXOSMITHKLINE INTELLECTUAL PROPERTY DEVELOPMENT LIMITED, Brentford, Middlesex (GB)

( * ) Notice: Subject to any disclaimer, the term of this patent is extended or adjusted under 35 U.S.C. 154(b) by 0 days.

(21) Appl. No.: 15/314,111

(22) PCT Filed: May 26, 2015

(86) PCT No.: PCT/CN2015/079753
§ 371 (c)(1),
(2) Date: Nov. 28, 2016

(87) PCT Pub. No.: WO2015/180612
PCT Pub. Date: Dec. 3, 2015

(65) Prior Publication Data
US 2017/0197978 A1    Jul. 13, 2017

(30) Foreign Application Priority Data
May 28, 2014  (WO) ............... PCT/CN2014/000540

(51) Int. Cl.
C07D 401/12  (2006.01)
A61K 31/496  (2006.01)
(Continued)

(52) U.S. Cl.
CPC ....... *C07D 493/04* (2013.01); *C07D 295/185* (2013.01); *C07D 401/12* (2013.01);
(Continued)

(58) Field of Classification Search
None
See application file for complete search history.

(56) References Cited

U.S. PATENT DOCUMENTS 8,604,069 B2  12/2013  Maeba et al.
9,242,972 B2   1/2016  Birault et al.
(Continued)

FOREIGN PATENT DOCUMENTS

WO  WO 2007022257 A2   2/2007
WO  WO 2007/070626 A2  6/2007
(Continued)

OTHER PUBLICATIONS

Leipe et al. Arthritis & Rheumatism vol. 62, No. 10, Oct. 2010, pp. 2876-2885.*
(Continued)

*Primary Examiner* — Emily Bernhardt
(74) *Attorney, Agent, or Firm* — Dara L. Dinner; Edward R. Gimmi; William R. Majarian

(57) ABSTRACT

The present invention relates to novel retinoid-related orphan receptor gamma (RORγ) modulators of Formula (I) and their use in the treatment of diseases mediated by RORγ.

(Continued)

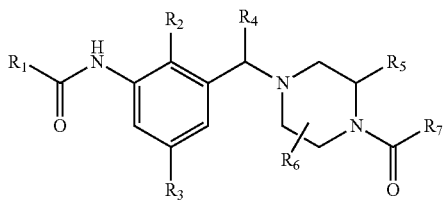

Formula I

13 Claims, 1 Drawing Sheet

(51) Int. Cl.
    *C07D 493/04*     (2006.01)
    *C07D 405/12*     (2006.01)
    *C07D 295/185*    (2006.01)
    *C07D 413/12*     (2006.01)
    *C07D 403/12*     (2006.01)
    *C07D 409/12*     (2006.01)

(52) U.S. Cl.
    CPC ......... *C07D 403/12* (2013.01); *C07D 405/12* (2013.01); *C07D 409/12* (2013.01); *C07D 413/12* (2013.01)

(56) References Cited

U.S. PATENT DOCUMENTS

| | | |
|---|---|---|
| 2015/0299121 A1 | 10/2015 | Han et al. |
| 2016/0257664 A1 | 9/2016 | Birault et al. |
| 2016/0304478 A1 | 10/2016 | Birault et al. |
| 2017/0081278 A1 | 3/2017 | Birault et al. |
| 2017/0101399 A1 | 4/2017 | Lei et al. |
| 2017/0121313 A1 | 5/2017 | Deng et al. |

FOREIGN PATENT DOCUMENTS

| | | |
|---|---|---|
| WO | WO 2007/078839 A2 | 7/2007 |
| WO | WO 2007/089336 A2 | 8/2007 |
| WO | WO 2012/027965 A1 | 3/2012 |
| WO | WO 2012/028100 A1 | 3/2012 |
| WO | WO 2012/100732 A1 | 8/2012 |
| WO | WO 2012/100734 A1 | 8/2012 |
| WO | WO 2012/145254 A2 | 10/2012 |
| WO | WO 2012139775 | 10/2012 |
| WO | WO 2012/147916 A1 | 11/2012 |
| WO | WO 2012158784 A2 | 11/2012 |
| WO | WO 2013/036912 A2 | 3/2013 |
| WO | WO 2013/045431 A1 | 4/2013 |
| WO | WO 2013/160418 A1 | 10/2013 |
| WO | WO 2013/160419 A1 | 10/2013 |
| WO | WO 2013/171729 A2 | 11/2013 |
| WO | 2014/086894 * | 6/2014 |
| WO | WO 2015/061515 A1 | 4/2015 |
| WO | WO 2015/061686 A2 | 4/2015 |
| WO | WO 2015/180613 A1 | 12/2015 |
| WO | WO 2015/180614 A1 | 12/2015 |

OTHER PUBLICATIONS

Rutz et al. Cytokine & Growth Factor Reviews 30 (2016) 1-17.*
Xue et al. Scientific Reports, pp. 1-17 (2016) available online at www.nature.com/scientificreports/.*
Silverman. The Organic Chemistry of Drug Design and Action, 25-34 (2004).

* cited by examiner

| | BID Dose (mg/kg by oral gavage) | Ear thickness following 4 daily applications of 10 mg Aldara to the ears (microns ± S.E.M., n=8 mice per group) | | | | Ear Th17 Gene Expression (number of mRNA copies per 100 ng of whole ear RNA, mean copy number ± S.E.M., n=8-10 mice per group) | | | | Cytokine expression in *ex vivo* whole blood assay from Study A (mean pg/ml ± S.E.M., n=8-10 mice per group) |
|---|---|---|---|---|---|---|---|---|---|---|
| | | Study 1 | Study 2 | Study 3 | Study 4 | Study | IL-17A | IL-17F | IL-22 | IL-17A |
| Vehicle | 0 | 344.3 ± 27.7 | 301.0 ± 17.7 | 352.5 ± 19.5 | 370.7 ± 14.3 | A | 21012 ± 1581 | 59488 ± 5078 | 8737 ± 945 | 4189 ± 321 |
| | | | | | | B | 13240 ± 2182 | 43310 ± 4612 | 9224 ± 933 | not in study |
| | | | | | | C | 8997 ± 2986 | 9016 ± 1333 | 2123 ± 392 | not in study |
| E43 | 10 | * 233.3 ± 6.3 | * 244.7 ± 10.6 | * 296.6 ± 16.1 | * 297.8 ± 16.5 | A | 16811 ± 3028 | 52579 ± 8614 | 6547 ± 1239 | * 1678 ± 314 |
| | | | | | | B | 7129 ± 1285 | 25610 ± 3623 | † 5612 ± 840 | not in study |
| | | | | | | C | † 1883 ± 273 | 4426 ± 850 | 978 ± 202 | not in study |
| | 30 | * 264.5 ± 14.6 | * 248.6 ± 9.0 | not in study | not in study | | not in study | not in study | not in study | not in study |

HETEROARYL SUBSTITUTED COMPOUNDS AS RORγ INHIBITORS

This application is a 371 of International Application No PCT/CN2015/079753, filed 26 May 2015, which claims priority of PCT Application PCT/CN2014/000540 filed 28 May 2014

The present invention relates to novel retinoid-related orphan receptor gamma (RORγ) modulators and their use in the treatment of diseases mediated by RORγ.

BACKGROUND OF THE INVENTION

Retinoid-related orphan receptors (RORs) are transcription factors which belong to the steroid hormone nuclear receptor superfamily (Jetten & Joo (2006) *Adv. Dev. Biol.* 16:313-355). The ROR family consists of three members, ROR alpha (RORα), ROR beta (RORβ) and ROR gamma (RORγ), each encoded by a separate gene (RORA, RORB and RORC, respectively). RORs contain four principal domains shared by the majority of nuclear receptors: an N-terminal A/B domain, a DNA-binding domain, a hinge domain, and a ligand binding domain. Each ROR gene generates several isoforms which differ only in their N-terminal A/B domain. Two isoforms of RORγ have been identified: RORγ1 and RORγt (also known as RORγ2). RORγ is a term used to describe both RORγ1 and/or RORγt.

While RORγ1 is expressed in a variety of tissues including thymus, muscle, kidney and liver, RORγt is exclusively expressed in the cells of the immune system. RORγt has been identified as a key regulator of Th17 cell differentiation. Th17 cells are a subset of T helper cells which produce IL-17 and other proinflammatory cytokines. Th17 cells have been shown to have key functions in several mouse autoimmune disease models including experimental autoimmune encephalomyelitis (EAE) and collagen-induced arthritis (CIA). In addition, Th17 cells or their products have been shown to be associated with the pathology of a variety of human inflammatory and autoimmune disorders including multiple sclerosis, rheumatoid arthritis, psoriasis, ankylosing spondylitis, Crohn's disease and asthma (Jetten (2009) *Nucl. Recept. Signal.* 7: e003; Manel et al. (2008) *Nat. Immunol.* 9:641-649; Miossec & Kolls (2012) *Nat. Rev. Drug. Discov.* 10:763-776). The pathogenesis of chronic autoimmune diseases including multiple sclerosis and rheumatoid arthritis arises from the break in tolerance towards self-antigens and the development of auto-aggressive effector T cells infiltrating the target tissues. Studies have shown that Th17 cells are one of the important drivers of the inflammatory process in tissue-specific autoimmunity (Steinman (2008) *J. Exp. Med.* 205:1517-1522; Leung et al. (2010) *Cell. Mol. Immunol.* 7:182-189). There is evidence that Th17 cells are activated during the disease process and are responsible for recruiting other inflammatory cells types, especially neutrophils, to mediate pathology in the target tissues (Korn et al. (2009) *Annu. Rev. Immunol.* 27:485-517).

RORγt plays a critical role in the pathogenic responses of Th17 cells (Ivanov et al. (2006) *Cell* 126:1121-1133). RORγt deficient mice show very little Th17 cells. In addition, RORγt deficiency resulted in amelioration of EAE. Further support for the role of RORγt in the pathogensis of autoimmune or inflammatory diseases can be found in the following references: Jetten & Joo (2006) *Adv. Dev. Biol.* 16:313-355; Meier et al. (2007) *Immunity* 26:643-654; Aloisi & Pujol-Borrell (2006) *Nat. Rev. Immunol.* 6:205-217; Jager et al. (2009) *J. Immunol.* 183:7169-7177; Serafini et al. (2004) *Brain Pathol.* 14:164-174; Magliozzi et al. (2007) *Brain* 130:1089-1104; Barnes (2008) *Nat. Rev. Immunol.* 8:183-192; Miossec & Kolls (2012) *Nat. Rev. Drug. Discov.* 10:763-776.

In light of the role RORγ plays in the pathogenesis of diseases, it is desirable to prepare compounds that modulate RORγ activity, which can be used in the treatment of diseases mediated by RORγ.

SUMMARY OF THE INVENTION

The invention is directed to novel RORγ modulators and their use in the treatment of diseases mediated by RORγ. Specifically, the invention is directed to compounds according to Formula I.

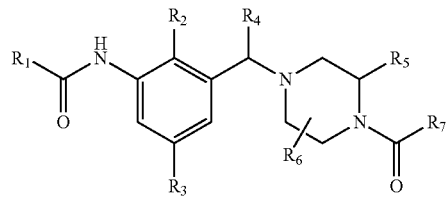

Formula I wherein $R_1$ to $R_7$ are defined below, and to pharmaceutically-acceptable salts thereof.

The invention is also directed to novel RORγ modulators and their use in the treatment of diseases mediated by RORγ wherein the compounds are according to Formula II:

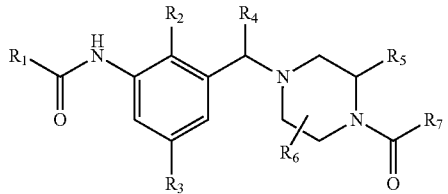

Formula II wherein $R_1$ to $R_7$ are defined below, and to pharmaceutically-acceptable salts thereof.

In another aspect, this invention provides for the use of the compounds of Formula I and Formula II for the treatment of diseases mediated by RORγ. Examples of such diseases include but are not limited to autoimmune or inflammatory diseases such as multiple sclerosis, rheumatoid arthritis, psoriasis and ankylosing spondylitis. In yet another aspect, the invention is directed to methods of treating such diseases.

This invention also provides for the use of compounds of Formula I and Formula II, or a pharmaceutically acceptable salt thereof of, for the treatment of diseases mediated by RORγ. Examples of such diseases include but are not limited to autoimmune or inflammatory diseases such as multiple sclerosis, rheumatoid arthritis, psoriasis and ankylosing spondylitis. In yet another aspect, the invention is directed to methods of treating such diseases.

BRIEF DESCRIPTION OF THE DRAWINGS

FIG. 1 shows statistically significant reduction of compound E43 versus vehicle in imiquimod-induced ear thickening studies.

DETAILED DESCRIPTION OF THE INVENTION

The present invention provides for, a compound of Formula I or a pharmaceutically acceptable salt thereof.

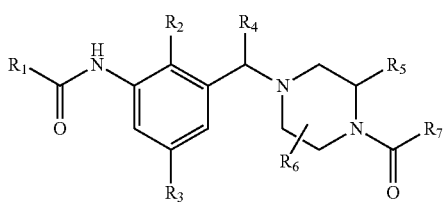

Formula I wherein R1 is:
a) a 6 membered heteroaryl optionally substituted with one substituent selected from the group consisting of: C(O)NHRfRf, CN, CHF2 and CH2F, and said Rf is independently selected from hydrogen or methyl; or
b) a 6 membered heteroaryl substituted with two substituents selected from the group consisting of: i) F and methyl, ii) CN and methyl, and iii) Cl and methyl; or
c) a methyl substituted with a substituent selected from the group consisting of:
  i) a C4-C6 cycloalkyl substituted with OH or two F;
  ii) a 4 to 8 membered heterocycloalkyl optionally substituted one or more times, suitably 1 to 2 times, with C(O)Ra, OH, CN, oxo or C1-C3 alkyl, wherein said heterocycloalkyl containing 1 or 2 heteroatoms independently selected from O and N, and said Ra is C1-C2 alkyl optionally substituted with methyl or ethyl;
  iii) a 4 to 6 membered monocyclic sulfone;
  iv) oxazolyl or isooxozolyl substituted with methyl;
  v) difluoromethoxy or difluoroethoxy; and
  vi) NRaSO2CH3, wherein Ra is C1-C2 alkyl; or
d) a C2-C5 alkyl substituted with
  i) SO2Rb,
  ii) CF3,
  iii) CN,
  iv) methoxy,
  v) OH,
  vi) C(O)NRbRb,
  vii) NRbRc,
  viii) a 5 or 6 membered heterocycloalkyl containing one (1) oxygen (O),
  ix) a cyclopropyl substituted with CN, or
  x) O—CHF2,
  wherein Rb is independently selected from methyl or ethyl, and Rc is C(O)CH3; or
e) CH2-O-Rd, wherein Rd is a C1-C4 alkyl optionally substituted with i) methoxy, ii) CN, iii) CHF2 or iv) cyclopropyl substituted with CN; or
f) C3-C6 cycloalkyl substituted with a substituent selected from the group consisting of
  i) NHC(O)CH3,
  ii) SO2CH3,
  vii) OH, and
  viii) C1-C3 alkyl substituted with OH; or
g) a 4 to 6 membered monocyclic heterocycloalkyl containing one (1) nitrogen (N) heteroatom, and optionally a second heteroatom which is oxygen (O), wherein said heterocycloalkyl is substituted with SO2CH3 or C(O)Re, and said Re is C1-C3 alkyl; or
h) -tetrahydro-2H-thiopyran 1,1-dioxide;
R2 is C1-C3 alkyl or halo;
R3 is halo or CN;
R4 is H;
R5 is C1-C3 alkyl;
R6 is H or methyl; and
R7 is selected from the group consisting of:
  C3-C6 cycloalkyl optionally substituted with methyl;
  methyl substituted with C3-C5 cycloalkyl; and
  C2 or C3 alkyl optionally substituted with two F.

The present invention provides, in one embodiment, a compound of Formula I or a pharmaceutically acceptable salt thereof, wherein R1 is:
a) 6 membered heteroaryl containing 1 or 2 N, wherein said heteroaryl is optionally substituted with C(O)NH2 or CN;
b) 6 membered heteroaryl containing 1 or 2N, wherein said heteroaryl is substituted with i) F and methyl, or ii) CN and methyl;
c) C2-C3 alkyl substituted with i) SO2Rb, ii) CF3, or iii) CN, wherein Rb is methyl or ethyl; or
d) methyl substituted with a substituent selected from the group consisting of:
  i) C4-C6 cycloalkyl substituted with OH or two F;
  ii) 4 or 5 membered heterocycloalkyl optionally substituted one or more times, suitably 1 or 2 times with C(O)Ra, wherein said heterocycloalkyl contains 1 O or 1 N, and said Ra is C1-C2 alkyl;
R2 is C1-C3 alkyl;
R3 is halo or CN;
R4 is H;
R5 is C1-C3 alkyl;
R6 is H; and
R7 is a C3-C6 cycloalkyl or a methyl substituted with C3-C5 cycloalkyl.

The present invention provides in another embodiment for a compound of Formula Ia or a pharmaceutically acceptable salt thereof.

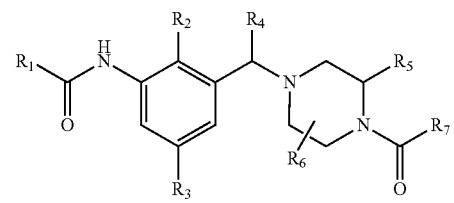

Formula Ia wherein R1 is:
  6 membered heteroaryl optionally substituted with one substituent selected from the group consisting of: C(O)NH2, CN, CHF2 and CH2F;
  6 membered heteroaryl substituted with two substituents selected from the group consisting of: i) F and methyl, ii) CN and methyl, and iii) Cl and methyl;
  methyl substituted with a substituent selected from the group consisting of:
    i) C4-C6 cycloalkyl substituted with OH or two F;
    ii) 4 to 8 membered heterocycloalkyl optionally substituted with C(O)Ra, OH, CN, oxo or C1-C3 alkyl, wherein said heterocycloalkyl containing 1 or 2 heteroatoms independently selected from O and N, and said Ra is C1-C2 alkyl optionally substituted with methyl or ethyl;
  iii) 4 to 6 membered monocyclic sulfone;
  iv) oxazolyl or isooxozolyl substituted with methyl;
  v) difluoromethoxy or difluoroethoxy; and
  vi) NRaSO$_2$CH$_3$, wherein Ra is C1-C2 alkyl;
C2-C5 alkyl substituted with i) SO$_2$Rb, ii) CF$_3$, iii) CN, iv) methoxy, v) OH, vi) C(O)NRbRb, vii) NRbRc, viii) 5 or 6 membered heterocycloalkyl containing 1 O, ix) cyclopropyl substituted with CN, or x) O—CHF$_2$, wherein Rb is methyl or ethyl, and Rc is C(O)CH$_3$;
CH2-O-Rd, wherein Rd is C1-C4 alkyl optionally substituted with i) methoxy, ii) CN, iii) CHF2 or iv) cyclopropyl substituted with CN;
C3-C6 cycloalkyl substituted with a substituent selected from the group consisting of:
  i) NHC(O)CH$_3$, ii) SO$_2$CH$_3$, iii) OH, and iv) C1-C3 alkyl substituted with OH;
4 to 6 membered monocyclic heterocycloalkyl containing 1 N heteroatom, wherein said heterocycloalkyl is substituted with SO$_2$CH$_3$ or C(O)Re, and said Re is C1-C3 alkyl; or
R1 is tetrahydro-2H-thiopyran 1,1-dioxide;
R2 is C1-C3 alkyl or halo;
R3 is halo or CN;
R4 is H;
R5 is C1-C3 alkyl;
R6 is H or methyl; and
R7 is selected from the group consisting of:
  C3-C6 cycloalkyl optionally substituted with methyl;
  methyl substituted with C3-C5 cycloalkyl; and
  C2 or C3 alkyl optionally substituted with two F.

One embodiment of the invention, is a compound of Formula Ia or a pharmaceutically acceptable salt thereof, wherein R1 is:
  6 membered heteroaryl containing 1 or 2 N, wherein said heteroaryl is optionally substituted with C(O)NH$_2$ or CN;
  6 membered heteroaryl containing 1 or 2 N, wherein said heteroaryl is substituted with i) F and methyl, or ii) CN and methyl;
  C2-C3 alkyl substituted with i) SO$_2$Rb, ii) CF$_3$, or iii) CN, wherein Rb is methyl or ethyl; or
  methyl substituted with a substituent selected from the group consisting of:
    i) C4-C6 cycloalkyl substituted with OH or two F;
    ii) 4 or 5 membered heterocycloalkyl optionally substituted with C(O)Ra, wherein said heterocycloalkyl containing 1 O or 1 N, and said Ra is C1-C2 alkyl;
R2 is C1-C3 alkyl;
R3 is halo or CN;
R4 is H;
R5 is C1-C3 alkyl;
R6 is H; and
R7 is i) C3-C6 cycloalkyl or ii) methyl substituted with C3-C5 cycloalkyl.

As will be discussed further herein, compounds of Formulas Ia, and Formulas III-IX are all subsets of Formula I. Unless specifically noted to the contrary all of the following embodiments are applicable to all compounds of Formula I, Formula Ia and Formulas III-IX. In one embodiment, the invention relates to the compounds of Formula I, wherein R1 is a pyridinyl substituted with C(O)NH$_2$, or C(O)NHCH$_3$, or CN. In one embodiment, this invention also relates to compounds of any of the above embodiments, wherein R1 is pyridinyl substituted with C(O)NH$_2$, or C(O)NHCH$_3$, preferably C(O)NH$_2$. In one embodiment, this invention also relates to compounds of any of the above embodiments, wherein R1 is pyridinyl substituted with CN.

In one embodiment, the invention relates to the compounds of Formula I, wherein R1 is methyl substituted with tetrahydrofuran. In one embodiment, this invention also relates to compounds of any of the above embodiments, wherein R1 is methyl substituted with hydroxycyclohexyl.

In another embodiment, the invention relates to compounds of Formula I wherein R1 is a methyl substituted with difluorocyclobutyl. In another embodiment, this invention relates to compounds of Formula I wherein R1 is methyl substituted with acetylpyrrolidinyl. In another embodiment, this invention relates to compounds of Formula I wherein R1 is a methyl substituted with propionylazetidine.

In another embodiment, the invention relates to the compounds of Formula I, wherein R1 is an ethyl substituted with CF$_3$. In another embodiment, this invention also relates to compounds of Formula I wherein R1 is propyl substituted with CN. In another embodiment, this invention also relates to compounds of Formula I, wherein R1 is ethyl substituted with SO$_2$Rb wherein Rb is methyl or ethyl. In one embodiment, the Rb in the SO$_2$Rb is methyl.

In one embodiment, the invention also relates to compounds of Formula I wherein R2 is methyl.

In one embodiment, the invention also relates to compounds of any of the above embodiments, wherein R3 is Cl. In one embodiment, this invention also relates to compounds of any of the above embodiments, wherein R3 is F. In one embodiment, the invention also relates to compounds of any of the above embodiments, wherein R3 is CN.

In one embodiment, the invention also relates to compounds of any of the above embodiments, wherein R5 is methyl. In one embodiment, the invention also relates to compounds of any of the above, wherein R6 is H.

In one embodiment, this invention also relates to compounds of any of the above embodiments, wherein R7 is a C3-C6 cycloalkyl. In one embodiment, R7 is cyclopentyl. In another embodiment, R7 is cyclohexyl.

In another embodiment, this invention also relates to compounds of any of the above embodiments, wherein R7 is a methyl substituted with C3-C5 cycloalkyl. In one embodiment the C3-C5 cycloalkyl is cyclopropyl. In one embodiment, R7 is a methyl substituted with cyclopropyl.

In one embodiment, a compound of the present invention, or a pharmaceutically acceptable salt thereof, is selected from:
(S)—N-(5-chloro-3-((4-(cyclopentanecarbonyl)-3-methylpiperazin-1-yl)methyl)-2-methylphenyl)-3-(methylsulfonyl)propanamide;
(S)—N-(5-chloro-3-((4-(cyclopentanecarbonyl)-3-methylpiperazin-1-yl)methyl)-2-methylphenyl)-4-(methylsulfonyl)butanamide;
(S)—N-(5-chloro-3-((4-(cyclopentanecarbonyl)-3-methylpiperazin-1-yl)methyl)-2-methylphenyl)-3-(ethylsulfonyl)propanamide;
(S)—N-(5-chloro-3-((4-(cyclohexanecarbonyl)-3-methylpiperazin-1-yl)methyl)-2-methylphenyl)-3-(methylsulfonyl)propanamide;
(S)—N-(5-chloro-3-((4-(cyclopentanecarbonyl)-3-methylpiperazin-1-yl)methyl)-2-methylphenyl)-4,4,4-trifluorobutanamide;
(S)—N-(5-chloro-3-((4-(cyclopentanecarbonyl)-3-methylpiperazin-1-yl)methyl)-2-methylphenyl)-2-(3,3-difluorocyclobutyl)acetamide;

(S)—N-(5-chloro-3-((4-(cyclopentanecarbonyl)-3-methyl-piperazin-1-yl)methyl)-2-methylphenyl)-4-cyanobutana-mide;
N-(5-chloro-3-(((S)-4-(cyclopentanecarbonyl)-3-methylpip-erazin-1-yl)methyl)-2-methylphenyl)-2-((S)-tetrahydro-furan-3-yl)acetamide;
N-(5-chloro-3-(((S)-4-(cyclopentanecarbonyl)-3-methylpip-erazin-1-yl)methyl)-2-methylphenyl)-2-((R)-tetrahydro-furan-3-yl)acetamide;
N-(5-chloro-3-(((S)-4-(cyclopentanecarbonyl)-3-methylpip-erazin-1-yl)methyl)-2-methylphenyl)-2-((1s,4R)-4-hy-droxycyclohexyl)acetamide;
N-(5-chloro-3-(((S)-4-(cyclopentanecarbonyl)-3-methylpip-erazin-1-yl)methyl)-2-methylphenyl)-2-((1r,4S)-4-hy-droxycyclohexyl)acetamide;
(S)—N-(5-chloro-3-((4-(cyclopentanecarbonyl)-3-methyl-piperazin-1-yl)methyl)-2-methylphenyl)-2-cyanoisonico-tinamide;
(S)—N-(5-chloro-3-((4-(cyclopentanecarbonyl)-3-methyl-piperazin-1-yl)methyl)-2-methylphenyl)-2-cyanoisonico-tinamide;
(S)—N-(5-chloro-3-((4-(2-cyclopropylacetyl)-3-methylpip-erazin-1-yl)methyl)-2-methylphenyl)-6-cyanonicotina-mide;
(S)—N-(5-chloro-3-((4-(2-cyclopropylacetyl)-3-methylpip-erazin-1-yl)methyl)-2-methylphenyl)-6-cyanonicotina-mide;
(S)—N-(5-chloro-3-((4-(cyclopentanecarbonyl)-3-methyl-piperazin-1-yl)methyl)-2-methylphenyl)-6-cyanonicoti-namide;
(S)—N-(5-chloro-3-((4-(cyclopentanecarbonyl)-3-methyl-piperazin-1-yl)methyl)-2-methylphenyl)-6-cyanonicoti-namide;
(S)—N-(5-chloro-3-((4-(2-cyclopropylacetyl)-3-methylpip-erazin-1-yl)methyl)-2-methylphenyl)-5-cyano-6-methyl-nicotinamide;
(S)—N-(5-chloro-3-((4-(2-cyclopropylacetyl)-3-methylpip-erazin-1-yl)methyl)-2-methylphenyl)-5-cyano-6-methyl-nicotinamide;
(S)—N-(5-chloro-3-((4-(2-cyclopropylacetyl)-3-methylpip-erazin-1-yl)methyl)-2-methylphenyl)-5-fluoro-6-methyl-nicotinamide;
(S)—N-(5-chloro-3-((4-(2-cyclopropylacetyl)-3-methylpip-erazin-1-yl)methyl)-2-methylphenyl)-6-cyano-5-methyl-nicotinamide;
2-(1-acetylpyrrolidin-3-yl)-N-(3-(((S)-4-(cyclopentanecar-bonyl)-3-methylpiperazin-1-yl)methyl)-5-fluoro-2-meth-ylphenyl)acetamide;
(S)—N-(5-chloro-3-((4-(cyclopentanecarbonyl)-3-methyl-piperazin-1-yl)methyl)-2-methylphenyl)-2-(1-propio-nylazetidin-3-yl)acetamide;
(S)—N$^5$-(5-chloro-3-((4-(cyclopentanecarbonyl)-3-methyl-piperazin-1-yl)methyl)-2-methylphenyl)pyridine-2,5-di-carboxamide;
(S)—N-(5-cyano-3-((4-(2-cyclopropylacetyl)-3-methylpip-erazin-1-yl)methyl)-2-methylphenyl)-5-fluoro-6-methyl-nicotinamide; or
(S)—N-(5-cyano-3-((4-(2-cyclopropylacetyl)-3-methylpip-erazin-1-yl)methyl)-2-methylphenyl)-5-fluoro-6-methyl-nicotinamide.

One aspect of the invention is a pharmaceutical composition comprising a compound of Formula I, or a pharmaceutically acceptable salt thereof, and a pharmaceutically acceptable carrier or diluent.

The present invention provides, in another aspect, a compound of Formula II or a pharmaceutically acceptable salt thereof:

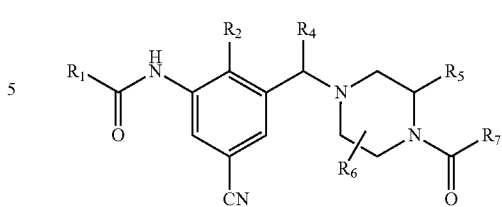

Formula II wherein
R1 is
i) 6 membered heteroaryl containing 1 or 2 N, said heteroaryl is substituted with methyl or methoxy; or
ii) phenyl substituted with i) CN or ii) methyl substituted with 1 to 3 F;
R2 is C1-C3 alkyl;
R4 is H;
R5 is C1-C3 alkyl;
R6 is H; and
R7 is i) C3-C6 cycloalkyl; or ii) methyl substituted with C3-C5 cycloalkyl.

In one embodiment, compounds of Formula II, or a pharmaceutically acceptable salt, is selected from:
(S)—N-(5-cyano-3-((4-(cyclopentanecarbonyl)-3-methyl-piperazin-1-yl)methyl)-2-methylphenyl)-6-methylnicoti-namide;
(S)—N-(5-cyano-3-((4-(cyclopentanecarbonyl)-3-methyl-piperazin-1-yl)methyl)-2-methylphenyl)-2-methylisoni-cotinamide;
(S)—N-(5-cyano-3-((4-(2-cyclopropylacetyl)-3-methylpip-erazin-1-yl)methyl)-2-methylphenyl)-2-methylpyrimi-dine-5-carboxamide;
(S)—N-(5-cyano-3-((4-(2-cyclopropylacetyl)-3-methylpip-erazin-1-yl)methyl)-2-methylphenyl)-6-methylnicotina-mide;
(S)—N-(5-cyano-2-methyl-3-((3-methyl-4-(spiro[2.3]hexane-5-carbonyl)piperazin-1-yl)methyl)phenyl)-6-methylnicotinamide;
N-(3-(((3S)-4-(bicyclo[3.1.0]hexane-3-carbonyl)-3-methyl-piperazin-1-yl)methyl)-5-cyano-2-methylphenyl)-6-methylnicotinamide;
(S)—N-(5-cyano-3-((4-(2-cyclopropylacetyl)-3-methylpip-erazin-1-yl)methyl)-2-methylphenyl)-6-methoxynicoti-namide;
(S)—N-(5-cyano-3-((4-(2-cyclopropylacetyl)-3-methylpip-erazin-1-yl)methyl)-2-methylphenyl)-6-methoxynicoti-namide;
(S)—N-(5-cyano-3-((4-(cyclobutanecarbonyl)-3-methyl-piperazin-1-yl)methyl)-2-methylphenyl)-6-methylnicoti-namide;
(S)-3-cyano-N-(5-cyano-3-((4-(cyclopentanecarbonyl)-3-methylpiperazin-1-yl)methyl)-2-methylphenyl)benz-amide; or
(S)—N-(5-cyano-3-((4-(cyclopentanecarbonyl)-3-methyl-piperazin-1-yl)methyl)-2-methylphenyl)-2-methylpy-rimidine-5-carboxamide.

One aspect of the invention is a pharmaceutical composition comprising a compound of Formula II, or a pharmaceutically acceptable salt thereof, and a pharmaceutically acceptable carrier or diluent.

In one embodiment, the invention also relates to compounds of Formula II wherein R2 is methyl.

In one embodiment, the invention also relates to compounds of Formula II wherein R5 is methyl.

In one embodiment, this invention also relates to compounds of Formula II wherein R7 is a C3-C6 cycloalkyl. In one embodiment, R7 is cyclopentyl. In another embodiment, R7 is cyclohexyl.

In another embodiment, this invention also relates to compounds of Formula II wherein R7 is a methyl substituted with C3-C5 cycloalkyl. In one embodiment the C3-C5 cycloalkyl is cyclopropyl. In another embodiment the C3-C5 cycloalkyl is cyclopentyl The present invention provides, in another aspect, a compound of Formula III or a pharmaceutically acceptable salt thereof:

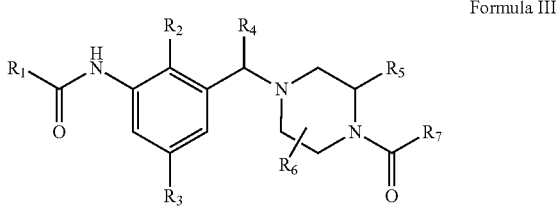

Formula III wherein

R1 is a 6 membered heteroaryl ring optionally substituted with one substituent selected from the group consisting of C(O)NRfRf, CN, CHF$_2$ and CH$_2$F;
Rf is independently selected from hydrogen or methyl;
R2 is C1-C3 alkyl or halo;
R3 is halo or CN;
R4 is H;
R5 is C1-C3 alkyl;
R6 is H or methyl; and
R7 is selected from the group consisting of:
a C3-C6 cycloalkyl optionally substituted with methyl;
a methyl substituted with C3-C5 cycloalkyl; and
a C2 or C3 alkyl optionally substituted with two F.

Suitably, for a compound of Formula III, R1 is a 6 membered heteroaryl ring optionally substituted with one substituent selected from the group consisting of C(O)NRfRf, CN, CHF$_2$ and CH$_2$F. In one embodiment, Rf is independently selected from hydrogen or methyl. In one embodiment both Rf groups are hydrogen. In another embodiment one of Rf is hydrogen and the other is methyl. In another embodiment both Rf groups are methyl.

In one embodiment, the 6 membered heteroaryl R1 ring is a pyridinyl or a pyrimidinyl ring. In another embodiment, the R1 ring is a pyridine. In another embodiment the R1 ring is a pyridimine ring.

In one embodiment the pyridine ring is a 2-pyridinyl, a 3-pyridinyl or a 4-pyridinyl ring which is substituted. In one embodiment the 3-pyridinyl ring (also called a nicotinamide when coupled with the adjacent amide linkage), and is substituted in the 6-position by cyano or C(O)NH2 or C(O)NHCH3. In another embodiment the pyridine ring is an isonicotinamde and substituted in the adjacent 2-position by cyano.

Suitably, for a compound of Formula III, R7 is a C3-C6 cycloalkyl optionally substituted with methyl. The C3-C6 cycloalkyl which may be optionally substituted is suitably a cyclopropyl or cyclopentyl ring. In one embodiment the R7 ring is a cyclopentyl ring. In another embodiment, R7 is a cyclopropyl ring.

Suitably, for a compound of Formula III, R7 is methyl substituted with C3-C5 cycloalkyl. Suitably, the C3-C5 ring is a cyclopropyl or a cyclopentyl ring. In one embodiment, R7 is a cyclopropylmethyl.

Suitably, for a compound of Formula III, R7 is a C2 or C3 alkyl optionally substituted with two F, the alkyl chain is a straight of branched C3 carbon chain, such as propyl or isopropyl. In one embodiment the first carbon in the chain attached to the carbonyl is the one optionally substituted with two fluorines.

Suitably, for compounds of Formula III, R2 is C1-C3 alkyl or halo. In one embodiment, R2 is a C1-C3. In another embodiment, R2 is methyl.

Suitably, for compounds of Formula III, R3 is halo or CN. In one embodiment, R3 is halo. In another embodiment, R3 is fluorine or chlorine. In one embodiment, R3 is fluorine. In another embodiment, R3 is chlorine. In another embodiment, R3 is cyano. In one embodiment, when R3 is fluorine, chlorine or cyano, R2 is methyl.

Suitably, for compounds of Formula III, R5 is C1-C3 alkyl. In one embodiment R5 is methyl.

Suitably, for compounds of Formula III, R6 is H or methyl. In one embodiment, R6 is hydrogen.

In one embodiment, a compound of the Formula III, or a pharmaceutically acceptable salt thereof is selected from:

(S)—N-(5-chloro-3-((4-(cyclopentanecarbonyl)-3-methylpiperazin-1-yl)methyl)-2-methylphenyl)-2-cyanoisonicotinamide;

(S)—N-(5-chloro-3-((4-(2-cyclopropylacetyl)-3-methylpiperazin-1-yl)methyl)-2-methylphenyl)-2-cyanoisonicotinamide;

(S)—N-(5-chloro-3-((4-(2-cyclopropylacetyl)-3-methylpiperazin-1-yl)methyl)-2-methylphenyl)-6-cyanonicotinamide;

(S)—N-(5-chloro-3-((4-(cyclopentanecarbonyl)-3-methylpiperazin-1-yl)methyl)-2-methylphenyl)-6-cyanonicotinamide;

(S)—N$^5$-(5-chloro-3-((4-(cyclopentanecarbonyl)-3-methylpiperazin-1-yl)methyl)-2-methylphenyl)pyridine-2,5-dicarboxamide;

S)—N$^5$-(3-((4-(cyclopentanecarbonyl)-3-methylpiperazin-1-yl)methyl)-5-fluoro-2-methylphenyl)pyridine-2,5-dicarboxamide;

(S)—N$^5$-(5-chloro-3-((4-(2-cyclopropylacetyl)-3-methylpiperazin-1-yl)methyl)-2-methylphenyl)pyridine-2,5-dicarboxamide;

(S)—N$^5$-(3-((4-(cyclopentanecarbonyl)-3-methylpiperazin-1-yl)methyl)-5-fluoro-2-methylphenyl)-N$^2$-methylpyridine-2,5-dicarboxamide;

(S)—N$^5$-(3-((4-(cyclopentanecarbonyl)-3-methylpiperazin-1-yl)methyl)-5-fluoro-2-methylphenyl)-N$^2$-methylpyridine-2,5-dicarboxamide;

(S)—N-(5-cyano-3-((4-(2-cyclopropylacetyl)-3-methylpiperazin-1-yl)methyl)-2-methylphenyl)-6-(fluoromethyl)nicotinamide;

(S)—N-(5-cyano-3-((4-(2-cyclopropylacetyl)-3-methylpiperazin-1-yl)methyl)-2-methylphenyl)-6-(fluoromethyl)nicotinamide;

(S)—N-(5-cyano-3-((4-(cyclopentanecarbonyl)-3-methylpiperazin-1-yl)methyl)-2-methylphenyl)-3-(difluoromethyl)benzamide;

(S)—N-(5-cyano-3-((4-(cyclopentanecarbonyl)-3-methylpiperazin-1-yl)methyl)-2-methylphenyl)-2-(difluoromethyl)isonicotinamide; or (S)—N-(5-cyano-3-((4-(cyclopentanecarbonyl)-3-methylpiperazin-1-yl)methyl)-2-methylphenyl)-2-(difluoromethyl)isonicotinamide.

One aspect of the invention is a pharmaceutical composition comprising a compound of Formula III, or a pharmaceutically acceptable salt thereof, and a pharmaceutically acceptable carrier or diluent.

The present invention provides, in another aspect, a compound of Formula IV or a pharmaceutically acceptable salt thereof

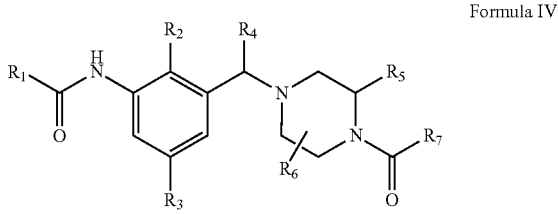

Formula IV wherein R1 is a 6 membered heteroaryl ring substituted with two substituents selected from the group consisting of: i) F and methyl, ii) CN and methyl, and iii) Cl and methyl;
R2 is C1-C3 alkyl or halo;
R3 is halo or CN;
R4 is H;
R5 is C1-C3 alkyl;
R6 is H or methyl; and
R7 is selected from the group consisting of a C3-C6 cycloalkyl optionally substituted with methyl; a methyl substituted with C3-C5 cycloalkyl; and a C2 or C3 alkyl optionally substituted with two F.

Suitably for a compound of Formula IV, R1 is a 6 membered heteroaryl ring substituted with two substituents selected from F and methyl. In another embodiment, R1 is a 6 membered heteroaryl ring substituted with two substituents selected from CN and methyl. In another embodiment R1 is a 6 membered heteroaryl ring substituted with two substituents selected from Cl and methyl.

In one embodiment, the 6 membered heteroaryl R1 ring is a pyridinyl or a pyrimidinyl ring. In another embodiment, the R1 ring is a pyridine. In another embodiment the R1 ring is a pyridimine ring.

When R1 is a pyridinyl, it is suitably di-substituted in the 5, 6 position (the core being called a nictoinamide derivative). In one embodiment the methyl is in the 6-position. In another embodiment, the methyl is in the 5-position.

Suitably, for a compound of Formula IV, R7 is a C3-C6 cycloalkyl optionally substituted with methyl. The C3-C6 cycloalkyl which may be optionally substituted is suitably a cyclopropyl or cyclopentyl ring. In one embodiment the R7 ring is a cyclopentyl ring. In another embodiment, R7 is a cyclopropyl ring.

Suitably, for a compound of Formula IV, R7 is methyl substituted with C3-C5 cycloalkyl. Suitably, the C3-C5 ring is a cyclopropyl or a cyclopentyl ring. In one embodiment, R7 is a cyclopropylmethyl.

Suitably, for a compound of Formula IV, R7 is a C2 or C3 alkyl optionally substituted with two F, the alkyl chain is a straight of branched C3 carbon chain, such as propyl or isopropyl. In one embodiment the first carbon in the chain attached to the carbonyl is the one optionally substituted with two fluorines.

Suitably, for compounds of Formula IV, R2 is C1-C3 alkyl or halo. In one embodiment, R2 is a C1-C3. In another embodiment, R2 is methyl.

Suitably, for compounds of Formula IV, R3 is halo or CN. In one embodiment, R3 is halo. In another embodiment, R3 is fluorine or chlorine. In one embodiment, R3 is fluorine. In another embodiment, R3 is chlorine. In another embodiment, R3 is cyano. In one embodiment, when R3 is fluorine, chlorine or cyano, R2 is methyl.

Suitably, for compounds of Formula IV, R5 is C1-C3 alkyl. In one embodiment R5 is methyl.

Suitably, for compounds of Formula IV, R6 is H or methyl. In one embodiment, R6 is hydrogen.

In one embodiment, a compound of the Formula IV, or a pharmaceutically acceptable salt thereof is selected from:
(S)—N-(5-chloro-3-((4-(cyclopentanecarbonyl)-3-methyl-piperazin-1-yl)methyl)-2-methylphenyl)-5-cyano-6-methylnicotinamide;
(S)—N-(5-chloro-3-((4-(cyclopentanecarbonyl)-3-methyl-piperazin-1-yl)methyl)-2-methylphenyl)-5-cyano-6-methylnicotinamide;
(S)-5-chloro-N-(5-chloro-3-((4-(2-cyclopropylacetyl)-3-methylpiperazin-1-yl)methyl)-2-methylphenyl)-6-methylnicotinamide;
(S)—N-(5-chloro-3-((4-(2-cyclopropylacetyl)-3-methylpiperazin-1-yl)methyl)-2-methylphenyl)-5-cyano-6-methylnicotinamide;
(S)—N-(5-chloro-3-((4-(2-cyclopropylacetyl)-3-methylpiperazin-1-yl)methyl)-2-methylphenyl)-5-cyano-6-methylnicotinamide;
(S)—N-(5-chloro-3-((4-(2-cyclopropylacetyl)-3-methylpiperazin-1-yl)methyl)-2-methylphenyl)-5-fluoro-6-methylnicotinamide;
(S)-5-chloro-N-(5-cyano-3-((4-(2-cyclopropylacetyl)-3-methylpiperazin-1-yl)methyl)-2-methylphenyl)-6-methylnicotinamide;
(S)-5-chloro-N-(3-((4-(2,2-difluorobutanoyl)-3-methylpiperazin-1-yl)methyl)-5-fluoro-2-methylphenyl)-6-methylnicotinamide;
(S)—N-(5-chloro-3-((4-(2-cyclopropylacetyl)-3-methylpiperazin-1-yl)methyl)-2-methylphenyl)-6-cyano-5-methylnicotinamide;)
(S)-5-chloro-N-(5-fluoro-3-((4-isobutyryl-3-methylpiperazin-1-yl)methyl)-2-methylphenyl)-6-methylnicotinamide;
(S)—N-(3-((4-butyryl-3-methylpiperazin-1-yl)methyl)-5-fluoro-2-methylphenyl)-5-chloro-6-methylnicotinamide;
(S)-5-chloro-N-(5-chloro-3-((4-(cyclopropanecarbonyl)-3-methylpiperazin-1-yl)methyl)-2-methylphenyl)-6-methylnicotinamide;
(S)—N-(5-cyano-3-((4-(2-cyclopropylacetyl)-3-methylpiperazin-1-yl)methyl)-2-methylphenyl)-5-fluoro-6-methylnicotinamide;
(S)—N-(5-cyano-3-((4-(2-cyclopropylacetyl)-3-methylpiperazin-1-yl)methyl)-2-methylphenyl)-5-fluoro-6-methylnicotinamide;
(S)—N-(3-((4-butyryl-3-methylpiperazin-1-yl)methyl)-5-chloro-2-methylphenyl)-5-fluoro-6-methylnicotinamide;
(S)-5-chloro-N-(3-((4-(2-cyclopropylacetyl)-3-methylpiperazin-1-yl)methyl)-5-fluoro-2-methylphenyl)-6-methylnicotinamide; or
(S)—N-(5-chloro-3-((4-(2,2-difluorobutanoyl)-3-methylpiperazin-1-yl)methyl)-2-methylphenyl)-5-fluoro-6-methylnicotinamide.

One aspect of the invention is a pharmaceutical composition comprising a compound of Formula IV, or a pharmaceutically acceptable salt thereof, and a pharmaceutically acceptable carrier or diluent.

Suitably, a compound of Formula IV is (S)—N-(5-chloro-3-((4-(2-cyclopropylacetyl)-3-methylpiperazin-1-yl)methyl)-2-methylphenyl)-5-fluoro-6-methylnicotinamide, or a pharmaceutically acceptable salt thereof.

One embodiment of the invention is a pharmaceutical composition comprising (S)—N-(5-chloro-3-((4-(2-cyclopropylacetyl)-3-methylpiperazin-1-yl)methyl)-2-methylphenyl)-5-fluoro-6-methylnicotinamide, or a pharmaceutically acceptable salt thereof and a pharmaceutically acceptable carrier or excipient.

The present invention provides, in another aspect, a compound of Formula V or a pharmaceutically acceptable salt thereof

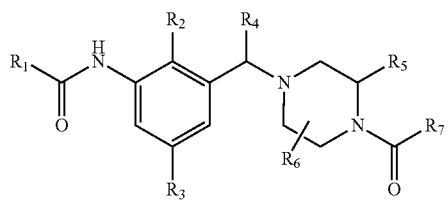

Formula V wherein
R1 is a methyl substituted with a substituent selected from the group consisting of:
   i) a C4-C6 cycloalkyl substituted with OH or two F;
   ii) a 4 to 8 membered heterocycloalkyl ring optionally substituted one or more times, suitably 1 or 2 times, with C(O)Ra, OH, CN, oxo or C1-C3 alkyl, wherein said heterocycloalkyl contains 1 or 2 heteroatoms each independently selected from O and N, and said Ra is a C1-C2 alkyl optionally substituted with methyl or ethyl;
   iii) a 4 to 6 membered monocyclic sulfone;
   iv) oxazolyl or isooxozolyl substituted with methyl;
   v) difluoromethoxy or difluoroethoxy; and
   NRa'SO$_2$CH$_3$, wherein Ra' is a C1-C2 alkyl;
R2 is C1-C3 alkyl or halo;
R3 is halo or CN;
R4 is H;
R5 is C1-C3 alkyl;
R6 is H or methyl; and
R7 is selected from the group consisting of
   i) a C3-C6 cycloalkyl optionally substituted with methyl;
   ii) a methyl substituted with a C3-C5 cycloalkyl; and
   iii) a C2 or C3 alkyl optionally substituted with two F.
Suitably, for compounds of Formula V, R1 is a methyl substituted with a substituent selected from the group consisting of:
   i) a C4-C6 cycloalkyl substituted with OH or two F;
   ii) a 4 to 8 membered heterocycloalkyl ring optionally substituted with C(O)Ra, OH, CN, oxo or C1-C3 alkyl, wherein said heterocycloalkyl contains 1 or 2 heteroatoms each independently selected from O and N, and said Ra is a C1-C2 alkyl optionally substituted with methyl or ethyl;
   iii) a 4 to 6 membered monocyclic sulfone;
   iv) oxazolyl or isooxozolyl substituted with methyl;
   v) difluoromethoxy or difluoroethoxy; and
   vi) NRa'SO$_2$CH$_3$, wherein Ra' is a C1-C2 alkyl.

In one embodiment, R1 is a methyl substituted with a C4-C6 cycloalkyl ring substituted with OH or two F. In one embodiment, the C4-C6 ring is a cyclohexyl ring. In another embodiment, the C4-C6 ring is a cyclobutyl ring.

In one embodiment, R1 is a methyl substituted with a 4 to 8 membered heterocycloalkyl ring optionally substituted one or more times, suitably 1 or 2 times, with C(O)Ra, OH, CN, oxo or C1-C3 alkyl; the heterocycloalkyl ring contains 1 or 2 heteroatoms each independently selected from O and N, and Ra is a C1-C2 alkyl optionally substituted with methyl or ethyl. In another embodiment, the heterocycloalkyl ring is a 4 or 5 membered heterocycloalkyl ring. The 4 to 5 membered heterocyclic alkyl ring is optionally substituted with C(O)Ra, wherein said heterocycloalkyl contains a O or a N, and said Ra is C1-C2 alkyl. It is recognized that the substitution on the heterocyclic ring may be on a ring carbon or on the ring nitrogen, such as in a 1-acetylpyrrolidin-3-yl ring, etc.

In one embodiment the 4 to 8 membered heterocycloalkyl ring is a tetrahydro-2H-pyranyl ring, such as a tetrahydro-2H-pyran-2-yl, a tetrahydro-2H-pyran-4-yl, or a tetrahydro-2H-pyran-3-yl; a tetrahydrofuranyl ring, such as tetrahydrofuran-2-yl or tetrahydrofuran-3-yl; a morpholino; a pyrrolidinyl, such as a pyrrolidin-1-yl, or a pyrrolidin-3-yl; or an oxazolidinyl ring, such as a oxazolidin-3-yl.

In one embodiment, the R1 methyl substituted by a 4 to 8 membered heterocycloalkyl ring is substituted by oxo. In another embodiment R1 methyl substituted by a 4 to 8 membered heterocycloalkyl ring is substituted by C(O)Ra. In another embodiment, the R1 methyl substituted by a 4 to 8 membered heterocycloalkyl ring is disubstituted with an oxo and a C1-C3 alkyl, suitably methyl or ethyl. In one embodiment the R1 methyl substituted by a 4 to 8 membered heterocycloalkyl ring is a pyrrolidnyl ring disubstituted with oxo and methyl or ethyl. It is recognized that the nitrogen in the heterocyclic ring may be substituted by the optional substitutent, such as the C1-3 alkyl, e.g. a 1-methyl-2-oxopyrrolidin-3-yl, or a 1-ethyl-5-oxopyrrolidin-3-yl.

Suitably, for a compound of Formula V, R7 is a C3-C6 cycloalkyl optionally substituted with methyl. The C3-C6 cycloalkyl which may be optionally substituted is suitably a cyclopropyl or cyclopentyl ring. In one embodiment the R7 ring is a cyclopentyl ring. In another embodiment, R7 is a cyclopropyl ring.

Suitably, for a compound of Formula V, R7 is methyl substituted with C3-C5 cycloalkyl. Suitably, the C3-C5 ring is a cyclopropyl or a cyclopentyl ring. In one embodiment, R7 is a cyclopropylmethyl group.

Suitably, for a compound of Formula V, R7 is a C2 or C3 alkyl optionally substituted with two F, the alkyl chain is a straight of branched C3 carbon chain, such as propyl or isopropyl. In one embodiment the first carbon in the chain attached to the carbonyl is the one optionally substituted with two fluorines.

Suitably, for compounds of Formula V, R2 is C1-C3 alkyl or halo. In one embodiment, R2 is a C1-C3 alkyl. In another embodiment, R2 is methyl.

Suitably, for compounds of Formula V, R3 is halo or CN. In one embodiment, R3 is halo. In another embodiment, R3 is fluorine or chlorine. In one embodiment, R3 is fluorine. In another embodiment, R3 is chlorine. In another embodiment, R3 is cyano. In one embodiment, when R3 is fluorine, chlorine or cyano, R2 is methyl.

Suitably, for compounds of Formula V, R5 is C1-C3 alkyl. In one embodiment R5 is methyl.

Suitably, for compounds of Formula V, R6 is H or methyl. In one embodiment, R6 is hydrogen.

In one embodiment, a compound of the Formula V, or a pharmaceutically acceptable salt thereof is selected from:
(S)—N-(3-((4-(cyclopentanecarbonyl)-3-methylpiperazin-1-yl)methyl)-5-fluoro-2-methylphenyl)-2-(oxetan-3-yl)acetamide;
N-(3-(((S)-4-(cyclopentanecarbonyl)-3-methylpiperazin-1-yl)methyl)-5-fluoro-2-methylphenyl)-3-(tetrahydrofuran-2-yl)propanamide;

N-(3-(((S)-4-(cyclopentanecarbonyl)-3-methylpiperazin-1-yl)methyl)-5-fluoro-2-methylphenyl)-3-(tetrahydrofuran-2-yl)propanamide;

N-(3-(((S)-4-(cyclopentanecarbonyl)-3-methylpiperazin-1-yl)methyl)-5-fluoro-2-methylphenyl)-2-(tetrahydrofuran-3-yl)acetamide;

N-(3-(((S)-4-(cyclopentanecarbonyl)-3-methylpiperazin-1-yl)methyl)-5-fluoro-2-methylphenyl)-2-(tetrahydrofuran-2-yl)acetamide;

N-(3-(((S)-4-(cyclopentanecarbonyl)-3-methylpiperazin-1-yl)methyl)-5-fluoro-2-methylphenyl)-2-(tetrahydrofuran-2-yl)acetamide;

(S)—N-(3-((4-(cyclopentanecarbonyl)-3-methylpiperazin-1-yl)methyl)-5-fluoro-2-methylphenyl)-2-(tetrahydro-2H-pyran-4-yl)acetamide;

N-(3-(((S)-4-(cyclopentanecarbonyl)-3-methylpiperazin-1-yl)methyl)-5-fluoro-2-methylphenyl)-2-(tetrahydro-2H-pyran-2-yl)acetamide;

N-(3-(((S)-4-(cyclopentanecarbonyl)-3-methylpiperazin-1-yl)methyl)-5-fluoro-2-methylphenyl)-2-(tetrahydro-2H-pyran-2-yl)acetamide;

cis-N-(3-(((S)-4-(cyclopentanecarbonyl)-3-methylpiperazin-1-yl)methyl)-5-fluoro-2-methylphenyl)-2-(3-hydroxycyclopentyl)acetamide;

N-(3-(((S)-4-(cyclopentanecarbonyl)-3-methylpiperazin-1-yl)methyl)-5-fluoro-2-methylphenyl)-2-(3-hydroxycyclohexyl)acetamide, N-(3-(((S)-4-(cyclopentanecarbonyl)-3-methylpiperazin-1-yl)methyl)-5-fluoro-2-methylphenyl)-2-(hexahydrofuro[2,3-b]furan-3-yl)acetamide;

(S)—N-(3-((4-(cyclopentanecarbonyl)-3-methylpiperazin-1-yl)methyl)-5-fluoro-2-methylphenyl)-2-(2-methyloxazol-4-yl)acetamide;

(S)—N-(3-((4-(cyclopentanecarbonyl)-3-methylpiperazin-1-yl)methyl)-5-fluoro-2-methylphenyl)-2-(2-methyloxazol-4-yl)acetamide;

(S)—N-(3-((4-(cyclopentanecarbonyl)-3-methylpiperazin-1-yl)methyl)-5-fluoro-2-methylphenyl)-2-(3-methylisoxazol-5-yl)acetamide;

(S)—N-(3-((4-(cyclopentanecarbonyl)-3-methylpiperazin-1-yl)methyl)-5-chloro-2-methylphenyl)-2-(3-methylisoxazol-5-yl)acetamide;

N-(5-chloro-3-(((S)-4-(cyclopentanecarbonyl)-3-methylpiperazin-1-yl)methyl)-2-methylphenyl)-2-(tetrahydrofuran-2-yl)acetamide;

N-(5-chloro-3-(((S)-4-(cyclopentanecarbonyl)-3-methylpiperazin-1-yl)methyl)-2-methylphenyl)-2-(tetrahydrofuran-2-yl)acetamide;

N-(5-chloro-3-(((S)-4-(cyclopentanecarbonyl)-3-methylpiperazin-1-yl)methyl)-2-methylphenyl)-2-(2-methyltetrahydrofuran-3-yl)acetamide;

N-(5-chloro-3-(((S)-4-(cyclopentanecarbonyl)-3-methylpiperazin-1-yl)methyl)-2-methylphenyl)-2-(2-methyltetrahydrofuran-3-yl)acetamide;

(S)—N-(5-chloro-3-((4-(cyclopentanecarbonyl)-3-methylpiperazin-1-yl)methyl)-2-methylphenyl)-2-(tetrahydro-2H-pyran-4-yl)acetamide;

(S)—N-(5-chloro-3-((4-(cyclopentanecarbonyl)-3-methylpiperazin-1-yl)methyl)-2-methylphenyl)-2-(tetrahydro-2H-pyran-4-yl)acetamide;

N-(5-chloro-3-(((S)-4-(cyclopentanecarbonyl)-3-methylpiperazin-1-yl)methyl)-2-methylphenyl)-2-(tetrahydro-2H-pyran-2-yl)acetamide;

N-(5-chloro-3-(((S)-4-(cyclopentanecarbonyl)-3-methylpiperazin-1-yl)methyl)-2-methylphenyl)-2-(tetrahydro-2H-pyran-2-yl)acetamide;

(S)—N-(5-chloro-3-((4-(cyclopentanecarbonyl)-3-methylpiperazin-1-yl)methyl)-2-methylphenyl)-2-morpholinoacetamide;

(S)—N-(5-chloro-3-((4-(cyclopentanecarbonyl)-3-methylpiperazin-1-yl)methyl)-2-methylphenyl)-2-morpholinoacetamide;

(S)—N-(5-chloro-3-((4-(cyclopentanecarbonyl)-3-methylpiperazin-1-yl)methyl)-2-methylphenyl)-4-hydroxycyclohexanecarboxamide;

N-(5-chloro-3-(((S)-4-(cyclopentanecarbonyl)-3-methylpiperazin-1-yl)methyl)-2-methylphenyl)-2-(5-methyltetrahydrofuran-3-yl)acetamide;

N-(5-chloro-3-(((S)-4-(cyclopentanecarbonyl)-3-methylpiperazin-1-yl)methyl)-2-methylphenyl)-2-(5-methyltetrahydrofuran-3-yl)acetamide;

N-(5-chloro-3-(((S)-4-(cyclopentanecarbonyl)-3-methylpiperazin-1-yl)methyl)-2-methylphenyl)-2-(tetrahydro-2H-pyran-3-yl)acetamide;

N-(5-chloro-3-(((S)-4-(cyclopentanecarbonyl)-3-methylpiperazin-1-yl)methyl)-2-methylphenyl)-2-(tetrahydro-2H-pyran-3-yl)acetamide;

N-(5-chloro-3-(((S)-4-(cyclopentanecarbonyl)-3-methylpiperazin-1-yl)methyl)-2-methylphenyl)-2-(2-methyltetrahydro-2H-pyran-4-yl)acetamide;

N-(5-chloro-3-(((S)-4-(cyclopentanecarbonyl)-3-methylpiperazin-1-yl)methyl)-2-methylphenyl)-2-(4-methyltetrahydrofuran-3-yl)acetamide;

N-(5-chloro-3-(((S)-4-(cyclopentanecarbonyl)-3-methylpiperazin-1-yl)methyl)-2-methylphenyl)-2-(4-methyltetrahydrofuran-3-yl)acetamide;

N-(5-chloro-3-(((S)-4-(cyclopentanecarbonyl)-3-methylpiperazin-1-yl)methyl)-2-methylphenyl)-2-(3-methyltetrahydro-2H-pyran-4-yl)acetamide;

N-(5-chloro-3-(((S)-4-(cyclopentanecarbonyl)-3-methylpiperazin-1-yl)methyl)-2-methylphenyl)-2-(3-methyltetrahydro-2H-pyran-4-yl)acetamide;

(S)—N-(5-chloro-3-((4-(cyclopentanecarbonyl)-3-methylpiperazin-1-yl)methyl)-2-methylphenyl)-2-(2-oxopyrrolidin-1-yl)acetamide;

(S)—N-(5-chloro-3-((4-(cyclopentanecarbonyl)-3-methylpiperazin-1-yl)methyl)-2-methylphenyl)-2-(2-oxopyrrolidin-1-yl)acetamide;

(S)—N-(5-chloro-3-((4-(cyclopentanecarbonyl)-3-methylpiperazin-1-yl)methyl)-2-methylphenyl)-2-(2-oxooxazolidin-3-yl)acetamide;

N-(5-chloro-3-(((S)-4-(2-cyclopropylacetyl)-3-methylpiperazin-1-yl)methyl)-2-methylphenyl)-2-(tetrahydrofuran-3-yl)acetamide;

N-(5-cyano-3-(((S)-4-(cyclopentanecarbonyl)-3-methylpiperazin-1-yl)methyl)-2-methylphenyl)-2-(tetrahydrofuran-3-yl)acetamide;

(S)—N-(5-chloro-3-((4-(cyclopentanecarbonyl)-3-methylpiperazin-1-yl)methyl)-2-methylphenyl)-2-(1,1-dioxidotetrahydro-2H-thiopyran-4-yl)acetamide;

(S)—N-(5-chloro-3-((4-(cyclopentanecarbonyl)-3-methylpiperazin-1-yl)methyl)-2-methylphenyl)-2-(3-oxomorpholino)acetamide;

(S)—N-(5-chloro-3-((4-(cyclopentanecarbonyl)-3-methylpiperazin-1-yl)methyl)-2-methylphenyl)-2-(1,1-dioxidothietan-3-yl)acetamide;

(S)—N-(5-chloro-3-((4-(cyclopentanecarbonyl)-3-methylpiperazin-1-yl)methyl)-2-methylphenyl)-2-(3,3-difluorocyclobutyl)acetamide;

(S)—N-(3-((4-(cyclopentanecarbonyl)-3-methylpiperazin-1-yl)methyl)-5-fluoro-2-methylphenyl)-2-(3,3-difluorocyclobutyl)acetamide;

(S)—N-(5-chloro-3-((4-(cyclopentanecarbonyl)-3-methyl-piperazin-1-yl)methyl)-2-methylphenyl)-4-cyanobutana-mide;
N-(5-chloro-3-(((S)-4-(cyclopentanecarbonyl)-3-methylpip-erazin-1-yl)methyl)-2-methylphenyl)-2-((S)-tetrahydro-furan-3-yl)acetamide;
N-(5-chloro-3-(((S)-4-(cyclopentanecarbonyl)-3-methylpip-erazin-1-yl)methyl)-2-methylphenyl)-2-((R)-tetrahydro-furan-3-yl)acetamide;
N-(2,5-dichloro-3-(((S)-4-(cyclopentanecarbonyl)-3-meth-ylpiperazin-1-yl)methyl)phenyl)-2-(tetrahydrofuran-3-yl) acetamide;
N-(2,5-dichloro-3-(((S)-4-(cyclopentanecarbonyl)-3-meth-ylpiperazin-1-yl)methyl)phenyl)-2-((S)-tetrahydrofuran-3-yl)acetamide;
N-(2,5-dichloro-3-(((S)-4-(cyclopentanecarbonyl)-3-meth-ylpiperazin-1-yl)methyl)phenyl)-2-((R)-tetrahydrofuran-3-yl) acetamide;
N-(5-chloro-3-(((S)-4-(cyclopentanecarbonyl)-3-methylpip-erazin-1-yl)methyl)-2-methylphenyl)-2-((1s,4R)-4-hy-droxycyclohexyl)acetamide;
N-(5-chloro-3-(((S)-4-(cyclopentanecarbonyl)-3-methylpip-erazin-1-yl)methyl)-2-methylphenyl)-2-((1r,4S)-4-hy-droxycyclohexyl)acetamide;
N-(3-(((S)-4-(cyclopentanecarbonyl)-3-methylpiperazin-1-yl)methyl)-5-fluoro-2-methylphenyl)-2-((1r,4S)-4-hy-droxycyclohexyl)acetamide;
N-(3-(((S)-4-(cyclopentanecarbonyl)-3-methylpiperazin-1-yl)methyl)-5-fluoro-2-methylphenyl)-2-((1s,4R)-4-hy-droxycyclohexyl)acetamide;
N-(5-chloro-3-(((S)-4-(cyclopentanecarbonyl)-3-methylpip-erazin-1-yl)methyl)-2-methylphenyl)-2-((S)-1-methyl-5-oxopyrrolidin-3-yl)acetamide;
N-(5-chloro-3-(((S)-4-(cyclopentanecarbonyl)-3-methylpip-erazin-1-yl)methyl)-2-methylphenyl)-2-((R)-1-methyl-5-oxopyrrolidin-3-yl)acetamide;
N-(5-chloro-3-(((S)-4-(cyclopentanecarbonyl)-3-methylpip-erazin-1-yl)methyl)-2-methylphenyl)-2-((S)-1-ethyl-5-oxopyrrolidin-3-yl)acetamide;
N-(5-chloro-3-(((S)-4-(cyclopentanecarbonyl)-3-methylpip-erazin-1-yl)methyl)-2-methylphenyl)-2-((R)-1-ethyl-5-oxopyrrolidin-3-yl)acetamide;
N-(5-chloro-3-(((S)-4-(cyclopentanecarbonyl)-3-methylpip-erazin-1-yl)methyl)-2-methylphenyl)-2-((R)-1-methyl-2-oxopyrrolidin-3-yl)acetamide; E69
N-(5-chloro-3-(((S)-4-(cyclopentanecarbonyl)-3-methylpip-erazin-1-yl)methyl)-2-methylphenyl)-2-((S)-1-methyl-2-oxopyrrolidin-3-yl)acetamide;
(S)—N-(5-chloro-3-((4-(2-cyclopropylacetyl)-3-methylpip-erazin-1-yl)methyl)-2-methylphenyl)-2-(4-hydroxycyclo-hexyl)acetamide;
(S)—N-(5-chloro-3-((4-(2-cyclopropylacetyl)-3-methylpip-erazin-1-yl)methyl)-2-methylphenyl)-2-(4-hydroxycyclo-hexyl)acetamide;
cis N-(3-(((S)-4-(cyclopentanecarbonyl)-3-methylpiper-azin-1-yl)methyl)-5-fluoro-2-methylphenyl)-2-(2-hy-droxycyclopentyl)acetamide;
trans N-(3-(((S)-4-(cyclopentanecarbonyl)-3-methylpiper-azin-1-yl)methyl)-5-fluoro-2-methylphenyl)-2-(2-hy-droxycyclopentyl)acetamide;
Cis (S)—N-(5-chloro-3-((4-(cyclopentanecarbonyl)-3-methylpiperazin-1-yl)methyl)-2-methylphenyl)-2-(3-hy-droxycyclobutyl)acetamide;
trans (S)—N-(5-chloro-3-((4-(cyclopentanecarbonyl)-3-methylpiperazin-1-yl)methyl)-2-methylphenyl)-2-(3-hy-droxycyclobutyl)acetamide;

N-(3-(((S)-4-(cyclopentanecarbonyl)-3-methylpiperazin-1-yl)methyl)-5-fluoro-2-methylphenyl)-2-(2-hydroxycyclo-hexyl)acetamide;
(S)—N-(5-chloro-3-((4-(cyclopentanecarbonyl)-3-methyl-piperazin-1-yl)methyl)-2-methylphenyl)-2-(3-hy-droxyazetidin-1-yl)acetamide;
N-(5-chloro-3-(((S)-4-(cyclopentanecarbonyl)-3-methylpip-erazin-1-yl)methyl)-2-methylphenyl)-2-(1,1-dioxidotet-rahydrothiophen-3-yl)acetamide;
N-(5-chloro-3-(((S)-4-(cyclopentanecarbonyl)-3-methylpip-erazin-1-yl)methyl)-2-methylphenyl)-2-(1,1-dioxidotet-rahydrothiophen-3-yl)acetamide;
N-(5-chloro-3-(((S)-4-(cyclopentanecarbonyl)-3-methylpip-erazin-1-yl)methyl)-2-methylphenyl)-2-(1,1-dioxidotet-rahydrothiophen-2-yl)acetamide;
N-(5-chloro-3-(((S)-4-(cyclopentanecarbonyl)-3-methylpip-erazin-1-yl)methyl)-2-methylphenyl)-2-(1,1-dioxidotet-rahydro-2H-thiopyran-3-yl)acetamide;
N-(5-chloro-3-(((S)-4-(cyclopentanecarbonyl)-3-methylpip-erazin-1-yl)methyl)-2-methylphenyl)-2-(1,1-dioxidotet-rahydro-2H-thiopyran-3-yl)acetamide;
2-(1-acetylpyrrolidin-3-yl)-N-(3-(((S)-4-(cyclopentanecar-bonyl)-3-methylpiperazin-1-yl)methyl)-5-fluoro-2-meth-ylphenyl)acetamide;
(S)-2-(1-acetylazetidin-3-yl)-N-(5-chloro-3-((4-(cyclopen-tanecarbonyl)-3-methylpiperazin-1-yl)methyl)-2-methyl-phenyl)acetamide;
(S)—N-(5-chloro-3-((4-(cyclopentanecarbonyl)-3-methyl-piperazin-1-yl)methyl)-2-methylphenyl)-2-(N-methylm-ethylsulfonamido)acetamide;
(S)—N-(5-chloro-3-((4-(cyclopentanecarbonyl)-3-methyl-piperazin-1-yl)methyl)-2-methylphenyl)-2-(N-methylm-ethylsulfonamido)acetamide;
2-(1-acetylpyrrolidin-3-yl)-N-(5-chloro-3-(((S)-4-(cyclo-pentanecarbonyl)-3-methylpiperazin-1-yl)methyl)-2-methylphenyl)acetamide;
2-(1-acetylpyrrolidin-3-yl)-N-(5-chloro-3-(((S)-4-(cyclo-pentanecarbonyl)-3-methylpiperazin-1-yl)methyl)-2-methylphenyl)acetamide;
2-((R)-1-acetylpyrrolidin-2-yl)-N-(5-chloro-3-(((S)-4-(cy-clopentanecarbonyl)-3-methylpiperazin-1-yl)methyl)-2-methylphenyl)acetamide;
2-((S)-1-acetylpyrrolidin-2-yl)-N-(5-chloro-3-(((S)-4-(cy-clopentanecarbonyl)-3-methylpiperazin-1-yl)methyl)-2-methylphenyl)acetamide;
2-((S)-1-acetylpiperidin-3-yl)-N-(5-chloro-3-(((S)-4-(cyclo-pentanecarbonyl)-3-methylpiperazin-1-yl)methyl)-2-methylphenyl)acetamide; or
2-((R)-1-acetylpiperidin-3-yl)-N-(5-chloro-3-(((S)-4-(cy-clopentanecarbonyl)-3-methylpiperazin-1-yl)methyl)-2-methylphenyl)acetamide.

One aspect of the invention is a pharmaceutical composition comprising a compound of Formula V, or a pharmaceutically acceptable salt thereof, and a pharmaceutically acceptable carrier or diluent.

The present invention provides, in another aspect, a compound of Formula VI or a pharmaceutically acceptable salt thereof:

Formula VI

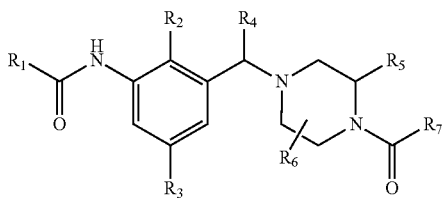

wherein R1 is a C2-C5 alkyl substituted with
i) SO₂Rb,
ii) CF₃,
iii) CN,
iv) methoxy,
v) OH,
vi) C(O)NRbRb,
vii) NRbRc
viii) 5 or 6 membered heterocycloalkyl containing an Oxygen
ix) cyclopropyl substituted with CN, or
x) O—CHF₂,
Rb is independently selected from methyl or ethyl,
Rc is —C(O)CH₃;
R2 is a C1-C3 alkyl or halo;
R3 is halo or CN;
R4 is H;
R5 is C1-C3 alkyl;
R6 is H or methyl; and
R7 is selected from the group consisting of
i) a —C3-C6 cycloalkyl optionally substituted with methyl;
ii) a methyl substituted with a C3-C5 cycloalkyl; and
iii) a —C2 or C3 alkyl optionally substituted with two F.

Suitably, for a compound of Formula VI, R1 is a C2-C5 alkyl substituted with
i) SO₂Rb,
ii) CF₃,
iii) CN,
iv) methoxy,
v) OH,
vi) C(O)NRbRb,
vii) NRbRc
viii) 5 or 6 membered heterocycloalkyl containing 1 O,
ix) cyclopropyl substituted with CN, or
x) O—CHF₂.

Suitably, Rb is independently selected from methyl or ethyl.
Suitably, Rc is —C(O)CH₃.

The R1 C2-C5 alkyl carbon chain may be branched or straight. In one embodiment the C3-C5 alkyl is a branched chain. Suitably, the C2-C5 alkyl carbon is ethyl, propyl, butyl or an isobutyl.

Suitably, for a compound of Formula VI, R7 is a C3-C6 cycloalkyl optionally substituted with methyl. The C3-C6 cycloalkyl which may be optionally substituted is suitably a cyclopropyl or cyclopentyl ring. In one embodiment the R7 ring is a cyclopentyl ring. In another embodiment, R7 is a cyclopropyl ring.

Suitably, for a compound of Formula VI, R7 is methyl substituted with C3-C5 cycloalkyl. Suitably, the C3-C5 ring is a cyclopropyl or a cyclopentyl ring. In one embodiment, R7 is a cyclopropyl methyl.

Suitably, for a compound of Formula VI, R7 is a C2 or C3 alkyl optionally substituted with two F, the alkyl chain is a straight of branched C3 carbon chain, such as propyl or isopropyl. In one embodiment the first carbon in the chain attached to the carbonyl is the one optionally substituted with two fluorines.

Suitably, for compounds of Formula VI, R2 is C1-C3 alkyl or halo. In one embodiment, R2 is a C1-C3 alkyl. In another embodiment, R2 is methyl.

Suitably, for compounds of Formula VI, R3 is halo or CN. In one embodiment, R3 is halo. In another embodiment, R3 is fluorine or chlorine. In one embodiment, R3 is fluorine. In another embodiment, R3 is chlorine. In another embodiment, R3 is cyano. In one embodiment, when R3 is fluorine, chlorine or cyano, R2 is methyl.

Suitably, for compounds of Formula VI, R5 is C1-C3 alkyl. In one embodiment R5 is methyl.

Suitably, for compounds of Formula VI, R6 is H or methyl. In one embodiment, R6 is hydrogen.

In one embodiment, a compound of the Formula VI, or a pharmaceutically acceptable salt thereof is selected from:
N-(5-chloro-3-(((S)-4-(cyclopentanecarbonyl)-3-methylpiperazin-1-yl)methyl)-2-methylphenyl)-2-(tetrahydrofuran-2-yl)propanamide;
N-(5-chloro-3-(((S)-4-(cyclopentanecarbonyl)-3-methylpiperazin-1-yl)methyl)-2-methylphenyl)-2-(tetrahydrofuran-2-yl)propanamide;
N-(5-chloro-3-(((S)-4-(cyclopentanecarbonyl)-3-methylpiperazin-1-yl)methyl)-2-methylphenyl)-2-(tetrahydrofuran-3-yl)propanamide;
(S)—N-(5-chloro-3-((4-(cyclopentanecarbonyl)-3-methylpiperazin-1-yl)methyl)-2-methylphenyl)-4-methoxybutanamide;
(S)—N-(5-chloro-3-((4-(cyclopentanecarbonyl)-3-methylpiperazin-1-yl)methyl)-2-methylphenyl)-4-methoxybutanamide;
(S)—N-(5-chloro-3-((4-(cyclopentanecarbonyl)-3-methylpiperazin-1-yl)methyl)-2-methylphenyl)-2-(2-methoxyethoxy)acetamide;
(S)—N-(5-chloro-3-((4-(2-cyclopropylacetyl)-3-methylpiperazin-1-yl)methyl)-2-methylphenyl)-4-methoxybutanamide;
(S)—N-(5-chloro-3-((4-(cyclopentanecarbonyl)-3-methylpiperazin-1-yl)methyl)-2-methylphenyl)-3-(1-cyanocyclopropyl)propanamide;
(S)—N-(5-chloro-3-((4-(cyclopentanecarbonyl)-3-methylpiperazin-1-yl)methyl)-2-methylphenyl)-4-cyano-4-methylpentanamide;
(S)—N-(5-chloro-3-((4-(cyclopentanecarbonyl)-3-methylpiperazin-1-yl)methyl)-2-methylphenyl)-2-hydroxy-2-methylpropanamide;
(S)—N-(5-chloro-3-((4-(cyclopentanecarbonyl)-3-methylpiperazin-1-yl)methyl)-2-methylphenyl)-3-hydroxy-3-methylbutanamide;
(S)—N-(5-chloro-3-((4-(cyclopentanecarbonyl)-3-methylpiperazin-1-yl)methyl)-2-methylphenyl)-3-(methylsulfonyl)propanamide;
(S)—N-(5-chloro-3-((4-(cyclopentanecarbonyl)-3-methylpiperazin-1-yl)methyl)-2-methylphenyl)-4-(methylsulfonyl)butanamide;
(S)—N-(5-cyano-3-((4-(cyclopentanecarbonyl)-3-methylpiperazin-1-yl)methyl)-2-methylphenyl)-4-(methylsulfonyl)butanamide;
(S)—N-(5-chloro-3-((4-(cyclopentanecarbonyl)-3-methylpiperazin-1-yl)methyl)-2-methylphenyl)-3-(ethylsulfonyl)propanamide;
(S)—N-(5-cyano-3-((4-(cyclopentanecarbonyl)-3-methylpiperazin-1-yl)methyl)-2-methylphenyl)-3-(ethylsulfonyl)propanamide;

(S)—N-(5-cyano-3-((4-(cyclopentanecarbonyl)-3-methyl-piperazin-1-yl)methyl)-2-methylphenyl)-3-(ethylsulfonyl)propanamide;

(S)—N-(5-chloro-3-((4-(2-cyclopentylacetyl)-3-methylpiperazin-1-yl)methyl)-2-methylphenyl)-3-(methylsulfonyl)propanamide;

(S)—N-(5-chloro-3-((4-(2-cyclopentylacetyl)-3-methylpiperazin-1-yl)methyl)-2-methylphenyl)-3-(methylsulfonyl)propanamide;

(S)—N-(5-chloro-3-((4-(cyclohexanecarbonyl)-3-methyl-piperazin-1-yl)methyl)-2-methylphenyl)-3-(methylsulfonyl)propanamide;

(S)—N-(5-chloro-3-((4-(cyclopentanecarbonyl)-3-methyl-piperazin-1-yl)methyl)-2-methylphenyl)-4,4,4-trifluorobutanamide;

(S)—N-(5-chloro-3-((4-(cyclopentanecarbonyl)-3-methyl-piperazin-1-yl)methyl)-2-methylphenyl)-5,5,5-trifluoropentanamide;

(S)—N-(5-chloro-3-((4-(cyclopentanecarbonyl)-3-methyl-piperazin-1-yl)methyl)-2-methylphenyl)-4-cyanobutanamide, (S)—N-(5-chloro-3-((4-(cyclopentanecarbonyl)-3-methyl-piperazin-1-yl)methyl)-2-methylphenyl)-4-cyanobutanamide;

(S)—N-(5-chloro-3-((4-(2-cyclopropylacetyl)-3-methylpiperazin-1-yl)methyl)-2-methylphenyl)-4-cyano-4-methylpentanamide;

(S)—N-(5-chloro-2-methyl-3-((3-methyl-4-(spiro[2.3]hexane-5-carbonyl)piperazin-1-yl)methyl)phenyl)-3-(methylsulfonyl)propanamide;

N-(3-(((3S)-4-(bicyclo[3.1.0]hexane-3-carbonyl)-3-methyl-piperazin-1-yl)methyl)-5-chloro-2-methylphenyl)-3-(methylsulfonyl)propanamide;

(S)—N-(5-chloro-3-((4-(cyclopentanecarbonyl)-3-methyl-piperazin-1-yl)methyl)-2-methylphenyl)-3-(N-methylacetamido) propanamide;

(S)—N-(5-chloro-3-((4-(cyclopentanecarbonyl)-3-methyl-piperazin-1-yl)methyl)-2-methylphenyl)-4-(Nmethylacetamido) butanamide; or (S)—N$^1$-(5-chloro-3-((4-(cyclopentanecarbonyl)-3-methyl-piperazin-1-yl)methyl)-2-methylphenyl)-N$^4$,N$^4$-dimethylsuccinamide.

One aspect of the invention is a pharmaceutical composition comprising a compound of Formula VI, or a pharmaceutically acceptable salt thereof, and a pharmaceutically acceptable carrier or diluent.

The present invention provides, in another aspect, a compound of Formula VII or a pharmaceutically acceptable salt thereof:

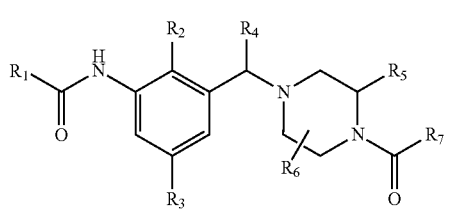

Formula VII wherein
R1 is —CH$_2$—O-Rd,
Rd is a C1-C4 alkyl optionally substituted with i) methoxy, ii) CN, iii) CHF$_2$ or iv) cyclopropyl substituted with CN;
R2 is C1-C3 alkyl or halo;
R3 is halo or CN;
R4 is H;
R5 is C1-C3 alkyl;
R6 is H or methyl; and
R7 is selected from the group consisting of
  i) a —C3-C6 cycloalkyl optionally substituted with methyl;
  ii) a methyl substituted with a C3-C5 cycloalkyl; and
  iii) a —C2 or C3 alkyl optionally substituted with two F.

Suitably, for a compound of Formula VII, R1 is —CH$_2$—O-Rd, and Rd is a C1-C4 alkyl optionally substituted with i) methoxy, ii) CN, iii) CHF$_2$ or iv) cyclopropyl substituted with CN. The Rd C1-4 alkyl carbon chain may be branched or straight. In one embodiment, the C1-C4 carbon chain is methyl or is a methylene group. When the C1-C4alkyl group of Rd is substituted with a cyclopropyl, it is recognized that the cyano may be substituted on the 1-position of the cyclopropyl ring (the same position substituted to the C1-4 carbon chain).

Suitably, for a compound of Formula VII, R7 is a C3-C6 cycloalkyl optionally substituted with methyl. The C3-C6 cycloalkyl which may be optionally substituted is suitably a cyclopropyl or cyclopentyl ring. In one embodiment the R7 ring is a cyclopentyl ring. In another embodiment, R7 is a cyclopropyl ring.

Suitably, for a compound of Formula VII, R7 is methyl substituted with C3-C5 cycloalkyl. Suitably, the C3-C5 ring is a cyclopropyl or a cyclopentyl ring. In one embodiment, R7 is a methyl cyclopropyl.

Suitably, for a compound of Formula VII, R7 is a C2 or C3 alkyl optionally substituted with two F, the alkyl chain is a straight of branched C3 carbon chain, such as propyl or isopropyl. In one embodiment the first carbon in the chain attached to the carbonyl is the one optionally substituted with two fluorines.

Suitably, for compounds of Formula VII, R2 is C1-C3 alkyl or halo. In one embodiment, R2 is a C1-C3 alkyl. In another embodiment, R2 is methyl.

Suitably, for compounds of Formula VII, R3 is halo or CN. In one embodiment, R3 is halo. In another embodiment, R3 is fluorine or chlorine. In one embodiment, R3 is fluorine. In another embodiment, R3 is chlorine. In another embodiment, R3 is cyano. In one embodiment, when R3 is fluorine, chlorine or cyano, R2 is methyl.

Suitably, for compounds of Formula VII, R5 is C1-C3 alkyl. In one embodiment R5 is methyl.

Suitably, for compounds of Formula VII, R6 is H or methyl. In one embodiment, R6 is hydrogen.

In one embodiment, a compound of the Formula VI is selected from:

(S)—N-(5-chloro-3-((4-(cyclopentanecarbonyl)-3-methyl-piperazin-1-yl)methyl)-2-methylphenyl)-2-(difluoromethoxy)acetamide;

(S)—N-(5-chloro-3-((4-(cyclopentanecarbonyl)-3-methyl-piperazin-1-yl)methyl)-2-methylphenyl)-3-(difluoromethoxy)propanamide;

(S)—N-(5-chloro-3-((4-(cyclopentanecarbonyl)-3-methyl-piperazin-1-yl)methyl)-2-methylphenyl)-2-((1-cyanocyclopropyl)methoxy)acetamide;

(S)—N-(5-chloro-3-((4-(cyclopentanecarbonyl)-3-methyl-piperazin-1-yl)methyl)-2-methylphenyl)-2-(2,2-difluoroethoxy)acetamide; or (S)—N-(5-chloro-3-((4-(cyclopentanecarbonyl)-3-methyl-piperazin-1-yl)methyl)-2-methylphenyl)-2-(2-cyano-2-methylpropoxy)acetamide.

One aspect of the invention is a pharmaceutical composition comprising a compound of Formula VI, or a pharmaceutically acceptable salt thereof, and a pharmaceutically acceptable carrier or diluent.

The present invention provides, in another aspect, a compound of Formula VIII or a pharmaceutically acceptable salt thereof:

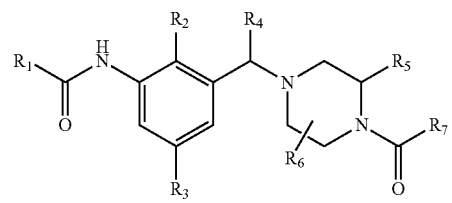

Formula VIII wherein
R1 is a C3-C6 cycloalkyl substituted with a substituent selected from the group consisting of
  i) —NHC(O)CH$_3$, ii) SO$_2$CH$_3$, iii) OH, and iv) C1-C3 alkyl substituted with OH;
R2 is C1-C3 alkyl or halo;
R3 is halo or CN;
R4 is H;
R5 is C1-C3 alkyl;
R6 is H or methyl; and
R7 is selected from the group consisting of
  i) a —C3-C6 cycloalkyl optionally substituted with methyl;
  ii) a methyl substituted with a C3-C5 cycloalkyl; and
  iii) a —C2 or C3 alkyl optionally substituted with two F.

Suitably, for a compound of Formula VIII, R1 is a C3-C6 cycloalkyl substituted with a substituent selected from the group consisting of i) —NHC(O)CH$_3$, ii) —SO$_2$CH$_3$, iii) —OH, and iv) a —C1-C3 alkyl substituted with OH.

Suitably, for a compound of Formula VIII, R7 is a C3-C6 cycloalkyl optionally substituted with methyl. The C3-C6 cycloalkyl which may be optionally substituted is suitably a cyclopropyl or cyclopentyl ring. In one embodiment the R7 ring is a cyclopentyl ring. In another embodiment, R7 is a cyclopropyl ring.

Suitably, for a compound of Formula VIII, R7 is methyl substituted with C3-C5 cycloalkyl. Suitably, the C3-C5 ring is a cyclopropyl or a cyclopentyl ring. In one embodiment, R7 is a methyl cyclopropyl.

Suitably, for a compound of Formula VIII, R7 is a C2 or C3 alkyl optionally substituted with two F, the alkyl chain is a straight of branched C3 carbon chain, such as propyl or isopropyl. In one embodiment the first carbon in the chain attached to the carbonyl is the one optionally substituted with two fluorines.

Suitably, for compounds of Formula VIII, R2 is C1-C3 alkyl or halo. In one embodiment, R2 is a C1-C3 alkyl. In another embodiment, R2 is methyl.

Suitably, for compounds of Formula VIII, R3 is halo or CN. In one embodiment, R3 is halo. In another embodiment, R3 is fluorine or chlorine. In one embodiment, R3 is fluorine. In another embodiment, R3 is chlorine. In another embodiment, R3 is cyano. In one embodiment, when R3 is fluorine, chlorine or cyano, R2 is methyl.

Suitably, for compounds of Formula VIII, R5 is C1-C3 alkyl. In one embodiment R5 is methyl.

Suitably, for compounds of Formula VIII, R6 is H or methyl. In one embodiment, R6 is hydrogen.

In one embodiment, a compound of the Formula VIII, or a pharmaceutically acceptable salt thereof is selected from:
N-(5-chloro-3-(((S)-4-(cyclopentanecarbonyl)-3-methylpiperazin-1-yl)methyl)-2-methylphenyl)-2-(methylsulfonyl)cyclobutanecarboxamide;
(S)—N-(5-chloro-3-((4-(cyclopentanecarbonyl)-3-methylpiperazin-1-yl)methyl)-2-methylphenyl)-3-(methylsulfonyl)cyclobutanecarboxamide;
(1r,3S)-3-acetamido-N-(3-(((S)-4-(cyclopentanecarbonyl)-3-methylpiperazin-1-yl)methyl)-5-fluoro-2-methylphenyl)cyclobutanecarboxamide;
(1r,3 S)-3-acetamido-N-(3-(((S)-4-(cyclopentanecarbonyl)-3-methylpiperazin-1-yl)methyl)-5-fluoro-2-methylphenyl)cyclobutanecarboxamide;
(1s,3R)-3-acetamido-N-(3-(((S)-4-(cyclopentanecarbonyl)-3-methylpiperazin-1-yl)methyl)-5-fluoro-2-methylphenyl)cyclobutanecarboxamide;
(1s,3R)-3-acetamido-N-(3-(((S)-4-(cyclopentanecarbonyl)-3-methylpiperazin-1-yl)methyl)-5-fluoro-2-methylphenyl)cyclobutanecarboxamide;
(cis) N-(5-chloro-3-(((S)-4-(cyclopentanecarbonyl)-3-methylpiperazin-1-yl)methyl)-2-methylphenyl)-2-(2-hydroxypropan-2-yl)cyclopropanecarboxamide; or
N-(5-chloro-3-(((S)-4-(cyclopentanecarbonyl)-3-methylpiperazin-1-yl)methyl)-2-methylphenyl)-2-(2-hydroxypropan-2-yl)cyclopropanecarboxamide.

One aspect of the invention is a pharmaceutical composition comprising a compound of Formula VIII, or a pharmaceutically acceptable salt thereof, and a pharmaceutically acceptable carrier or diluent.

The present invention provides, in another aspect, a compound of Formula IX or a pharmaceutically acceptable salt thereof:

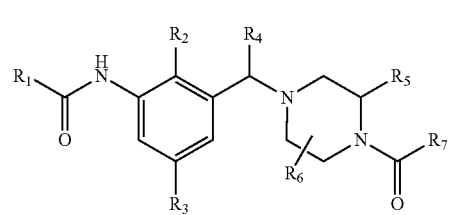

Formula IX wherein
R1 is a 4 to 6 membered monocyclic heterocycloalkyl containing one (1) nitrogen (N) heteroatom, and optionally an additional heteroatom which is oxygen (O), wherein said heterocycloalkyl is substituted with SO$_2$CH$_3$ or C(O)Re, and said Re is a C1-C3 alkyl; or
R1 is a tetrahydro-2H-thiopyran 1,1-dioxide;
R2 is C1-C3 alkyl or halo;
R3 is halo or CN;
R4 is H;
R5 is C1-C3 alkyl;
R6 is H or methyl; and
R7 is selected from the group consisting of
  i) a —C3-C6 cycloalkyl optionally substituted with methyl;
  ii) a methyl substituted with a C3-C5 cycloalkyl; and
  iii) a —C2 or C3 alkyl optionally substituted with two F.

In one embodiment of the invention, R1 is a 4 to 6 membered monocyclic heterocycloalkyl containing one (1) nitrogen (N) heteroatom, and optionally an additional heteroatom which is oxygen (O), and wherein said heterocycloalkyl ring is substituted with SO$_2$CH$_3$ or C(O)Re, and Re is a C1-C3 alkyl Suitably when R1 is a 4 to 6 membered monocyclic heterocycloalkyl it is a piperidinyl ring, a pyrrolidonyl ring or an azetidinyl ring. Suitably, the ring is a piperidinyl or pyrrolidonyl ring. In another embodiment the ring is a morpholinyl ring. It is recognized that either the ring carbon atom or the ring nitrogen atom of the heterocyclic ring may be substituted.

In another embodiment R1 is a tetrahydro-2H-thiopyran 1,1-dioxide.

Suitably, for a compound of Formula IX, R7 is a C3-C6 cycloalkyl optionally substituted with methyl. The C3-C6 cycloalkyl which may be optionally substituted is suitably a cyclopropyl or cyclopentyl ring. In one embodiment the R7 ring is a cyclopentyl ring. In another embodiment, R7 is a cyclopropyl ring.

Suitably, for a compound of Formula IX, R7 is methyl substituted with C3-C5 cycloalkyl. Suitably, the C3-C5 ring is a cyclopropyl or a cyclopentyl ring. In one embodiment, R7 is a cyclopropylmethyl.

Suitably, for a compound of Formula IX, R7 is a C2 or C3 alkyl optionally substituted with two F, the alkyl chain is a straight of branched C3 carbon chain, such as propyl or isopropyl. In one embodiment the first carbon in the chain attached to the carbonyl is the one optionally substituted with two fluorines.

Suitably, for compounds of Formula IX, R2 is C1-C3 alkyl or halo. In one embodiment, R2 is a C1-C3 alkyl. In another embodiment, R2 is methyl.

Suitably, for compounds of Formula IX, R3 is halo or CN. In one embodiment, R3 is halo. In another embodiment, R3 is fluorine or chlorine. In one embodiment, R3 is fluorine. In another embodiment, R3 is chlorine. In another embodiment, R3 is cyano. In one embodiment, when R3 is fluorine, chlorine or cyano, R2 is methyl.

Suitably, for compounds of Formula IX, R5 is C1-C3 alkyl. In one embodiment R5 is methyl.

Suitably, for compounds of Formula IX, R6 is H or methyl. In one embodiment, R6 is hydrogen.

In one embodiment, a compound of the Formula IX, or a pharmaceutically acceptable salt thereof is selected from:

(S)-1-acetyl-N-(3-((4-(cyclopentanecarbonyl)-3-methylpiperazin-1-yl)methyl)-5-fluoro-2-methylphenyl)azetidine-3-carboxamide;

(S)—N-(5-chloro-3-((4-(cyclopentanecarbonyl)-3-methylpiperazin-1-yl)methyl)-2-methylphenyl)-2-(1-propionylazetidin-3-yl)acetamide;

(R)-1-acetyl-N-(5-chloro-3-(((S)-4-(cyclopentanecarbonyl)-3-methylpiperazin-1-yl)methyl)-2-methylphenyl)pyrrolidine-3-carboxamide;

(S)-1-acetyl-N-(5-chloro-3-(((S)-4-(cyclopentanecarbonyl)-3-methylpiperazin-1-yl)methyl)-2-methylphenyl)pyrrolidine-3-carboxamide;

(R)-1-acetyl-N-(5-chloro-3-(((S)-4-(cyclopentanecarbonyl)-3-methylpiperazin-1-yl)methyl)-2-methylphenyl)pyrrolidine-2-carboxamide;

(S)-1-acetyl-N-(5-chloro-3-((4-(cyclopentanecarbonyl)-3-methylpiperazin-1-yl)methyl)-2-methylphenyl)piperidine-4-carboxamide;

(S)-1-acetyl-N-(5-chloro-3-(((S)-4-(cyclopentanecarbonyl)-3-methylpiperazin-1-yl)methyl)-2-methylphenyl)piperidine-3-carboxamide;

(R)-1-acetyl-N-(5-chloro-3-(((S)-4-(cyclopentanecarbonyl)-3-methylpiperazin-1-yl)methyl)-2-methylphenyl)piperidine-3-carboxamide;

(S)-1-acetyl-N-(5-chloro-3-(((S)-4-(cyclopentanecarbonyl)-3-methylpiperazin-1-yl)methyl)-2-methylphenyl)pyrrolidine-2-carboxamide;

(S)—N-(5-chloro-3-(((S)-4-(cyclopentanecarbonyl)-3-methylpiperazin-1-yl)methyl)-2-methylphenyl)-1-propionylpyrrolidine-2-carboxamide;

(S)—N-(5-chloro-3-(((S)-4-(cyclopentanecarbonyl)-3-methylpiperazin-1-yl)methyl)-2-methylphenyl)-1-isobutyrylpyrrolidine-2-carboxamide;

(S)-2-(1-acetylpiperidin-4-yl)-N-(5-chloro-3-((4-(cyclopentanecarbonyl)-3-methylpiperazin-1-yl)methyl)-2-methylphenyl)acetamide;

4-Acetyl-N-(5-chloro-3-(((S)-4-(cyclopentanecarbonyl)-3-methylpiperazin-1-yl)methyl)-2-methylphenyl)morpholine-2-carboxamide;

4-Acetyl-N-(5-chloro-3-(((S)-4-(cyclopentanecarbonyl)-3-methylpiperazin-1-yl)methyl)-2-methylphenyl)morpholine-2-carboxamide;

(S)—N-(3-((4-(cyclopentanecarbonyl)-3-methylpiperazin-1-yl)methyl)-5-fluoro-2-methylphenyl)-1-(methylsulfonyl)azetidine-3-carboxamide;

(S)—N-(5-chloro-3-((4-(cyclopentanecarbonyl)-3-methylpiperazin-1-yl)methyl)-2-methylphenyl)tetrahydro-2H-thiopyran-4-carboxamide 1,1-dioxide; or N-(5-chloro-3-(((S)-4-(cyclopentanecarbonyl)-3-methylpiperazin-1-yl)methyl)-2-methylphenyl)tetrahydro-2H-thiopyran-3-carboxamide 1,1-dioxide.

One aspect of the invention is a pharmaceutical composition comprising a compound of Formula IX, or a pharmaceutically acceptable salt thereof, and a pharmaceutically acceptable carrier or diluent.

Compounds outside the scope of Formulas I-IX include:

(S)—N-(5-chloro-3-((4-(cyclopentanecarbonyl)-3-methylpiperazin-1-yl)methyl)-2-methylphenyl)-4-oxo-4-(pyrrolidin-1-yl)butanamide, or a pharmaceutically acceptable salt thereof.

TERMS AND DEFINITIONS

"Alkyl" refers to a monovalent saturated hydrocarbon chain having the specified number of member atoms. For example, C1-C6 alkyl refers to an alkyl group having from 1 to 6 member atoms. Alkyl groups may be optionally substituted with one or more substituent as defined herein. The alkyl groups as used herein, may be straight or branched. Representative branched alkyl groups have one, two, or three branches. Examples of alkyl include methyl, ethyl, propyl (n-propyl and isopropyl), butyl (n-butyl, isobutyl, and t-butyl), pentyl (n-pentyl, isopentyl, and neopentyl), and hexyl.

"Cycloalkyl" refers to a saturated hydrocarbon ring having the specified number of member atoms. Cycloalkyl groups are monocyclic ring systems or are fused or bridged bicyclic ring systems. For example, C3-C7 cycloalkyl refers to a cycloalkyl group having from 3 to 7 member atoms. Cycloalkyl groups may be optionally substituted with one or more substituent as defined herein. Examples of cycloalkyl include cyclopropyl, cyclobutyl, cyclopentyl, and cyclohexyl.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" refers to the time required for half of a quantity of a substance to be converted to another chemically distinct species in vitro or in vivo.

"Halo" refers to the halogen radicals fluoro, chloro, bromo, and iodo.

"Heteroaryl" refers to an aromatic ring containing from 1 to 4 heteroatoms as member atoms in the ring. Heteroaryl rings containing more than one heteroatom may contain different heteroatoms. Heteroaryl rings may be optionally substituted with one or more substituent as defined herein. Heteroaryl rings are monocyclic ring systems, or are fused or bridged bicyclic ring systems. Monocyclic heteroaryl rings have from 5 to 7 member atoms. Bicyclic heteroaryl rings have from 7 to 11 member atoms. Bicyclic heteroaryl rings include those rings wherein phenyl and a monocyclic heterocycloalkyl ring are attached forming a fused, spiro, or bridged bicyclic ring system, and those rings wherein a monocyclic heteroaryl ring and a monocyclic cycloalkyl, cycloalkenyl, heterocycloalkyl, or heteroaryl ring are attached forming a fused, spiro, or bridged bicyclic ring system. Suitable examples of heteroaryl include but are not limited to pyrrolyl, pyrazolyl, imidazolyl, oxazolyl, isoxazolyl, oxadiazolyl, thiazolyl, isothiazolyl, thiadiazolyl, furanyl, furazanyl, thienyl, triazolyl, pyridinyl, pyrimidinyl, pyridazinyl, pyrazinyl, triazinyl, tetrazinyl, tetrazolyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, furopyridinyl, and naphthyridinyl. Suitable examples of 6 membered heteroaryls include but are not limited to pyridinyl, pyrimidinyl, pyridazinyl, pyrazinyl, and triazinyl.

Suitable examples of 5 membered heteroaryls include but are not limited to pyrrolyl, pyrazolyl, imidazolyl, oxazolyl, isoxazolyl, oxadiazolyl, thiazolyl, isothiazolyl, thiadiazolyl, furanyl, furazanyl, thienyl, triazolyl, and tetrazolyl.

"Heteroatom" refers to a nitrogen, sulphur, or oxygen atom, also abbreviated herein as N, S or O respectively.

"Heterocycloalkyl" refers to a saturated ring containing from 1 to 4 heteroatoms as member atoms in the ring, unless otherwise indicated. Heterocycloalkyl rings are not aromatic. Heterocycloalkyl groups containing more than one heteroatom may contain different heteroatoms. Heterocycloalkyl groups may be optionally substituted with one or more substituents as defined herein. Heterocycloalkyl groups are monocyclic ring systems or are fused, spiro, or bridged bicyclic ring systems. Monocyclic heterocycloalkyl rings have from 4 to 7 member atoms. Bicyclic heterocycloalkyl rings have from 7 to 11 member atoms. Examples of heterocycloalkyl include pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, azepinyl, 1,3-dioxolanyl, 1,3-dioxanyl, 1,3-oxathiolanyl, 1,3-dithianyl, azetidinyl, oxetanyl, azabicylo[3.2.1]octyl, and oxabicylo[2.2.1]heptyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as alkyl, alkenyl, alkynyl, aryl, cycloalkyl, cycloalkenyl, heterocycloalkyl, or heteroaryl, may be unsubstituted, or the group may be substituted with one or more substituent as defined.

"RORγ" refers to all isoforms encoded by the RORC gene which include RORγ1 and RORγt.

"RORγ modulator" refers to a chemical compound that inhibits, either directly or indirectly, the activity of RORγ. RORγ modulators include antagonists and inverse agonists of RORγ.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom.

The compounds according to Formula I may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formula I, or in any chemical structure illustrated herein, is not specified the structure is intended to encompass all individual stereoisomers and all mixtures thereof. Thus, compounds according to Formula I containing one or more chiral center may be used as racemic mixtures, enantiomerically enriched mixtures, or as enantiomerically pure individual stereoisomers.

Individual stereoisomers of a compound according to Formula I which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to Formula I may also contain double bonds or other centers of geometric asymmetry.

Where the stereochemistry of a center of geometric asymmetry present in Formula I, or in any chemical structure illustrated herein, is not specified, the structure is intended to encompass the trans (E) geometric isomer, the cis (Z) geometric isomer, and all mixtures thereof. Likewise, all tautomeric forms are also included in Formula I whether such tautomers exist in equilibrium or predominately in one form.

In certain embodiments, compounds according to Formula I may be present as a free base or free acid.

In certain embodiments, compounds according to Formula I may contain an acidic functional group. In certain other embodiments, compounds according to Formula I may contain a basic functional group. Thus, the skilled artisan will appreciate that pharmaceutically-acceptable salts of the compounds according to Formula I or II may be prepared. Indeed, in certain embodiments of the invention, pharmaceutically-acceptable salts of the compounds according to Formula I or II may be preferred over the respective free base or free acid because such salts may impart greater stability or solubility to the molecule thereby facilitating formulation into a dosage form. Accordingly, the invention is further directed to the use of pharmaceutically-acceptable salts of the compounds according to Formula I or II.

As used herein, the term "pharmaceutically acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively. Suitable pharmaceutically acceptable salts include those described by Berge, Bighley, and Monkhouse, *J. Pharm. Sci.* (1977) 66, pp 1-19.

Salts of the disclosed compounds containing a basic amine or other basic functional group may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing an acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bis-dehydroabietylamine, glucamine, N-methylglucamine, collidine, choline, quinine, quinoline, and basic amino acid such as lysine and arginine.

Other salts, which are not pharmaceutically acceptable, may be useful in the preparation of compounds of this invention and these should be considered to form a further aspect of the invention. These salts, such as trifluoroacetate, while not in themselves pharmaceutically acceptable, may be useful in the preparation of salts useful as intermediates in obtaining the compounds of the invention and their pharmaceutically acceptable salts.

If a compound of the invention containing a basic amine or other basic functional group is isolated as a salt, the corresponding free base form of that compound may be prepared by any suitable method known to the art, including treatment of the salt with an inorganic or organic base, suitably an inorganic or organic base having a higher $pK_a$ than the free base form of the compound. Similarly, if a compound of the invention containing an acidic functional group is isolated as a salt, the corresponding free acid form of that compound may be prepared by any suitable method known to the art, including treatment of the salt with an inorganic or organic acid, suitably an inorganic or organic acid having a lower $pK_a$ than the free acid form of the compound.

As used herein, the term "compounds of the invention" means both the compounds according to Formula I and II (as a free base or free acid), and the pharmaceutically-acceptable salts thereof. The term "a compound of the invention" also appears herein and refers to both a compound according to Formula I or II (as a free base or free acid), and its pharmaceutically-acceptable salts.

The invention also includes various deuterated forms of the compounds of Formula I. Each available hydrogen atom attached to a carbon atom may be independently replaced with a deuterium atom. A person of ordinary skill in the art will know how to synthesize deuterated forms of the compounds of Formula I. Commercially available deuterated starting materials may be employed in the preparation of deuterated forms of the compounds of Formula I, or they may be synthesized using conventional techniques employing deuterated reagents (e.g. lithium aluminum deuteride).

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The compounds of Formula I and pharmaceutically acceptable salts thereof may be employed alone or in combination with other therapeutic agents. Combination therapies according to the present invention thus comprise the administration of at least one compound of Formula I or a pharmaceutically acceptable salt thereof, and the use of at least one other therapeutically active agent. A compound of Formula I or pharmaceutically acceptable salt thereof, and the other therapeutically active agent(s) may be administered together in a single pharmaceutical composition or separately and, when administered separately this may occur simultaneously or sequentially in any order.

In a further aspect, there is provided a combination product comprising a compound of Formula I or a pharmaceutically acceptable salt thereof, together with one or more other therapeutically active agents, and optionally a pharmaceutically acceptable carrier or excipient.

Suitable other therapeutic agents include, but are not limited to, (1) TNF-alpha inhibitors; (2) non-selective COX-1/COX-2 inhibitors; (3) COX-2 inhibitors; (4) other agents for treatment of inflammatory and autoimmune diseases including glucocorticoids, methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors, such as belimumab, and CTLA-4-Ig or mimetics thereof; (5) leukotriene biosynthesis inhibitor, 5-lipoxygenase (5-LO) inhibitor or 5-lipoxygenase activating protein (FLAP) antagonist; (6) LTD4 receptor antagonist; (7) PDE4 inhibitor; (8) antihistamine H1 receptor antagonists; (9) α1- and α2-adrenoceptor agonist; (10) anticholinergic agents; (11) β-adrenoceptor agonists; (12) insulin-like growth factor type I (IGF-1) mimetic; (13) glucocorticosteroids; (14) kinase inhibitors such as inhibitors of the Janus Kinases (JAK 1 and/or JAK2 and/or JAK 3 and/or TYK2), p38 MAPK and IKK2; (15) B-cell targeting biologies such as rituximab; (16) selective costimulation modulators such as abatacept; (17) interleukin inhibitors, such as IL-1 inhibitor anakinra, IL-6 inhibitors tocilizumab or sirukumab, IL-12/IL-23 inhibitor ustekinumab, IL-23 inhibitor guselkumab, and anti-IL17 antibodies; (18) anti-GM-CSF antibodies; (19) checkpoint blockade and other immunotherapies, such as anti-PD-1/anti-PD-L1 antibodies, including pembrolizumab and nivolumab, and anti-CTLA4 antibodies, including ipilimumab; (20) BET inhibitors, such as GSK525762; and (21) other oncology agents, such as fluorouracil, bevacizumab, irinotecan hydrochloride, capecitabine, cetuximab, ramucirumab, oxaliplatin, leucovorin calcium, panitumumab, regorafenib, ziv-aflibercept, trastuzumab, imatinib mesylate, sunitinib malate, sorafenib tosylate, paclitaxel, everolimus, erlotinib hydrochloride, gemcitabine hydrochloride, mitomycin C, dabrafenib, trametinib, lapatinib, ofatumumab, topotecan, doxorubicin hydrochloride, and ibrutinib.

Compound Preparation

The compounds according to Formula I may be prepared using conventional organic syntheses. Suitable synthetic routes are depicted below in the following general reaction scheme.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

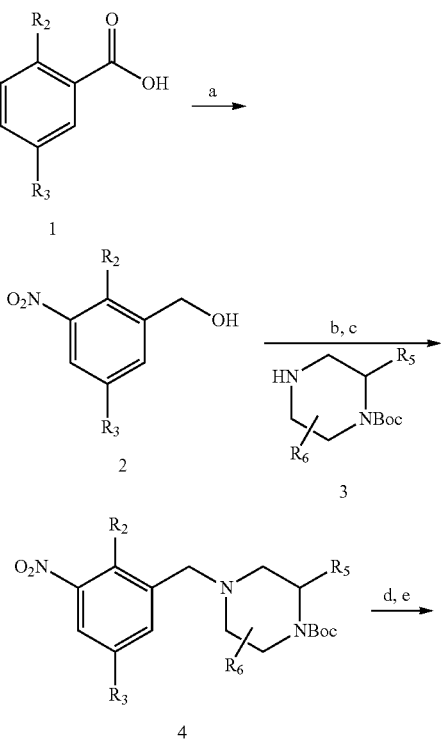

Scheme 1

-continued

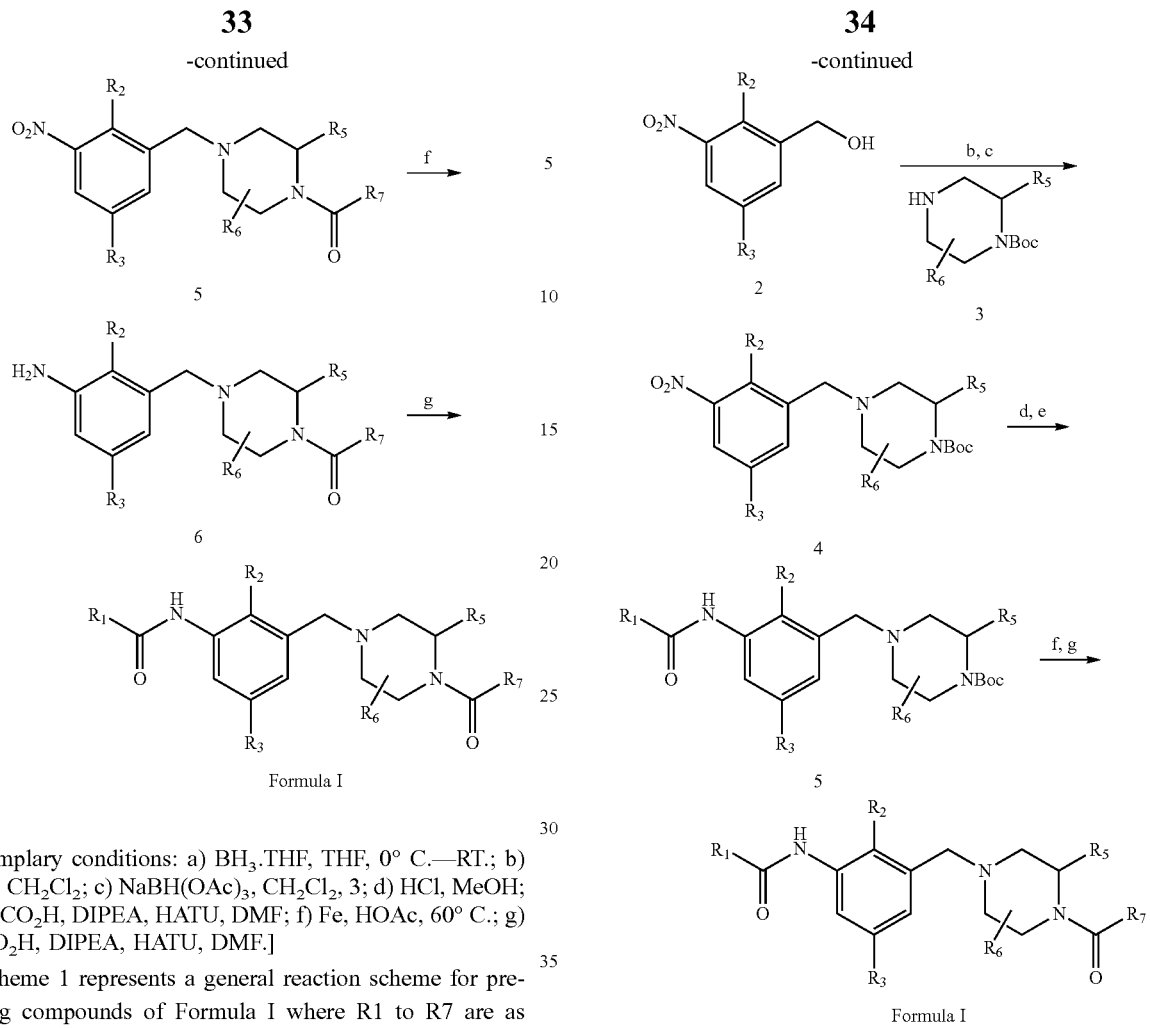

Formula I

[Exemplary conditions: a) $BH_3.THF$, THF, 0° C.—RT.; b) PCC, $CH_2Cl_2$; c) $NaBH(OAc)_3$, $CH_2Cl_2$, 3; d) HCl, MeOH; e) $R_7CO_2H$, DIPEA, HATU, DMF; f) Fe, HOAc, 60° C.; g) $R_1CO_2H$, DIPEA, HATU, DMF.]

Scheme 1 represents a general reaction scheme for preparing compounds of Formula I where R1 to R7 are as defined above. The starting material or reagents described are either commercially available or is made from commercially available starting materials using methods known to those skilled in the art.

Benzoic acids 1 may be reduced by $BH_3$-THF to provide benzyl alcohol 2. Alcohol 2 may be oxidized by PCC to the corresponding aldehyde followed by reductive amination with 3 to provide nitro compound 4. The Boc protection of 4 may be removed by treatment with HCl and the resulting amine reacted with various acids to provide nitro compound 5. Nitro compound 5 may be reduced to amine 6 which is then reacted with various acids to give final compounds of Formula I.

Scheme 2

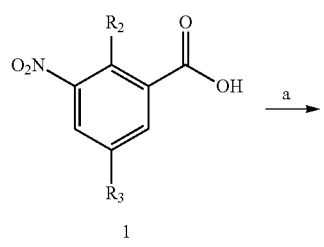

[Exemplary conditions: a) $BH_3.THF$, THF, 0° C.—RT; b) PCC, $CH_2Cl_2$; c) $NaBH(OAc)_3$, $CH_2Cl_2$, 3; d) Pd/C, MeOH, $H_2$; e) $R_1CO_2H$, DIPEA, HATU, DMF, f) HCl, MeOH; g) $R_7CO_2H$, DIPEA, HATU, DMF].

Scheme 2 represents another reaction scheme for preparing compounds of Formula I where R1 to R7 are as defined above. The starting material or reagents described are either commercially available or is made from commercially available starting materials using methods known to those skilled in the art.

Benzoic acids 1 may be reduced by $BH_3$-THF to provide benzyl alcohol 2. Alcohol 2 may be oxidized by PCC to corresponding aldehyde followed by reductive amination with 3 to provide nitro compound 4. Reduction of nitro compound 4 with Pd/C in the presence of $H_2$ afforded the amine which may be reacted with various acids to give amide 5. The Boc protection of 5 may be removed by treatment with HCl and the resulting amine reacted with various acids to provide final compounds of Formula I.

EXAMPLES

Abbreviations
ACN Acetonitrile
AIBN 2,2'-Azobisisobutyronitrile
Aq. Aqueous
Boc t-Butoxycarbonyl
Bn Benzyl DAST Diethylaminosulfur trifluoride
DCC Dicyclohexylcarbodiimide
DCM Dichloromethane
DIPEA N,N-diisopropylethylamine
DMAP Dimethylaminopyridine
DMF N,N-dimethylformamide
DMSO Dimethylsulphoxide
Dppf 1'-Bis(diphenylphosphino)ferrocene
DPPP Diphenyl-1-pyrenylphosphine
EDC N-(3-Dimethylaminopropyl)-N'-ethylcarbodiimide hydrochloride
ESI Electron Spray Ionization
EtOAc ethyl acetate
HATU O-(7-Azabenzotriazol-1-yl)-N,N,N',N'-tetramethyl-uronium hexafluorophosphate
HOBt Hydroxybenzotriazole
LCMS Liquid Chromatography Mass Spectrometry
LDA Lithium diisopropylamide
MDAP Mass Directed Automated Preparative liquid chromatography
MS mass spectrometry
MsCl Methanesulfonyl chloride
NBS N-bromosuccinamide
PCC Pyridinium chlorochromate
RT room temperature
sat. saturated
SM starting material
TEA Triethylamine
TFA Trifluoroacetic acid
THF Tetrahydrofuran
TsCl 4-Methyl-benzenesulfonyl chloride
Chromatography Unless stated otherwise, all chromatography was carried out using silica columns.
LCMS Conditions:
1) Acidic conditions:
 Mobile phase: water containing 0.05% TFA/acetonitrile
 Column: Agilent SB-C18 4.6×30 mm 1.8 μm
 Detection: MS and photodiode array detector (PDA)
2) Basic Conditions:
 Mobile phase: 10 mM $NH_4HCO_3$ aqueous/acetonitrile
 Column: Waters XBridge C18 4.6×50 mm 3.5 μm
 Detection: MS and photodiode array detector (PDA)
MDAP Conditions:
1) Acidic conditions: f
 Instrument: Waters Mass Directed Auto-purification System
 Column: Waters Sunfire Prep C18 column (5 um, 19×50 mm)
 Mobile phase: water containing 0.05% TFA/acetonitrile.
2) Basic Conditions:
 Instrument: Mass Directed Auto-purification System
 Column: Xbridge Prep C18 column (5 um, 19×50 mm)
 Mobile phase: water containing 0.05% ammonia/acetonitrile.

In the procedures that follow, after each starting material, reference to an intermediate is typically provided. This is provided merely for assistance to the skilled chemist. The starting material may not necessarily have been prepared from the batch referred to.

Description 1 cis-2-(3-Hydroxycyclopentyl)acetic acid (D1)

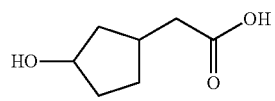

The mixture of 2-oxabicyclo[3.2.1]octan-3-one (300 mg) and potassium hydroxide (267 mg) in methanol (30 mL) and water (5 mL) was stirred at 20° C. for 12 hours and then concentrated under vacuum, 1 M HCl (aq.) was added to pH=5, extracted with EtOAc (3×10 mL), combined organic layer was dried and concentrated, the crude product was purified by column chromatography (silica gel, petroleum ether/EtOAc=1:1) to afford the title compound (150 mg) as sticky oil. MS (ESI): $C_7H_{12}O_3$ requires 144; found 143 [M−H]−.

Description 2

Methyl 2-(4-hydroxycyclohexyl)acetate (D2)

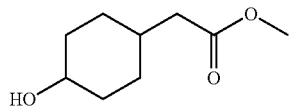

The mixture of Rh/Al (1 g) and methyl 2-(4-hydroxyphenyl)acetate (6 g) was dissolved in MeOH (150 mL). The reaction mixture was hydrogenated at 50° C. for 6 hours under 30 bar of $H_2$. The reaction mixture was filtered and the filtrate was concentrated to afford the title compound (4 g) as yellow solid. MS (ESI): $C_9H_{16}O_3$ requires 172; found 195 [M+Na]+.

Description 3

2-(4-Hydroxycyclohexyl)acetic acid (D3)

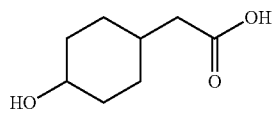 [SMILES: O=C(O)CC1CCC(O)CC1]

The mixture of potassium hydroxide (2.61 g) and methyl 2-(4-hydroxycyclohexyl)acetate (D2, 4 g) was dissolved in MeOH (30 mL) and water (30 mL). The reaction mixture was stirred for 6 hours at 80° C. The reaction mixture was concentrated and acidified with 2 M HCl (aq.) to pH=1, then extracted with DCM (2×50 mL). The organic layer was dried with anhydrous sodium sulfate. Filtered, the filtrate was concentrated to afford the title compound (3 g) as yellow solid. MS (ESI): $C_8H_{14}O_3$ requires 158; found 157 [M−H]−.

Description 4

2-(3-Hydroxycyclohexyl)acetic acid (D4)

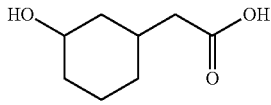

The mixture of NaOH (0.5 g), Rh/C (1 g) and 2-(3-hydroxyphenyl)acetic acid (1.1 g) in water (60 mL) was hydrogenated at 80° C. for 12 hours under 10 bar of $H_2$. Filtered, the filtrate was acidified with 1 M HCl (aq.) to pH=5 and then extracted with EtOAc (3×10 mL). Combined organic layer was dried and evaporated to afford the title compound (600 mg) as yellow oil. MS (ESI): $C_8H_{14}O_3$ requires 158; found 157 [M−H]$^-$.

Description 5

(E)-ethyl 4-hydroxybut-2-enoate (D5)

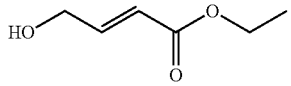

To a solution of (E)-4-ethoxy-4-oxobut-2-enoic acid (9 g) in THF (50 mL), $BH_3$-THF (1 M, 45 mL) solution in THF (100 mL) was added dropwise at −10° C. The reaction mixture was gradually warmed to RT and stirred for 12 hours. The reaction was quenched by adding AcOH/$H_2O$ (1:1, v/v, 5 mL) with stirring until no more gas evolution occurred. The mixture was concentrated under vacuum, the residue was treated with saturated $NaHCO_3$ solution (50 mL) and then extracted with EtOAc (2×50 mL). The combined organic layer was dried over anhydrous $MgSO_4$ and concentrated to afford the title compound (2 g) as yellow oil. MS (ESI): $C_6H_{10}O_3$ requires 130; found 131 [M+H]$^+$.

Description 6

Trans-(E)-ethyl 4-((3-bromotetrahydrofuran-2-yl)oxy)but-2-enoate (D6)

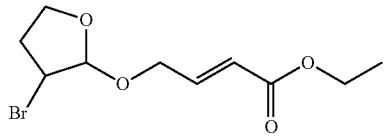

To a solution of (E)-ethyl 4-hydroxybut-2-enoate (D5, 1 g) in DCM (50 mL), 2,3-dihydrofuran (0.539 g) and NBS (1.368 g) were added at 0° C. The reaction mixture was gradually warmed to RT and stirred for 12 hours. To the resulting mixture was added water (100 mL) and then extracted with EtOAc (2×30 mL). The combined organic layer was washed with brine (30 mL), dried over anhydrous $MgSO_4$ and concentrated. The residue was purified by column chromatography (silica gel, petroleum ether/EtOAc=10:1) to afford the title compound (500 mg) as yellow oil. MS (ESI): $C_{10}H_{15}BrO_4$ requires 278; found 279 [M+H]$^+$.

Description 7

Ethyl 2-(hexahydrofuro[2,3-b]furan-3-yl)acetate (D7)

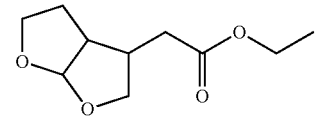

To a solution of trans-(E)-ethyl 4-((3-bromotetrahydrofuran-2-yl)oxy)but-2-enoate (D6, 300 mg) in benzene (30 mL) was added tributylstannane (313 mg) and AIBN (1 mg) at 0° C. The reaction mixture was gradually warm to 80° C. and stirred for 4 hours. Water (10 mL) was added, extracted with EtOAc (2×10 mL). The combined organic layer was washed with brine (10 mL), dried over anhydrous $MgSO_4$ and concentrated. The residue was purified by column chromatography (silica gel, petroleum ether/EtOAc=5:1) to afford the title compound (200 mg) as yellow oil. MS (ESI): $C_{10}H_{16}O_4$ requires 200; found 201 [M+H]$^+$.

Description 8

2-(Hexahydrofuro[2,3-b]furan-3-yl)acetic acid (D8)

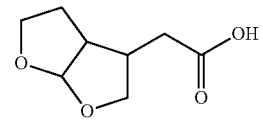 [SMILES: O=C(O)CC1COC2OCCC12]

The mixture of ethyl 2-(hexahydrofuro[2,3-b]furan-3-yl)acetate (D7, 180 mg) and sodium hydroxide (36.0 mg) in ethanol (20 mL) and water (10 mL) was stirred at 80° C. for 2 hours and then concentrated. The residue was acidified with 2 M HCl (aq.) to pH=1 and extracted with EtOAc (10 mL). The organic layer was dried and concentrated under vacuum to afford the title compound (100 mg) as white solid. MS (ESI): $C_8H_{12}O_4$ requires 172; found 173 [M+H]$^+$.

Description 9

(5-Methyltetrahydrofuran-3-yl)methanol (D9)

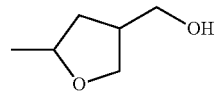

The mixture of 4-methylbenzenesulfonic acid (1.925 g) and 2-(hydroxymethyl)pentane-1,4-diol (1.5 g) in toluene (30 mL) was stirred at 130° C. for 3 hours and then diluted with EtOAc (100 mL), washed with water (100 mL). The organic layer was dried and concentrated under vacuum. The residue was purified by column chromatography (silica gel, petroleum ether/EtOAc=4:1) to afford the title compound (200 mg) as yellow oil. $^1$H NMR (500 MHz, DMSO-d$_6$): 4.61-4.60 (m, 1H), 3.89-3.83 (m, 2H), 3.60-3.56 (m, 1H), 3.37-3.27 (m, 2H), 2.38-2.33 (m, 1H), 1.73-1.71 (m, 1H), 1.42-1.40 (m, 1H), 1.15-1.10 (m, 3H).

Description 10

(3,3-Difluorocyclobutyl)methanol (D10)

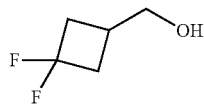

To the mixture of 3,3-difluorocyclobutanecarboxylic acid (1 g) in THF (20 mL) was added borane (1 M in THF, 29.4 mL) during 30 min. The reaction mixture was stirred at 20° C. for 6 hours, then concentrated under vacuum to afford the title compound (1 g) as white solid. $^1$H NMR (500 MHz, CDCl$_3$): 3.72-3.70 (m, 2H), 2.68-2.62 (m, 2H), 2.40-2.33 (m, 3H).

Description 11

(5-Methyltetrahydrofuran-3-yl)methyl 4-methylbenzenesulfonate (D11)

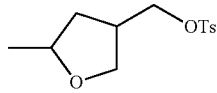 [SMILES: Cc1ccc(S(=O)(=O)OCC2COC(C)C2)cc1]

To the mixture of (5-methyltetrahydrofuran-3-yl)methanol (D9, 200 mg) in pyridine (5 mL) was added 4-methylbenzene-1-sulfonyl chloride (985 mg). The reaction mixture was stirred at RT overnight and then diluted with EtOAc (25 mL) and water (20 mL). The organic layer was separated and washed with water (20 mL) and brine (20 mL), dried over Na$_2$SO$_4$ and concentrated. The residue was purified by column chromatography (silica gel, petroleum ether/EtOAc=8:1) to afford the title compound (300 mg) as yellow oil. MS (ESI): C$_{13}$H$_{18}$O$_4$S requires 270; found 271 [M+H]$^+$.

Description 12

(3,3-Difluorocyclobutyl)methyl 4-methylbenzenesulfonate (D12)

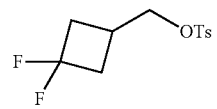 [SMILES: Cc1ccc(S(=O)(=O)OCC2CC(F)(F)C2)cc1]

D12 was prepared using a similar procedure to that described for D11. MS (ESI): C$_{12}$H$_{14}$F$_2$O$_3$S requires 276; found 294 [M+NH$_4$]$^+$.

Description 13

2-(5-Methyltetrahydrofuran-3-yl)acetonitrile (D13)

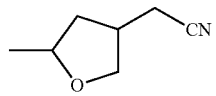

The mixture of (5-methyltetrahydrofuran-3-yl)methyl 4-methylbenzenesulfonate (D11, 300 mg) and NaCN (65.3 mg) in DMSO (5 mL) was stirred at 80° C. overnight. The reaction mixture was poured into water (50 mL) and extracted with EtOAc (2×10 mL). The combined organic layer was washed with water (10 mL) and brine (10 mL), dried and concentrated under vacuum to afford the title compound (180 mg). $^1$H NMR (500 MHz, CDCl$_3$): 4.24-3.90 (m, 2H), 3.51-3.44 (m, 1H), 2.62 (brs, 1H), 2.55-2.42 (m, 2H), 1.92-1.75 (m, 2H), 1.28-1.24 (m, 3H).

Description 14

2-(3,3-Difluorocyclobutyl)acetonitrile (D14)

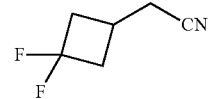

D14 was prepared using a similar procedure to that described for D13. $^1$H NMR (500 MHz, DMSO-d$_6$): 2.84-2.82 (m, 2H), 2.63-2.49 (m, 3H), 2.43-2.39 (m, 2H).

Description 15

2-(5-Methyltetrahydrofuran-3-yl)acetic acid (D15)

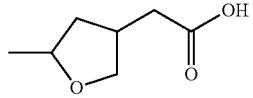

The mixture of 2-(5-methyltetrahydrofuran-3-yl)acetonitrile (D13, 180 mg) and potassium hydroxide (161 mg) in ethanol (2 mL) and water (2 mL) was added stirred at 70° C. overnight and then evaporated under vacuum. The residue was acidified to pH=1 with 2 M HCl (aq.) and then extracted with DCM (10 mL). The organic layer was dried over MgSO$_4$ and concentrated to afford the title compound (100 mg) as yellow oil (cis/trans mixture). $^1$H NMR (500 MHz, CDCl$_3$): 4.15-3.87 (m, 2H), 3.62-3.32 (m, 1H), 2.79-2.19 (nm, 3H), 1.81-1.66 (m, 2H), 1.31-1.18 (m, 3H).

Description 16

2-(3,3-difluorocyclobutyl)acetic acid (D16)

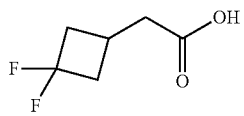

D16 was prepared using a similar procedure to that described for D15. $^1$H NMR (500 MHz, DMSO-$d_6$): 12.21 (brs, 1H), 2.72-2.62 (m, 2H), 2.55-2.26 (m, 5H).

Description 17

2-Methyltetrahydro-2H-pyran-4-ol (D17)

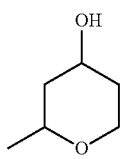

A mixture of but-3-en-1-ol (7.21 g), 2,4,6-trimethyl-1,3,5-trioxane (4.40 g) and 20% $H_2SO_4$ (12 g) was heated to 85° C. for 2 days. The mixture was cooled to RT and extracted with ether (4×50 mL). Combined organic layer was dried and evaporated to afford the title compound (7.5 g). MS (EI): $C_6H_{12}O_2$ requires 116; found 116 [M]$^+$.

Description 18

2-Methyldihydro-2H-pyran-4(3H)-one (D18)

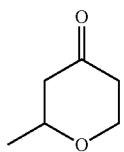

To a solution of 2-methyltetrahydro-2H-pyran-4-ol (D17, 12.5 g) in DCM (200 mL), PCC (23.20 g) was added in several portions at 0° C. After addition, the mixture was stirred at RT overnight. To the mixture was added petroleum ether (200 mL) and silica gel (100 g). The mixture was stirred for 30 min then filtered through Celite, and the cake was washed with EtOAc-petroleum ether (1:4, 100 mL). Filtrate was dried and evaporated to leave the crude product, which was purified by column chromatography (silica gel, petroleum ether/EtOAc=20:1 to 10:1) to afford the title compound (6.5 g) as pale yellow oil. $^1$H NMR (400 MHz, CDCl$_3$): 4.31-4.26 (m, 1H), 3.78-3.66 (m, 2H), 2.63-2.54 (m, 1H), 2.43-2.25 (m, 3H), 1.32 (d, J=6.4 Hz, 3H).

Description 19

Ethyl 2-(2-methyldihydro-2H-pyran-4(3H)-ylidene)acetate (D19)

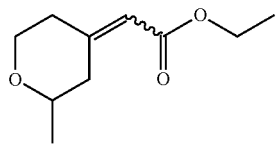

To an ice-cooled solution of ethyl 2-(diethoxyphosphoryl)acetate (14.04 g) in DMF (100 mL), sodium hydride (2.505 g) was added in several portions. After addition, the mixture was stirred at 0° C. for 30 min, and 2-methyldihydro-2H-pyran-4(3H)-one (D18, 6.5 g) was added dropwise. The reaction mixture was stirred at 0° C. for 1 hour, poured into ice water (200 mL), extracted with EtOAc (3×100 mL). The combined organic layer was washed with brine (200 mL), dried and evaporated to leave the crude product, which was purified by column chromatography (silica gel, petroleum ether/EtOAc=20:1) to afford title compound (12.5 g) as colorless oil. MS (EI): $C_{10}H_{16}O_3$ requires 184; found 184 [M]$^+$.

Descriptions 20-21

Descriptions 20-21 were prepared using a similar procedure to that described for D19.

D20 Ethyl 2-(3-methyldihydro-2H-pyran-4(3H)-ylidene)acetate

D21 Ethyl 2-(2-methyldihydrofuran-3(2H)-ylidene)acetate

| D20 | 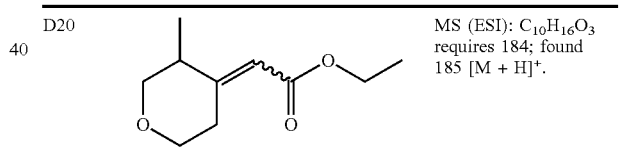 | MS (ESI): $C_{10}H_{16}O_3$ requires 184; found 185 [M + H]$^+$. |
|---|---|---|
| D21 | 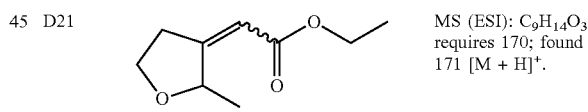 | MS (ESI): $C_9H_{14}O_3$ requires 170; found 171 [M + H]$^+$. |

Description 22

Ethyl 2-(2-methyltetrahydro-2H-pyran-4-yl)acetate (D22)

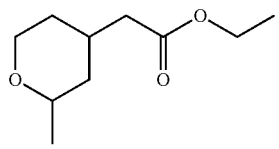

A mixture of ethyl 2-(2-methyldihydro-2H-pyran-4(3H)-ylidene)acetate (D19, 12.5 g) and Pd/C (1 g) in ethanol (150 mL) was stirred at RT overnight under $H_2$ atmosphere (1 atm). The mixture was filtered through Celite, and the cake was washed with DCM, The filtrate was concentrated under vacuum to afford the title compound (12.2 g) as colorless oil. MS (EI): $C_{10}H_{18}O_3$ requires 186; found 186 $[M]^+$.

Descriptions 23-24

Descriptions 23 and 24 were prepared using a similar procedure to that described for D22.
D23 Ethyl 2-(3-methyltetrahydro-2H-pyran-4-yl)acetate
D24 Ethyl 2-(2-methyltetrahydrofuran-3-yl)acetate

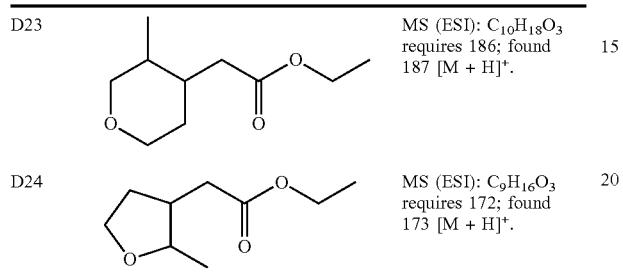

| D23 | | MS (ESI): $C_{10}H_{18}O_3$ requires 186; found 187 $[M + H]^+$. |
|---|---|---|
| D24 | | MS (ESI): $C_9H_{16}O_3$ requires 172; found 173 $[M + H]^+$. |

Description 25

2-(2-Methyltetrahydro-2H-pyran-4-yl)acetic acid (D25)

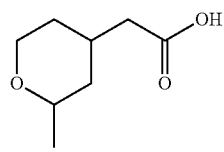

A mixture of ethyl 2-(2-methyltetrahydro-2H-pyran-4-yl)acetate (D22, 12.2 g) and sodium hydroxide (3.93 g) THF (40 mL) and water (80 mL) was heated to 60° C. for 3 hours. The mixture was concentrated, and the residual aqueous phase was adjusted to pH=2 with dilute HCl, extracted with EtOAc (3×50 mL). Combined organic layer was dried and evaporated to leave the crude product, which was purified by column chromatography (silica gel, petroleum ether/EtOAc=4:1 to 2:1) to afford the title compound (7.15 g) as colorless oil. MS (EI): $C_8H_{14}O_3$ requires 158; found 158 $[M]^+$.

Descriptions 26-27

Descriptions 26 and 27 were prepared using a similar procedure to that described for D25.
D26 2-(3-Methyltetrahydro-2H-pyran-4-yl)acetic acid
D27 2-(2-Methyltetrahydrofuran-3-yl)acetic acid

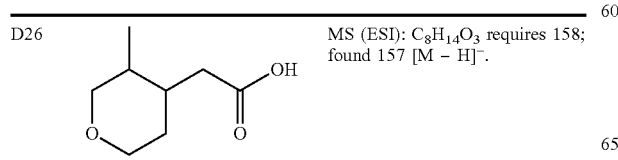

| D26 | | MS (ESI): $C_8H_{14}O_3$ requires 158; found 157 $[M - H]^-$. |
|---|---|---|
| D27 | | MS (ESI): $C_7H_{12}O_3$ requires 144; found 143 $[M - H]^-$. |

Description 28

3-(Chloromethyl)-4-methyltetrahydrofuran (D28)

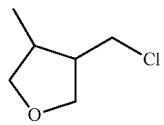

A mixture of 3-(allyloxy)prop-1-ene (5 g) and iron III chloride (9.92 g) in THF (100 mL) was cooled to 0° C. and then NaBH$_4$ (2.89 g) was added. The resulting suspension was stirred at RT overnight under $O_2$ atmosphere. The mixture was poured into water (100 mL) and extracted with ether (3×50 mL). The combined organic layer was dried and evaporated to afford the crude title compound (7.5 g). MS (EI): $C_6H_{11}ClO$ requires 134; found 134 $[M]^+$.

Description 29

2-(4-Methyltetrahydrofuran-3-yl)acetonitrile (D29)

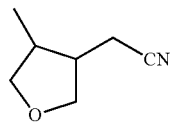

A mixture of 3-(chloromethyl)-4-methyltetrahydrofuran (D28, 7.5 g) and NaCN (4 g) in DMSO (100 mL) was heated to 90° C. for 20 hours, then poured into ice (200 g), extracted with EtOAc (4×50 mL). The combined organic layer was washed with saturated LiCl aqueous solution (2×100 mL), dried and evaporated to afford the crude title compound (4.0 g) as brown oil. MS (ESI): $C_7H_{11}NO$ requires 125; found 124 $[M-H]^-$.

Description 30

2-(4-Methyltetrahydrofuran-3-yl)acetic acid (D30)

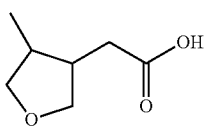

A mixture of 2-(4-methyltetrahydrofuran-3-yl)acetonitrile (D29, 4.0 g) and potassium hydroxide (1.793 g) in ethanol (50 mL) was heated at 85° C. for 24 hours. The mixture was evaporated to dryness, and the residue was dissolved in water (100 mL) and washed with ether (2×50 mL). The aqueous layer was acidified to pH=3 with KHSO₄ solution and then extracted with ether (3×50 mL). The combined organic layer was dried and evaporated. The residue was purified by column chromatography (silica gel, petroleum ether/EtOAc=5:1) to afford title compound (800 mg) as yellow oil (cis and trans isomers). ¹H NMR (400 MHz, CDCl₃): 4.14-3.94 (m, 2H), 3.57-3.33 (m, 2H), 2.68-2.10 (m, 3H), 2.19-1.80 (m, 1H), 1.05-0.95 (m, 3H).

Description 31

2-(1-Iodoethyl)tetrahydrofuran (D31)

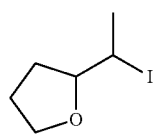

The mixture of (Z)-hex-4-en-1-ol (2.2 g), PdCl₂(dppf)-CH₂Cl₂ adduct (0.538 g) and 1-iodopyrrolidine-2,5-dione (5.93 g) in toluene (100 mL) was a stirred at RT for 2 hours and then filtered through Celite. The filtrate was concentrated under vacuum, and the residue was partitioned between water (100 mL) and EtOAc (100 mL). The organic layer was dried over Na₂SO₄, filtered and concentrated. The crude product was purified by column chromatography (silica gel, petroleum ether/EtOAc=8:1) to afford the title compound (2.78 g). ¹H NMR (400 MHz, CDCl₃): 4.20-4.14 (m, 1H), 3.98-3.93 (m. 1H), 3.87-3.82 (m, 1H), 3.75-3.70 (m, 1H), 2.10-1.91 (m, 3H), 1.92 (d, J=7.0 Hz, 3H), 1.69-1.60 (n 1H). MS (EI): C₆H₁₁IO requires 226; found 226 [M]⁺.

Description 32

2-(Tetrahydrofuran-2-yl)propanenitrile (D32)

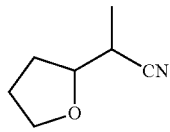

The mixture of 2-(1-iodoethyl)tetrahydrofuran (D31, 2.71 g) and NaCN (1.176 g) in water (12 mL) and ethanol (20 mL) was refluxed for 18 hours. The mixture was evaporated under vacuum to afford the crude title compound (1.5 g). MS (ESI): C₇H₁₁NO requires 125; found no mass.

Description 33

2-(Tetrahydrofuran-2-yl)propanoic acid (D33)

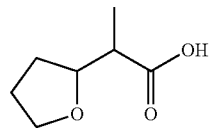

The mixture of 2-(tetrahydrofuran-2-yl)propanenitrile (1D32, 1.5 g) and KOH (4.5 g) in ethanol (16 mL) were heated at 85° C. for 18 hours and then concentrated. The residue was acidified to pH=5 with 4 M HCl (aq.) and extracted with DCM (8 mL). The organic layer was dried over Na₂SO₄, filtered and concentrated. The crude product was purified by column chromatography (silica gel, petroleum ether/EtOAc=3:1) to afford the title compound (410 mg) as orange oil. MS (ESI): C₇H₁₂O₃ requires 144; found 145 [M+H]⁺.

Description 34

Ethyl 2-(dihydrofuran-3(2H)-ylidene)propanoate (D34)

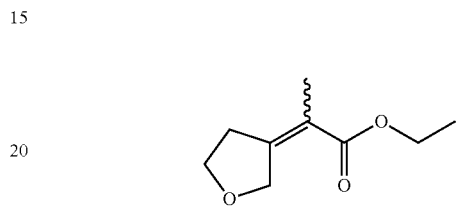

To a solution of sodium hydride (1.394 g) in THF (60 mL) at 0° C. was added dropwise ethyl 2-(diethoxyphosphoryl)propanoate (8.29 g) under N₂. The mixture was stirred at 0° C. for 30 min until the mixture became clear, then dihydrofuran-3(2H)-one (1.5 g) was added. The mixture was stirred at RT for 2 hours and then quenched by water (100 mL). The mixture was extracted with EtOAc (3×50 mL). The combined organic layer was washed with brine (100 mL), dried and evaporated under vacuum. The crude product was purified by column chromatography (silica gel, petroleum ether/EtOAc=30:1) to afford the title compound (1.3 g). MS (ESI): C₉H₁₄O₃ requires 170; found 171 [M+H]⁺.

Description 35

Ethyl 2-(tetrahydrofuran-3-yl)propanoate (D35)

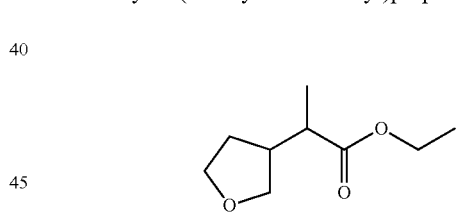

The mixture of ethyl 2-(dihydrofuran-3(2H)-ylidene)propanoate (D34, 2.0 g) and 10% palladium on carbon (0.250 g) in methanol (15 mL) was stirred at 30° C. under H₂ (1 atm) for 2 hours. The mixture was filtered through Celite, and the filtrate was concentrated under vacuum to afford the title compound (2.1 g) as yellow oil. MS (ESI): C₉H₁₆O₃ requires 172; found 173 [M+H]⁺.

Description 36

2-(Tetrahydrofuran-3-yl)propanoic acid (D36)

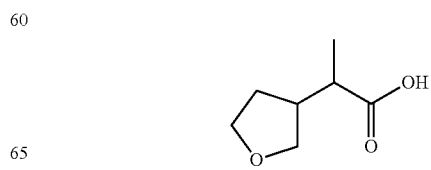

To a mixture of ethyl 2-(tetrahydrofuran-3-yl)propanoate (D35, 2.1 g) in ethanol (10 mL) and water (10 mL) was added LiOH aqueous solution (4 M, 15.24 mL). The mixture was stirred at 30° C. for 4 hours and then evaporated to remove most EtOH. The residue was washed with EtOAc (2×50 mL), the aqueous layer was adjusted to pH=3 with 3 M HCl (aq.) and then extracted with EtOAc (4×50 mL). The combined organic was dried and evaporated under vacuum to afford the title compound (1.2 g) as yellow oil. $^1$H NMR (500 MHz, DMSO-$d_6$): 12.18 (s, 1H), 3.79-3.58 (m, 3H), 3.35-3.28 (m, 1H), 2.28-2.23 (m, 2H), 2.00-1.91 (m, 1H), 1.55-1.50 (m, 1H), 1.10-1.00 (m, 3H). MS (EI): $C_7H_{12}O_3$ requires 144; found 143 [M−H]$^-$.

Description 37

4-Methoxybutanoic acid (D37)

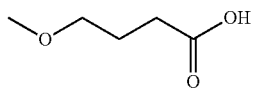

To a solution of methyl 4-methoxybutanoate (555.6 mg) in THF (6 mL), sodium hydroxide (6.31 mL) (2M aqueous solution) was added, the reaction mixture was stirred overnight. Most solvent was removed by rotavap, diluted with water (5 mL), washed with DCM (5 mL). The aqueous layer was acidified with 3 M HCl (aq.) to pH=2, extracted with EtOAc twice (2×15 mL). The combined organic layer was dried over Na$_2$SO$_4$ and filtered. The filtrate was concentrated to afford the title compound (491.3 mg) as colorless oil. $^1$H NMR (400 MHz, DMSO-$d_6$): 12.02 (s, 1H), 3.30 (t, J=6.6 Hz, 2H), 3.21 (s, 3H), 2.23 (t, J=7.3 Hz, 2H), 1.71 (quin, J=6.9 Hz, 2H).

Description 38

Ethyl 2-(2-oxocyclohexyl)acetate (D38)

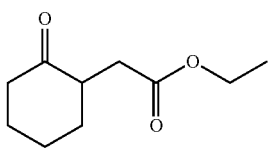

The mixture of 4-(cyclohex-1-en-1-yl)morpholine (2.0 g) and ethyl 2-bromoacetate (3.0 g) in benzene (30 mL) was stirred at 50° C. overnight. The reaction mixture was concentrated. Water (50 mL) and EtOAc (50 mL) were added to the residue. The resulting mixture was extracted. The organic layer was dried over Na$_2$SO$_4$ and concentrated to afford the title compound (1 g) as yellow oil. MS (ESI): $C_{10}H_{16}O_3$ requires 184; found 185 [M+H]$^+$.

Description 39

2-(2-Oxocyclohexyl)acetic acid (D39)

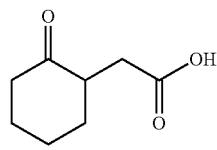 [SMILES: O=C(O)CC1CCCCC1=O]

The mixture of ethyl 2-(2-oxocyclohexyl)acetate (D38, 1 g) and potassium hydroxide (0.305 g) in methanol (20 mL) and water (20 mL) was stirred at 60° C. for 2 hours and then concentrated under vacuum. The residue was acidified with 2 M HCl (aq.) to pH=1 and then extracted with EtOAc (50 mL). The organic layer was dried and concentrated afford the title compound (300 mg) as white solid. MS (ESI): $C_8H_{12}O_3$ requires 156; found 155 [M−H]$^-$.

Description 40

2-(2-Oxocyclopentyl)acetic acid (D40)

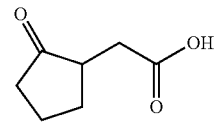

The mixture of ethyl 2-(2-oxocyclopentyl)acetate (600 mg) and potassium hydroxide (396 mg) in methanol (20 mL) and water (20 mL) was stirred at 60° C. for 3 hours and then concentrated under vacuum. The residue was acidified with 2 M HCl (aq.) to pH=1 and extracted with EtOAc (10 mL). The organic layer was dried and concentrated under vacuum to afford the title compound (300 mg) as oil. MS (ESI): $C_7H_{10}O_3$ requires 142; found 141 [M−H]$^-$.

Description 41

Methyl 4-(methylthio)butanoate (D41)

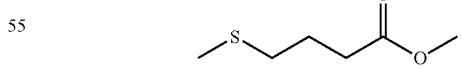

The mixture of methyl 4-bromobutanoate (905 mg) and sodium methanethiolate (526 mg) in DMF (16 mL) was heated at 80° C. overnight. The mixture was diluted with water (15 mL) and extracted with EtOAc (40 mL). The organic layer was dried over Na$_2$SO$_4$, filtered and concentrated to afford the title compound (760 mg) as colorless oil. $^1$H NMR (400 MHz, CDCl$_3$): 3.67 (s, 3H), 2.53 (t, J=7.2 Hz, 2H), 2.44 (t, J=7.4 Hz, 2H), 2.09 (s, 3H), 1.92 (quin, J=7.2 Hz, 2H). MS (EI): $C_6H_{12}O_2S$ requires 148; found 148 [M]$^+$.

Description 42

Methyl 4-(methylsulfonyl)butanoate (D42)

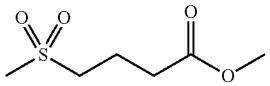

Methyl 4-(methylthio)butanoate (D41, 741 mg) was added into acetic anhydride (2.363 mL) and acetic acid (2.4 mL) cooling with ice bath and stirred for 30 min, then $H_2O_2$ (30%) (5.11 mL) was added dropwise during 15 min. The mixture was stirred at 0° C. for 18 hours, a trace amount of $MnO_2$ was added to quench excess $H_2O_2$, and the mixture was stirred for another 30 min. The organic solvents was removed under vacuum. The residue was partitioned between saturated $Na_2CO_3$ solution (10 mL) and EtOAc (30 mL). The organic layer was washed with brine (30 mL), dried over $Na_2SO_4$ and concentrated to afford the title compound (440 mg) as colorless oil. $^1$H NMR (400 MHz, CDCl$_3$): 3.69 (s, 3H), 3.13-3.07 (m, 2H), 2.92 (s, 3H), 2.54 (t, J 7.0 Hz, 2H), 2.21-2.11 (m, 2H). MS (ESI): $C_6H_{12}O_4S$ requires 180; found 181 [M+H]$^+$.

Description 43

4-(Methylsulfonyl)butanoic acid (D43)

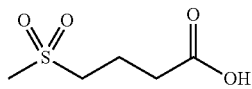

The mixture of methyl 4-(methylsulfonyl)butanoate (D42, 0.44 g) and LiOH aqueous solution (2 M, 3.66 mL) in THF (10 mL) were stirred at RT overnight. The mixture was diluted with water (8 mL) and EtOAc (16 mL). The organic layer was discarded, and the aqueous phase was acidified to pH=5~6 with 1 M HCl (aq.), extracted with EtOAc (20 mL). The organic layer was dried over $Na_2SO_4$, filtered and concentrated to afford the title compound (310 mg) as white solid. $^1$H NMR (400 MHz, DMSO-d$_6$): 12.21 (brs, 1H), 3.13 (t, J=7.7 Hz, 2H), 2.96 (s, 3H), 2.39 (t, J=7.2 Hz, 2H), 1.89 (quin, J=7.7 Hz, 2H). MS (ESI): $C_5H_{10}O_4S$ requires 166; found 167 [M+H]$^+$.

Description 44

Ethyl 2-(thietan-3-ylidene)acetate (D44)

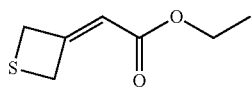

To a solution of thietan-3-one (8 g) in DCM (100 mL), ethyl 2-(triphenylphosphoranylidene)acetate (31.6 g) in DCM (50 mL) was added dropwise over 30 min at 0° C. The reaction mixture was gradually warmed to RT and stirred 6 hours. The mixture was concentrated and the residue was partitioned between brine (50 mL) and EtOAc (50 mL). The aqueous layer was extracted with EtOAc (2×50 mL). Combined organic layer was dried over anhydrous MgSO$_4$ and concentrated to afford the title compound (5 g) as yellow oil. MS (ESI): $C_7H_{10}O_2S$ requires 158; found 159 [M+H]$^+$.

Description 45

D45 Ethyl 2-(dihydro-2H-thiopyran-4(3H)-ylidene)acetate

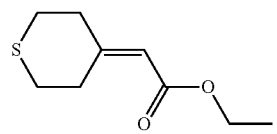

Description 45 was prepared using a similar procedure to that described for D44. MS (ESI): $C_9H_{14}O_2S$ requires 186; found 187 [M+H]$^+$.

Description 46

Ethyl 2-(1,1-dioxidothietan-3-ylidene)acetate (D46)

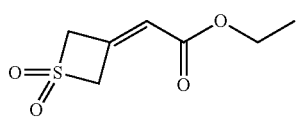

To a solution of ethyl 2-(thietan-3-ylidene)acetate (D44, 500 mg) in DCM (50 mL) was added 3-chlorobenzoperoxoic acid (1091 mg). The mixture was stirred overnight at RT. The mixture was filtered, and the filtrate was concentrated. The residue was partitioned between saturated NaHCO$_3$ solution (20 mL) and EtOAc (20 mL). The aqueous layer was extracted with EtOAc (2×10 mL). Combined organic layer was dried over anhydrous MgSO$_4$ and concentrated to afford the title compound (300 mg) as yellow solid. MS (ESI): $C_7H_{10}O_4S$ requires 190; found 191 [M+H]$^+$.

Description 47

Ethyl 2-(1,1-dioxidodihydro-2H-thiopyran-4(3H)-ylidene)acetate (D47)

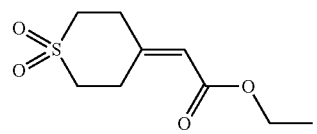

Description 47 was prepared using a similar procedure to that described for D46. MS (ESI): $C_9H_{14}O_4S$ requires 218; found 219 [M+H]$^+$.

Description 48

Ethyl 2-(1,1-dioxidothietan-3-yl)acetate (D48)

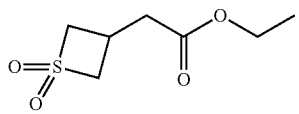

The mixture of ethyl 2-(1,1-dioxidothietan-3-ylidene)acetate (D46, 300 mg) and 10% Pd/C (168 mg) in methanol (10 mL) was hydrogenated at 20° C. for 12 hours under $H_2$ atmosphere (1 atm). The mixture was filtered through Celite and the filtrate was concentrated under vacuum to afford the title compound (200 mg) as yellow oil. MS (ESI): $C_7H_{12}O_4S$ requires 192; found 193 $[M+H]^+$.

Description 49

Ethyl 2-(1,1-dioxidotetrahydro-2H-thiopyran-4-yl)acetate (D49)

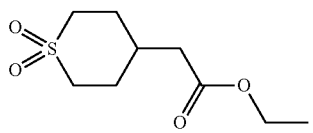

To the mixture of nickel II chloride (594 mg) and $NaBH_4$ (433 mg) in ethanol (20 mL) was added ethyl 2-(1,1-dioxidodihydro-2H-thiopyran-4(3H)-ylidene)acetate (D47, 500 mg) at 0° C. The reaction mixture was gradually allowed to warm to RT and stirred at RT for 6 hr. The mixture was concentrated and the residue was treated with saturated NaCl solution (50 mL) and extracted with EtOAc (2×50 mL). The combined organic layer was washed with brine (2×50 mL), dried over anhydrous $MgSO_4$, separated and concentrated to give the title compound (300 mg) as yellow oil. MS (ESI): $C_9H_{16}O_4S$ requires 220; found 221 $[M+H]^+$.

Description 50

2-(1,1-Dioxidothietan-3-yl)acetic acid (D50)

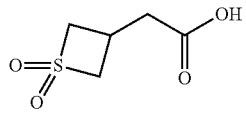

The mixture of potassium hydroxide (88 mg) and ethyl 2-(1,1-dioxidothietan-3-yl)acetate (D48, 150 mg) in methanol (20 mL) and water (20 mL) was stirred at 80° C. for 2 hours. The reaction mixture was concentrated under vacuum. The residue was acidified with 2 M HCl (aq.) to pH=1 and extracted with EtOAc (20 mL). The organic layer was dried and concentrated under vacuum to afford the title compound (120 mg) as white solid. MS (ESI): $C_5H_8O_4S$ requires 164; found 163 $[M-H]^-$.

Description 51

2-(1,1-Dioxidotetrahydro-2H-thiopyran-4-yl)acetic acid (D51)

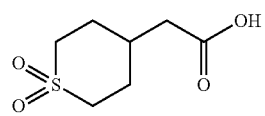 [SMILES: O=C(O)CC1CCS(=O)(=O)CC1]

Description 51 was prepared using a similar procedure to that described for D50. MS (ESI): $C_7H_{12}O_4S$ requires 192; found 215 $[M+Na]+$.

Description 52

Ethyl 3-(tosyloxy)cyclobutanecarboxylate (D52)

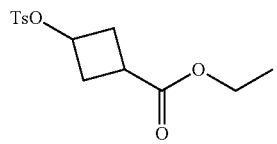 [SMILES: CCOC(=O)C1CC(OS(=O)(=O)c2ccc(C)cc2)C1]

To a solution of ethyl 3-hydroxycyclobutanecarboxylate (800 mg) in DCM (40 mL) was added TsCl (1.14 g) and pyridine (0.898 mL) at RT. The mixture was then stirred at RT overnight. The mixture was washed with water (2×20 mL). The combined organic layer was dried over $Na_2SO_4$, filtered and concentrated under vacuum to leave the crude as yellow oil, which was purified by flash chromatography (silica gel, petroleum ether/EtOAc=20:1) to afford the title compound (600 mg) as colorless oil. MS (ESI): $C_{14}H_{18}O_5S$ requires 298; found 299 $[M+H]^+$.

Description 53

Ethyl 3-(methylthio)cyclobutanecarboxylate (D53)

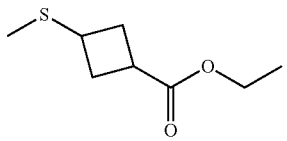

To a solution of ethyl 3-(tosyloxy)cyclobutanecarboxylate (D52, 1.6 g) in DMF (50 mL) was added sodium methanethiolate (3.76 g). The reaction mixture was stirred at 90° C. overnight. Solvent was removed under vacuum, and the residue was partition between EtOAc (20 mL) and water (20 mL). The organic layer was dried and concentrated under vacuum to afford the title compound (600 mg) as brown oil. MS (EI): $C_8H_{14}O_2S$ requires 174; found 174 $[M]^+$.

Description 54

3-(Methylthio)cyclobutanecarboxylic acid (D54)

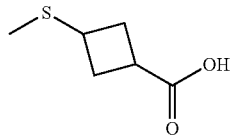

To a solution of ethyl 3-(methylthio)cyclobutanecarboxylate (D53, 400 mg) in methanol (10 mL) was added a solution of NaOH (184 mg) in water (5 mL) at RT, the mixture was stirred at RT overnight and then concentrated under vacuum, the residue was acidified to pH=5 with 1M HCl. The resulting solid was collected by filtration to afford the title compound (300 mg) as yellow solid. MS (ESI): $C_6H_{10}O_2S$ requires 146; found no mass.

Description 55

Ethyl 2-(dihydro-2H-thiopyran-3(4H)-ylidene)acetate (D55)

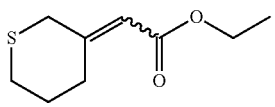

To a mixture of dihydro-2H-thiopyran-3(4H)-one (410 mg) in DMF (3 mL) were added ethyl 2-(diethoxyphosphoryl)acetate (1187 mg) and $K_2CO_3$ (488 mg). The reaction mixture was stirred at 80° C. for 3 hours. The mixture was poured into water (50 mL) and extracted with EtOAc (30 mL). The organic layer was dried over anhydrous sodium sulfate and concentrated. The residue was purified by column chromatography (silica gel, petroleum ether) to afford the title compound (584 mg) as colorless oil. MS (ESI): $C_9H_{14}O_2S$ requires 186; found 187 $[M+H]^+$.

Description 56

Ethyl 2-(tetrahydro-2H-thiopyran-3-yl)acetate (D56)

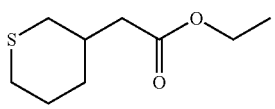

To ethanol (6 mL) was added $NaBH_4$ (471 mg). The mixture was cooled in an ice bath and nickel II chloride (404 mg) was added. Ethyl 2-(tetrahydro-2H-thiopyran-3-yl)acetate (D55, 500 mg) in ethanol (1 mL) was added slowly into above mixture. The reaction mixture was warmed to RT and stirred at RT overnight. The mixture was concentrated under vacuo to afford the title compound (500 mg) as dark oil. MS (ESI): $C_9H_{16}O_2S$ requires 188; found 189 $[M+H]^+$.

Description 57

2-(Tetrahydro-2H-thiopyran-3-yl)acetic acid (D57)

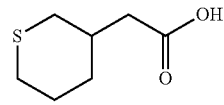

To the solution of ethyl 2-(tetrahydro-2H-thiopyran-3-yl)acetate (D56, 500 mg) in MeOH (12 mL) was added a solution of sodium hydroxide (212 mg) in water (12.00 mL). The mixture was stirred at 18° C. overnight. After the reaction completed, the organic solvent was removed under vacuo. The aqueous layer was washed with DCM (10 mL) and acidified with 1 M HCl (aq.) to pH=6 and extracted with EtOAc (50 mL). The organic layer was washed with brine (50 mL), dried and evaporated to afford the title compound (400 mg) as yellow solid. MS (ESI): $C_7H_{12}O_2S$ requires 160; found no mass.

Description 58

Ethyl 2-(dihydrothiophen-3(2H)-ylidene)acetate (D58)

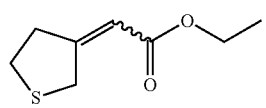

To a solution of ethyl 2-(diethoxyphosphoryl)acetate (346 mg) in anhydrous THF (2 mL) in water-bath, sodium hydride (37.0 mg) was added portion wise. The mixture was stirred for 0.5 hour at 18° C. Then the reaction mixture was cooled to −70° C. and added dihydrothiophen-3(2H)-one (105 mg). The reaction mixture was stirred for 1 hour at −70° C., then poured into water (2 mL), extracted with EtOAc (2×10 mL). The organic layer was dried over $Na_2SO_4$, filtered and concentrated. The residue was purified by column chromatography (silica gel, petroleum ether/THF=100:1) to afford the title compound (142 mg) as colorless oil. MS (ESI): $C_8H_{12}O_2S$ requires 172; found 173 $[M+H]^+$.

Description 59

Ethyl 2-(tetrahydrothiophen-3-yl)acetate (D59)

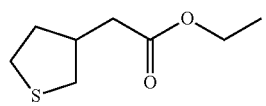

$NaBH_4$ (156 mg) was dissolved in ethanol (4 mL), which was added nickelII chloride (107 mg) in ice-water bath. Ethyl 2-(dihydrothiophen-3(2H)-ylidene)acetate (D58, 142 mg) was added into above mixture slowly, and then the reaction mixture was warmed to RT slowly and stirred overnight. The mixture was concentrated under vacuo, and the residue was purified by column chromatography (silica

Description 60

2-(Tetrahydrothiophen-3-yl)acetic acid (D60)

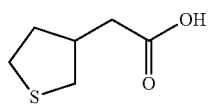

To a solution of ethyl 2-(tetrahydrothiophen-3-yl)acetate (D59, 118 mg) in MeOH (5 mL) was added a solution of sodium hydroxide (54.2 mg) in water (5.00 mL). The mixture was stirred overnight at RT. After removal of the organic solvent under vacuo, the residue was acidified with 3 M HCl (aq.) to pH<6, extracted with EtOAc (15 mL). The organic layer was separated and condensed to afford the title compound (88 mg) as white solid. MS (ESI): $C_6H_{10}O_2S$ requires 146; found 145 $[M-H]^-$.

Description 61

2-(Tetrahydrothiophen-2-yl)acetic acid (D61)

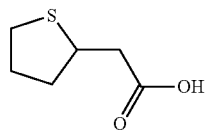

To a mixture of 2,2,2-trifluoroacetic acid (8.02 g) and triethylsilane (9.81 g) were added 2-(thiophen-2-yl)acetic acid (2 g) and $BF_3$-$Et_2O$ (1.908 g). The reaction mixture was gradually warm to RT and stirred at 90° C. for 4 days. The mixture was concentrated and brine (50 mL) was added to the residue. The mixture was extracted with EtOAc (2×50 mL). The combined organic layer was washed with brine (50 mL), dried over anhydrous $MgSO_4$ and concentrated to afford the title compound (1 g) as yellow oil. MS (ESI): $C_6H_{10}O_2S$ requires 146; found 145 $[M-H]^-$.

Description 62

Ethyl 1-bromocyclo butanecarboxylate (D62)

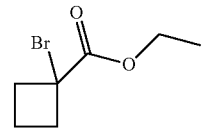

To a solution of ethyl cyclobutanecarboxylate (10 g) in $CCl_4$ (100 mL) was added NBS (20.83 g) and AIBN (1.281 g). The mixture was stirred at 80° C. for 2 hours. Water (50 mL) was added and the mixture was extracted with EtOAc (3×50 mL). The combined organic was washed with saturated $NaHCO_3$ (50 mL), water (50 mL) and brine (50 mL), dried over $MgSO_4$ and evaporated. The residue was purified by column chromatography (silica gel, petroleum ether/EtOAc=100:1) to afford the title compound (10 g) as yellow oil. $^1$H NMR (400 MHz, $CDCl_3$): 4.26 (q, J=14.4, 7.2 Hz, 2H), 2.95-2.88 (m, 2H), 2.67-2.59 (m. 2H) 2.26-2.21 (m, 1H), 1.91-1.86 (m, 1H), 1.32 (t, J=7.2 Hz, 3H).

Description 63

Cyclobut-1-enecarboxylic acid (D63)

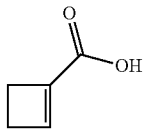

To a solution of ethyl 1-bromocyclobutanecarboxylate (D62, 4 g) in toluene (50 mL) was added potassium hydroxide (5.42 g). The mixture was stirred at 110° C. for 2 hours and evaporated under vacuum. To the residue was added water (50 mL). The mixture was adjusted to pH=6 and extracted with EtOAc (3×50 mL). The combined organic layer was washed with saturated $NaHCO_3$ (50 mL), water (50 mL) and brine (50 mL), dried over $MgSO_4$ and evaporated to afford the title compound (1.8 g) as brown solid. $^1$H NMR (400 MHz. DMSO-$d_6$): 12.25 (brs. 1H). 6.75 (s, 1H), 2.58 (t, J=3.2 Hz, 2H), 2.38 (t, J=2.8 Hz, 2H).

Description 64

2-(Acetylthio)cyclobutanecarboxylic acid (D64)

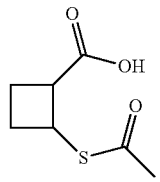

To a solution of cyclobut-1-enecarboxylic acid (D63, 500 mg) in $CCl_4$ (10 mL) was added thioacetic acid (776 mg). The mixture was stirred at RT for 48 hours and evaporated under vacuum. To the residue was added water (50 mL), and the mixture was extracted with EtOAc (3×50 mL). The combined organic layer was washed with water (50 mL) and brine (50 mL), dried over $MgSO_4$ and evaporated to afford the crude title compound (300 mg) as brown oil. MS (ESI): $C_7H_{11}O_3S$ requires 174; found no mass.

Description 65

3-Methylenecyclobutanecarboxylic acid (D65)

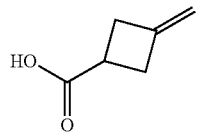

To a solution of 3-methylenecyclobutanecarbonitrile (5.0 g) in ethanol (20 mL) was added KOH aqueous solution (35%, 34.4 g) and the resulting mixture was heated to reflux overnight. The ethanol was removed under reduced pressure. The residue was cooled to below 10° C. and acidified with concentrated HCl to pH=5. The mixture was extracted with EtOAc (2×50 mL). The combined organic extracts were dried over anhydrous sodium sulfate and concentrated under vacuum to afford the title compound (6.01 g) as yellow oil. MS (ESI): $C_6H_8O_2$ requires 112; found 111 [M−H]⁻.

Description 66

Methyl 3-Methylenecyclobutanecarboxylate (D66)

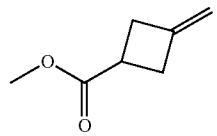

The mixture of 3-methylenecyclobutanecarboxylic acid (D65, 6.0 g), $K_2CO_3$ (14.79 g) and $Me_2SO_4$ (7.67 mL) in acetone (100 mL) was heated to reflux for 2 hours. The reaction mixture was cooled to RT and filtered. The solvent was removed under reduced pressure, and the residue was purified with column chromatography (silica gel, petroleum ether/EtOAc=20:1) to afford the title compound (2.1 g) as colorless oil. ¹H NMR (500 MHz, DMSO-d₆): 4.80-4.75 (m, 2H), 3.62 (s, 3H), 3.20-3.12 (m, 1H), 2.89-2.81 (m, 4H).

Description 67

Methyl spiro[2.3]hexane-5-carboxylate (D67)

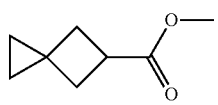

To an ice-cooled (0° C.) solution of diethylzinc (1.0 M in hexane) (39.6 mL) in DCM (30 mL) was added dropwise a solution of TFA (3.05 mL) in DCM (10 mL). After one hour of stirring, diiodomethane (10.62 g) in DCM (10 mL) was then introduced. After 40 min, the solution of methyl 3-methylene cyclobutanecarboxylate (D66, 2.0 g) in DCM (4 mL) was added dropwise. The reaction was stirred at RT for 2 hours and then quenched with saturated NH₄Cl solution (30 mL). The organic layer was separated, dried and concentrated to afford the title compound (1.9 g) as pale yellow oil. MS (ESI): $C_8H_{12}O_2$ requires 140; found 139 [M−H]⁻.

Description 68

Spiro[2.3]hexane-5-carboxylic acid (D68)

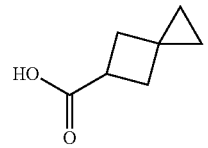

The mixture of methyl spiro[2.3]hexane-5-carboxylate (D67, 0.50 g) and LiOH aqueous solution (2 M, 5.35 mL) in THF (10 mL) was stirred at RT overnight. The mixture was diluted with water (8 mL) and EtOAc (16 mL). Extracted, the organic layer was discarded, and the aqueous layer was acidified with 1 M HCl (aq.) to pH=5-6 and then extracted with EtOAc (20 mL). The organic layer was dried over anhydrous sodium sulfate, filtered and concentrated to afford the title compound (200 mg) as pale yellow oil. MS (ESI): $C_7H_{10}O_2$ requires 126; found 125 [M−H]⁻.

Description 69

Benzyl 2-(difluoromethoxy)acetate (D69)

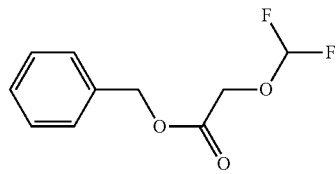 [SMILES: O=C(COC(F)F)OCc1ccccc1]

Benzyl 2-hydroxyacetate (1246 mg), sodium sulfate (213 mg), and acetonitrile (16 mL) were placed in a 100 ml two-necked flask fitted with a magnetic stirrer, a dropping funnel and a refluxing condenser. 2,2-difluoro-2-(fluorosulfonyl)acetic acid (3.10 mL) was then added with stirring at 45° C. After addition, the mixture was further stirred for 2 hours at this temperature. The reaction mixture was poured into 10% aqueous sodium carbonate solution (50 mL) and was extracted with EtOAc (2×50 mL). The combined extracts were washed with water (50 mL) and brine (50 mL), dried over sodium sulfate, and concentrated. The residue was purified by column chromatography (silica gel, petroleum ether/EtOAc=4:1) to afford the title compound (301 mg) as colorless oil. ¹H NMR (500 MHz, CDCl₃): 7.41-7.33 (m, 5H), 6.36 (t, J=73.2 Hz, 1H), 5.23 (s, 2H), 4.46 (s, 2H). ¹⁹F NMR (376 MHz, CDCl₃): −86.0, −86.2. MS (EI): $C_{10}H_{10}F_2O_3$ requires 216; found 216 [M]⁺.

Description 70

2-(Difluoromethoxy) acetic acid (D70)

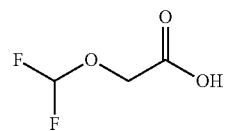

Benzyl 2-(difluoromethoxy)acetate (D169, 280 mg) was dissolved in EtOAc (12 mL). DIPEA (0.226 mL) was added. Then palladium on carbon (50 mg, 10%) was added under nitrogen atmosphere. The reaction was hydrogenated for 24 hours (1 bar of $H_2$). Filtered through a pad of Celite and concentrated to afford the title compound as ammonium salt (200 mg). MS (ESI): $C_3H_4F_2O_3$ requires 126; found 125 $[M-H]^-$.

Description 71

Benzyl 3-hydroxypropanoate (D71)

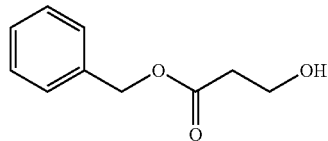 [SMILES: O=C(CCO)OCc1ccccc1]

Oxetan-2-one (8.0 g) was added slowly to a stirred solution of sodium methoxide (0.300 g) in phenylmethanol (72.0 g) at 0° C. Stirring was continued for a further 12 hours at 50° C. The reaction mixture was washed with water, dried and distilled to get the title compound as colorless oil. MS (ESI): $C_{10}H_{12}O_3$ requires 180; found 181 $[M+H]^+$.

Description 72

Benzyl 3-(difluoromethoxy)propanoate (D72)

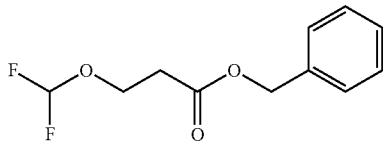 [SMILES: O=C(CCOC(F)F)OCc1ccccc1]

Benzyl 3-hydroxypropanoate (D71, 1.0 g), sodium sulfate (0.158 g), and acetonitrile (16 mL) were placed in a 100 ml two-necked flask fitted with a magnetic stirrer, a dropping funnel and a refluxing condenser. 2,2-Difluoro-2-(fluorosulfonyl)acetic acid (2.294 mL) was then added with stirring at 45° C. After addition, the mixture was further stirred for 2 hours at this temperature. The reaction mixture was poured into 10% aqueous sodium carbonate solution (30 mL) and was extracted with EtOAc (3×30 mL). The combined extracts were washed with water (30 mL) and brine (30 mL), dried over anhydrous sodium sulfate and concentrated. The residue was purified by column chromatography (silica gel, petroleum ether/EtOAc=5:1) to afford the title compound (100 mg) as colorless oil. $^1H$ NMR (400 MHz, CDCl$_3$): 7.41-7.38 (m, 5H), 6.22 (t, J=74.4 Hz 1H), 5.19 (s, 2H). 4.18 (t, J=6.4 Hz, 2H). 2.74 (t, J=6.0 Hz, 2H). $^{19}F$ (376 MHz, CDCl$_3$): −84.5, −84.7. MS (ESI): $C_{11}H_{12}F_2O_3$ requires 230; found no mass.

Description 73

3-(Difluoromethoxy)propanoic acid (D73)

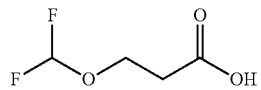

The mixture of benzyl 3-(difluoromethoxy)propanoate (D72, 100 mg), DIPEA (0.076 mL) and palladium on carbon (50 mg, 10%) in EtOAc (12 mL) was hydrogenated at RT under hydrogen atmosphere (1 atm) for 24 hours. The mixture was filtered through a pad of Celite and concentrated to afford the title compound as the ammonium salt (60 mg). MS (ESI): $C_4H_6F_2O_3$ requires 140; found 139 $[M-H]^-$.

Description 74

1-Methyl-5-oxopyrrolidine-3-carboxylic acid (D74)

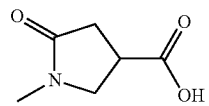

A mixture of 2-methylenesuccinic acid (20 g) and methanamine (17.90 g) (40% solution in $H_2O$) was heated to 115° C. for 2 hours and then cooled to RT. The mixture was evaporated to remove most of solvent. The residue was acidified to pH=3 with concentrated HCl acid, and the resulting white solid was collected by suction to leave the crude product as white solid, which was further purified by recrystallization from EtOAc (30 mL) to afford the title compound (12 g) as white solid. MS (ESI): $C_6H_9NO_3$ requires 143; found 142 $[M-H]^-$.

Description 75

4-(2-Diazoacetyl)-1-methylpyrrolidin-2-one (D75)

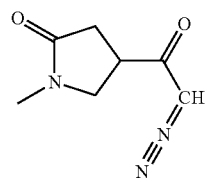

To a suspension of 1-methyl-5-oxopyrrolidine-3-carboxylic acid (D74, 2.86 g) in DCM (40 mL) was added 0.5 mL of DMF and then oxalyl chloride (5 mL) was added dropwise. After addition the mixture was stirred at RT for 1 hour and then evaporated to leave the crude acyl chloride. The above crude acyl chloride was re-dissolved in a mixture of THF (20 mL)/acetonitrile (20 mL) and then cooled to 0° C. TMS-diazomethane (20 mL) (2M solution in hexane) was added dropwise. After addition the mixture was stirred at RT overnight. The mixture was evaporated to give the crude product, which was purified by column chromatography (silica gel, DCM/MeOH=10:1) to afford the title compound (1 g) as brown oil. MS (ESI): C₇H9N₃O₂ requires 167; found 168 [M+H]⁺.

Description 76

2-(1-Methyl-5-oxopyrrolidin-3-yl)acetic acid (D76)

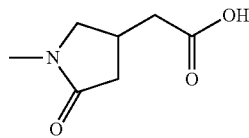

To a solution of 4-(2-diazoacetyl)-1-methylpyrrolidin-2-one (D75, 1 g) in THF (100 mL) and distillated water (50 mL) was added silver nitrate (1.016 g). The mixture was stirred at RT overnight. The mixture was evaporated to remove THF. The aqueous phase was adjusted to pH=3 with 1 M HCl (aq.) and then extracted with EtOAc (6×50 mL). The combined organic layer was dried, filtered, and evaporated to afford the title compound (800 mg) as brown oil. MS (ESI): $C_7H_{11}NO_3$ requires 157; found 156 [M−H]⁻.

Description 77

Tert-butyl 3-(2-ethoxy-2-oxoethyl)-2-oxopyrrolidine-1-carboxylate (D77)

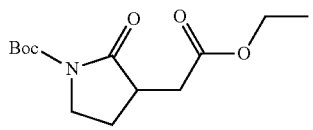 [SMILES: CCOC(=O)CC1CCN(C(=O)OC(C)(C)C)C1=O]

The solution of tert-butyl 2-oxopyrrolidine-1-carboxylate (5 g) in anhydrous THF (50 mL) was cooled to −78° C. and then LDA (2.89 g) solution in THF was added dropwise. The mixture was stirred at −78° C. for 1 hour, and then ethyl 2-bromoacetate (13.50 mL) was added dropwise. After addition the mixture was stirred at −78° C. for 1 hour and then warm to RT and stirred for 16 hours. The reaction mixture was partitioned between water (50 mL) and EtOAc (50 mL). The aqueous layer was extracted twice with EtOAc (2×50 mL). The combined extracts were dried, separated and concentrated under reduced pressure to leave the crude product, which was purified by column chromatography (silica gel, petroleum ether/EtOAc=1:1) to afford the title compound (3 g) as yellow oil. MS (ESI): $C_{13}H_{21}NO_5$ requires 271; found 172 [M+2H−Boc]⁺.

Description 78

Ethyl 2-(2-oxopyrrolidin-3-yl)acetate hydrochloride acid salt (D78)

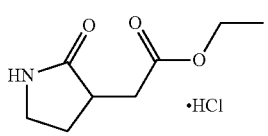

To a solution of tert-butyl 3-(2-ethoxy-2-oxoethyl)-2-oxopyrrolidine-1-carboxylate (D77, 3 g) in MeOH (20 mL) was added the solution of hydrogen chloride (13.82 mL) in dioxane. The mixture was stirred at RT for 2 hours and then concentrated to afford the title compound (2 g) as yellow solid. MS (ESI): $C_8H_{13}NO_3$ requires 171; found 172 [M+H]⁺.

Description 79

Ethyl 2-(1-methyl-2-oxopyrrolidin-3-yl)acetate (D79)

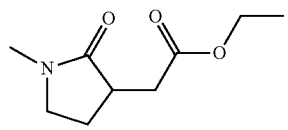

To a solution of ethyl 2-(2-oxopyrrolidin-3-yl)acetate hydrochloride acid salt (D78, 500 mg) in THF (10 mL) was added NaH (105 mg). The mixture was stirred at 0° C. for 10 minutes and then MeI (0.274 mL) was added. The mixture was stirred at RT overnight. Water (40 mL) was added and extracted with EtOAc (3×50 mL). The combined organic layer was washed with saturated NaHCO₃ (50 mL), water (50 mL) and brine (50 mL), dried over MgSO₄ and concentrated to afford the title compound (300 mg) as yellow oil. MS (ESI): $C_9H_{15}NO_3$ requires 185; found 186 [M+H]⁺.

Description 80

2-(1-Methyl-2-oxopyrrolidin-3-yl)acetic acid (D80)

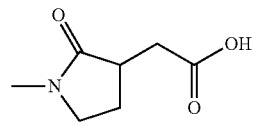

Ethyl 2-(1-methyl-2-oxopyrrolidin-3-yl)acetate (D79, 300 mg) was dissolved in THF (5 mL) and water (5 mL), then sodium hydroxide (4 M, 2.025 mL) aqueous solution was added. The mixture was stirred at RT for 1 hour. Water (30 mL) was added and the mixture was washed with EtOAc (30 mL). The water phase was adjusted to pH=6 with 2 M HCl (aq.) and lyophilized to afford the crude title compound (200 mg) as yellow oil. MS (ESI): $C_7H_{11}NO_3$ requires 157; found 158 [M+H]⁺.

Description 81

1-Ethyl-5-oxopyrrolidine-3-carboxylic acid (D81)

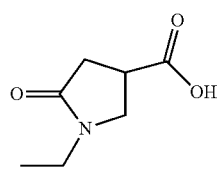

A mixture of 2-methylenesuccinic acid (10 g) and ethanamine (50 mL) (2M solution in THF) in isopropanol (50 mL) was heated to 120° C. overnight and then evaporated to remove most of solvent. The residue was acidified with concentrated HCl solution to pH=2 and then evaporated under vacuum. To the residue was added a mixture of DCM/MeOH (60 mL, 5:1), and then anhydrous sodium sulfate (20 g) was added. The mixture was stirred at RT for 2 hours and then filtered. The filtrate was evaporated to get the title compound (4 g) as sticky oil. MS (ESI): $C_7H_{11}NO_3$ requires 157; found 156 [M−H]⁻.

Description 82

1-Ethyl-5-oxopyrrolidine-3-carbonyl chloride (D82)

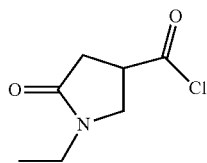

To a solution of 1-ethyl-5-oxopyrrolidine-3-carboxylic acid (D81, 1.6 g) in dry DCM (6 mL) was added sulfurous dichloride (4.84 g). The mixture was stirred at 40° C. overnight and then evaporated under vacuum. The residue was re-dissolved in anhydrous DCM (10 mL) and concentrated under reduced pressure to get the title compound (1.8 g) as brown oil. MS (ESI): C-$T_{13}NO_3$ requires 171; found 172 [M+H]⁺ (sample was converted to corresponding methyl ester by dissolved in MeOH and sent to LCMS).

Description 83

4-(2-Diazoacetyl)-1-ethylpyrrolidin-2-one (D83)

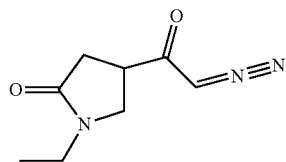

1-Ethyl-5-oxopyrrolidine-3-carbonyl chloride (D82, 1.6 g) was dissolved in acetonitrile (12 mL) and THF (12 mL). A solution of (diazomethyl)trimethylsilane (9.1 mL) in ether (2 M) was added. The reaction mixture was stirred at 25° C. for 5 hours. After the reaction completed, the solvents were removed under vacuum to leave the crude product, which was purified by column chromatography (silica gel, petroleum ether/THF=2:1) to afford the title compound (1.4 g) as yellow solid. MS (ESI): $C_8H_{11}N_3O_2$ requires 181; found 182 [M+H]⁺.

Description 84

2-(1-Ethyl-5-oxopyrrolidin-3-yl)acetic acid (D84)

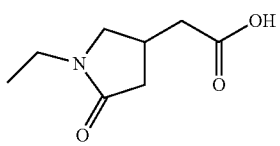

To the mixture of 4-(2-diazoacetyl)-1-ethylpyrrolidin-2-one (D83 1.4) in THF (50 mL) and water (25 mL) was added AgNO₃ (1.575 g). The reaction mixture was stirred at 26° C. for 2 days. The mixture was acidified with 1 M HCl (aq.) to pH=3 and concentrated under vacuum. The residue was washed with EtOAc and filtered. The filtrate was dried, separated and concentrated under vacuum to afford the title compound (700 mg) as yellow oil. MS (ESI): $C_8H_{13}NO_3$ requires 171; found 172 [M+H]⁺.

Description 85

Ethyl 1-cyanocyclopropanecarboxylate (D85)

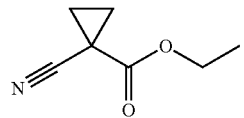

To the mixture of ethyl 2-cyanoacetate (5 g) and potassium carbonate (18.33 g) in acetone (20 mL) was added 1,2-dibromoethane (9.96 g) over a period of 10 min. The reaction mixture was heated to reflux overnight. More 1,2-dibromoethane (9.96 g) was added and the reaction mixture was refluxed for another 2 hours. The reaction mixture was filtered through a pad of Celite and the cake was rinsed with acetone (20 mL). The combined filtrate was concentrated under reduced pressure to give the title compound (5 g) as orange oil. MS (ESI): $C_7H_9NO_2$ requires 139; found 140 [M+H]⁺.

Description 86

1-(Hydroxymethyl)cyclopropanecarbonitrile (D86)

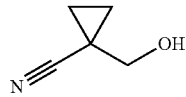

To a mixture of ethyl 1-cyanocyclopropanecarboxylate (D85, 4 g) in dimethoxyethane (80 mL) and methanol (8 mL) was added sodium borohydride (115 mmol). The mixture was stirred at RT for 18 hours. The solution was diluted with saturated NaHCO₃ aqueous solution (100 mL) and then extracted with 10% MeOH/DCM (3×100 mL). The combined organic layer was dried over anhydrous sodium sulfate, separated and concentrated under vacuum to afford the title compound (1.3 g) as pale brown oil. ¹H NMR (400

MHz, DMSO-d$_6$): 5.30 (t, J=6.0 Hz, 1H), 3.39 (d, J=5.8 Hz, 2H), 1.17-1.12 (m, 2H), 0.94-0.90 (m, 2H).

Description 87

1-Formylcyclopropanecarbonitrile (D87)

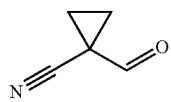

To a solution of 1-(hydroxymethyl)cyclopropanecarbonitrile (D86, 1.1 g) in DCM (10 mL) was added Dess-Martin reagent (4.80 g). The reaction mixture was stirred at 12° C. overnight and then poured into saturated NaHCO$_3$ aqueous solution (30 mL) until no gas released. Saturated Na$_2$S$_2$O$_3$ aqueous solution (30 mL) was added and then the mixture was extracted with EtOAc (30 mL). The organic layer was washed with brine (30 mL), dried, separated and evaporated under vacuo to afford the title compound (550 mg). MS (ESI): C$_5$H$_5$NO requires 95; found no mass.

Description 88

Ethyl 3-(1-cyanocyclopropyl)acrylate (D88)

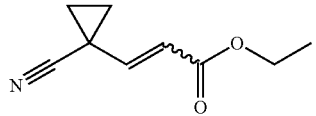

To the mixture of 1-formylcyclopropanecarbonitrile (D87, 550 mg) in anhydrous DCM (3 mL) was added ethyl 2-(triphenylphosphoranylidene)acetate (2418 mg). The mixture was stirred at RT for 16 hours and then concentrated under reduced pressure to leave the crude product, which was purified by column chromatography (silica gel, petroleum ether/EtOAc=25:1) to afford the title compound (289 mg) as white solid. MS (ESI): C$_9$H$_{11}$NO$_2$ requires 165; found 166 [M+H]$^+$.

Description 89

Ethyl 3-(1-cyanocyclopropyl)propanoate (D89)

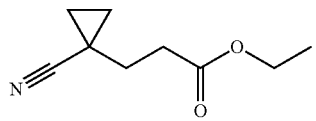

The mixture of ethyl 3-(1-cyanocyclopropyl)acrylate (D88, 200 mg) and Pd/C (30 mg, 10%) in ethanol (7 mL) was stirred under hydrogen atmosphere (1 atm) overnight. The mixture was filtrated and the filtrate was concentrated under vacuum to afford the title compound (170 mg) as colorless oil. MS (ESI): C$_9$H$_{13}$NO$_2$ requires 167; found 168 [M+H]$^+$.

Description 90

3-(1-Cyanocyclopropyl)-propanoic acid (D90)

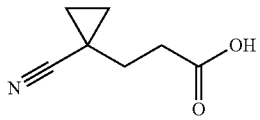

To a solution of ethyl 3-(1-cyanocyclopropyl)propanoate (189, 170 mg) in the mixture solvent of ethanol (10 mL) and water (10 mL) was added sodium hydroxide (81 mg). The reaction mixture was stirred at 18° C. overnight and then evaporated under vacuum. The aqueous layer was acidified with 1 M HCl (aq.) to pH=5-6 and extracted with EtOAc (20 mL). The organic layer was dried, separated and evaporated under vacuum to afford the title compound (80 mg) as yellow oil. MS (ESI): C$_7$H$_9$NO$_2$ requires 139; found 138 [M-H]$^-$.

Description 91

Methyl 4-cyano-4-methylpentanoate (D91)

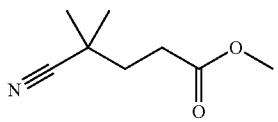

A solution of lithium diisopropylamide (11.2 g) in anhydrous THF (70 mL) was cooled to −78° C. and then isobutyronitrile (9.6 g) was added dropwise, the reaction mixture was stirred at −78° C. for additional 2 hours and then the solution of methyl acrylate (6 g) in anhydrous THF (15 mL) was added slowly, after addition the reaction mixture was stirred at −78° C. until the reaction was complete (approximately 60 min). The reaction mixture was then poured into aqueous saturated NH$_4$Cl solution (100 mL), the organic layer was separated and washed with water (100 mL) and brine (100 ml), dried and concentrated to afford the title compound (9 g) as yellow oil. MS (ESI): C$_8$H$_{13}$NO$_2$ requires 155; found 156 [M+H]$^+$.

Description 92

4-Cyano-4-methylpentanoic acid (D92)

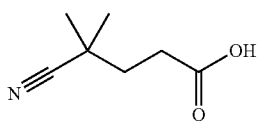

To a solution of methyl 4-cyano-4-methylpentanoate (D91, 1.2 g) in methanol (12 mL) and water (12 mL) was added potassium hydroxide (0.9 g), the reaction mixture was stirred at 25° C. overnight. The organic solvent was removed under vacuo, the residual aqueous phase was washed with DCM (10 mL), the aqueous phase was then acidified with 1 M HCl (aq.) to pH=6 and then extracted with EtOAc (20 mL), the organic layer was dried and evaporated under vacuo to afford the title compound (0.8 g) as brown solid. $^1$H NMR (400 MHz, DMSO-d$_6$): 12.30 (s, 1H), 2.36 (t, J=8.4 Hz, 2H), 1.78 (t, J=8.4 Hz, 2H), 1.30 (s, 6H). MS (ESI): C$_7$H$_{11}$NO$_2$ requires 141; found 140 [M−H]$^−$.

Description 93

3-Hydroxy-2,2-dimethylpropanenitrile (D93)

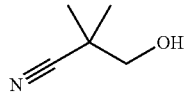

To a mixture of ethyl 2-cyano-2-methylpropanoate (2.5 g) in THF (20 mL) and water (50 mL) was added NaBH$_4$ (3.35 g) portionwise. After addition the mixture was stirred at RT for 6 hours. Hydrochloric acid (6 M) was added to quench the reaction mixture, and then extracted with EtOAc (50 mL). The extract was washed with water (50 mL), dried over anhydrous magnesium sulfate and concentrated under reduced pressure to afford the title compound (1 g). $^1$H NMR (400 MHz, MeOD-d$_4$): 5.45 (s, 1H), 3.36 (s, 2H), 1.21 (s, 6H).

Description 94

Tricyclo[2.2.1.0$^{2,6}$]heptan-3-yl acetate (D94)

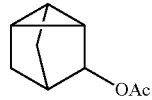

To a solution of acetic acid (10.17 g) and bicyclo[2.2.1]hepta-2,5-diene (15.6 g) was added BF$_3$.Et$_2$O (1.073 mL). The mixture was stirred at 100° C. for 6 hours and then evaporated. To the residue was added brine (200 mL) and then extracted with ether (2×200 mL). The combined organic layer was washed with brine (100 mL), dried over anhydrous MgSO$_4$, separated and concentrated to afford the title compound (8 g) as yellow oil. MS (ESI): C$_9$H$_{12}$O$_2$ requires 152; found 153 [M+H]$^+$.

Description 95

Tricyclo[2.2.1.0$^{2,6}$]heptan-3-ol (D95)

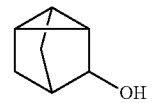

To the mixture of sodium (1.511 g) in MeOH (60 mL), was added tricyclo[2.2.1.0$^{2,6}$]heptan-3-yl acetate (D94, 6 g). The mixture was stirred at 80° C. for 6 hours and then evaporated. To the residue was added brine (50 mL) and then extracted with ether (2×50 mL). The combined organic layer was washed with brine (50 mL), dried over anhydrous MgSO$_4$, separated and concentrated to afford the title compound (1.5 g) as yellow oil. MS (ESI): C$_7$H$_{10}$O requires 110; found 111 [M+H]$^+$.

Description 96

Tricyclo[2.2.1.0$^{2,6}$]heptan-3-one (D96)

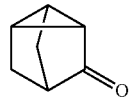

To the mixture of water (10 mL), sulfuric acid (17.81 g) and chromiumVI oxide (4.54 g) was added tricyclo[2.2.1.0$^{2,6}$]heptan-3-ol (D95, 1 g). The mixture was stirred at 0° C. for 6 hours. Water (50 mL) was added and the resulting mixture was extracted with ether (2×50 mL). The combined organic layer was dried over anhydrous MgSO$_4$ and concentrated to afford the title compound (800 mg) as yellow oil. MS (ESI): C$_7$H$_8$O requires 108; found 109 [M+H]$^+$.

Description 97

Bicyclo[3.1.0]hexane-3-carboxylic acid (D97)

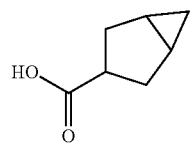

To the solution of KOtBu (2594 mg) in diethyl ether (20 mL) was added tricyclo[2.2.1.0$^{2,6}$]heptan-3-one (D96, 500 mg) at 0° C. The mixture was stirred at 0° C. for 6 hours and then poured into water (50 mL). The mixture was extracted with ether (2×20 mL), dried over anhydrous MgSO$_4$ and concentrated to afford the title compound (200 mg) as yellow oil. MS (ESI): C$_6$H$_8$O$_4$ requires 126; found 125 [M−H]$^−$.

Description 98

2-(Methoxycarbonyl) cyclopropanecarboxylic acid (D98)

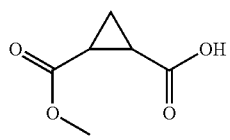

KOH (1.14 g) was added to the mixture of dimethyl cyclopropane-1,2-dicarboxylate (3 g) in MeOH (50 mL). The reaction mixture was heated to 80° C. for 5 hours. The reaction mixture was cooled to RT and was partition between water (100 mL) and EtOAc (50 mL). The organic layer was discarded. The water phase was adjusted to pH=2 with 1 M HCl (aq.) and extracted with EtOAc (50 mL). The organic layer was dried and concentrated under vacuum to afford the title compound (1.5 g) as yellow solid. MS (ESI): $C_6H_8O_4$ requires 144; found 143 [M–H]⁻.

Description 99

3-(2-Diazoacetyl) cyclobutanone (D99)

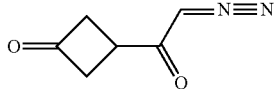

To a solution of 3-oxocyclobutanecarboxylic acid (2 g) in DCM (10 mL) was added $SOCl_2$ (3.84 mL). The reaction mixture was stirred at 20° C. for 2 hours. The mixture was evaporated under reduced pressure to give acyl chloride. To a solution of the above crude acyl chloride in THF (5 mL) and acetonitrile (5 mL) was added (diazomethyl)trimethylsilane (1 M in hexane, 35 mL). The reaction mixture was stirred at 20° C. overnight and then evaporated under vacuum to leave the crude product, which was purified by column chromatography (silica gel, petroleum ether/EtOAc=2:1) to afford the title compound (400 mg) as yellow oil. MS (ESI): $C_6H_6N_2O_2$ requires 138; found 139 [M+H]⁺.

Description 100

2-(3-Oxocyclobutyl)acetic acid (D100)

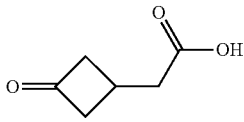

To a solution of 3-(2-diazoacetyl)cyclobutanone (D99, 400 mg) in THF (20 mL) and water (10 mL) was added $AgNO_3$ (590 mg). The reaction mixture was stirred at RT overnight and then evaporated under vacuum to remove most of THF. The water phase was extracted with EtOAc (3×10 mL). The combined organic layer was dried over anhydrous $Na_2SO_4$ and evaporated under vacuum to afford the title compound (360 mg) as yellow oil. MS (ESI): $C_6H_8O_3$ requires 128; found 129 [M+H]⁺.

Description 101

(R)-2-((tert-butoxycarbonyl)amino)pentanoic acid (D101)

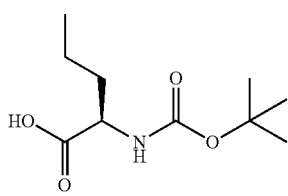

To a mixture of (R)-2-aminopentanoic acid (2.343 g) and $Na_2CO_3$ (2.120 g) in water (60.00 mL) was added dropwise a solution of $Boc_2O$ (4.88 mL) in THF (20 mL). The mixture was stirred at RT overnight. The mixture was washed with ether (2×20 mL), and the water phase was adjusted to pH=3 with $KHSO_4$ solution and then extracted with EtOAc (2×30 mL). The combined organic was dried and evaporated to afford the title compound (4 g) as sticky oil. MS (ESI): $C_{10}H_{19}NO_4$ requires 217; found 216 [M–H]⁻.

Description 102

(R)-ethyl 2-(N-benzyl-2-((tert-butoxycarbonyl) amino) pentanamido)acetate (D102)

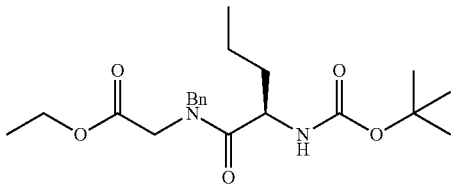 [SMILES: CCC[C@@H](NC(=O)OC(C)(C)C)C(=O)N(CC(=O)OCC)Cc1ccccc1]

To a mixture of ethyl 2-(benzylamino)acetate (3.38 g), (R)-2-((tert-butoxycarbonyl)amino)pentanoic acid (D101, 8.9 g) and DIPEA (3.05 mL) in DCM (50 mL) was added HATU (6.65 g). The mixture was stirred at RT for 2 days. To the mixture was added 1 M $KHSO_4$ solution (50 mL), which resulted in large amount of precipitate. The mixture was filtered, and the filtrate was stirred at RT for 5 min and then the organic layer was separated. The organic layer was then washed with saturated $NaHCO_3$ solution (50 mL), $KHSO_4$ solution (50 mL, 1 M) and then sat $NaHCO_3$ solution (50 mL), dried over $Na_2SO_4$, filtered and evaporated to afford the title compound (8.9 g) as yellow oil. MS (ESI): $C_{21}H_{32}N_2O_5$ requires 392; found 393 [M+H]⁺.

Description 103

(R)-1-benzyl-3-propylpiperazine-2,5-dione (D103)

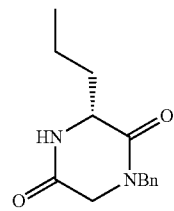

The (R)-ethyl 2-(N-benzyl-2-((tert-butoxycarbonyl) amino)pentanamido)acetate (D102, 3.2 g) in toluene was heated at 85° C. overnight and then concentrated to leave the crude as brown oil, which was diluted with saturated $NaHCO_3$ solution (50 mL) and EtOAc (50 mL). The organic layer was dried over $Na_2SO_4$, filtered and concentrated to leave a brown oil, which was purified by reverse phase column chromatography (C18 column, 10~95% $CH_3CN$ in $H_2O$ with 0.01% $NH_4HCO_3$) to afford the title compound (900 mg) as white solid. MS (ESI): $C_{14}H_{18}N_2O_2$ requires 246; found 247 [M+H]⁺.

Description 104

(R)-1-benzyl-3-propylpiperazine (D104)

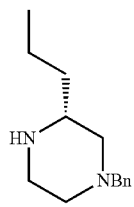

A solution of (R)-1-benzyl-3-propylpiperazine-2,5-dione (D103, 1100 mg) in dry THF (25 mL) was flushed with nitrogen for 5 min. The solution was cooled to 0° C. in an ice bath, and LiAlH$_4$ (678 mg) was added in portions. The reaction was stirred at RT for 1 hour, then another batch of LiAlH$_4$ (275 mg) was added, and the reaction was stirred at RT for 36 hours. The mixture was quenched with Na$_2$SO$_4$ 10H$_2$O in an ice bath. The white precipitate was filtered and washed with a mixture of DCM (20 mL) and MeOH (20 mL). The filtrate was concentrated to give the crude as green oil, which was purified by reverse phase column chromatography (C18 column, 10~95% CH$_3$CN in H$_2$O with 0.01% NH$_4$HCO$_3$) to afford the title compound (750 mg) as pale orange solid. MS (ESI): C$_{14}$H$_{22}$N$_2$ requires 218; found 219 [M+H]$^+$.

Description 105

(R)-(4-benzyl-2-propylpiperazin-1-yl) (cyclopentyl)methanone (D105)

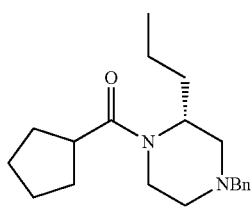 [SMILES: CCC[C@@H]1CN(Cc2ccccc2)CCN1C(=O)C1CCCC1]

To the mixture of (R)-1-benzyl-3-propylpiperazine (D104, 180 mg) and TEA (0.230 mL) in DCM (10 mL) was added slowly cyclopentanecarbonyl chloride (120 mg) at RT and stirred for 15 min. The mixture was diluted with water (5 mL), and the organic layer was washed with brine and dried over Na$_2$SO$_4$, filtered and concentrated to afford the title compound (250 mg) as white solid. MS (ESI): C$_{20}$H$_{30}$N$_2$O requires 314; found 315 [M+H]$^+$.

Description 106

(R)-cyclopentyl(2-propylpiperazin-1-yl)methanone (D106)

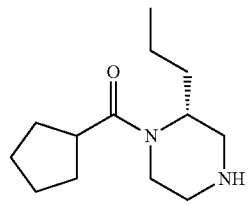 [SMILES: CCC[C@@H]1CNCCN1C(=O)C1CCCC1]

The mixture of (R)-(4-benzyl-2-propylpiperazin-1-yl)(cyclopentyl)methanone (D105, 240 mg) and 10% palladium-carbon (50 mg) in ethanol (5 mL) was hydrogenated at RT under hydrogen atmosphere (1 atm) for 16 hours. The mixture was filtered through Celite and the filtrate was concentrated under reduced pressure to afford the title compound (150 mg) as oil. MS (ESI): C$_{13}$H$_{24}$N$_2$O requires 224; found 225 [M+H]$^+$.

Description 107

Ethyl 2-(2-methyloxazol-4-yl)acetate (D107)

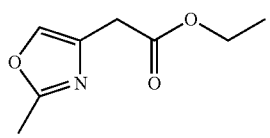

The mixture of acetamide (200 mg) and ethyl 4-chloro-3-oxobutanoate (1672 mg) in ethanol (20 mL) was stirred at 50° C. for 1 hour and then concentrated. The crude product was purified by column chromatography (silica gel, petroleum ether/EtOAc=5:1) to afford the title compound (150 mg) as yellow solid. MS (ESI): C$_8$H$_{11}$NO$_3$ requires 169; found 170 [M+H]$^+$.

Description 108

2-(2-methyloxazol-4-yl) acetic acid (D108)

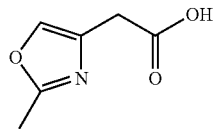

The mixture of ethyl 2-(2-methyloxazol-4-yl)acetate (D107,150 mg) and potassium hydroxide (149 mg) in ethanol (20 mL) was stirred at 80° C. for 3 hours. The reaction mixture was concentrated under vacuum, 1M HCl (aq.) was added to pH=5, extracted with EtOAc (3×10 mL). Combined organic layer was dried and evaporated to afford the title (100 mg) as yellow solid. MS (ESI): C$_6$H$_7$NO$_3$ requires 141; found 142 [M+H]$^+$.

Description 109

2-(3-Methylisoxazol-5-yl)acetic acid (D109)

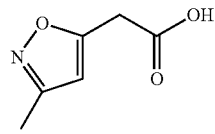

To a solution of 3,5-dimethylisoxazole (4.5 g) in dry THF (60 mL), n-butyllithium (23.17 mL, 2.5 M) was added dropwise under nitrogen at −75° C. During the addition, temperature was kept below −55° C. After addition, the mixture was stirred for 30 min then poured onto dry ice (50 g). Water (50 mL) and EtOAc (30 mL) were added and the mixture was stirred at RT for 30 min, the organic layer was discarded, the aqueous layer was adjust to pH=2 with HCl, extracted with EtOAc (2×20 mL). Combined organic layer was dried over magnesium sulfate, filtered and concentrated under reduced pressure, the crude product was triturated with petroleum ether/EtOAc (10:1, 30 mL) to afford the title compound (2.3 g) as brown solid. MS (ESI): $C_6H_7NO_3$ requires 141; found 142 $[M+H]^+$.

Description 110

Methyl 2,6-dichloro-5-fluoronicotinate (D110)

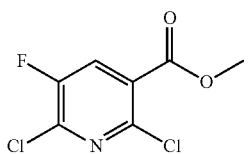

To a mixture of 2,6-dichloro-5-fluoronicotinic acid (5 g) and one drop of DMF in DCM (20 mL), oxalyl chloride (5 mL) was added dropwise at RT. The mixture was stirred at RT for 1 hour, and then concentrated. The resulting acyl chloride was re-dissolved in DCM (10 mL), and then added dropwise to a mixture of DCM (20 mL) and MeOH (20 mL). The resulting mixture was stirred at RT for another 1 hour, and then concentrated to afford the title compound (6 g) as pale yellow oil. MS (ESI): $C_7H_4Cl_2FNO_2$ requires 223; found 224 $[M+H]^+$.

Description 111

Methyl 2-chloro-5-fluoro-6-methylnicotinate (D111)

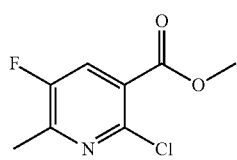

A mixture of methyl 2,6-dichloro-5-fluoronicotinate (D110, 6 g), 2,4,6-trimethyl-1,3,5,2,4,6-trioxatriborinane (3.36 g), $K_2CO_3$ (9.99 g) and $Pd(Ph_3P)_4$ (1.548 g) in 1,4-dioxane (50 mL) was heated to 110° C. for 20 hours. The mixture was filtered, and the filtrate was concentrated. The residue was purified by column chromatography (silica gel, petroleum ether/EtOAc=10:1) to afford the title compound (3.5 g) as yellow oil. MS (ESI): $C_8H_7ClFNO_2$ requires 203; found 204 $[M+H]^+$.

Description 112

Methyl 5-fluoro-6-methylnicotinate (D112)

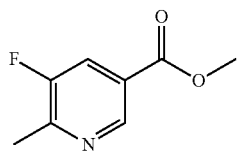

A mixture of methyl 2-chloro-5-fluoro-6-methylnicotinate (D111, 4.2 g), Pd/C (0.5 g) and sodium acetate (6.77 g) in EtOAc (50 mL) was stirred at RT overnight under hydrogen atmosphere (1 atm). The mixture was filtered, and the filtrate was concentrated. The residue was purified by column chromatography (silica gel, petroleum ether/EtOAc=10:1) to afford the title compound (3.5 g) as white solid. MS (ESI): $C_8H_8FNO_2$ requires 169; found 170 $[M+H]^+$.

Description 113

5-Fluoro-6-methylnicotinic acid (D113)

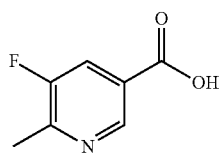

To a solution of methyl 5-fluoro-6-methylnicotinate (D112, 2.3 g) in THF (10 mL) and methanol (10 mL) was added a solution of NaOH (0.707 g) in water (5 mL). The mixture was stirred at RT for 1 hour, and then concentrated under vacuum. To the residue was added water (5 ml). The pH of the mixture was adjusted to 3. The solid was collected and dried under vacuum to afford the title compound (800 mg) as white solid. $^1$H NMR (400 MHz, DMSO-$d_6$): 8.83 (s, 1H), 8.00 (dd, J=9.6, 1.2 Hz, 1H), 2.57 (s, 3H). MS (ESI): $C_7H_6FNO_2$ requires 155; found 156 $[M+H]^+$.

Description 114

Ethyl 5-cyano-2-hydroxy-6-methylnicotinate (D114)

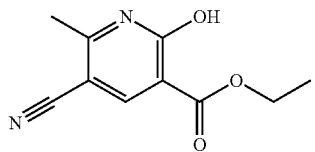

A mixture of diethyl 2-(ethoxymethylene)malonate (21.6 g) and 3-aminobut-2-enenitrile (8.2 g) was stirred at 150° C. for 2 hours and standing overnight. Filtered, the solid was washed with ice-cold methanol to give the title compound (5 g) as yellow solid. MS (ESI): $C_{10}H_{10}N_2O_3$ requires 206; found 207 $[M+H]^+$.

Description 115

Ethyl 2-chloro-5-cyano-6-methylnicotinate (D115)

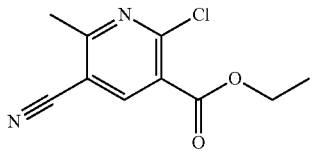

A mixture of ethyl 5-cyano-2-hydroxy-6-methylnicotinate (D114, 3.0 g) in phosphoryl trichloride (22.3 g) was stirred at 90° C. for 5 hours and standing overnight. The solution was concentrated under vacuum. The residue was poured into ice. The resulting mixture was filtered to afford the title compound (3 g) as yellow solid. MS (ESI): $C_{10}H_9ClN_2O_2$ requires 224; found 225 $[M+H]^+$.

Description 116

Ethyl 5-cyano-6-methylnicotinate (D116)

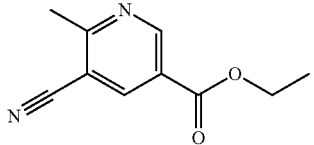

To a mixture of ethyl 2-chloro-5-cyano-6-methylnicotinate (D115, 1.5 g), methanol (50 mL) and palladium (10% on carbon, 0.071 g) was added ammonium formate (6.32 g). The mixture was stirred at RT for 3 hours, and then filtered. The solution was concentrated under vacuum. The residue was purified by column chromatography (silica gel, petroleum ether/EtOAc=4:1) to afford the title compound (1 g) as white solid. MS (ESI): $C_{10}H_{10}N_2O_2$ requires 190; found 191 $[M+H]^+$.

Description 117

5-Cyano-6-methylnicotinic acid (D117)

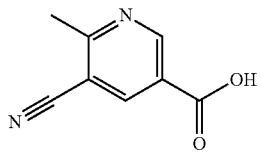

To a mixture of ethyl 5-cyano-6-methylnicotinate (D116, 1 g), methanol (15 mL) and water (30 mL) was added sodium hydroxide (2.1 g). The mixture was stirred at RT for 30 min. The pH of the solution was adjusted to 4 with hydrochloric acid, extracted with EtOAc (2×100 mL). Combined organic layer was concentrated under vacuum to afford the title compound (800 mg) as white solid. $^1$H NMR (400 MHz, MeOD-d$_4$): 9.20 (s, 1H), 8.62 (s, 1H), 2.83 (s, 3H). MS (ESI): $C_8H6N_2O_2$ requires 162; found 163 $[M+H]^+$.

Description 118

Methyl 6-(hydroxymethyl)nicotinate (D118)

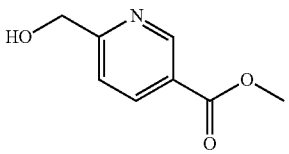

A solution of dimethyl pyridine-2,5-dicarboxylate (5 g) in THF (50 mL) was cooled to 0° C. and then NaBH$_4$ (1.454 g) was added in several portions. The reaction mixture was stirred at RT overnight, aq NH$_4$Cl solution (50 mL) was added and the mixture was extracted with EtOAc (3×20 mL). The combined organic layer was dried over Na$_2$SO$_4$, Filtered, the filtrate was concentrated under vacuum. The residue was purified by column chromatography (silica gel, petroleum ether/EtOAc=5:1) to afford the title compound (3 g) as white solid. MS (ESI): $C_8H_9NO_3$ requires 167; found 168 $[M+H]^+$.

Description 119

Methyl 6-(fluoromethyl)nicotinate (D119)

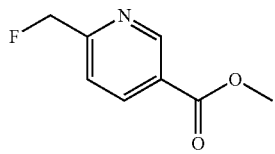

A solution of methyl 6-(hydroxymethyl)nicotinate (D118, 2.0 g) in DCM (40 mL) was cooled to −78° C. and then DAST (1.9 g) was added dropwise. The reaction mixture was stirred at −78° C. for 4 hours, quenched with saturated NaHCO$_3$ aqueous solution (40 mL). The organic layer was separated, dried over Na$_2$SO$_4$. Filtered, the filtrate was concentrated under vacuum, the residue was purified by column chromatography (silica gel, petroleum ether/EtOAc=10:1) to afford the title compound (250 mg) as white solid. MS (ESI): $C_8H_8FNO_2$ requires 169; found 170 $[M+H]^+$.

Description 120

6-(Fluoromethyl)nicotinic acid (D120)

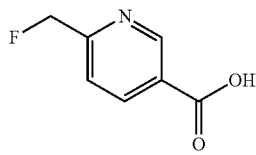 [SMILES: O=C(O)c1ccc(CF)nc1]

To a solution of methyl 6-(fluoromethyl)nicotinate (D119, 250 mg) in methanol (20 mL), NaOH (118 mg) solution in water (10 mL) was added. The reaction mixture was stirred at 30° C. overnight. Most solvent was evaporated off, the residue was acidified to pH=3 with 1 M hydrochloric acid and then lyophilized to get the crude title compound (200 mg) as white solid. $^1$H NMR (400 MHz, DMSO-$d_6$): 9.04 (d, J=2.0 Hz, 1H), 8.35 (dd, J=8.0, 2.3 Hz, 1H), 7.62 (d, J=8.0 Hz, 1H), 5.53 (d, J=46.4 Hz, 2H). MS (ESI): $C_7H_6FNO_2$ requires 155; found 156 [M+H]$^+$.

Description 121

Methyl 6-carbamnoylnicotinate (D121)

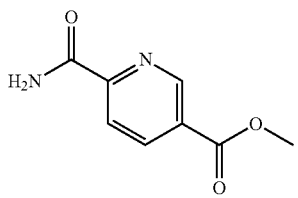

To a solution of 5-(methoxycarbonyl)picolinic acid (12 g) in DCM (80 mL), oxalyl dichloride (8.41 g) was added dropwise over 15 minutes. This mixture stirred at RT for 3 hours and then solvent was removed under vacuum. The crude acyl chloride was re-dissolved with DCM (40 mL), added dropwise over 15 minutes into concentrated ammonia aqueous solution (20 mL) at 0° C. The reaction mixture was stirred for 15 minutes, filtered, the filtrate was concentrated to afford the title compound (11 g) as white solid. MS (ESI): $C_8H_8N_2O_3$ requires 180; found 181 [M+H]$^+$.

Description 122

6-Carbamoylnicotinic acid (D122)

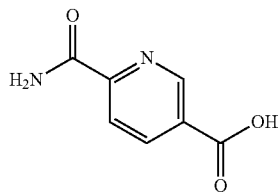 [SMILES: NC(=O)c1ccc(C(=O)O)cn1]

To a solution of methyl 6-carbamoylnicotinate (D121, 11 g) in THF (20 mL) and water (20 mL), NaOH (24.42 g) was added portion-wise over 15 minutes. This mixture stirred at RT for 3 hours. The solution was neutralized with 2 M HCl (aq.) to pH=5, and extracted with EtOAc (2×60 mL). The combined organic layer was washed with water (3×80 mL) and brine (2×40 mL), dried over $Na_2SO_4$ and filtered. The filtrate was concentrated under vacuum to afford the title compound (2 g) as white solid. MS (ESI): $C_7H_6N_2O_3$ requires 166; found 167 [M+H]$^+$.

Description 123

Methyl 5,6-dichloronicotinate (D123)

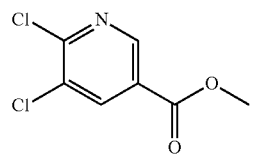

The mixture of 5,6-dichloronicotinic acid (5 g) and sulfurous dichloride (3.10 g) in methanol (20 mL) was stirred overnight at 25° C. Cold water (100 mL) was added and the resulted mixture was neutralized with saturated $NaHCO_3$ solution. The aqueous layer was extracted with DCM (2×100 mL). The combined organic layers were dried over $Na_2SO_4$, filtered, and concentrated under vacuum to afford the title compound (5 g) as white solid. MS (ESI): $C_7H_5Cl_2NO_2$ requires 205; found 206 [M+H]$^+$.

Description 124

Methyl 5-chloro-6-methylnicotinate (D124)

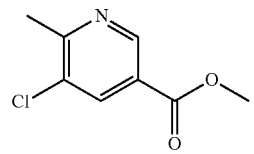

To a solution of methyl 5,6-dichloronicotinate (D123, 2 g), methylboronic acid (0.581 g), $K_2CO_3$ (2.68 g) and Pd(PPh$_3$)$_4$ (0.561 g) in 1,4-dioxane (100 mL) was stirred at 75° C. overnight. The reaction was filtered and the filtrate concentrated under vacuum to give the residue, which was purified by column chromatography (silica gel, petroleum ether/EtOAc=1:1) to afford the title compound (420 mg) as yellow solid. MS (ESI): $C_8H_8ClNO_2$ requires 185; found 186 [M+H]$^+$.

Description 125

5-Chloro-6-methylnicotinic acid (D125)

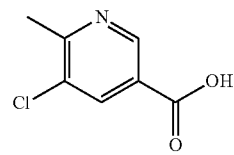

The mixture of methyl 5-chloro-6-methylnicotinate (D124, 450 mg), sodium hydroxide (485 mg) in methanol (20 mL) and water (5 mL) was stirred at RT for 1 hour. 4 M HCl (aq.) was used to adjusted the solution to pH=4. The solution was concentrated under vacuum then treated with EtOAc (20 mL) and washed with water (2×10 mL). The combined organic layer was dried over $Na_2SO_4$, concentrated to give the title compound (400 mg) as white solid. MS (ESI): $C_7H_6ClNO_2$ requires 171; found 172 $[M+H]^+$.

Description 126

5-Chloro-6-methylnicotinoyl chloride (D126)

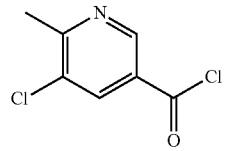

To a solution of 5-chloro-6-methylnicotinic acid (D125, 80 mg) in DCM (5 mL) were added oxalyl chloride (0.122 mL) and a drop of DMF. The mixture was stirred for 30 min. The mixture was concentrated to afford the title compound (100 mg) as yellow solid. MS (ESI): $C_8H_8ClNO_2$ requires 185; found 186 $[M+H]^+$ (sample was converted to corresponding methyl ester by dissolved in MeOH and sent to LCMS).

Description 127

3-(Difluoromethyl)benzoyl chloride (D127)

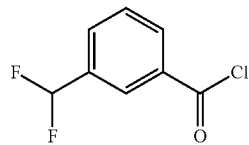 [SMILES: O=C(Cl)c1cccc(C(F)F)c1]

To the mixture of 3-(difluoromethyl)benzoic acid (202 mg) and two drop of DMF in dry DCM (3 mL) was added dropwise oxalyl dichloride (298 mg). After addition the mixture was stirred at RT for 30 min. The solvent was removed under vacuum. The residue was re-dissolved in dry DCM (2 mL) and concentrated to give the title compound (230 mg) as colorless oil. MS (ESI): $C_9H8F_2O_2$ requires 186; found no mass (sample was converted to corresponding methyl ester by dissolved in MeOH and sent to LCMS).

Description 128

4-Bromo-2-(difluoromethyl)pyridine (D128)

To a solution of 4-bromopicolinaldehyde (1 g) in DCM (20 mL) stirred under nitrogen atmosphere at 0° C. was added DAST (1.065 mL). The reaction mixture was stirred at RT overnight. To the mixture was added water, and then extracted with DCM (3×50 mL). The organic phase was washed with saturated $NaHCO_3$, water, and brine, then dried over $MgSO_4$ and filtered to give the title compound (800 mg) as yellow oil. MS (ESI): $C_6H4BrF_2N$ requires 207; found no mass.

Description 129

Methyl 2-(difluoromethyl)isonicotinate (D129)

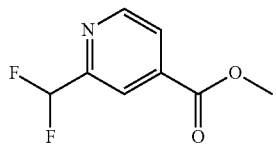

To a mixture of 4-bromo-2-(difluoromethyl)pyridine (D128, 900 mg), DPPP (357 mg), triethylamine (0.603 mL) in methanol (20 mL) and DMF (5 mL) was passed CO gas for 3 min. The mixture was then heated to 120° C. in a sealed vial at 16 atm for 8 hours. After cooling to RT, the mixture was concentrated. Water was added, extracted with EtOAc (3×50 mL). The organic layer was washed with saturated $NaHCO_3$ solution (10 mL), water (10 mL), and brine (10 mL), dried over $MgSO_4$, filtered and concentrated. The residue was purified by column chromatography (silica gel, petroleum ether/EtOAc=5:1) to afford the title compound (500 mg) as yellow oil. MS (ESI): $C_8H_7F_2NO_2$ requires 187; found 188 $[M+H]^+$.

Description 130

2-(Difluoromethyl)isonicotinic acid (D130)

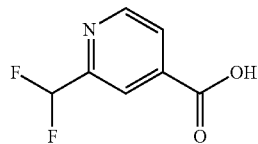 [SMILES: O=C(O)c1ccnc(C(F)F)c1]

A mixture of methyl 2-(difluoromethyl)isonicotinate (D129, 500 mg), NaOH (1069 mg) in water (10 mL) and MeOH (10 mL) was stirred at RT overnight. The mixture was concentrated and adjusted to pH<7 with 2 M HCl, then extracted with EtOAc (3×50 mL). The organic layer was washed with saturated $NaHCO_3$ solution (10 mL), water (10 mL), and brine (10 mL), dried over $MgSO_4$, filtered and concentrated to afford the title compound (400 mg) as white solid. MS (ESI): $C_7H_5F_2NO_2$ requires 173; found 174 $[M+H]^+$.

Description 131

2-(Difluoromethyl)isonicotinoyl chloride (D131)

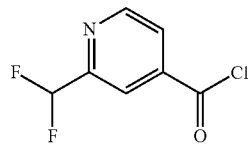 [SMILES: O=C(Cl)c1ccnc(C(F)F)c1]

To a suspension of 2-(difluoromethyl)isonicotinic acid (D130, 160 mg) and two drop of DMF in anhydrous DCM (2 mL) was added dropwise oxalyl dichloride (176 mg). After addition the mixture was stirred for 1 hour at RT, then evaporated under vacuum. The residue was re-dissolved in anhydrous DCM (2 mL) and concentrated again to afford the title compound (245 mg) as colorless oil. MS (ESI): $C_8H_7F_2NO_2$ requires 187; found 188 $[M+H]^+$ (sample was converted to corresponding methyl ester by dissolved in MeOH and sent to LCMS).

Description 132

5-Bromo-3-methylpicolinonitrile (D132)

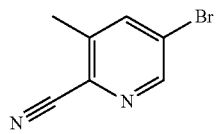

To a solution of 2,5-dibromo-3-methylpyridine (5 g) in DMF (20 mL) was added cyanocopper (1.785 g). The mixture was stirred at 120° C. overnight and then cooled to RT. The mixture was partitioned between EtOAc (50 mL) and water (50 mL). The organic layer was washed with brine (50 mL), dried over $Na_2SO_4$ and concentrated under vacuum to leave the crude, which was purified by column chromatography (silica gel, petroleum ether/EtOAc=4:1) to afford the title compound (600 mg, 13.14% yield) as white solid. MS (ESI): $C_7H_5BrN_2$ requires 195; found 196 $[M+H]^+$.

Description 133

Methyl 6-cyano-5-methylnicotinate (D133)

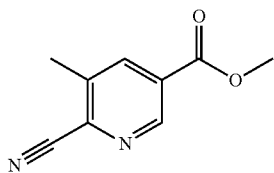

A mixture of 5-bromo-3-methylpicolinonitrile (D132, 700 mg), palladiumII acetate (160 mg), DPPP (394 mg) and TEA (1.486 mL) in methanol (12 mL) and DMF (3 mL) was heated to 120° C. for 12 hours under CO atmosphere (10 atm). After cooling to RT, the mixture was concentrated under vacuum, the residue was purified by column chromatography (silica gel, petroleum ether/EtOAc=4:1) to afford the title compound (300 mg) as sticky oil. MS (ESI): $C_9H_8N_2O_2$ requires 176; found 177 $[M+H]^+$.

Description 134

6-Cyano-5-methylnicotinic acid (D134)

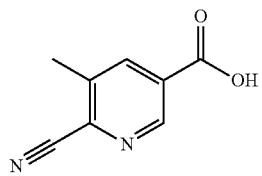

A mixture of methyl 6-cyano-5-methylnicotinate (D133, 250 mg) and LiOH (68.0 mg) in THF (15 mL) and water (5 mL) was stirred at RT overnight. The mixture was diluted with water (10 mL) and EA (16 mL), the organic phase was discarded, the water phase was acidified to pH=6 with 1M HCl (aq.) and then extracted with EtOAc (20 mL), the organic phase was dried over $Na_2SO_4$, filtered and concentrated to afford the title compound (160 mg) as pale solid. MS (ESI): $C_8H_6N_2O_2$ requires 162; found 163 $[M+H]^+$.

Description 135

5-Fluoro-2-methyl-3-nitrobenzoic acid (D135)

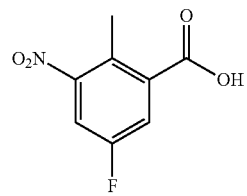

5-Fluoro-2-methylbenzoic acid (20 g) was added portion-wise to ice-cooled con. sulfuric acid (98%, 80 mL), the mixture was stirred at 0° C. until all solid dissolved, and then the mixture of nitric acid (65%, 6 mL) and $H_2SO_4$ (98%, 12 mL) was added portion-wise, the mixture was warmed gradually to RT and stirred at RT for 6 hours. The mixture was poured into ice (500 g), the resulting solid was collected and washed with water (100 mL), the solid was re-dissolved in EtOAc (200 mL) and washed with brine. The organic layer was dried over anhydrous $Na_2SO_4$. Filtered, the filtrate was concentrated under vacuum to afford the title compound (11 g) as brown solid. $^1$H NMR (400 MHz, MeOD-$d_4$): 7.84 (dd, J=8.7, 2.6 Hz, 1H), 7.78 (dd, J=7.8, 2.8 Hz, 1H), 2.55 (s, 3H). MS (ESI): $C_8H_6FNO_4$ requires 199; found 198 $[M-H]^-$.

Description 136

5-Chloro-2-methyl-3-nitrobenzoic acid (D136)

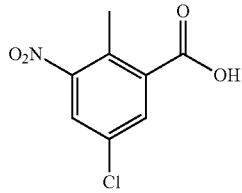

To a solution of 5-chloro-2-methylbenzoic acid (8.5 g) in con. sulfuric acid (98%, 150 mL), nitric acid (65%, 17.1 mL) was added dropwise at 0° C. and the mixture was warmed gradually to RT and stirred at RT for 5 hours. The mixture was poured into ice (~500 g), the resulting solid was collected and washed with water three times, dried to afford title compound (10.7 g), with its regio-isomer. $^1$H NMR (400 MHz, DMSO-$d_6$): 8.19 (d, J=2.3 Hz, 1H), 8.02 (d, J=2.3 Hz, 1H), 2.47 (s, 4H). MS (ESI): $C_8H_6ClNO_4$ requires 215; found 238 [M+Na]$^+$.

Description 137

5-Bromo-2-methyl-3-nitrobenzoic acid (D137)

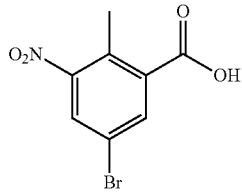

2-Methyl-3-nitrobenzoic acid (5.0 g) was dissolved in conc. $H_2SO_4$ (20 mL) at 0° C. To this solution, NBS (6.2 g) was added gradually. The resulting mixture was stirred at 0° C. for 2 hours, and then warmed to 40° C. After stirring at 40° C. for 3 hours, the mixture was poured into ice water. The white solid precipitate was filtered and dried to give the title compound (7.0 g) as off-white solid. MS (ESI): $C_8H_6BrNO_4$ requires 259; found no mass.

Description 138

(5-Fluoro-2-methyl-3-nitrophenyl) methanol (D138)

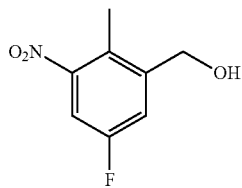

A mixture of 5-fluoro-2-methyl-3-nitrobenzoic acid (D135, 11 g) and $BH_3$-THF (1 M, 72 mL) was heated to 80° C. for 2 hours. MeOH (20 mL) was added slowly to the mixture to quench the reaction, then the mixture was concentrated under vacuum to remove the solvents. The residue was dissolved in DCM (50 mL) and washed with saturated $NaHCO_3$ solution (2×50 mL) and brine (2×50 mL). The organic phase was dried over $Na_2SO_4$, filtered and the filtrate was concentrated to afford the title compound (9 g) as yellow solid. $^1$H NMR (400 MHz, MeOD-$d_4$): 7.54-7.44 (m, 2H), 4.68 (s, 2H), 2.31 (s, 3H). MS (ESI): $C_8H_8FNO_3$ requires 185; found 186 [M+H]$^+$.

Description 139

(5-Chlorol-2-methyl-3-nitrophenyl) methanol (D139)

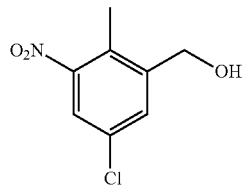

To a solution of 5-chloro-2-methyl-3-nitrobenzoic acid (D136, 23.8 g) in THF (400 mL) was added $BH_3$THF (166 mL, 1 M in THF) dropwise at 0° C. The mixture was warmed gradually to RT and stirred overnight. MeOH was added dropwise until no gas released. The mixture was poured into water (100 mL), extracted with EtOAc (2×100 mL). Combined organic layer was dried over $Na_2SO_4$. Filtered, the filtrate was concentrated under vacuum. The residue was purified by column chromatography (silica gel, petroleum ether/EtOAc=4:1) to afford the title compound (20.5 g). MS (ESI): $C_8H_8ClNO_3$ requires 201; found 200 [M−H]$^−$.

Description 140

(2,5-Dichloro-3-nitrophenyl)methanol (D140)

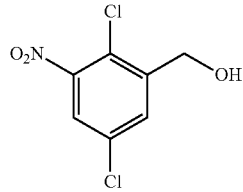 [SMILES: O=[N+]([O-])c1cc(Cl)cc(CO)c1Cl]

2,5-Dichloro-3-nitrobenzoic acid (2.2 g) was dissolved in THF (50 mL) at 0° C. Then to this solution, $NaBH_4$ (1.64 g) was added gradually under ice bath. Then $BF_3$-$Et_2O$ (5.5 mL) was added dropwise carefully at 0° C. Subsequently the reaction mixture was stirred at RT overnight. Methanol was added slowly to quench the reaction. After remove of the solvent, the residue was extracted by EtOAc (2×20 mL) and water (2×20 mL). The combined organic phases were dried over sodium sulfate and concentrated in vacuo to afford the title compound (1.9 g) as yellow solid. $^1$H NMR (400 MHz, $CDCl_3$): 7.83 (d, J=2.2 Hz, 1H), 7.73 (d, J=2.4 Hz, 1H), 4.86 (s, 2H), 2.20 (brs, 1H). MS (ESI): $C_7H_5Cl_2NO_3$ requires 221; found 222 [M+]H$^+$.

Description 141

5-Chloro-1-(chloromethyl)-2-methyl-3-nitrobenzene (D141)

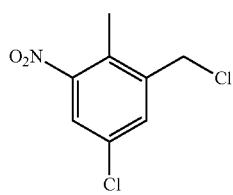

(5-Chloro-2-methyl-3-nitrophenyl) methanol (D139, 7 g) was dissolved in sulfurous dichloride (24.78 g). After stirred at 80° C. overnight, the mixture was concentrated to give the title compound (7 g) as yellow solid. MS (ESI): $C_8H_7Cl_2NO_2$ requires 219; found no mass.

Description 142

5-Fluoro-2-methyl-3-nitrobenzaldehyde (D142)

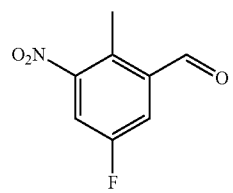

To a mixture of (5-fluoro-2-methyl-3-nitrophenyl)methanol (D138, 9 g) in DCM (100 mL) was added PCC (14 g) in several portions. The mixture was stirred at RT overnight. The solvent was removed under vacuum to give a crude product, which was purified by column chromatography (silica gel, petroleum ether/EtOAc=20:1) to afford the title compound (5 g) as pale yellow solid. $^1$H NMR (400 MHz, CDCl$_3$): 10.37 (d, J=2.2 Hz, 1H), 7.80 (dd, J=7.8, 2.9 Hz, 1H), 7.74 (dd, J=7.2, 2.8 Hz, 1H), 2.75 (d, J=0.7 Hz, 3H). MS (ESI): $C_8H_6FNO_3$ requires 185; found no mass.

Description 143

5-Chloro1-2-methyl-3-nitrobenzaldehyde (D143)

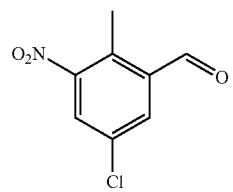

To a solution of (5-chloro-2-methyl-3-nitrophenyl)methanol (D139, 1.823 g) in DCM (20 mL) was added PCC (2.047 g) portionwise at RT. The reaction mixture was stirred at RT overnight. The mixture was extracted by DCM (2×20 mL) and water (2×20 mL). The combined organic phase was dried over Na$_2$SO$_4$. Filtered, the filtrate was concentrated under vacuum to afford the title compound (1 g). $^1$H NMR (400 MHz, CDCl$_3$): 10.34 (s, 1H), 8.02 (d, J=2.0 Hz, 1H), 7.97 (d, J=2.3 Hz, 1H), 2.75 (s, 3H). MS (ESI): $C_8H_6ClNO_3$ requires 199; found 200 [M+H]$^+$.

Description 144

2,5-Dichloro-3-nitrobenzaldehyde (D144)

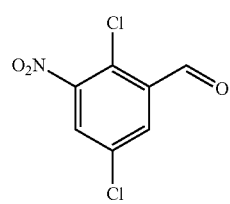

D144 was prepared using a similar procedure to that described for D143. $^1$H NMR (400 MHz, CDCl$_3$): 10.49 (s, 1H), 8.30-7.73 (m, 2H). MS (ESI): $C_7H_3Cl_2NO_3$ requires 219 found 219 [M]$^-$

Description 145

(S)-tert-butyl 4-(5-bromo-2-methyl-3-nitrobenzoyl)-2-methylpiperazine-1-carboxylate (D145)

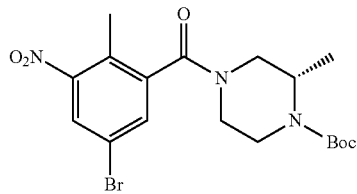 [SMILES: Cc1c(C(=O)N2CCN(C(=O)OC(C)(C)C)[C@@H](C)C2)cc(Br)cc1[N+](=O)[O-]]

5-Bromo-2-methyl-3-nitrobenzoic acid (D137, 7 g) and DIPEA (9.40 mL) were dissolved in DMF (10 mL). To this solution, HATU (12.28 g) was added gradually. After stirring at RT for 30 min, (S)-tert-butyl 2-methylpiperazine-1-carboxylate (6.47 g) was added. The mixture was stirred at RT overnight. As the starting material (5-bromo-2-methyl-3-nitrobenzoic acid) still remained, more (S)-tert-butyl 2-methylpiperazine-1-carboxylate (2.0 g) and HATU (4.0 g) were added. The mixture was stirred at RT overnight. Water (30 mL) was added, extracted with EtOAc (2×30 mL). The organic phase was dried over Na$_2$SO$_4$. Filtered, the filtrate was concentrated to dryness. The residue was triturated with EtOAc, the resulting solid was filtered through a Buchner funnel, to afford the title compound (3.8 g). MS (ESI): $C_{18}H_{24}BrN_3O_5$ requires 441; found 464 [M+Na]$^+$.

Description 146

(S)-tert-butyl 3-methylpiperazine-1-carboxylate (D146)

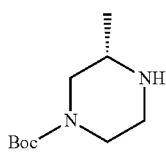

To a solution of (S)-2-methylpiperazine (500 mg) in DCM (5 mL) was added Et$_3$N (1010 mg) and (Boc)$_2$O (1198 mg) in DCM (3 mL) dropwise. The mixture was stirred at 0° C. for 2 hours. DCM (10 mL), water (5 mL) and 30% NaHSO$_4$ (10 mL) aqueous solution were added to the reaction mixture. The resulted mixture was stirred for 10 min, and to the aqueous layer was added saturated Na$_2$CO$_3$ solution until pH=8, extracted with isopropyl alcohol:chloroform=1:3 (5×20 mL). The combined organic layer was washed with brine (5 mL), dried over Na$_2$SO$_4$, filtered and concentrated to afford the title compound (562 mg) as pale yellow oil, MS (ESI): C$_{10}$H$_{20}$N$_2$O$_2$ requires 200; found 201 [M+H]$^+$.

Description 147

(S)-tert-butyl 4-(cyclopentanecarbonyl)-3-methyl-piperazine-1-carboxylate (D147)

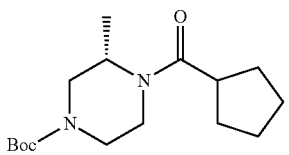 [SMILES: C[C@H]1CN(C(=O)OC(C)(C)C)CCN1C(=O)C1CCCC1]

To a solution of (S)-tert-butyl 3-methylpiperazine-1-carboxylate (D146, 15 g) and triethylamine (31.3 mL) in DCM (300 mL) stirred at RT under nitrogen was added cyclopentanecarbonyl chloride (12.91 g) dropwise. The reaction mixture was stirred at RT overnight. The mixture was concentrated to afford the title compound (24 g) as yellow oil, MS (ESI): C$_{16}$H$_{28}$N$_2$O$_3$ requires 296; found 297 [M+H]$^+$.

Description 148

(S)-cyclopentyl(2-methylpiperazin-1-yl)methanone (D148)

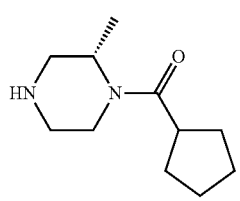

To a solution of (S)-tert-butyl 4-(cyclopentanecarbonyl)-3-methylpiperazine-1-carboxylate (D147, 24 g) in DCM (300 mL) stirred at RT was added TFA (31.2 mL) slowly. The mixture was stirred at RT overnight. The reaction mixture was evaporated. Saturated NaHCO$_3$ solution (100 mL) was added and extracted with EtOAc (3×50 mL). The organic layer was dried over Na$_2$SO$_4$, filtered, the filtrate was evaporated to give the title compound (15 g) as yellow oil, MS (ESI): C$_{11}$H$_{20}$N$_2$O requires 196; found 197 [M+H]$^+$.

Description 149

(S)-tert-butyl 4-(5-fluoro-2-methyl-3-nitrobenzyl)-2-methylpiperazine-1-carboxylate (D149)

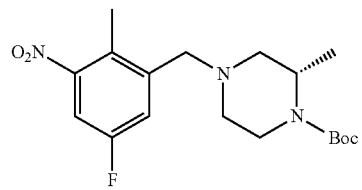

To a solution of 5-fluoro-2-methyl-3-nitrobenzaldehyde (D142, 10 g) and (S)-tert-butyl 2-methylpiperazine-1-carboxylate (12.03 g) in DCM (120 mL) was added drops of acetic acid (3.28 g) and the mixture was stirred at RT for 1 hour. Sodium triacetoxyhydroborate (23.15 g) was added to the mixture in ice-bath and the mixture was stirred at RT overnight and quenched with saturated NaHCO$_3$ solution. The organic layer was dried with anhydrous Na$_2$SO$_4$, filtered and the filtrate evaporated in vacuo to give the title compound (22.17 g) as a syrup. MS (ESI): C$_{18}$H$_{26}$FN$_3$O$_4$ requires 367; found 368 [M+H]$^+$.

Descriptions 150

(S)-tert-butyl 4-(5-chloro-2-methyl-3-nitrobenzyl)-2-methylpiperazine-1-carboxylate (D150)

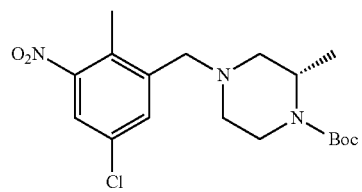 [SMILES: Cc1c(CN2CCN(C(=O)OC(C)(C)C)[C@@H](C)C2)cc(Cl)cc1[N+](=O)[O-]]

To a solution of 5-chloro-2-methyl-3-nitrobenzaldehyde (D143, 20 g) in DCM (260 mL), (S)-tert-butyl 2-methylpiperazine-1-carboxylate (24.08 g) was added. The mixture was stirred for 10 min at room temperature, sodium triacetoxyhydroborate (25.4 g) was added portionwise. The reaction mixture was stirred overnight at 20° C. The mixture was washed with brine, dried with anhydrous Na$_2$SO$_4$. Filtered, the filtrate was concentrated to give crude product, which was purified by column chromatography (silica gel, petroleum ether/EtOAc=20:1) to afford the title compound (37 g) as white solid. MS (ESI): C$_{18}$H$_{26}$ClN$_3$O$_4$ requires 383; found 384 [M+H]$^+$.

Description 151

(S)-tert-butyl 4-(5-bromo-2-methyl-3-nitrobenzyl)-2-methylpiperazine-1-carboxylate (D151)

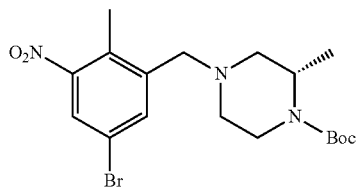

(S)-tert-butyl 4-(5-bromo-2-methyl-3-nitrobenzoyl)-2-methylpiperazine-1-carboxylate (D145, 3.8 g) was dissolved in THF (20 mL) at 0° C. To this solution, NaBH$_4$ (1.625 g) was added gradually under an ice bath, then BF$_3$.Et$_2$O (5.44 mL) was added dropwise carefully. The mixture was stirred at 0° C. for 2 hours and at RT overnight. Methanol was added to quench the reaction. After removal of the solvent, the residue was extracted with EtOAc (2×20 mL) and water (2×20 mL). The combined organic phases were dried over Na$_2$SO$_4$ and concentrated in vacuo to afford the title compound (4.28 g) as pale yellow oil. MS (ESI): C$_{18}$H$_{26}$BrN$_3$O$_4$ requires 427; found 428 [M+H]$^+$.

Description 152

(S)-tert-butyl 4-(5-cyano-2-methyl-3-nitrobenzyl)-2-methylpiperazine-1-carboxylate (D152)

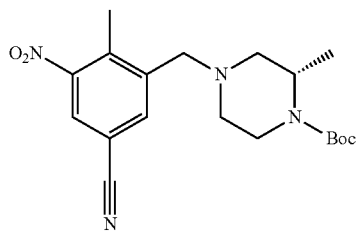

A mixture of (S)-tert-butyl 4-(5-bromo-2-methyl-3-nitrobenzyl)-2-methylpiperazine-1-carboxylate (D151, 1.28 g), dicyanozinc (0.505 g) and tetrakis(triphenylphosphine)palladium(0) (0.276 g) in a sealed tube was stirred at 150° C. in the microwave for 5 hours. The reaction mixture was diluted with EtOAc (20 mL), poured into water (50 mL), and then filtrated. The filtrate was extracted with EtOAc (20 mL). The organic phase was dried and concentrated. The residue was purified by column chromatography (silica gel, petroleum ether/EtOAc=9:1 to 2:1) to afford the title compound (370 mg). MS (ESI): C$_{19}$H$_{26}$N$_4$O$_4$ requires 374; found 397 [M+Na]+.

Description 153

(S)-cyclopentyl(4-(5-fluoro-2-methyl-3-nitrobenzyl)-2-methylpiperazin-1-yl)methanone (D153)

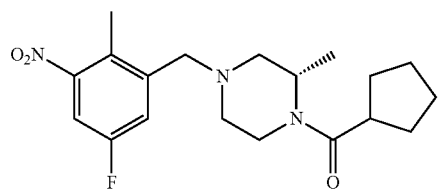

A mixture of 5-fluoro-2-methyl-3-nitrobenzaldehyde (D142, 4.4 g) and (S)-cyclopentyl(2-methylpiperazin-1-yl)methanone (D148, 4.6 g) in anhydrous DCM (50 mL) was stirred at RT for 10 min. NaBH(OAc)$_3$ (4.9 g) was added in several portions. The reaction mixture was stirred at RT overnight. After the reaction completed, MeOH was added dropwise to quench the reaction. When the gaseous evaluation had ceased, the solvents was removed under vacuum to give the crude product, which was purified by column chromatography (silica gel, petroleum ether/EtOAc=100:1) to afford the title compound (7 g) as yellow oil. MS (ESI): C$_{19}$H$_{26}$FN$_3$O$_3$ requires 363; found 364 [M+H]$^+$.

Descriptions 154-155

Descriptions 154-155 were prepared using a similar procedure to that described for D153.

D154 (S)-(4-(5-chloro-2-methyl-3-nitrobenzyl)-2-methylpiperazin-1-yl)(cyclopentyl)methanone D155 (S)-cyclopentyl(4-(2,5-dichloro-3-nitrobenzyl)-2-methylpiperazin-1-yl)methanone

D154

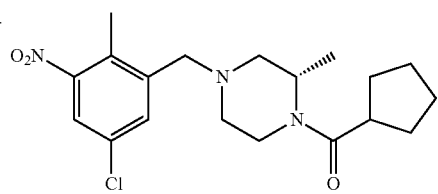

MS (ESI): C$_{19}$H$_{26}$ClN$_3$O$_3$ requires 379; found 380 [M + H]$^+$.

D155

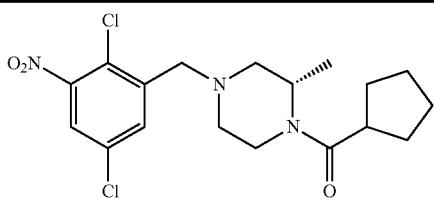

MS (ESI): $C_{18}H_{23}Cl_2N_3O_3$ requires 399; found 400 [M + H]⁺.

Description 156

(S)-(4-(3-amino-5-fluoro-2-methylbenzyl)-2-methyl-piperazin-1-yl)(cyclopentyl)methanone (D156)

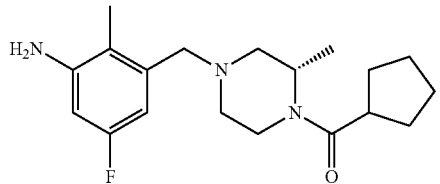

A mixture of (S)-cyclopentyl(4-(5-fluoro-2-methyl-3-nitrobenzyl)-2-methylpiperazin-1-yl)methanone (D153, 7.0 g), HCOONH₄ (1.8 g) and zinc powder (1.44 g) in methanol (60 mL) and water (60 mL) was stirred at 80° C. for 4 hours. After the reaction completed, the solvent was removed in vacuo, the residue was extracted with EtOAc (4×50 mL). The combined organic extract was washed with brine (100 mL), dried over anhydrous sodium sulfate and concentrated to afford the title compound (5.1 g) as pale yellow oil. MS (ESI): $C_{19}H_{28}FN_3O$ requires 333; found 334

Description 157

(S)-(4-(3-amino-5-chloro-2-methylbenzyl)-2-methyl-piperazin-1-yl)(cyclopentyl)methanone (D157)

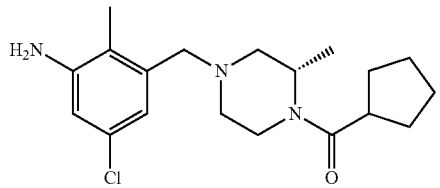 [SMILES: Cc1c(CN2CCN(C(=O)C3CCCC3)[C@@H](C)C2)cc(Cl)cc1[N+](=O)[O-]]

To a solution of (S)-(4-(5-chloro-2-methyl-3-nitrobenzyl)-2-methylpiperazin-1-yl)(cyclopentyl)methanone (D154, 2.4 g) in acetic acid (40 mL) was added iron (3.53 g) portion-wise under vigorous stirring. After addition, the resulting mixture was stirred for another 4 hours. The solid was filtered off and the cake was washed three times with EtOAc (3×10 mL). The filtrate was collected and the solvent was removed in vacuo. The residue was dissolved in EtOAc and washed with aqueous Na₂CO₃ solution and brine. The organic layer was separated, dried over Na₂SO₄, filtered and solvent removed to afford the title compound (1.8 g). MS (ESI): $C_{19}H_{28}ClN_3O$ requires 349; found 350 [M+H]⁺.

Description 158

(S)-(4-(3-amino-2,5-dichlorobenzyl)-2-methylpiperazin-1-yl)(cyclopentyl)methanone (D158)

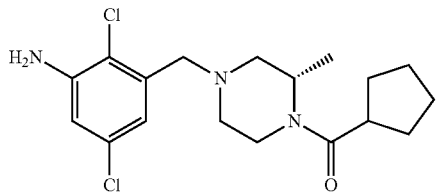 [SMILES: C[C@H]1CN(Cc2cc(Cl)cc([N+](=O)[O-])c2Cl)CCN1C(=O)C1CCCC1]

To a solution of compound (S)-cyclopentyl(4-(2,5-dichloro-3-nitrobenzyl)-2-methylpiperazin-1-yl)methanone (D155, 122 mg) in DCM (20 mL), tinII chloride dihydrate (492 mg) was added and the mixture was stirred at RT for 2 days. The pH value of the mixture was adjusted to about 8 by NaHCO₃ solution. Subsequently it was extracted with DCM (2×10 mL), washed by water (2×10 mL). The organic layer was concentrated in vacuo to give the title compound (91 mg) as yellow oil. MS (ESI): $C_{18}H_{25}Cl_2N_3O$ requires 369; found 370 [M+H]⁻.

Description 159

(S)-tert-butyl 4-(3-amino-5-chloro-2-methylbenzyl)-2-methylpiperazine-1-carboxylate (D159)

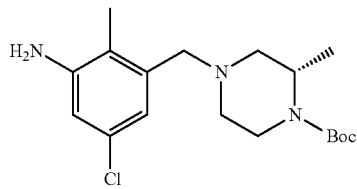

Iron (7.54 g) was added in to a solution of (S)-tert-butyl 4-(5-chloro-2-methyl-3-nitrobenzyl)-2-methylpiperazine-1-carboxylate (D150, 3.7 g) in acetic acid (20 mL) at 0° C. and stirred at this temperature for 5 min and then at RT for 3 hours. After the reaction was complete, the reaction mixture was concentrated to remove most of the solvent. The residue was taken up in DCM (100 mL) and the mixture was filtered through Celite. The filtrate was concentrated and the pH adjusted to about 8 by saturated NaHCO₃ solution. The mixture was extracted with DCM (3×30 mL), the organic layer was dried via Na₂SO₄, filtered and the filtrate was concentrated to give the title compound as brown oil. MS (ESI): $C_{18}H_{28}ClN_3O_2$ requires 353; found 354 [M+H]⁺.

Description 160

(S)-tert-butyl 4-(3-amino-5-cyano-2-methylbenzyl)-2-methylpiperazine-1-carboxylate (D160)

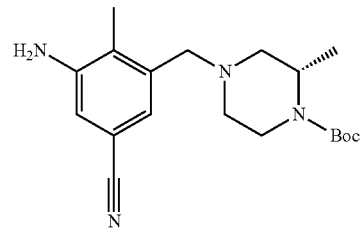 [SMILES: Cc1c(N)cc(C#N)cc1CN1CCN(C(=O)OC(C)(C)C)[C@@H](C)C1]

To a solution of (S)-tert-butyl 4-(5-cyano-2-methyl-3-nitrobenzyl)-2-methylpiperazine-1-carboxylate (D152, 1010 mg) in ethanol (10 mL) was added tinII chloride dihydrate (2587 mg). The mixture was stirred at RT overnight. The pH value of the mixture was adjusted to about 8 by NaHCO$_3$ solution. The white precipitate was filtered through Celite and the filtrate was concentrated, and then extracted with EtOAc (2×20 mL). The combined organic phases were washed with water (2×10 mL). The resulting organic phase was concentrated in vacuo to afford the title compound (630 mg) as yellow oil. MS (ESI): C$_{19}$H$_{28}$N$_4$O$_2$ requires 344; found 345 [M+H]$^+$.

Description 161

(S)-1-(5-chloro-2-methyl-3-nitrobenzyl)-3-methylpiperazine (D161)

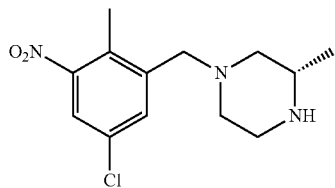 [SMILES: Cc1c(CN2CCN[C@@H](C)C2)cc(Cl)cc1[N+](=O)[O-]]

To a solution of (S)-tert-butyl 4-(5-chloro-2-methyl-3-nitrobenzyl)-2-methylpiperazine-1-carboxylate (D150, 10 g) in DCM (20 mL), TFA (16 mL) was added dropwise at room temperature. After addition, the reaction mixture was stirred for 3.5 hours at room temperature. Solvent was removed under vacuum. The residue was diluted with DCM (40 mL), neutralized with saturated Na$_2$CO$_3$ solution to pH=10, then 2 M NaOH was added until pH=11. Extracted, the aqueous layer was extracted with DCM (20 mL) again. Combined organic layer was dried over Na$_2$SO$_4$. Filtered, the filtrate was concentrated to dryness to afford the title compound (7.96 g) as pale yellow oil. MS (ESI): C$_{13}$H$_{18}$ClN$_3$O$_2$ requires 283; found 284 [M+H]$^+$.

Description 162

(S)-4-methyl-3-((3-methylpiperazin-1-yl)methyl)-5-nitrobenzonitrile (D162)

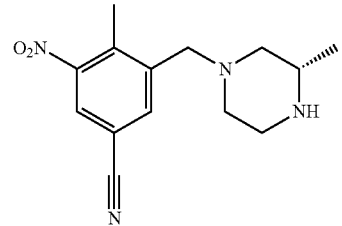 [SMILES: Cc1c(CN2CCN[C@@H](C)C2)cc(C#N)cc1[N+](=O)[O-]]

A mixture of (S)-tert-butyl 4-(5-cyano-2-methyl-3-nitrobenzyl)-2-methylpiperazine-1-carboxylate (D152, 1.0 g) in methanol (10 mL) was added HCl (4 M in dioxane, 6.68 mL). The mixture was stirred at RT for 18 hours, and then concentrated. The residue was diluted with DCM (40 mL), neutralized with saturated Na$_2$CO$_3$ solution to pH=10. Extracted, the aqueous layer was extracted with DCM (20 mL) again. Combined organic layer was dried over Na$_2$SO$_4$. Filtered, the filtrate was concentrated to dryness to afford the title compound (724 mg) as pale yellow oil. MS (ESI): C$_{14}$H$_{18}$N$_4$O$_2$ requires 274; found 275 [M+H]$^+$.

Description 163

(S)-1-(4-(5-chloro-2-methyl-3-nitrobenzyl)-2-methylpiperazin-1-yl)-2-cyclopropylethanone (D163)

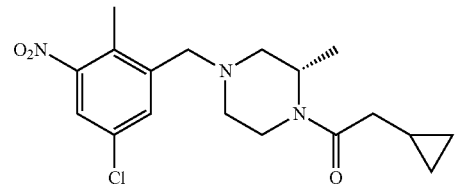 [SMILES: Cc1c(CN2CCN(C(=O)CC3CC3)[C@@H](C)C2)cc(Cl)cc1[N+](=O)[O-]]

2-Cyclopropylacetic acid (2.84 mL) and DIPEA (10.80 mL) were dissolved in DMF (10 mL), to this solution, HATU (12.54 g) was added gradually. The reaction mixture was stirred at RT for 1 hour. Then (S)-1-(5-chloro-2-methyl-3-nitrobenzyl)-3-methylpiperazine (D161, 6.5 g) in DMF (2 mL) was added into the mixture, which was stirred at RT overnight. Water (30 mL) was added, extracted with EtOAc (2×20 mL), combined organic layer was dried over Na$_2$SO$_4$. Filtered, the filtrate was concentrated to dryness to afford the title compound (8 g) as yellow oil. MS (ESI): C$_{18}$H$_{24}$ClN$_3$O$_3$ requires 365; found 366 [M+H]$^+$.

Descriptions 164-165

Descriptions 164 and 165 were prepared using a similar procedure to that described for D163.

D164 (S)-1-(4-(5-chloro-2-methyl-3-nitrobenzyl)-2-methylpiperazin-1-yl)-2-cyclopentylethanone D165 (S)-(4-(5-chloro-2-methyl-3-nitrobenzyl)-2-methylpiperazin-11)(cyclohexyl)methanone D164 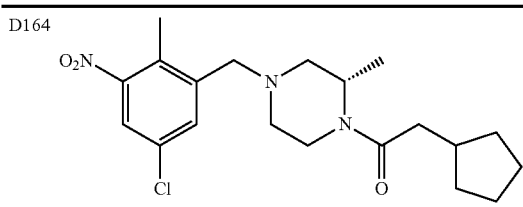

MS (ESI): $C_{20}H_{28}ClN_3O_3$ requires 393; found 394 [M + H]$^+$.

D165 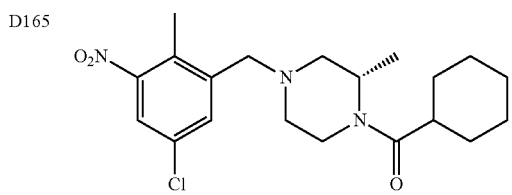

MS (ESI): $C_{20}H_{28}ClN_3O_3$ requires 393, found 394 [M + H]$^+$.

Description 166

(S)-1-(4-(5-chloro-2-methyl-3-nitrobenzyl)-2-methylpiperazin-1-yl) butan-1-one (D166)

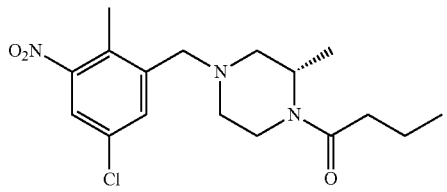 [SMILES: CCCC(=O)N1CCN(Cc2cc(Cl)cc([N+](=O)[O-])c2C)C[C@@H]1C]

To a solution of (S)-1-(5-chloro-2-methyl-3-nitrobenzyl)-3-methylpiperazine (D161, 1 g) and DIPEA (0.911 g) in DCM (20 mL) was added dropwise butyryl chloride (0.563 g). The reaction was stirred at RT overnight. The reaction was quenched with saturated NaHCO$_3$ aqueous solution (3 mL), extracted with DCM (2×20 mL). The combined organic layer was dried over Na$_2$SO$_4$, filtered, and concentrated in vacuo. The residue was purified by column chromatography (silica gel, petroleum ether/EtOAc=1:1 to 0:1) to afford the title compound (1 g) as white solid. MS (ESI): $C_{17}H_{24}ClN_3O_3$ requires 353; found 354 [M+H]$^+$.

Description 167

(S)-3-((4-(cyclopentanecarbonyl)-3-methylpiperazin-1-yl)methyl)-4-methyl-5-nitrobenzonitrile (D167)

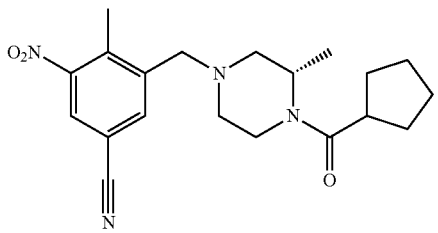

To the mixture of (S)-4-methyl-3-((3-methylpiperazin-1-yl)methyl)-5-nitrobenzonitrile (D162, 0.5 g) and triethylamine (0.922 g) in DCM (6 mL), cyclopentanecarbonyl chloride (0.242 g) was added dropwise. The mixture was stirred at 23° C. for 30 min. The mixture was washed with brine (10 mL), and the organic layer was dried and evaporated under vacuum to afford the crude title compound (0.5 g). MS (ESI): $C_{20}H_{26}N_4O_3$ requires 370; found 371 [M+H]$^+$.

Description 168

(S)-3-((4-(2-cyclopropylacetyl)-3-methylpiperazin-1-yl)methyl)-4-methyl-5-nitrobenzonitrile (D168)

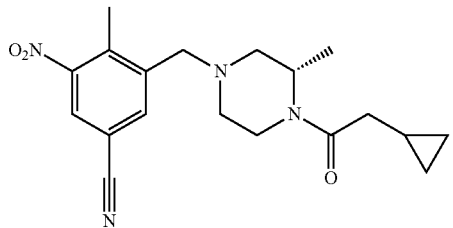 [SMILES: Cc1c(CN2CCN(C(=O)CC3CC3)[C@@H](C)C2)cc(C#N)cc1[N+](=O)[O-]]

2-Cyclopropylacetic acid (281 mg), DIPEA (0.979 mL) and HATU (1421 mg) were dissolved in DMF (2 mL). To this solution, (S)-4-methyl-3-((3-methylpiperazin-1-yl)methyl)-5-nitrobenzonitrile (D162, 512 mg) was added. The reaction mixture was stirred at RT overnight. EtOAc (20 mL) and water (10 mL) was added, extracted, the organic layer was dried over Na$_2$SO$_4$. Filtered, the filtrate was concentrated to dryness. The residue was purified by column chromatography (silicon gel, petroleum ether/EtOAc=1:0 to 1:1.5) to afford the title compound (320 mg) as yellow oil. MS (ESI): $C_{19}H_{24}N_4O_3$ requires 356, found 357 [M+H]$^+$.

Description 169

(S)-1-(4-(3-amino-5-chloro-2-methylbenzyl)-2-methylpiperazin-1-yl)-2-cyclopropylethanone (D169)

To a solution of (S)-1-(4-(5-chloro-2-methyl-3-nitrobenzyl)-2-methylpiperazin-1-yl)-2-cyclopropylethanone (D163, 600 mg) in methanol (50 mL), Raney nickel (96 mg) was added under nitrogen. The mixture was warmed to 50° C., hydrazine hydrate (0.257 mL, 6.56 mmol) was added. The reaction mixture was stirred at 50° C. for 1 hour. Filtered, the filtrate was concentrated under vacuum to afford the title compound (500 mg) as pale yellow oil. MS (ESI): $C_{18}H_{26}ClN_3O$ requires 335, found 336 [M+H]+.

Description 170

(S)-1-(4-(3-amino-5-chloro-2-methylbenzyl)-2-methylpiperazin-1-yl)-2-cyclopentylethanone (170)

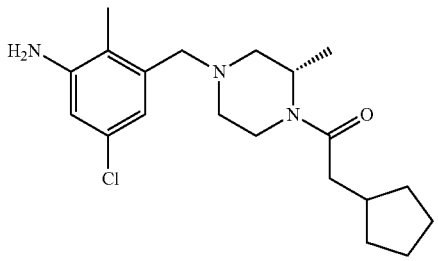 [SMILES: Cc1c(N)cc(Cl)cc1CN1CCN(C(=O)CC2CCCC2)[C@@H](C)C1]

To a solution of compound (S)-1-(4-(5-chloro-2-methyl-3-nitrobenzyl)-2-methylpiperazin-1-yl)-2-cyclopentylethanone (D162, 980 mg) in ethanol (10 mL), tinII chloride dihydrate (2386 mg) was added and the mixture was stirred at RT overnight. The pH value of the mixture was adjusted to about 8 by $NaHCO_3$ solution. The white precipitate was filtered through Celite and the filtrate was concentrated, and then extracted with EtOAc (2×20 mL). The combined organic phases were washed with water (2×10 mL). The resulting organic phase was concentrated in vacuo to afford the title compound (730 mg) as yellow oil. MS (ESI): $C_{20}H_{30}ClN_3O$ requires 363, found 364 [M+H]+.

Description 171

(S)-(4-(3-amino-5-chloro-2-methylbenzyl)-2-methylpiperazin-1-yl)(cyclohexyl)methanone (D171)

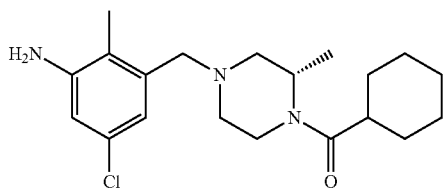

D171 was prepared using a similar procedure to that described for 0170. MS (ESI): $C_{20}H_{30}ClN_3O$ requires 363, found 364 [M+H]+.

Description 172

(S)-1-(4-(3-amino-5-chloro-2-methylbenzyl)-2-methylpiperazin-1-yl)butan-1-one (D9172)

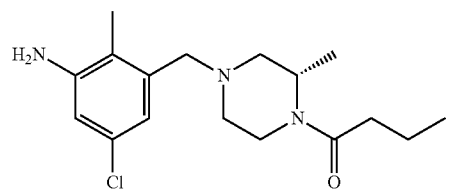

To a mixture of (S)-1-(4-(5-chloro-2-methyl-3-nitrobenzyl)-2-methylpiperazin-1-yl)butan-1-one (D166, 1 g) and iron (1.578 g) in MeOH (50 mL) was added a solution of $NH_4Cl$ (1.512 g) in water (5 mL). The mixture was stirred at 70° C. for 1 hour. The mixture was filtered and the filtrate was concentrated and dissolved with EtOAc (200 mL) and water (50 mL). The organic layer was washed by brine, dried over $Na_2SO_4$, and concentrated to afford the title compound (800 mg) as yellow solid. MS (ESI): $C_{17}H_{26}ClN_3O$ requires 323; found 324 [M+H]+.

Description 173

(S)-3-amino-5-((4-(cyclopentanecarbonyl)-3-methylpiperazin-1-yl)methyl)-4-methylbenzonitrile (D173)

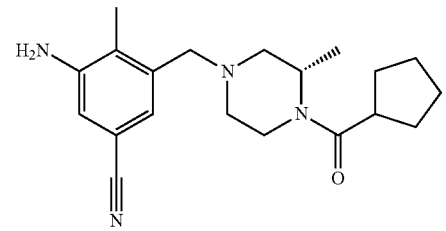 [SMILES: Cc1c(N)cc(C#N)cc1CN1CCN(C(=O)C2CCCC2)[C@@H](C)C1]

The mixture of (S)-3-((4-(cyclopentanecarbonyl)-3-methylpiperazin-1-yl) methyl)-4-methyl-5-nitrobenzonitrile (D167, 0.4 g) and Pd/C (20 mg, 10%) in MeOH (30 mL) was stirred at 28° C. for 4 hours under hydrogen atmosphere (1 atm). After filtration, the filtrate was concentrated under vacuo to afford the title compound (0.35 g) as colorless oil. MS (ESI): $C_{20}H_{28}N_4O$ requires 340; found 341 [M+H]+.

Description 174

(S)-3-amino-5-((4-(2-cyclopropylacetyl)-3-methylpiperazin-1-yl)methyl)-4-methylbenzonitrile (D174)

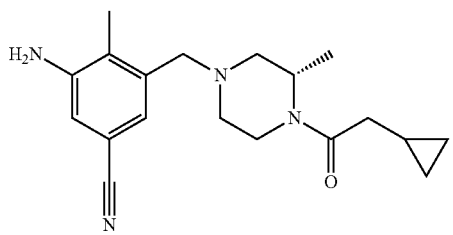

D174 was prepared using a similar procedure to that described for D173. MS (ESI): $C_{19}H_{26}N_4O$ requires 326, found 327 $[M+H]^+$.

Description 175

(S)-tert-butyl 4-(3-amino-5-(methoxycarbonyl)-2-methylbenzyl)-2-methylpiperazine-1-carboxylate (D175)

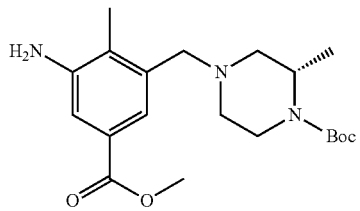

The mixture of (S)-tert-butyl-4-(5-bromo-2-methyl-3-nitrobenzyl)-2-methylpiperazine-1-carboxylate (D151, 16 g), DPPP (1.541 g), diacetoxypalladium (0.419 g) and triethylamine (10.41 mL) in DMF (10 mL) and methanol (200 mL) was heated to 120° C. for 12 hours under CO atmosphere (10 atm). The mixture was filtered, the filtrate was concentrated under vacuum. The residue was re-dissolved in EtOAc (20 mL) and then washed with brine (50 mL), the organic layer was dried over anhydrous sodium sulfate and evaporated under vacuum to leave the crude product, which was purified by column chromatography (silica gel, petroleum ether/EtOAc=5:1) to afford the title compound (13 g) as yellow solid. MS (ESI): $C_{20}H_{31}N_3O_4$ requires 377, found 378 $[M+H]^+$.

Description 176

(R)-(4-(5-chloro-2-methyl-3-nitrobenzyl)-2-propylpiperazin-1-yl)(cyclopentyl)methanone (D176)

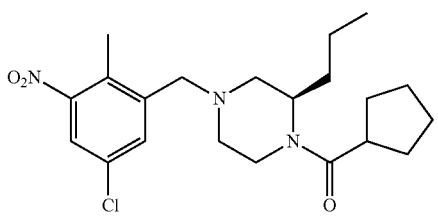 [SMILES: CCC[C@@H]1CN(Cc2cc(Cl)cc([N+](=O)[O-])c2C)CCN1C(=O)C1CCCC1]

The mixture of (R)-cyclopentyl(2-propylpiperazin-1-yl)methanone (D106, 150 mg) and 5-chloro-1-(chloromethyl)-2-methyl-3-nitrobenzene (D141, 147 mg) in DMF (6 mL) was heated at 60° C. for 2 hours, and then cooled to RT. The mixture was diluted with water (20 mL) and extracted with EtOAc (20 mL). The organic layer was dried over $Na_2SO_4$, filtered and concentrated to leave the crude as brown oil, which was purified by column chromatography (silica gel, petroleum ether/EtOAc=20:1) to afford the title compound (101 mg) as pale yellow solid. MS (ESI): $C_{21}H_{30}ClN_3O_3$ requires 407; found 408 $[M+H]^+$.

Description 177

(R)-(4-(3-amino-5-chloro-2-methylbenzyl)-2-propylpiperazin-1-yl)(cyclopentyl) methanone (D177)

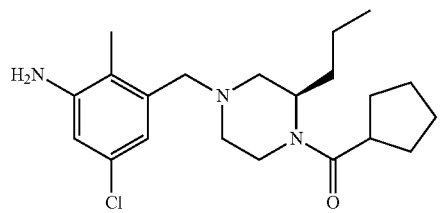

To a solution of (R)-(4-(5-chloro-2-methyl-3-nitrobenzyl)-2-propylpiperazin-1-yl) (cyclopentyl)methanone (DI76, 100 mg) in MeOH (10 mL) was added Raney Ni (46.0 mg) portionwise. The mixture was heated to 50° C. and hydrazine monohydrate (0.084 mL) was slowly added during 10 min. After addition the mixture was stirred at 50° C. for 5 min. The mixture was filtered through a thin pad of Celite and concentrated to afford the title compound (90 mg) as pale orange solid. MS (ESI): $C_{21}H_{32}ClN_3O$ requires 377; found 378 $[M+H]^+$.

Description 178

(R)-tert-butyl 2-((5-chloro-3-(((S)-4-(cyclopentanecarbonyl)-3-methylpiperazin-1-yl)methyl)-2-methylphenyl)carbamoyl)pyrrolidine-1-carboxylate

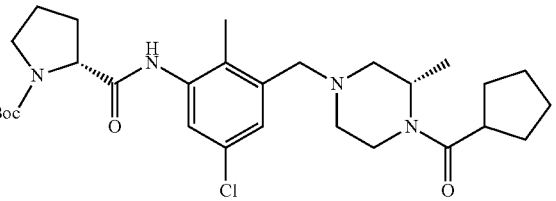

To the solution of (R)-1-(tert-butoxycarbonyl)pyrrolidine-2-carboxylic acid (176 mg) and (S)-(4-(3-amino-5-chloro-2-methylbenzyl)-2-methylpiperazin-1-yl)(cyclopentyl) methanone (D157, 260 mg) in DCM (18 mL) was added HATU (424 mg) at RT. After stirred at RT for 10 min, DIPEA (0.260 mL) was added to the mixture. Then the mixture was stirred at 45° C. for 2 days. The mixture was washed with saturated $NaHCO_3$ aqueous solution and brine, dried by anhydrous sodium sulfate, filtrated and concentrated under vacuum to get crude product which was purified by column chromatography (silica gel, petroleum ether/EtOAc=10:1) to afford the title compound (310 mg) as oil. MS (ESI): $C_{29}H_{43}ClN_4O_4$ requires 546; found 547 $[M+H]^+$.

Descriptions 179-201

Descriptions 179-201 were prepared using a similar procedure to that described for D178, with the specified reaction base or solvent listed in the table.

D179 Tert-butyl 2-(2-((5-chloro-3-(((S)-4-(cyclopentanecarbonyl)-3-methylpiperazin-1-yl)methyl)-2-methylphenyl)amino)-2-oxoethyl)pyrrolidine-1-carboxylate D180 Tert-butyl 3-(2-((5-chloro-3-(((S)-4-(cyclopentanecarbonyl)-3-methylpiperazin-1-yl)methyl)-2-methylphenyl)amino)-2-oxoethyl)piperidine-1-carboxylate
D181 (S)-tert-butyl 4-((5-chloro-3-((4-(cyclopentanecarbonyl)-3-methylpiperazin-1-yl)methyl)-2-methylphenyl)carbamoyl)piperidine-1-carboxylate
D182 (S)-tert-butyl 3-((5-chloro-3-(((S)-4-(cyclopentanecarbonyl)-3-methylpiperazin-1-yl)methyl)-2-methylphenyl)carbamoyl)piperidine-1-carboxylate
D183 (R)-tert-butyl 3-((5-chloro-3-(((S)-4-(cyclopentanecarbonyl)-3-methylpiperazin-1-yl)methyl)-2-methylphenyl)carbamoyl)piperidine-1-carboxylate
D184 (S)-tert-butyl 2-((5-chloro-3-(((S)-4-(cyclopentanecarbonyl)-3-methylpiperazin-1-yl)methyl)-2-methylphenyl)carbamoyl)pyrrolidine-1-carboxylate
D185 (S)-tert-butyl 4-(2-((5-chloro-3-((4-(cyclopentanecarbonyl)-3-methylpiperazin-1-yl)methyl)-2-methylphenyl)amino)-2-oxoethyl)piperidine-1-carboxylate
D186 (S)-tert-butyl (3-((5-chloro-3-((4-(cyclopentanecarbonyl)-3-methylpiperazin-1-yl)methyl)-2-methylphenyl)amino)-3-oxopropyl)(methyl)carbamate
D187 (S)-tert-butyl 3-(2-((5-chloro-3-((4-(cyclopentanecarbonyl)-3-methylpiperazin-1-yl)methyl)-2-methylphenyl)amino)-2-oxoethyl)azetidine-1-carboxylate,Trifluoroacetic acid salt
D188 (S)-tert-butyl (4-((5-chloro-3-((4-(cyclopentanecarbonyl)-3-methylpiperazin-1-yl)methyl)-2-methylphenyl)amino)-4-oxobutyl)(methyl)carbamate
D189 Tert-butyl 2-((5-chloro-3-(((S)-4-(cyclopentanecarbonyl)-3-methylpiperazin-1-yl)methyl)-2-methylphenyl)carbamoyl)morpholine-4-carboxylate
D190 Tert-butyl 3-(2-((3-(((S)-4-(cyclopentanecarbonyl)-3-methylpiperazin-1-yl)methyl)-5-fluoro-2-methylphenyl)amino)-2-oxoethyl)pyrrolidine-1-carboxylate
D191 Tert-butyl ((1S,3r)-3-((3-(((S)-4-(cyclopentanecarbonyl)-3-methylpiperazin-1-yl)methyl)-5-fluoro-2-methylphenyl)carbamoyl)cyclobutyl)carbamate
D192 Tert-butyl ((1R,3s)-3-((3-(((S)-4-(cyclopentanecarbonyl)-3-methylpiperazin-1-yl)methyl)-5-fluoro-2-methylphenyl)carbamoyl)cyclobutyl)carbamate
D193 (S)-tert-butyl 3-((3-((4-(cyclopentanecarbonyl)-3-methylpiperazin-1-yl)methyl)-5-fluoro-2-methylphenyl)carbamoyl)azetidine-1-carboxylate
D194 (S)-tert-butyl (2-((5-chloro-3-((4-(cyclopentanecarbonyl)-3-methylpiperazin-1-yl)methyl)-2-methylphenyl)amino)-2-oxoethyl)(methyl)carbamate
D195 Methyl 2-((5-chloro-3-(((S)-4-(cyclopentanecarbonyl)-3-methylpiperazin-1-yl)methyl)-2-methylphenyl)carbamoyl)cyclopropanecarboxylate
D196 N-(5-chloro-3-(((S)-4-(cyclopentanecarbonyl)-3-methylpiperazin-1-yl)methyl)-2-methylphenyl)-2-(tetrahydrothiophen-2-yl)acetamide
D197 N-(5-chloro-3-(((S)-4-(cyclopentanecarbonyl)-3-methylpiperazin-1-yl)methyl)-2-methylphenyl)-2-(tetrahydro-2H-thiopyran-3-yl)acetamide
D198 S-(2-((5-chloro-3-(((S)-4-(cyclopentanecarbonyl)-3-methylpiperazin-1-yl)methyl)-2-methylphenyl)carbamoyl)cyclobutyl) ethanethioate
D199 (S)—N-(5-chloro-3-((4-(cyclopentanecarbonyl)-3-methylpiperazin-1-yl)methyl)-2-methylphenyl)-3-(methylthio)cyclobutanecarboxamide
D200 N-(3-(((S)-4-(cyclopentanecarbonyl)-3-methylpiperazin-1-yl)methyl)-5-fluoro-2-methylphenyl)-2-(2-oxocyclohexyl)acetamide
D201 N-(3-(((S)-4-(cyclopentanecarbonyl)-3-methylpiperazin-1-yl)methyl)-5-fluoro-2-methylphenyl)-2-(2-oxocyclopentyl)acetamide

| | Structure | Base/Solvent | Characterization |
|---|---|---|---|
| D179 | 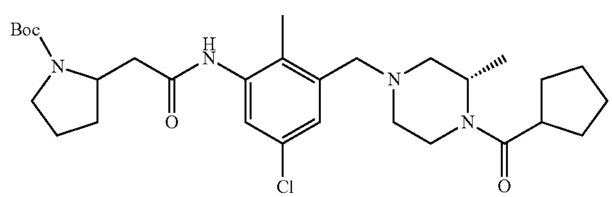 [SMILES: Cc1c(CN2CCN(C(=O)C3CCCC3)[C@@H](C)C2)cc(Cl)cc1NC(=O)CC1CCCN1C(=O)OC(C)(C)C] | DIPEA/DMF | MS (ESI): $C_{30}H_{45}ClN_4O_4$ requires 560; found 561 $[M + H]^+$. |
| D180 | 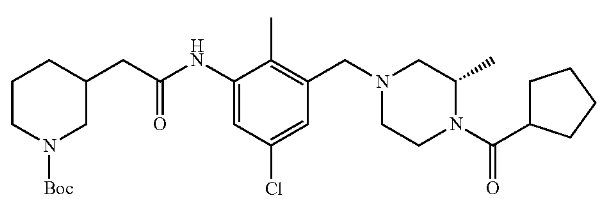 [SMILES: Cc1c(CN2CCN(C(=O)C3CCCC3)[C@@H](C)C2)cc(Cl)cc1NC(=O)CC1CCCN(C(=O)OC(C)(C)C)C1] | DIPEA/DMF | MS (ESI): $C_{31}H_{47}ClN_4O_4$ requires 574; found 575 $[M + H]^+$. |
| D181 | 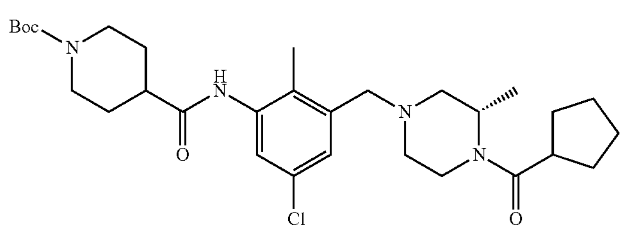 [SMILES: Cc1c(CN2CCN(C(=O)C3CCCC3)[C@@H](C)C2)cc(Cl)cc1NC(=O)C1CCN(C(=O)OC(C)(C)C)CC1] | DIPEA/DMF | MS (ESI): $C_{30}H_{45}ClN_4O_4$ requires 560; found 561 $[M + H]^+$. |

-continued

| | Structure | Base/Solvent | Characterization |
|---|---|---|---|
| D182 | 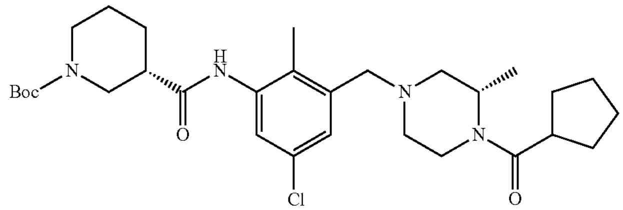 [SMILES: Cc1c(CN2CCN(C(=O)C3CCCC3)[C@@H](C)C2)cc(Cl)cc1NC(=O)[C@H]1CCCN(C(=O)OC(C)(C)C)C1] | DIPEA/DMF | MS (ESI): $C_{30}H_{45}ClN_4O_4$ requires 560; found 561 $[M + H]^+$. |
| D183 | 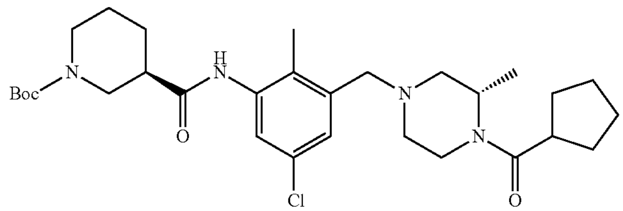 [SMILES: Cc1c(CN2CCN(C(=O)C3CCCC3)[C@@H](C)C2)cc(Cl)cc1NC(=O)[C@@H]1CCCN(C(=O)OC(C)(C)C)C1] | DIPEA/DMF | MS (ESI): $C_{30}H_{45}ClN_4O_4$ requires 560; found 561 $[M + H]^+$. |
| D184 | 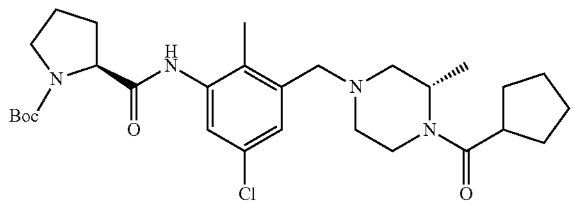 [SMILES: Cc1c(CN2CCN(C(=O)C3CCCC3)[C@@H](C)C2)cc(Cl)cc1NC(=O)[C@@H]1CCCN1C(=O)OC(C)(C)C] | DIPEA/DCM | MS (ESI): $C_{29}H_{43}ClN_4O_4$ requires 546; found 547 $[M + H]^+$. |
| D185 | 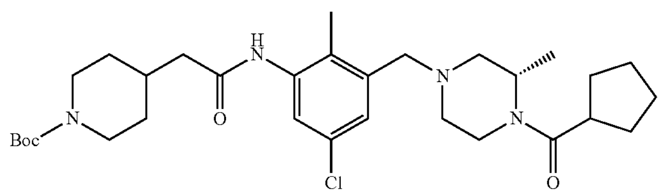 [SMILES: Cc1c(CN2CCN(C(=O)C3CCCC3)[C@@H](C)C2)cc(Cl)cc1NC(=O)CC1CCN(C(=O)OC(C)(C)C)CC1] | DIPEA/DMF | MS (ESI): $C_{31}H_{47}ClN_4O_4$ requires 574; found 575 $[M + H]^+$. |
| D186 | 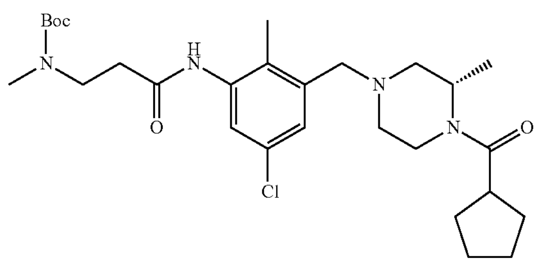 [SMILES: Cc1c(CN2CCN(C(=O)C3CCCC3)[C@@H](C)C2)cc(Cl)cc1NC(=O)CCN(C)C(=O)OC(C)(C)C] | DIPEA/DMF | MS (ESI): $C_{28}H_{43}ClN_4O_4$ requires 534; found 535 $[M + H]^+$. |
| D187 | · TFA | DIPEA/DMF | MS (ESI): $C_{29}H_{43}ClN_4O_4$ requires 546; found 547 $[M + H]^+$. |
| D188 | 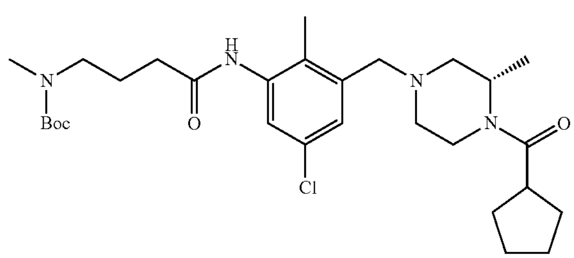 [SMILES: Cc1c(CN2CCN(C(=O)C3CCCC3)[C@@H](C)C2)cc(Cl)cc1NC(=O)CCCN(C)C(=O)OC(C)(C)C] | DIPEA/DMF | MS (ESI): $C_{29}H_{45}ClN_4O_4$ requires 548; found 549 $[M + H]^+$. |

-continued

| | Structure | Base/Solvent | Characterization |
|---|---|---|---|
| D189 | 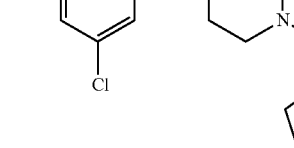 | DIPEA/DMF | MS (ESI): $C_{29}H_{43}ClN_4O_5$ requires 562; found 563 $[M + H]^+$. |
| D190 | 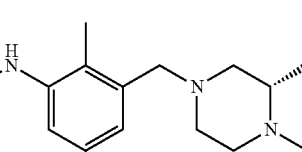 | DIPEA/DMF | MS (ESI): $C_{30}H_{45}FN_4O_4$ requires 544; found 545 $[M + H]^+$. |
| D191 | 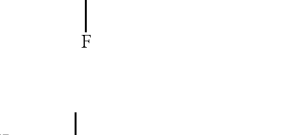 | DIPEA/DMF | MS (ESI): $C_{29}H_{43}FN_4O_4$ requires 530; found 531 $[M + H]^+$. |
| D192 | 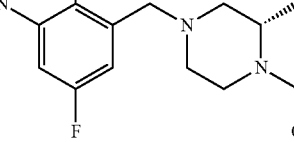 | DIPEA/DMF | MS (ESI): $C_{29}H_{43}FN_4O_4$ requires 530; found 531 $[M + H]^+$. |
| D193 | 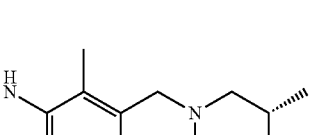 | DIPEA/DMF | MS (ESI): $C_{28}H_{41}FN_4O_4$ requires 516; found 517 $[M + H]^+$. |
| D194 | 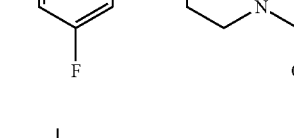 | DIPEA/DMF | MS (ESI): $C_{27}H_{41}ClN_4O_4$ requires 520; found 521 $[M + H]^+$. |
| D195 | 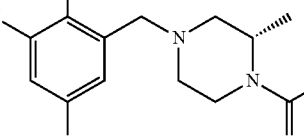 | TEA/DMF | MS (ESI): $C_{25}H_{34}ClN_3O_4$ requires 475; found 476 $[M + H]^+$. |

-continued

| | Structure | Base/Solvent | Characterization |
|---|---|---|---|
| D196 | 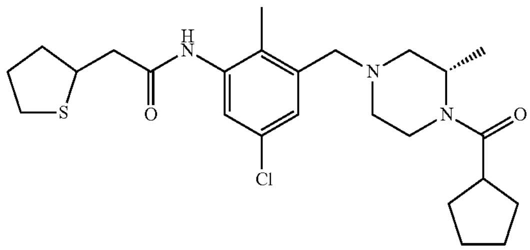 [SMILES: Cc1c(CN2CCN(C(=O)C3CCCC3)[C@@H](C)C2)cc(Cl)cc1NC(=O)CC1CCCS1] | No base/DMF | MS (ESI): $C_{25}H_{36}ClN_3O_2S$ requires 477; found 478 $[M + H]^+$. |
| D197 | 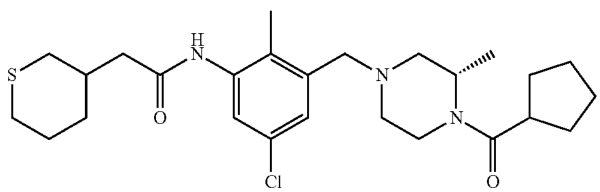 [SMILES: Cc1c(CN2CCN(C(=O)C3CCCC3)[C@@H](C)C2)cc(Cl)cc1NC(=O)CC1CCCSC1] | TEA/DCM | MS (ESI): $C_{26}H_{38}ClN_3O_2S$ requires 491; found 492 $[M - H]^-$. |
| D198 | 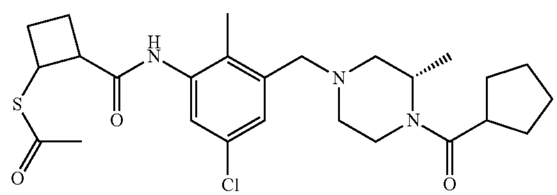 [SMILES: CC(=O)SC1CCC1C(=O)Nc1cc(Cl)cc(CN2CCN(C(=O)C3CCCC3)[C@@H](C)C2)c1C] | DIPEA/DMF | MS (ESI): $C_{26}H_{36}ClN_3O_3S$ requires 505; found 506 $[M + H]^+$. |
| D199 | 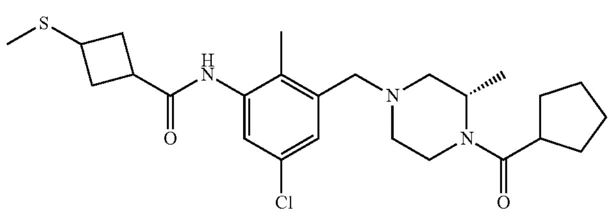 [SMILES: CSC1CC(C(=O)Nc2cc(Cl)cc(CN3CCN(C(=O)C4CCCC4)[C@@H](C)C3)c2C)C1] | TEA/DMF | MS (ESI): $C_{25}H_{36}ClN_3O_2S$ requires 477; found 478 $[M + H]^+$. |
| D200 | 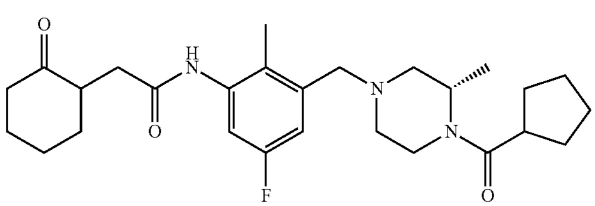 [SMILES: Cc1c(CN2CCN(C(=O)C3CCCC3)[C@@H](C)C2)cc(F)cc1NC(=O)CC1CCCCC1=O] | No base/DMF | MS (ESI): $C_{27}H_{38}FN_3O_3$ requires 471; found 472 $[M + H]^+$. |
| D201 | 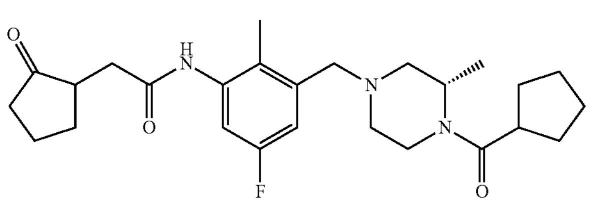 [SMILES: Cc1c(CN2CCN(C(=O)C3CCCC3)[C@@H](C)C2)cc(F)cc1NC(=O)CC1CCCC1=O] | No base/DMF | MS (ESI): $C_{26}H_{36}FN_3O_3$ requires 457; found 458 $[M + H]^+$. |

Description 202

(S)—N-(5-chloro-3-((4-(cyclopentanecarbonyl)-3-methylpiperazin-1-yl)methyl)-2-methylphenyl)-2-(3-oxocyclobutyl)acetamide (D202)

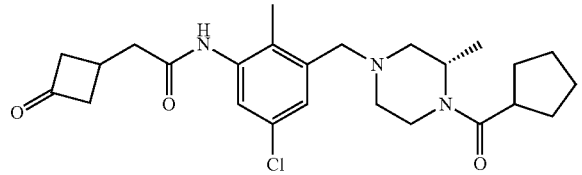 [SMILES: Cc1c(CN2CCN(C(=O)C3CCCC3)[C@@H](C)C2)cc(Cl)cc1NC(=O)CC1CC(=O)C1]

To a solution of 2-(3-oxocyclobutyl)acetic acid (D100, 360 mg) in DCM (5 mL) was added (S)-(4-(3-amino-5-chloro-2-methylbenzyl)-2-methylpiperazin-1-yl)(cyclopentyl)methanone (D157, 1475 mg), EDC (1077 mg), HOBt (861 mg) and DIPEA (1.472 mL). The reaction mixture was stirred at 40° C. overnight. The mixture was evaporated under vacuum to give the title compound (420 mg) as yellow oil. MS (ESI): $C_{25}H_{34}ClN_3O_3$ requires 459; found 460 $[M+H]^+$.

Description 203

(2S)-tert-butyl 4-(5-chloro-2-methyl-3-(2-(tetrahydrothiophen-3-yl)acetamido)benzyl)-2-methylpiperazine-1-carboxylate (D203)

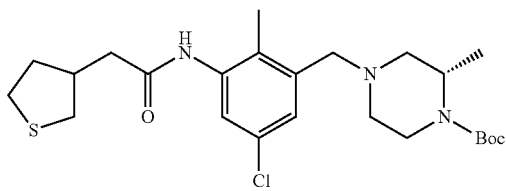 [SMILES: Cc1c(CN2CCN(C(=O)OC(C)(C)C)[C@@H](C)C2)cc(Cl)cc1NC(=O)CC1CCSC1]

To a suspension of (S)-tert-butyl 4-(3-amino-5-chloro-2-methylbenzyl)-2-methylpiperazine-1-carboxylate (D159, 146 mg) in DCM (4 mL) were added HATU (157 mg), 2-(tetrahydrothiophen-3-yl)acetic acid (D60, 100 mg) and triethylamine (83 mg). The mixture was stirred for overnight at RT. The mixture was washed with brine, separated, dried over sodium sulfate anhydrous and concentrated to give the title compound (320 mg) as yellow gum. MS (ESI): $C_{24}H_{36}ClN_3O_3S$ requires 481; found 482 $[M+H]^+$.

Description 204

(S)-tert-butyl 4-(5-chloro-3-(5-fluoro-6-methylnicotinamido)-2-methylbenzyl)-2-methylpiperazine-1-carboxylate (D204)

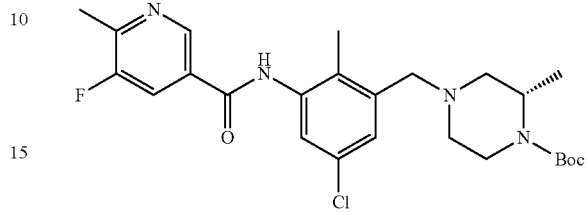

A solution of (S)-tert-butyl 4-(3-amino-5-chloro-2-methylbenzyl)-2-methylpiperazine-1-carboxylate (D159, 913 mg), 5-fluoro-6-methylnicotinic acid (D113, 400 mg), HATU (980 mg) and DIPEA (0.450 mL) in DCM (100 mL) was stirred at RT for 18 hours. The mixture was concentrated under vacuum to afford the title compound (1.2 g) as red oil which was used directly for next step without further purification. MS (ESI): $C_{25}H_{32}ClFN_4O_3$ requires 490, found 491 $[M+H]^+$.

Descriptions 205-211

Descriptions 205-211 were prepared using a similar procedure to that described for Description 204, with the specified reaction base or solvent listed in the table.

D205 (S)-tert-butyl 4-(5-chloro-3-(4-cyano-4-methylpentanamido)-2-methylbenzyl)-2-methylpiperazine-1-carboxylate D206 (S)-tert-butyl 4-(5-chloro-3-(2-(4-hydroxycyclohexyl)acetamido)-2-methylbenzyl)-2-methylpiperazine-1-carboxylate D207 (S)-tert-butyl 4-(5-chloro-2-methyl-3-(3-(methylsulfonyl)propanamido)benzyl)-2-methylpiperazine-1-carboxylate D208 (S)-tert-butyl 4-(3-(5-chloro-6-methylnicotinamido)-5-fluoro-2-methylbenzyl)-2-methylpiperazine-1-carboxylate D209 (S)-tert-butyl 4-(5-chloro-3-(5-chloro-6-methylnicotinamido)-2-methylbenzyl)-2-methylpiperazine-1-carboxylate D210 (S)-tert-butyl 4-(5-cyano-3-(6-methoxynicotinamido)-2-methylbenzyl)-2-methylpiperazine-1-carboxylate D211 (S)-tert-butyl 4-(3-(5-chloro-6-methylnicotinamido)-5-(methoxycarbonyl)-2-methylbenzyl)-2-methylpiperazine-1-carboxylate

| | Structure | Base/Solvent | Characterization |
|---|---|---|---|
| D205 | 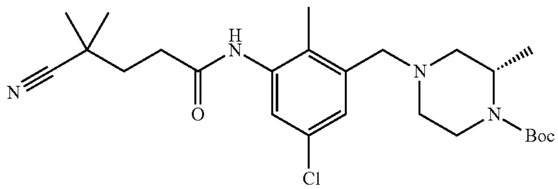 [SMILES: Cc1c(CN2CCN(C(=O)OC(C)(C)C)[C@@H](C)C2)cc(Cl)cc1NC(=O)CCC(C)(C)C#N] | TEA/DCM | MS (ESI): C$_{25}$H$_{37}$ClN$_4$O$_3$ requires 476; found 477 [M + H]$^+$. |
| D206 | 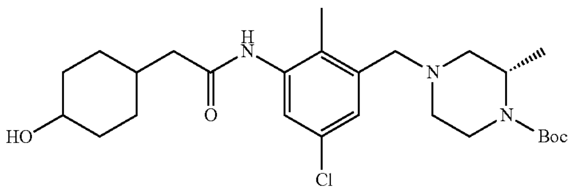 [SMILES: Cc1c(CN2CCN(C(=O)OC(C)(C)C)[C@@H](C)C2)cc(Cl)cc1NC(=O)CC1CCC(O)CC1] | No base/DMF | MS (ESI): C$_{26}$H$_{40}$ClN$_3$O$_4$ requires 493; found 494 [M + H]$^+$. |
| D207 | 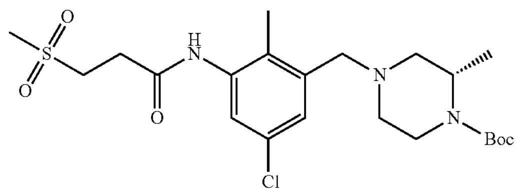 [SMILES: Cc1c(CN2CCN(C(=O)OC(C)(C)C)[C@@H](C)C2)cc(Cl)cc1NC(=O)CCS(C)(=O)=O] | DIPEA/DMF | MS (ESI): C$_{22}$H$_{34}$ClN$_3$O$_5$S requires 487; found 488 [M + H]$^+$. |
| D208 | 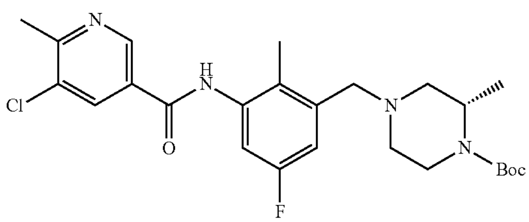 [SMILES: Cc1ncc(C(=O)Nc2cc(F)cc(CN3CCN(C(=O)OC(C)(C)C)[C@@H](C)C3)c2C)cc1Cl] | DIPEA/DMF | MS (ESI): C$_{25}$H$_{32}$ClFN$_4$O$_3$ requires 490; found 491 [M + H]$^+$. |
| D209 | 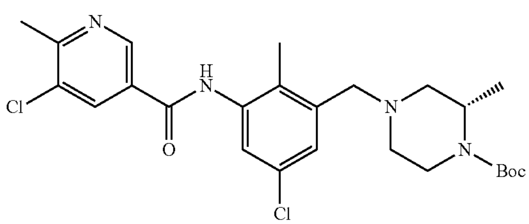 [SMILES: Cc1ncc(C(=O)Nc2cc(Cl)cc(CN3CCN(C(=O)OC(C)(C)C)[C@@H](C)C3)c2C)cc1Cl] | DIPEA/DMF | MS (ESI): C$_{25}$H$_{32}$Cl$_2$N$_4$O$_3$ requires 506; found 507 [M + H]$^+$. |
| D210 | 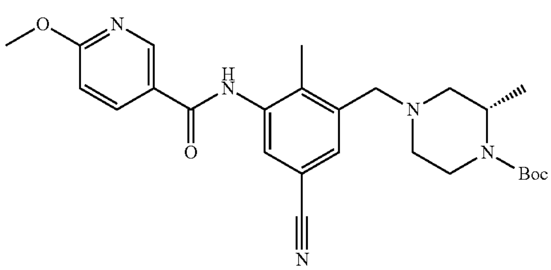 [SMILES: COc1ccc(C(=O)Nc2cc(C#N)cc(CN3CCN(C(=O)OC(C)(C)C)[C@@H](C)C3)c2C)cn1] | DIPEA/DMF | MS (ESI): C$_{26}$H$_{33}$N$_5$O$_4$ requires 479; found 480 [M + H]$^+$. |
| D211 | 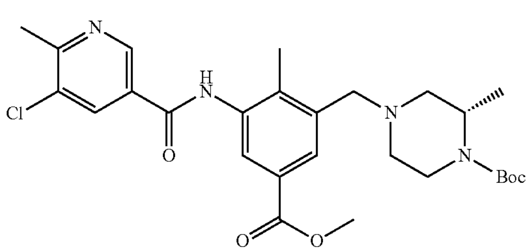 [SMILES: COC(=O)c1cc(CN2CCN(C(=O)OC(C)(C)C)[C@@H](C)C2)c(C)c(NC(=O)c2cnc(C)c(Cl)c2)c1] | TEA/DMF | MS (ESI): C$_{27}$H$_{35}$ClN$_4$O$_5$ requires 530; found 531 [M + H]$^+$. |

Description 212

(S)-tert-butyl 4-(5-cyano-2-methyl-3-(2-methylpyrimidine-5-carboxamido)benzyl)-2-methylpiperazine-1-carboxylate (D212)

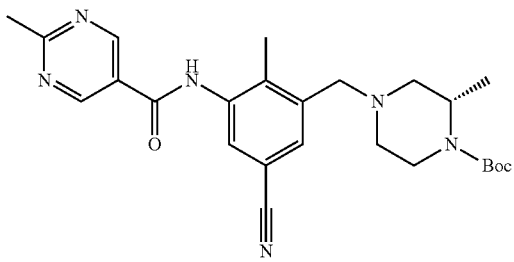 [SMILES: Cc1ncc(C(=O)Nc2cc(C#N)cc(CN3CCN(C(=O)OC(C)(C)C)[C@@H](C)C3)c2C)cn1]

To a solution of (S)-tert-butyl 4-(3-amino-5-cyano-2-methyl benzyl)-2-methylpiperazine-1-carboxylate (D160, 600 mg), 2-methylpyrimidine-5-carboxylic acid (300 mg) and DMAP (316 mg) in DCM (15 mL) was added DCC (530 mg). The mixture was stirred at RT overnight. Filtered, the filtrate was concentrated under reduced pressure to leave the crude product, which was purified by chromatography (silica gel, petroleum ether/EtOAc=1:1) to afford the title compound (800 mg) as white solid. MS (ESI): $C_{25}H_{32}N_6O_3$ requires 464; found 465 $[M+H]^+$.

Description 213

(S)-tert-butyl 4-(5-cyano-3-(3-cyanobenzamido)-2-methylbenzyl)-2-methylpiperazine-1-carboxylate (D213)

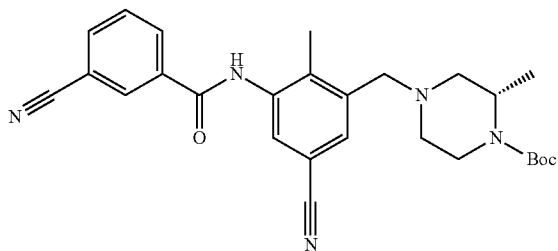 [SMILES: Cc1c(CN2CCN(C(=O)OC(C)(C)C)[C@@H](C)C2)cc(C#N)cc1NC(=O)c1cccc(C#N)c1]

To a suspension of 3-cyanobenzoic acid (431 mg) in DCM (10 mL) was added oxalyl chloride (0.288 mL) dropwise. The reaction mixture was stirred at 40° C. for 2 hours, and then concentrated. The residue was re-dissolved in pyridine (1 mL), and then added to a solution of (S)-tert-butyl 4-(3-amino-5-cyano-2-methylbenzyl)-2-methylpiperazine-1-carboxylate (D160, 630 mg) in pyridine (2 mL). The reaction mixture was stirred at RT overnight. The resulting mixture was diluted with EtOAc (20 mL), and then washed with brine (10 mL). The organic phase was separated, dried over MgSO₄, filtered and concentrated. The residue was purified by column chromatography (silica gel, petroleum ether/EtOAc=1:0 to 2.5:1) to afford the title compound (915 mg). MS (ESI): $C_{27}H_{31}N_5O_3$ requires 473; found 474 $[M+H]^+$.

Description 214

(S)-tert-butyl 4-(5-cyano-2-methyl-3-(6-methylnicotinamido)benzyl)-2-methylpiperazine-1-carboxylate (D214)

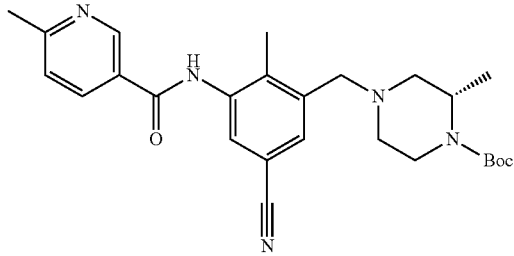 [SMILES: Cc1ccc(C(=O)Nc2cc(C#N)cc(CN3CCN(C(=O)OC(C)(C)C)[C@@H](C)C3)c2C)cn1]

Description 214 was prepared using a similar procedure to that described for D213. MS (ESI): $C_{26}H_{33}N_5O_3$ requires 463; found 464 $[M+H]^+$.

Description 215

(S)-tert-butyl 4-(5-chloro-3-(6-cyano-5-methylnicotinamido)-2-methylbenzyl)-2-methylpiperazine-1-carboxylate (D215)

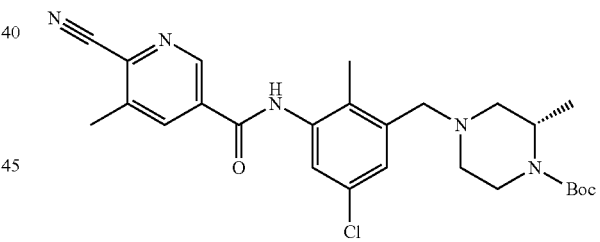

6-Cyano-5-methylnicotinic acid (D134, 160 mg) was dissolved in sulfurous dichloride (235 mg). The reaction mixture was stirred for 3 hours at 60° C. The mixture was then concentrated to dryness under reduced pressure, and the residue re-dissolved in DCM (10 mL) was slowly added to the mixture of (S)-tert-butyl 4-(3-amino-5-chloro-2-methylbenzyl)-2-methylpiperazine-1-carboxylate (D159, 349 mg) and DIPEA (383 mg) at 0° C. The reaction mixture was allowed to warm to RT and stirred for 1 hour. The mixture was diluted with water (15 mL), the organic layer was dried over anhydrous sodium sulfate, filtered and concentrated to afford the title compound (300 mg) as yellow oil. MS (ESI): $C_{26}H_{32}ClN_5O_3$ requires 497; found 498 $[M+H]^+$.

Description 216

(S)-3-((4-(tert-butoxycarbonyl)-3-methylpiperazin-1-yl)methyl)-5-(5-chloro-6-methylnicotinamido)-4-methylbenzoic acid (D216)

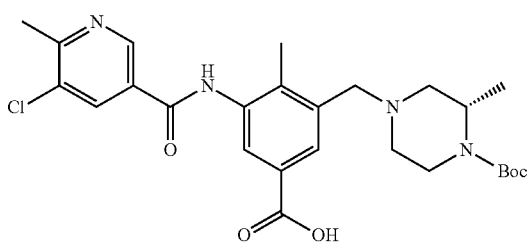 [SMILES: Cc1ncc(C(=O)Nc2cc(C(=O)O)cc(CN3CCN(C(=O)OC(C)(C)C)[C@@H](C)C3)c2C)cc1Cl]

To a solution of (S)-tert-butyl 4-(3-(5-chloro-6-methylnicotinamido)-5-(methoxycarbonyl)-2-methylbenzyl)-2-methylpiperazine-1-carboxylate (D211, 1.1 g) in the mixture solvents of ethanol (10 mL) and water (10 mL), was added lithium hydroxide (0.099 g). The reaction mixture was stirred for 10 hours at 40° C. After removal of the organic solvent under vacuum, the aqueous layer was acidified to pH-3 with 1 M HCl (aq.) and extracted with EtOAc (30 mL). The organic layer was dried over anhydrous sodium sulfate, filtered and concentrated to afford the title compound (1 g) as yellow solid. MS (ESI): $C_{26}H_{33}ClN_4O_5$ requires 516; found 517 $[M+H]^+$.

Description 217

(S)-tert-butyl 4-(5-carbamoyl-3-(5-chloro-6-methylnicotinamido)-2-methylbenzyl)-2-methylpiperazine-1-carboxylate (D217)

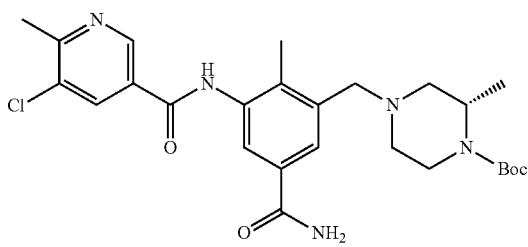 [SMILES: Cc1ncc(C(=O)Nc2cc(C(N)=O)cc(CN3CCN(C(=O)OC(C)(C)C)[C@@H](C)C3)c2C)cc1Cl]

To a suspension of (S)-3-((4-(tert-butoxycarbonyl)-3-methylpiperazin-1-yl)methyl)-5-(5-chloro-6-methylnicotinamido)-4-methylbenzoic acid (D216, 320 mg) in DMF (2 mL), was added HATU (282 mg) and $NH_4HCO_3$ (489 mg). The mixture was stirred overnight at RT. The mixture was washed with brine, dried over anhydrous sodium sulfate, filtered, and concentrated to afford the title compound (370 mg) as yellow solid. MS (ESI): $C_{26}H_{34}ClN_5O_4$ requires 515; found 516 $[M+H]^+$.

Description 218

(S)-tert-butyl 4-(3-(5-chloro-6-methylnicotinamido)-5-cyano-2-methylbenzyl)-2-methylpiperazine-1-carboxylate (D218)

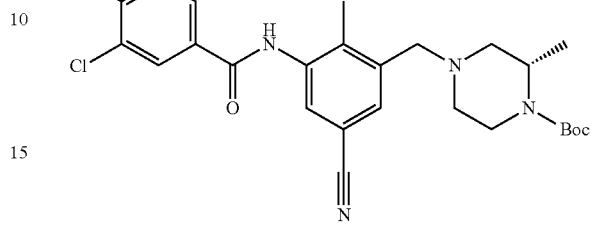

To a solution of (S)-tert-butyl 4-(5-carbamoyl-3-(5-chloro-6-methylnicotinamido)-2-methylbenzyl)-2-methylpiperazine-1-carboxylate (D217, 270 mg) in DCM (3 mL) was added triethylamine (106 mg) and 2,2,2-trifluoroacetic anhydride (330 mg). The mixture was stirred for 0.5 hour at 13° C. The mixture was washed with brine, dried over anhydrous sodium sulfate, filtered, and concentrated to afford the title compound (300 mg) as yellow solid. MS (ESI): $C_{26}H_{32}ClN_5O_3$ requires 497; found 498 $[M+H]^+$.

Description 219

(S)-tert-butyl 3-((5-chloro-3-(((S)-4-(cyclopentanecarbonyl)-3-methylpiperazin-1-yl)methyl)-2-methylphenyl)carbamoyl)pyrrolidine-1-carboxylate (D219)

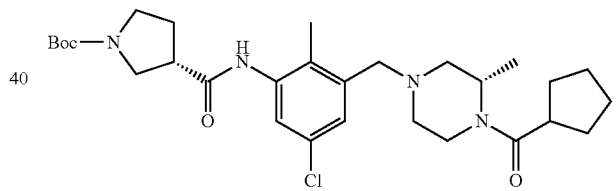

(S)-1-(Tert-butoxycarbonyl)pyrrolidine-3-carboxylic acid (50 mg) was dissolved in DCM (20 mL) and cooled to 0° C. Oxalyl chloride (0.024 mL) was added dropwise under a nitrogen atmosphere, followed by a few drops of DMF. The reaction mixture was allowed to warm to 25° C. and stirred for 1 h. The mixture was then concentrated to dryness under reduced pressure, and the residue redissolved in DCM (20 mL) was slowly added to the mixture of (S)-(4-(3-amino-5-chloro-2-methylbenzyl)-2-methylpiperazin-1-yl)(cyclopentyl)methanone (D157, 81 mg) and DIPEA (0.081 mL) at 0° C. The reaction mixture was allowed to warm to RT and stirred for 1 hour. The mixture was diluted with water (15 mL), the organic phase was dried over anhydrous sodium sulfate, filtered and concentrated to afford the title compound (80 mg) as yellow oil. MS (ESI): $C_{29}H_{43}ClN_4O_4$ requires 546; found 547 $[M+H]^+$.

Descriptions 220-222

Descriptions 220-222 were prepared using a similar procedure to that described for Description 219, with the specified reaction base or solvent listed in the table.

D220 Tert-butyl 3-(2-((5-chloro-3-(((S)-4-(cyclopentanecarbonyl)-3-methylpiperazin-1-yl)methyl)-2-methylphenyl)amino)-2-oxoethyl)pyrrolidine-1-carboxylate D221 (R)-tert-butyl 3-((5-chloro-3-(((S)-4-(cyclopentanecarbonyl)-3-methylpiperazin-1-yl)methyl)-2-methylphenyl)carbamoyl)pyrrolidine-1-carboxylate D222 (S)-6-cyano-N-(3-((4-(cyclopentanecarbonyl)-3-methylpiperazin-1-yl)methyl)-5-fluoro-2-methylphenyl)nicotinamide

Descriptions 224-242

Descriptions 224-242 were prepared using a similar procedure to that described for Description 223, with the specified reaction base or solvent listed in the table.

D224 (R)—N-(5-chloro-3-(((S)-4-(cyclopentanecarbonyl)-3-methylpiperazin-1-yl)methyl)-2-methylphenyl)pyrrolidine-3-carboxamide, 2 hydrochloride acid salt

| | Structure | Base/Solvent | Characterization |
|---|---|---|---|
| D220 | 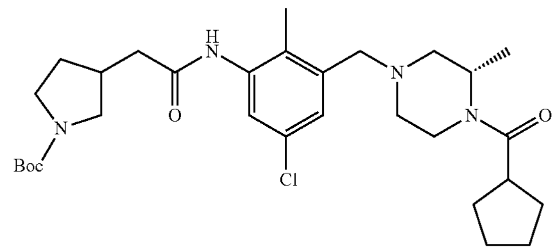 [SMILES: Cc1c(CN2CCN(C(=O)C3CCCC3)[C@@H](C)C2)cc(Cl)cc1NC(=O)CC1CCN(C(=O)OC(C)(C)C)C1] | DIPEA/DCM | MS (ESI): $C_{30}H_{45}ClN_4O_4$ requires 560; found 561 $[M + H]^+$. |
| D221 | 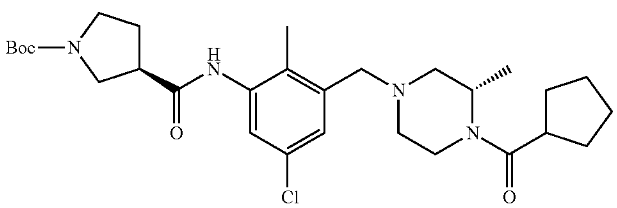 [SMILES: Cc1c(CN2CCN(C(=O)C3CCCC3)[C@@H](C)C2)cc(Cl)cc1NC(=O)[C@@H]1CCN(C(=O)OC(C)(C)C)C1] | TEA/DCM | MS (ESI): $C_{29}H_{43}ClN_4O_4$ requires 546; found 547 $[M + H]^+$. |
| D222 | 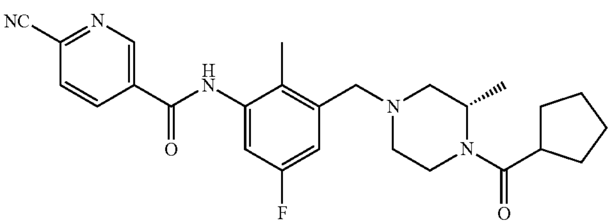 | $K_2CO_3/CH_3CN$ | MS (ESI): $C_{26}H_{30}FN_5O_2$ requires 563; found 564 $[M + H]^+$. |

Description 223

(S)—N-(5-chloro-3-(((S)-4-(cyclopentanecarbonyl)-3-methylpiperazin-1-yl)methyl)-2-methylphenyl)pyrrolidine-3-carboxamide, hydrochloride acid salt (D223)

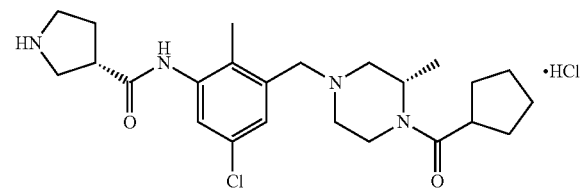 [SMILES: Cc1c(CN2CCN(C(=O)C3CCCC3)[C@@H](C)C2)cc(Cl)cc1NC(=O)[C@H]1CCNC1 ; Cl]

The mixture of (S)-tert-butyl 3-((5-chloro-3-(((S)-4-(cyclopentanecarbonyl)-3-methylpiperazin-1-yl)methyl)-2-methylphenyl)carbamoyl)pyrrolidine-1-carboxylate (D219, 200 mg) in MeOH (20 mL) was added HCl (0.022 mL) and the mixture was stirred at 60° C. for 1 hour. Then the reaction mixture was concentrated to afford the title compound (300 mg) as white solid. MS (ESI): $C_{24}H_{35}ClN_4O_2$ requires 446; found 447 $[M+H]^+$.

D225 N-(5-chloro-3-(((S)-4-(cyclopentanecarbonyl)-3-methylpiperazin-1-yl)methyl)-2-methylphenyl)-2-(pyrrolidin-3-yl)acetamide, 2 hydrochloride acid salt D226 (R)—N-(5-chloro-3-(((S)-4-(cyclopentanecarbonyl)-3-methylpiperazin-1-yl)methyl)-2-methylphenyl)pyrrolidine-2-carboxamide, 2 hydrochloride acid salt D227 (S)—N-(5-chloro-3-((4-(cyclopentanecarbonyl)-3-methylpiperazin-1-yl)methyl)-2-methylphenyl)piperidine-4-carboxamide, 2 hydrochloride acid salt D228 (S)—N-(5-chloro-3-(((S)-4-(cyclopentanecarbonyl)-3-methylpiperazin-1-yl)methyl)-2-methylphenyl)piperidine-3-carboxamide, 2 hydrochloride acid salt D229 (R)—N-(5-chloro-3-(((S)-4-(cyclopentanecarbonyl)-3-methylpiperazin-1-yl)methyl)-2-methylphenyl)piperidine-3-carboxamide, 2 hydrochloride acid salt D230 (S)—N-(5-chloro-3-(((S)-4-(cyclopentanecarbonyl)-3-methylpiperazin-1-yl)methyl)-2-methylphenyl)pyrrolidine-2-carboxamide, 2 hydrochloride acid salt D231 (S)—N-(5-chloro-3-((4-(cyclopentanecarbonyl)-3-methylpiperazin-1-yl)methyl)-2-methylphenyl)-2-(piperidin-4-yl)acetamide, 2 hydrochloride acid salt D232 N-(5-chloro-3-(((S)-4-(cyclopentanecarbonyl)-3-methylpiperazin-1-yl)methyl)-2-methylphenyl)-2-(pyrrolidin-2-yl)acetamide, 2 hydrochloride acid salt D233 N-(5-chloro-3-(((S)-4-(cyclopentanecarbonyl)-3-methylpiperazin-1-yl)methyl)-2-methylphenyl)-2-(piperidin-3-yl)acetamide, 2 hydrochloride acid salt D234 (S)—N-(5-chloro-3-((4-(cyclopentanecarbonyl)-3-methylpiperazin-1-yl)methyl)-2-methylphenyl)-3-(methylamino)propanamide
D235 (S)-2-(azetidin-3-yl)-N-(5-chloro-3-((4-(cyclopentanecarbonyl)-3-methylpiperazin-1-yl)methyl)-2-methylphenyl)acetamide,Trifluoroacetic acid salt
D236 (S)—N-(5-chloro-3-((4-(cyclopentanecarbonyl)-3-methylpiperazin-1-yl)methyl)-2-methylphenyl)-4-(methylamino)butanamide, 2 hydrochloride acid salt
D237 N-(5-chloro-3-(((S)-4-(cyclopentanecarbonyl)-3-methylpiperazin-1-yl)methyl)-2-methylphenyl)morpholine-2-carboxamide, 2 hydrochloride acid salt
D238 N-(3-(((S)-4-(cyclopentanecarbonyl)-3-methylpiperazin-1-yl)methyl)-5-fluoro-2-methylphenyl)-2-(pyrrolidin-3-yl)acetamide, 2 hydrochloride acid salt
D239 (1r,3 S)-3-amino-N-(3-(((S)-4-(cyclopentanecarbonyl)-3-methylpiperazin-1-yl)methyl)-5-fluoro-2-methylphenyl)cyclobutanecarboxamide, 2 hydrochloride acid salt
D240 (1s,3R)-3-amino-N-(3-(((S)-4-(cyclopentanecarbonyl)-3-methylpiperazin-1-yl)methyl)-5-fluoro-2-methylphenyl)cyclobutanecarboxamide, 2 hydrochloride acid salt
D241 (S)—N-(3-((4-(cyclopentanecarbonyl)-3-methylpiperazin-1-yl)methyl)-5-fluoro-2-methylphenyl)azetidine-3-carboxamide
D242 (S)—N-(5-chloro-3-((4-(cyclopentanecarbonyl)-3-methylpiperazin-1-yl)methyl)-2-methylphenyl)-2-(methylamino)acetamide

|  | Structure | Acid/Solvent | Characterization |
|---|---|---|---|
| D224 | 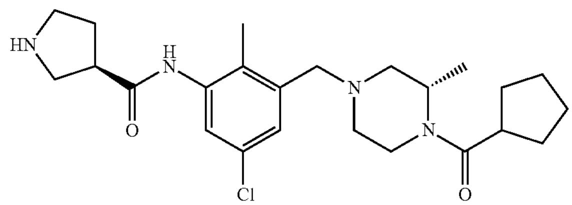 | HCl/MeOH | MS (ESI): $C_{24}H_{35}ClN_4O_2$ requires 446; found 447 $[M + H]^+$. |
| D225 | 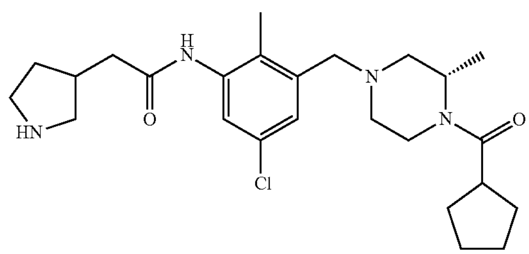 | HCl/MeOH | MS (ESI): $C_{25}H_{37}ClN_4O_2$ requires 460; found 461 $[M + H]^+$. |
| D226 | 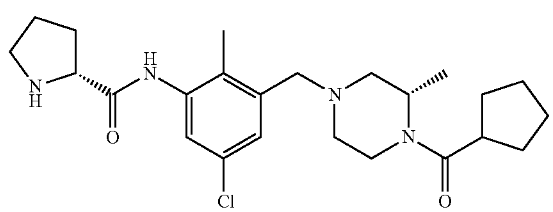 | HCl/MeOH | MS (ESI): $C_{24}H_{35}ClN_4O_2$ requires 446; found 447 $[M + H]^+$. |
| D227 | 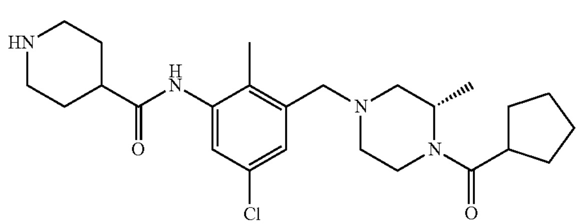 | HCl/THF | MS (ESI): $C_{25}H_{37}ClN_4O_2$ requires 460; found 461 $[M + H]^+$. |
| D228 | 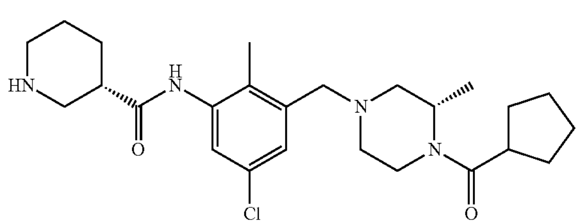 | HCl/THF | MS (ESI): $C_{25}H_{37}ClN_4O_2$ requires 460; found 461 $[M + H]^+$. |

| | Structure | Acid/Solvent | Characterization |
|---|---|---|---|
| D229 | · 2 HCl | HCl/THF | MS (ESI): $C_{25}H_{37}ClN_4O_2$ requires 460; found 461 $[M + H]^+$. |
| D230 | · 2 HCl | HCl/MeOH | MS (ESI): $C_{24}H_{35}ClN_4O_2$ requires 446; found 447 $[M + H]^+$. |
| D231 | · 2 HCl | HCl/EtOH | MS (ESI): $C_{26}H_{39}ClN_4O_2$ requires 474; found 473 $[M - H]^-$. |
| D232 | · 2 HCl | HCl/THF | MS (ESI): $C_{25}H_{37}ClN_4O_2$ requires 460; found 461 $[M + H]^+$. |
| D233 | · 2 HCl | HCl/MeOH | MS (ESI): $C_{26}H_{39}ClN_4O_2$ requires 474; found 475 $[M + H]^+$. |
| D234 | 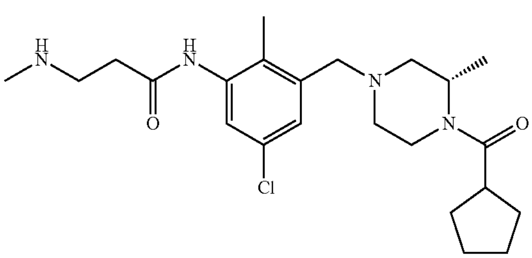 [SMILES: CNCCC(=O)Nc1cc(Cl)cc(CN2CCN(C(=O)C3CCCC3)[C@@H](C)C2)c1C] | HCl/MeOH | MS (ESI): $C_{23}H_{35}ClN_4O_2$ requires 434; found 435 $[M + H]^+$. |
| D235 | · TFA | TFA/DCM | MS (ESI): $C_{24}H_{35}ClN_4O_2$ requires 446; found 447 $[M + H]^+$. |

-continued

| | Structure | Acid/Solvent | Characterization |
|---|---|---|---|
| D236 | 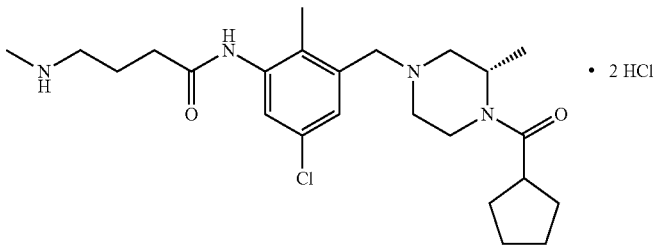 [SMILES: CNCCCC(=O)Nc1cc(Cl)cc(CN2CCN(C(=O)C3CCCC3)[C@@H](C)C2)c1C] • 2 HCl | HCl/MeOH | MS (ESI): $C_{24}H_{37}ClN_4O_2$ requires 448; found 449 $[M + H]^+$. |
| D237 | 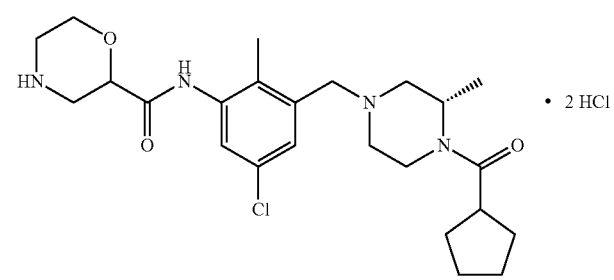 [SMILES: Cc1c(CN2CCN(C(=O)C3CCCC3)[C@@H](C)C2)cc(Cl)cc1NC(=O)C1CNCCO1] • 2 HCl | HCl/EtOH | MS (ESI): $C_{24}H_{35}ClN_4O_2$ requires 462; found 463 $[M + H]^+$. |
| D238 | 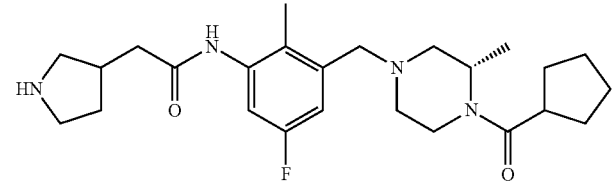 2 HCl | HCl/iPrOH | MS (ESI): $C_{25}H_{37}FN_4O_2$ requires 444; found 445 $[M + H]^+$. |
| D239 | 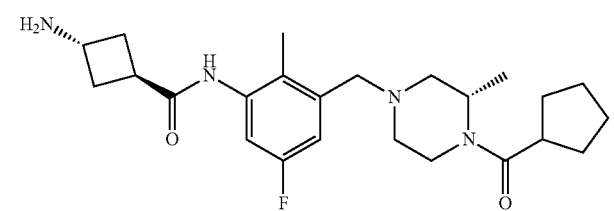 • 2 HCl | HCl/EtOH | MS (ESI): $C_{24}H_{35}FN_4O_2$ requires 430; found 431 $[M + H]^+$. |
| D240 | 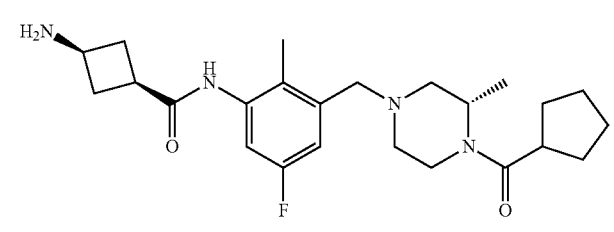 • 2 HCl | HCl/EtOH | MS (ESI): $C_{24}H_{35}FN_4O_2$ requires 430; found 431 $[M + H]^+$. |
| D241 | 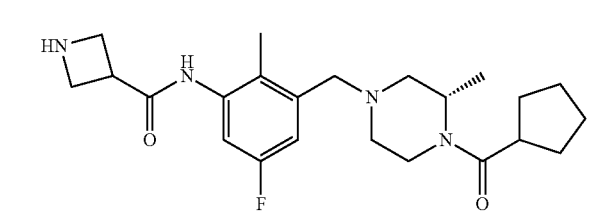 [SMILES: Cc1c(CN2CCN(C(=O)C3CCCC3)[C@@H](C)C2)cc(F)cc1NC(=O)C1CNC1] | HCl/iPrOH | MS (ESI): $C_{23}H_{33}FN_4O_2$ requires 416; found 417 $[M + H]^+$. |

| Structure | Acid/Solvent | Characterization |
|---|---|---|
| D242 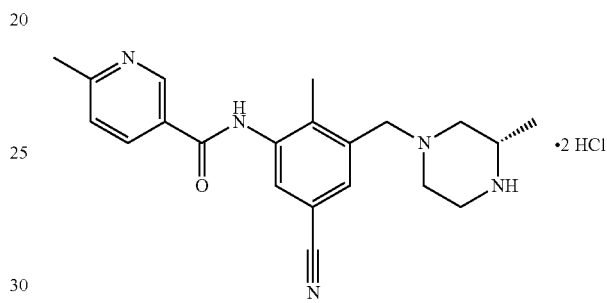 | HCl/EtOH | MS (ESI): C₂₂H₃₃ClN₄O₂ requires 420; found 421 [M + H]⁺. |

Description 243

(S)—N-(5-cyano-2-methyl-3-((3-methylpiperazin-1-yl)methyl)phenyl)-2-methylpyrimidine-5-carboxamide, 2 hydrochloride acid salt (D243)

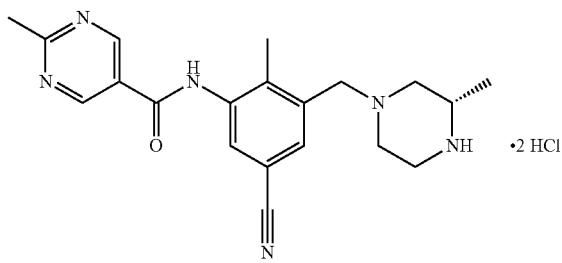

To a solution of (S)-tert-butyl 4-(5-cyano-2-methyl-3-(2-methyl pyrimidine-5-carboxamido)benzyl)-2-methylpiperazine-1-carboxylate (D212, 800 mg) in methanol (4 mL) and DCM (10 mL) was added hydrogen chloride in dioxane (4 M, 4.31 mL). The mixture was stirred at 50° C. for 30 min then concentrated under reduced pressure to afford the title compound (900 mg) as yellow solid. MS (ESI): C₂₀H₂₄N₆O requires 364; found 365 [M+H]⁺.

Description 244

(S)-3-cyano-N-(5-cyano-2-methyl-3-((3-methylpiperazin-1-yl)methyl)phenyl)benzamide, dihydrochloride, 2 hydrochloride acid salt (D244)

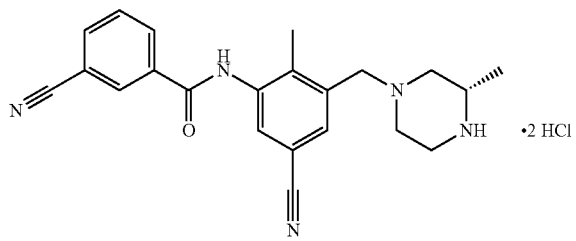 [SMILES: Cc1c(CN2CCN[C@@H](C)C2)cc(C#N)cc1NC(=O)c1cccc(C#N)c1]

(S)-tert-butyl 4-(5-cyano-3-(3-cyanobenzamido)-2-methylbenzyl)-2-methylpiperazine-1-carboxylate (D213, 915 mg) was added into aq. HCl solution (5 M, 3.48 mL) in isopropanol (20 mL). The reaction mixture was stirred at 50° C. overnight. The solvent was removed in vacuo to give the title compound (750 mg) as white solid. MS (ESI): C₂₂H₂₃N₅O requires 373; found 374 [M+H]⁺.

Description 245

(S)—N-(5-cyano-2-methyl-3-((3-methylpiperazin-1-yl)methyl)phenyl)-6-methylnicotinamide, 2 hydrochloride acid salt (D245)

To a solution of (S)-tert-butyl 4-(5-cyano-2-methyl-3-(6-methylnicotinamido)benzyl)-2-methylpiperazine-1-carboxylate (D214, 150 mg) in THF (2 mL) was added HCl in dioxane (0.809 mL). The mixture was stirred at RT for 18 hours. The mixture was concentrated to obtain the title compound (130 mg) as pale yellow solid. MS (ESI): C₂₁H₂₅N₅O requires 363; found 364 [M+H]⁺.

Descriptions 246-253

Descriptions 246-253 were prepared using a similar procedure to that described for Description 245, with the specified reaction base or solvent listed in the table.

D246 (S)—N-(5-chloro-2-methyl-3-((3-methylpiperazin-1-yl)methyl)phenyl)-4-cyano-4-methylpentanamide, 2 hydrochloride acid salt D247 (S)—N-(5-chloro-2-methyl-3-((3-methylpiperazin-1-yl)methyl)phenyl)-2-(4-hydroxycyclohexyl)acetamide, 2 hydrochloride acid salt D248 (S)—N-(5-chloro-2-methyl-3-((3-methylpiperazin-1-yl)methyl)phenyl)-3-(methylsulfonyl)propanamide, 2 hydrochloride acid salt D249 (S)-5-chloro-N-(5-fluoro-2-methyl-3-((3-methylpiperazin-1-yl)methyl)phenyl)-6-methylnicotinamide, 2 hydrochloride acid salt D250 (S)-5-chloro-N-(5-chloro-2-methyl-3-((3-methylpiperazin-1-yl)methyl)phenyl)-6-methylnicotinamide, 2 hydrochloride acid salt D251 (S)—N-(5-cyano-2-methyl-3-((3-methylpiperazin-1-yl)methyl)phenyl)-6-methoxynicotinamide, Trifluoroacetic acid salt D252 (S)—N-(5-chloro-2-methyl-3-((3-methylpiperazin-1-yl)methyl)phenyl)-6-cyano-5-methylnicotinamide, 2 hydrochloride acid salt D253 (S)-5-chloro-N-(5-cyano-2-methyl-3-((3-methylpiperazin-1-yl)methyl)phenyl)-6-methylnicotinamide, 2 hydrochloride acid salt

| | Structure | Base/Solvent | Characterization |
|---|---|---|---|
| D246 | • 2 HCl | HCl/MeOH | MS (ESI): $C_{20}H_{29}ClN_4O$ requires 376; found 377 $[M + H]^+$. |
| D247 | • 2 HCl | HCl/1,4-Dioxane | MS (ESI): $C_{21}H_{32}ClN_3O_2$ requires 393; found 394 $[M + H]^+$. |
| D248 | • 2 HCl | HCl/MeOH | MS (ESI): $C_{17}H_{26}ClN_3O_3S$ requires 387; found 388 $[M + H]^+$. |
| D249 | • 2 HCl | HCl/MeOH | MS (ESI): $C_{20}H_{24}ClFN_4O$ requires 390; found 391 $[M + H]^+$. |
| D250 | • 2 HCl | HCl/MeOH | MS (ESI): $C_{20}H_{24}Cl_2N_4O$ requires 406; found 407 $[M + H]^+$. |
| D251 | • TFA | TFA/DCM | MS (ESI): $C_{21}H_{25}N_5O_2$ requires 379; found 380 $[M + H]^+$. |

| | Structure | Base/Solvent | Characterization |
|---|---|---|---|
| D252 | HCl/MeOH | MS (ESI): $C_{21}H_{24}ClN_5O$ requires 397; found 398 $[M + H]^+$. |
| D253 | HCl/MeOH | MS (ESI): $C_{21}H_{24}ClN_5O$ requires 397; found 398 $[M + H]^+$. |

Description 254

(S)—N-(5-chloro-2-methyl-3-((3-methylpiperazin-1-yl)methyl)phenyl)-5-fluoro-6-methylnicotinamide, 3 Trifluoroacetic acid salt (D254)

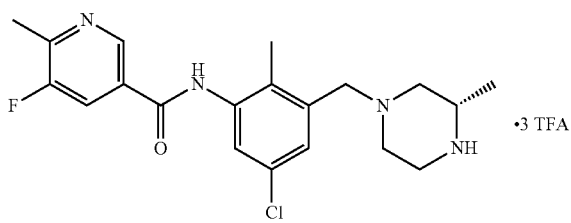

(S)-tert-butyl 4-(5-chloro-3-(5-fluoro-6-methylnicotinamido)-2-methylbenzyl)-2-methylpiperazine-1-carboxylate (D204, 6.5 g) was added into HCl solution (30 mL, 4 M in 1,4-Dioxane). The mixture was stirred at RT for 1 hour. The solvent was removed under vacuum and the crude product was washed with DCM/MeOH=10:1 (2×2 mL) to afford the title compound (7 g) as yellow solid. MS (ESI) $C_{20}H_{24}ClFN_4O$ requires: 390, found 391 $[M+H]^+$.

Description 255

N-(5-chloro-2-methyl-3-(((S)-3-methylpiperazin-1-yl)methyl)phenyl)-2-(tetrahydrothiophen-3-yl)acetamide, 2 hydrochloride acid salt (D255)

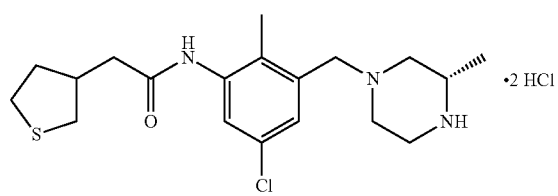 [SMILES: Cc1c(CN2CCN[C@@H](C)C2)cc(Cl)cc1NC(=O)CC1CCSC1]

To a solution of (2S)-tert-butyl 4-(5-chloro-2-methyl-3-(2-(tetrahydrothiophen-3-yl)acetamido)benzyl)-2-methylpiperazine-1-carboxylate (D203, 48 mg) in MeOH (1 mL), was added a solution of hydrogen chloride in dioxane (4 M, 1 mL). The mixture was stirred for 2 hours at 50° C. The solvent was removed under vacuum to give the title compound (210 mg) as yellow gum. MS (ESI): $C_{19}H_{28}ClN_3OS$ requires 381; found 382 $[M+H]^+$.

Description 256

N-(5-chloro-3-(((S)-4-(cyclopentanecarbonyl)-3-methylpiperazin-1-yl)methyl)-2-methylphenyl)-2-(tetrahydrothiophen-3-yl)acetamide (D256)

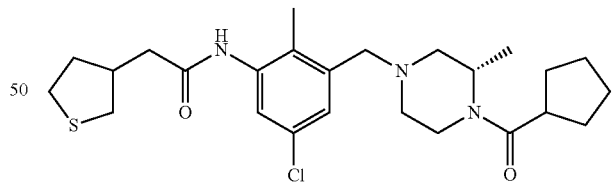

To a solution of N-(5-chloro-2-methyl-3-(((S)-3-methylpiperazin-1-yl)methyl)phenyl)-2-(tetrahydrothiophen-3-yl)acetamide (D255, 39 mg) in anhydrous DCM (2 mL) was added triethylamine (20.66 mg) and cyclopentanecarbonyl chloride (20.31 mg). The reaction mixture was stirred for 1 hour at 18° C. The mixture was washed with brine, and the organic phase was dried over anhydrous sodium sulfate, filtered and concentrated to give the title compound (220 mg) as yellow gum. MS (ESI): $C_{25}H_{36}ClN_3O_2S$ requires 477; found 478 $[M+H]^+$.

Description 257

(S)-2-chloro-N-(5-chloro-3-((4-(cyclopentanecarbonyl)-3-methylpiperazin-1-yl)methyl)-2-methylphenyl)acetamide (D257)

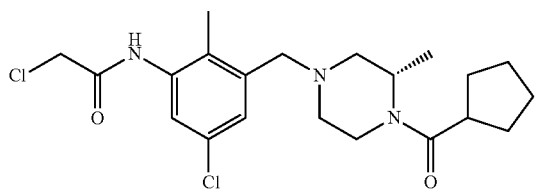 [SMILES: Cc1c(CN2CCN(C(=O)C3CCCC3)[C@@H](C)C2)cc(Cl)cc1NC(=O)CCl]

2-Chloroacetyl chloride (97 mg) solution in DCM (10 mL) was slowly added to the mixture of (S)-(4-(3-amino-5-chloro-2-methylbenzyl)-2-methylpiperazin-1-yl)(cyclopentyl)methanone (D157, 240 mg) and TEA (0.159 mL) in DCM (20 mL) at 0° C. The reaction mixture was allowed to warm to RT and stirred for 1 hour. The mixture was diluted with water (15 mL. The organic layer was dried over anhydrous sodium sulfate, filtered and concentrated. The residue was purified by column chromatography (silica gel, petroleum ether/EtOAc=5:1) to afford the title compound (240 mg) as white solid. MS (ESI): $C_{21}H_{29}Cl_2N_3O_2$ requires 425; found 426 $[M+H]^+$.

Description 258

(S)-5-((3-((4-(cyclopentanecarbonyl)-3-methylpiperazin-1-yl)methyl)-5-fluoro-2-methylphenyl)carbamoyl)picolinic acid, Trifluoroacetic acid salt (D258)

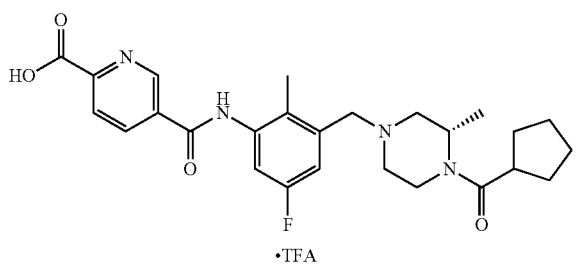 [SMILES: Cc1c(CN2CCN(C(=O)C3CCCC3)[C@@H](C)C2)cc(F)cc1NC(=O)c1ccc(C(=O)O)nc1]

To a suspension of (S)-6-cyano-N-(3-((4-(cyclopentanecarbonyl)-3-methylpiperazin-1-yl)methyl)-5-fluoro-2-methylphenyl)nicotinamide (D222, 120 mg) in ethanol (5 mL), 3 M NaOH solution (2.2 mL) was added dropwise. The reaction mixture was stirred at 100° C. for 3 hours. Solvent was removed by rotavap, 3 M HCl (aq.) was added dropwise to pH=5. The residue was diluted with EtOAc (10 mL) then washed with brine (10 mL). Organic layer was separated, dried over MgSO4, filtered and concentrated. The residue was purified by reverse phase column chromatography (C18 column, 0-35% $CH_3CN$ in $H_2O$ with 0.05% TFA) to afford the title compound (80 mg) as white solid. MS (ESI): $C_{26}H_{31}FN_4O_4$ requires 482; found 483 $[M+H]^+$.

Example 1

(S)—N-(3-((4-(cyclopentanecarbonyl)-3-methylpiperazin-1-yl)methyl)-5-fluoro-2-methylphenyl)-2-(oxetan-3-yl)acetamide (E1)

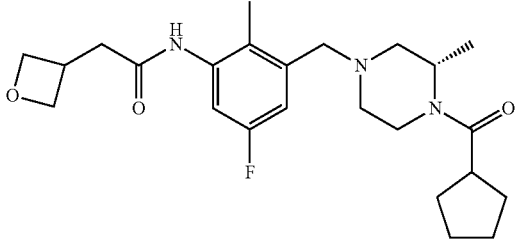 [SMILES: Cc1c(CN2CCN(C(=O)C3CCCC3)[C@@H](C)C2)cc(F)cc1NC(=O)CC1COC1]

2-(Oxetan-3-yl) acetic acid (0.035 mL) and DIPEA (0.157 mL) were dissolved in DMF (3 mL). To this solution, HATU (182 mg) was added gradually. The reaction mixture was stirred at RT for 1 hour. Then (S)-(4-(3-amino-5-fluoro-2-methylbenzyl)-2-methylpiperazin-1-yl)(cyclopentyl)methanone (D156, 100 mg) in DMF (2 mL) was added into the mixture, which was stirred at RT overnight. Water (10 mL) was added, extracted with EtOAc (2×10 mL). The combined organic layer was dried over $Na_2SO_4$ and filtered. The filtrate was concentrated to dryness, and the residue was purified by MADP to get the title (40 mg) as white solid. $^1H$ NMR (400 MHz, DMSO-$d_6$): 9.45 (s, 1H), 7.20 (dd, J=10.5, 2.0 Hz, 1H), 6.95 (d, J=9.5 Hz, 1H), 4.69 (dd, J=7.5, 6.2 Hz, 2H), 4.54 (brs, 0.5H), 4.35 (t, J=6.1 Hz, 2H), 4.19 (d, J=10.0 Hz, 1H), 3.74 (d, J=13.0 Hz, 0.5H), 3.45-3.38 (m, 2H), 3.32-3.25 (m, 1H), 3.18 (t, J=12.3 Hz, 0.5H), 2.96-2.86 (m, 1H), 2.77 (d, J=7.8 Hz, 2.5H), 2.72 (d, J=12.2 Hz, 1H), 2.66-2.58 (m, 1H), 2.14 (s, 3H), 2.11-1.44 (m, 10H), 1.28-1.04 (m, 3H). $^{19}F$ NMR (376 MHz, DMSO-$d_6$): −117.9. MS (ESI): $C_{24}H_{34}FN_3O_3$ requires 431; found 432 $[M+H]^+$.

Examples 2-42

Examples 2-42 were prepared using a similar procedure to that described for Example 1, with the specified reaction base or solvent listed in the table.

E2  N-(3-(((S)-4-(cyclopentanecarbonyl)-3-methylpiperazin-1-yl)methyl)-5-fluoro-2-methylphenyl)-3-(tetrahydrofuran-2-yl)propanamide, Trifluoroacetic acid salt E3  N-(3-(((S)-4-(cyclopentanecarbonyl)-3-methylpiperazin-1-yl)methyl)-5-fluoro-2-methylphenyl)-2-(tetrahydrofuran-3-yl)acetamide E4  N-(3-(((S)-4-(cyclopentanecarbonyl)-3-methylpiperazin-1-yl)methyl)-5-fluoro-2-methylphenyl)-2-(tetrahydrofuran-2-yl)acetamide, Trifluoroacetic acid salt E5  (S)—N-(3-((4-(cyclopentanecarbonyl)-3-methylpiperazin-1-yl)methyl)-5-fluoro-2-methylphenyl)-2-(tetrahydro-2H-pyran-4-yl)acetamide E6  N-(3-(((S)-4-(cyclopentanecarbonyl)-3-methylpiperazin-1-yl)methyl)-5-fluoro-2-methylphenyl)-2-(tetrahydro-2H-pyran-2-yl)acetamide, Trifluoroacetic acid salt E7  cis-N-(3-(((S)-4-(cyclopentanecarbonyl)-3-methylpiperazin-1-yl)methyl)-5-fluoro-2-methylphenyl)-2-(3-hydroxycyclopentyl)acetamide E8  N-(3-(((S)-4-(cyclopentanecarbonyl)-3-methylpiperazin-1-yl)methyl)-5-fluoro-2-methylphenyl)-2-(3-hydroxycyclohexyl)acetamide E9 N-(3-(((S)-4-(cyclopentanecarbonyl)-3-methylpiperazin-1-yl)methyl)-5-fluoro-2-methylphenyl)-2-(hexahydrofuro[2,3-b]furan-3-yl)acetamide E10 (S)—N-(3-((4-(cyclopentanecarbonyl)-3-methylpiperazin-1-yl)methyl)-5-fluoro-2-methylphenyl)-2-(2-methyloxazol-4-yl)acetamide, Trifluoroacetic acid salt E11 (S)—N-(3-((4-(cyclopentanecarbonyl)-3-methylpiperazin-1-yl)methyl)-5-fluoro-2-methylphenyl)-2-(3-methylisoxazol-5-yl)acetamide E12 (S)—N-(3-((4-(cyclopentanecarbonyl)-3-methylpiperazin-1-yl)methyl)-5-chloro-2-methylphenyl)-2-(3-methylisoxazol-5-yl)acetamide E13 N-(5-chloro-3-(((S)-4-(cyclopentanecarbonyl)-3-methylpiperazin-1-yl)methyl)-2-methylphenyl)-2-(tetrahydrofuran-2-yl)acetamide, Trifluoroacetic acid salt E14 N-(5-chloro-3-(((S)-4-(cyclopentanecarbonyl)-3-methylpiperazin-1-yl)methyl)-2-methylphenyl)-2-(2-methyltetrahydrofuran-3-yl)acetamide, Trifluoroacetic acid salt E15 (S)—N-(5-chloro-3-((4-(cyclopentanecarbonyl)-3-methylpiperazin-1-yl)methyl)-2-methylphenyl)-2-(tetrahydro-2H-pyran-4-yl)acetamide, Trifluoroacetic acid salt E16 N-(5-chloro-3-(((S)-4-(cyclopentanecarbonyl)-3-methylpiperazin-1-yl)methyl)-2-methylphenyl)-2-(tetrahydro-2H-pyran-2-yl)acetamide, Trifluoroacetic acid salt E17 (S)—N-(5-chloro-3-((4-(cyclopentanecarbonyl)-3-methylpiperazin-1-yl)methyl)-2-methylphenyl)-2-morpholinoacetamide, Trifluoroacetic acid salt E18 (S)—N-(5-chloro-3-((4-(cyclopentanecarbonyl)-3-methylpiperazin-1-yl)methyl)-2-methylphenyl)-4-hydroxycyclohexanecarboxamide E19 N-(5-chloro-3-(((S)-4-(cyclopentanecarbonyl)-3-methylpiperazin-1-yl)methyl)-2-methylphenyl)-2-(5-methyltetrahydrofuran-3-yl)acetamide, Trifluoroacetic acid salt E20 N-(5-chloro-3-(((S)-4-(cyclopentanecarbonyl)-3-methylpiperazin-1-yl)methyl)-2-methylphenyl)-2-(tetrahydro-2H-pyran-3-yl)acetamide, Trifluoroacetic acid salt E21 N-(5-chloro-3-(((S)-4-(cyclopentanecarbonyl)-3-methylpiperazin-1-yl)methyl)-2-methylphenyl)-2-(2-methyltetrahydro-2H-pyran-4-yl)acetamide E22 N-(5-chloro-3-(((S)-4-(cyclopentanecarbonyl)-3-methylpiperazin-1-yl)methyl)-2-methylphenyl)-2-(4-methyltetrahydrofuran-3-yl)acetamide, Trifluoroacetic acid salt E23 N-(5-chloro-3-(((S)-4-(cyclopentanecarbonyl)-3-methylpiperazin-1-yl)methyl)-2-methylphenyl)-2-(3-methyltetrahydro-2H-pyran-4-yl)acetamide, Trifluoroacetic acid salt E24 N-(5-chloro-3-(((S)-4-(cyclopentanecarbonyl)-3-methylpiperazin-1-yl)methyl)-2-methylphenyl)-2-(tetrahydrofuran-2-yl)propanamide, Trifluoroacetic acid salt E25 N-(5-chloro-3-(((S)-4-(cyclopentanecarbonyl)-3-methylpiperazin-1-yl)methyl)-2-methylphenyl)-2-(tetrahydrofuran-3-yl)propanamide E26 (S)—N-(5-chloro-3-((4-(cyclopentanecarbonyl)-3-methylpiperazin-1-yl)methyl)-2-methylphenyl)-4-methoxybutanamide, Trifluoroacetic acid salt E27 (S)—N-(5-chloro-3-((4-(cyclopentanecarbonyl)-3-methylpiperazin-1-yl)methyl)-2-methylphenyl)-2-(2-methoxyethoxy)acetamide E28 (S)—N-(5-chloro-3-((4-(cyclopentanecarbonyl)-3-methylpiperazin-1-yl)methyl)-2-methylphenyl)-2-(2-oxopyrrolidin-1-yl)acetamide, Trifluoroacetic acid salt E29 (S)—N-(5-chloro-3-((4-(cyclopentanecarbonyl)-3-methylpiperazin-1-yl)methyl)-2-methylphenyl)-2-(2-oxooxazolidin-3-yl)acetamide E30 N-(5-chloro-3-(((S)-4-(2-cyclopropylacetyl)-3-methylpiperazin-1-yl)methyl)-2-methylphenyl)-2-(tetrahydrofuran-3-yl)acetamide E31 (S)—N-(5-chloro-3-((4-(2-cyclopropylacetyl)-3-methylpiperazin-1-yl)methyl)-2-methylphenyl)-4-methoxybutanamide E32 N-(5-cyano-3-(((S)-4-(cyclopentanecarbonyl)-3-methylpiperazin-1-yl)methyl)-2-methylphenyl)-2-(tetrahydrofuran-3-yl)acetamide E33 (S)—N-(5-chloro-3-((4-(cyclopentanecarbonyl)-3-methylpiperazin-1-yl)methyl)-2-methylphenyl)-3-(1-cyanocyclopropyl)propanamide, Trifluoroacetic acid salt E34 (S)—N-(5-chloro-3-((4-(cyclopentanecarbonyl)-3-methylpiperazin-1-yl)methyl)-2-methylphenyl)-2-(difluoromethoxy)acetamide E35 (S)—N-(5-chloro-3-((4-(cyclopentanecarbonyl)-3-methylpiperazin-1-yl)methyl)-2-methylphenyl)-4-cyano-4-methylpentanamide E36 (S)—N-(5-chloro-3-((4-(cyclopentanecarbonyl)-3-methylpiperazin-1-yl)methyl)-2-methylphenyl)tetrahydro-2H-thiopyran-4-carboxamide 1,1-dioxide E37 N-(5-chloro-3-(((S)-4-(cyclopentanecarbonyl)-3-methylpiperazin-1-yl)methyl)-2-methylphenyl)tetrahydro-2H-thiopyran-3-carboxamide 1,1-dioxide E38 (S)—N-(5-chloro-3-((4-(cyclopentanecarbonyl)-3-methylpiperazin-1-yl)methyl)-2-methylphenyl)-2-(1,1-dioxidotetrahydro-2H-thiopyran-4-yl)acetamide E39 (S)—N-(5-chloro-3-((4-(cyclopentanecarbonyl)-3-methylpiperazin-1-yl)methyl)-2-methylphenyl)-3-(difluoromethoxy)propanamide, Trifluoroacetic acid salt E40 (S)—N-(5-chloro-3-((4-(cyclopentanecarbonyl)-3-methylpiperazin-1-yl)methyl)-2-methylphenyl)-2-(3-oxomorpholino)acetamide E41 (S)—N-(5-chloro-3-((4-(cyclopentanecarbonyl)-3-methylpiperazin-1-yl)methyl)-2-methylphenyl)-2-hydroxy-2-methylpropanamide E42 (S)—N-(5-chloro-3-((4-(cyclopentanecarbonyl)-3-methylpiperazin-1-yl)methyl)-2-methylphenyl)-3-hydroxy-3-methylbutanamide

| | Structure | Base/Solvent | Characterization |
|---|---|---|---|
| E2 | 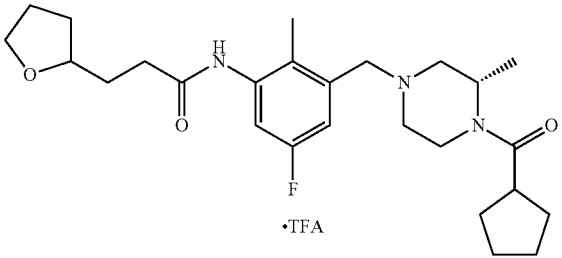 [SMILES: Cc1c(CN2CCN(C(=O)C3CCCC3)[C@@H](C)C2)cc(F)cc1NC(=O)CCC1CCCO1] | DIPEA/DMF | $^1$H NMR (400 MHz, DMSO-$d_6$): 9.34 (s, 1H), 7.21 (d, J = 10.1 Hz, 1H), 6.95 (d, J = 8.7 Hz, 1H), 4.55 (brs, 0.5H), 4.12 (brs, 1H), 3.84-3.65 (m, 2.5H), 3.65-3.52 (m, 1H), 3.41 (brs, 2H), 3.30 (brs, 2.5H), 2.99-2.55 (m, 3.5H), 2.47-2.35 (m, 2H), 2.15 (s, 3H), 2.05-1.37 (m, 14H), 1.33-0.96 (m, 3H). $^{19}$F NMR (376 MHz, DMSO-$d_6$): −74.4, −117.6. MS (ESI): $C_{26}H_{38}FN_3O_3$ requires 459; found 460 [M + H]$^+$. |

-continued

| | Structure | Base/Solvent | Characterization |
|---|---|---|---|
| E3 | 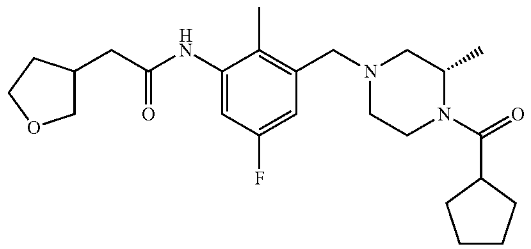 [SMILES: Cc1c(CN2CCN(C(=O)C3CCCC3)[C@@H](C)C2)cc(F)cc1NC(=O)CC1CCOC1] | DIPEA/DMF | ¹H NMR (400 MHz, DMSO-$d_6$): 9.37 (s, 1H), 7.20 (dd, J = 10.4, 2.6 Hz, 1H), 6.96 (dd, J = 9.4, 2.4 Hz, 1H), 4.55 (brs, 0.5H), 4.19 (brs, 1H), 3.87-3.58 (m, 3.5H), 3.45-3.31 (m, 3H), 3.25-3.12 (m, 0.5H), 2.98-2.85 (m, 1H), 2.85-2.52 (m, 3.5H), 2.47-2.38 (m, 2H), 2.16 (s, 3H), 2.10-1.40 (m, 11H), 1.30-1.04 (m, 3H). ¹⁹F NMR (376 MHz, DMSO-$d_6$): −73.4, −118.0. MS (ESI): $C_{25}H_{36}FN_3O_3$ requires 445; found 446 [M + H]⁺. |
| E4 | ·TFA | DIPEA/DMF | ¹H NMR (400 MHz, DMSO-$d_6$): 9.39 (s, 1H), 7.24 (dd, J = 10.4, 2.1 Hz, 1H), 6.95 (d, J = 9.3 Hz, 1H), 4.54 (brs, 0.5H), 4.26-4.09 (m, 2H), 3.86-3.70 (m, 1.5H), 3.68-3.57 (m, 1H), 3.46-3.38 (m, 2H), 3.25-3.10 (m, 0.5H), 2.98-2.53 (m, 4.5H), 2.48-2.42 (m, 1H), 2.15 (s, 3H), 2.10-1.43 (m, 14H), 1.32-1.03 (m, 3H). ¹⁹F NMR (376 MHz, DMSO-$d_6$): −74.0, −117.9. MS (ESI): $C_{25}H_{36}FN_3O_3$ requires 445; found 446 [M + H]⁺. |
| E5 | 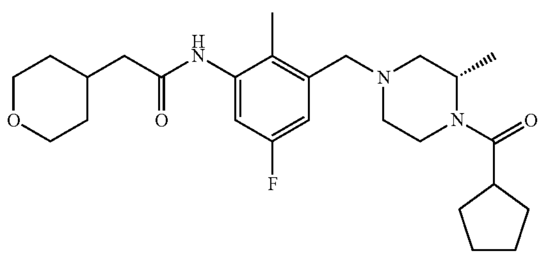 [SMILES: Cc1c(CN2CCN(C(=O)C3CCCC3)[C@@H](C)C2)cc(F)cc1NC(=O)CC1CCOCC1] | DIPEA/DMF | ¹H NMR (400 MHz, MeOD-$d_4$): 7.08 (dd, J = 9.8, 2.8 Hz, 1H), 6.99 (dd, J = 9.3, 2.8 Hz, 1H), 4.66 (brs, 0.5H), 4.36-4.22 (m, 1H), 3.95 (dd, J = 11.1, 3.4 Hz, 2H), 3.83 (d, J = 13.3 Hz, 0.5H), 3.54-3.41 (m, 4H), 3.40-3.33 (m, 0.5H), 3.08-2.91 (m, 1.5H), 2.83 (d, J = 11.6 Hz, 1H), 2.77-2.67 (m, 1H), 2.37 (d, J = 7.2 Hz, 2H), 2.28-2.21 (m, 3H), 2.19-1.56 (m, 13H), 1.50-1.14 (m, 5H). MS (ESI): $C_{26}H_{38}FN_3O_3$ requires 459; found 460 [M + H]⁺. |
| E6 | ·TFA | DIPEA/DMF | ¹H NMR (400 MHz, DMSO-$d_6$): 9.35 (s, 1H), 7.26 (d, J = 10.4 Hz, 1H), 6.94 (d, J = 8.1 Hz, 1H), 4.54 (brs, 0.5H), 4.26-4.11 (m, 1H), 3.87 (d, J = 11.4 Hz, 1H), 3.79-3.64 (m, 1.5H), 3.46-3.38 (m, 2H), 3.24-3.13 (m, 0.5H), 2.99-2.85 (m, 1H), 2.84-2.68 (m, 1.5H), 2.68-2.52 (m, 2H), 2.45-2.35 (m, 1H), 2.15 (s, 3H), 2.10-1.38 (m, 15H), 1.32-1.02 (m, 4H). ¹⁹F NMR (376 MHz, DMSO-$d_6$): −74.4, −116.3. MS (ESI): $C_{26}H_{38}FN_3O_3$ requires 459; found 460 [M + H]⁺. |
| E7 | 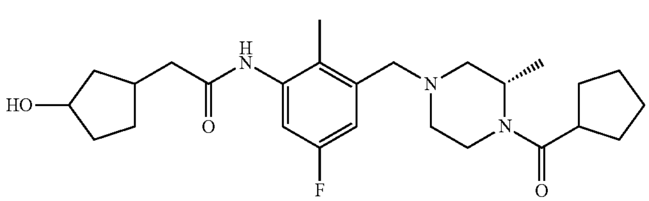 [SMILES: Cc1c(CN2CCN(C(=O)C3CCCC3)[C@@H](C)C2)cc(F)cc1NC(=O)CC1CCC(O)C1] | No base/ DMF | ¹H NMR (500 MHz, DMSO-$d_6$): 9.34 (s, 1H), 7.17 (dd, J = 10.6, 2.7 Hz, 1H), 6.96 (d, J = 9.1 Hz, 1H), 4.54 (brs, 0.5H), 4.50 (d, J = 3.8 Hz, 1H), 4.23-4.16 (m, 1H), 4.12-4.06 (m, 1H), 3.75 (d, J = 14.8 Hz, 0.5H), 3.45-3.35 (m, 2H), 3.24-3.15 (m, 0.5H), 2.95-2.87 (m, 1H), 2.81-2.70 (m, 1.5H), 2.66-2.59 (m, 1H), 2.42-2.37 (m, |

-continued

| | Structure | Base/Solvent | Characterization |
|---|---|---|---|
| | | | 2H), 2.24-2.18 (m, 1H), 2.15 (s, 3H), 2.12-1.37 (m, 15H), 1.26-1.05 (m, 4H). MS (ESI): $C_{26}H_{38}FN_3O_3$ requires 459; found 460 $[M + H]^+$. |
| E8 | 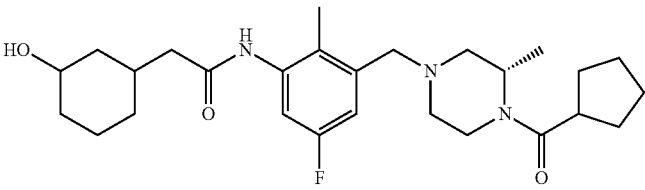 [SMILES: Cc1c(CN2CCN(C(=O)C3CCCC3)[C@@H](C)C2)cc(F)cc1NC(=O)CC1CCCC(O)C1] | No base/ DMF | $^1$H NMR (500 MHz, DMSO-$d_6$): 9.33 (s, 1H), 7.22-7.17 (dd, J = 10.0, 2.0 Hz, 1H), 6.97-6.95 (d, J = 9.8 Hz, 1H), 4.55 (brs, 0.5H), 4.36-4.19 (m, 2H), 3.85 (brs, 1H), 3.77-3.71 (m, 0.5H), 3.44-3.38 (m, 2H), 3.23-3.17 (m, 0.5H), 2.95-2.86 (m, 1H), 2.81-2.70 (m, 1.5H), 2.66-2.59 (m, 1H), 2.27-2.18 (m, 2H), 2.15 (brs, 3H), 2.08-1.34 (m, 16H), 1.28-0.98 (m, 6H), MS (ESI): $C_{27}H_{40}FN_3O_3$ requires 473; found 474 $[M + H]^+$. |
| E9 | 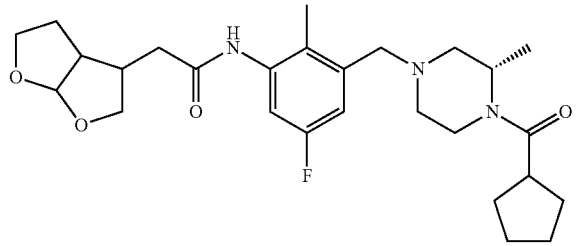 [SMILES: Cc1c(CN2CCN(C(=O)C3CCCC3)[C@@H](C)C2)cc(F)cc1NC(=O)CC1COC2OCCC12] | No base/ DMF | $^1$H NMR (500 MHz, DMSO-$d_6$): 9.44 (s, 1H), 7.21 (dd, J = 10.1, 2.2 Hz, 1H), 6.97 (d, J = 8.5 Hz, 1H), 5.61 (d, J = 5.0 Hz, 1H), 4.54 (brs, 0.5H), 4.25-4.14 (M, 1H), 3.88 (t, J = 7.7 Hz, 1H), 3.79-3.69 (m, 2.5H), 3.46-3.35 (m, 3H), 3.19 (t, J = 12.6 Hz, 0.5H), 2.96-2.69 (m, 3.5H), 2.68-2.52 (m, 3H), 2.16 (s, 3H), 2.14-1.45 (m, 13H), 1.30-1.05 (m, 3H). MS (ESI): $C_{27}H_{38}FN_3O_4$ requires 487; found 488 $[M + H]^+$. |
| E10 | 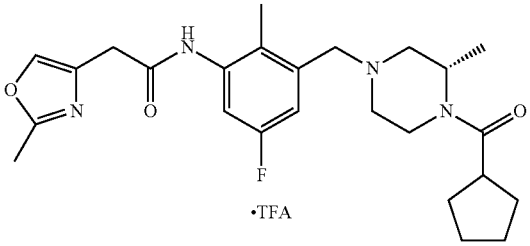 [SMILES: Cc1nc(CC(=O)Nc2cc(F)cc(CN3CCN(C(=O)C4CCCC4)[C@@H](C)C3)c2C)co1] | No base/ DMF | $^1$H NMR (400 MHz, DMSO-$d_6$): 9.67 (s, 1H), 7.83 (s, 1H), 7.50 (d, J = 9.5 Hz, 1H), 7.26 (d, J = 6.3 Hz, 1H), 4.80 (brs, 0.5H), 4.57-4.20 (m, 3H), 4.05 (d, J = 12.3 Hz, 0.5H), 3.62 (s, 2H), 3.44-2.85 (m, 6H), 2.38 (s, 3H), 2.23 (s, 3H), 1.86-1.43 (m, 8H), 1.37-1.10 (m, 3H). MS (ESI): $C_{25}H_{33}FN_4O_3$ requires 456; found 457 $[M + H]^+$. |
| E11 | 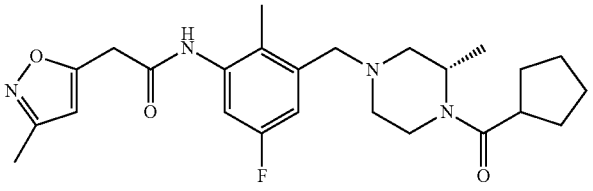 [SMILES: Cc1cc(CC(=O)Nc2cc(F)cc(CN3CCN(C(=O)C4CCCC4)[C@@H](C)C3)c2C)on1] | TEA/DMF | $^1$H NMR (400 MHz, DMSO-$d_6$): 9.75 (s, 1H), 7.22 (dd, J = 10.4, 2.6 Hz, 1H), 6.99 (dd, J = 9.3, 2.0 Hz, 1H), 6.28 (s, 1H), 4.54 (brs, 0.5H), 4.25-4.15 (m, 1H), 3.94 (s, 2H), 3.75 (d, J = 11.8 Hz, 0.5H), 3.46-3.37 (m, 2H), 3.19 (t, J = 12.2 Hz, 0.5H), 2.96-2.86 (m, 1H), 2.84-2.69 (m, 1.5H), 2.66-2.59 (m, 1H), 2.22 (s, 3H), 2.18 (s, 3H), 2.15-1.45 (m, 10H), 1.29-1.05 (m, 3H). MS (ESI): $C_{25}H_{33}FN_4O_3$ requires 456; found 457 $[M + H]^+$. |
| E12 | 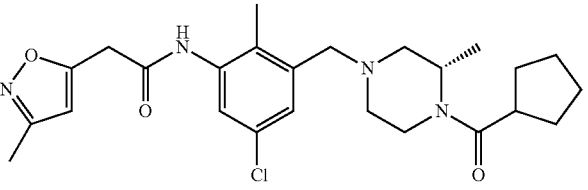 [SMILES: Cc1cc(CC(=O)Nc2cc(Cl)cc(CN3CCN(C(=O)C4CCCC4)[C@@H](C)C3)c2C)on1] | TEA/DMF | $^1$H NMR (400 MHz, DMSO-$d_6$): 9.78 (s, 1H), 7.41 (d, J = 2.3 Hz, 1H), 7.19 (s, 1H), 6.28 (s, 1H), 4.55 (brs, 0.5H), 4.25-4.15 (m, 1H), 3.93 (s, 2H), 3.75 (d, J = 12.8 Hz, 0.5H), 3.42 (brs, 2H), 3.23-3.13 (m, 0.5H), 2.96-2.86 (m, 1H), 2.83-2.67 (m, 1.5H), 2.65-2.56 (m, 1H), 2.21 (s, 3H), 2.19 (s, 3H), 2.15-1.45 (m, 10H), 1.29-1.03 (m, |

-continued

| | Structure | Base/Solvent | Characterization |
|---|---|---|---|
| | | | 3H). MS (ESI): $C_{25}H_{33}ClN_4O_3$ requires 472; found 473 [M + H]$^+$. |
| E13 | 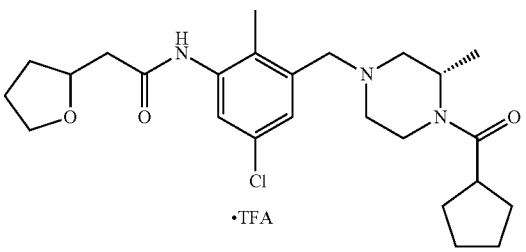 [SMILES: Cc1c(CN2CCN(C(=O)C3CCCC3)[C@@H](C)C2)cc(Cl)cc1NC(=O)CC1CCCO1] ·TFA | DIPEA/DMF | $^1$H NMR (400 MHz, MeOD-d$_4$): 7.59 (s, 1H), 7.48 (s, 1H), 4.60 (brs, 1H), 4.41-4.07 (m, 3.5H), 3.94 (q, J = 7.2 Hz, 1H), 3.88-3.70 (m, 1H), 3.64-3.34 (m, 2.5H), 3.25-2.91 (m, 3.5H), 2.69-2.56 (m, 2H), 2.30 (s, 3H), 2.21-1.51 (m, 12H), 1.48-1.15 (m, 3H). MS (ESI): $C_{25}H_{36}ClN_3O_3$ requires 461; found 462 [M + H]$^+$. |
| E14 | 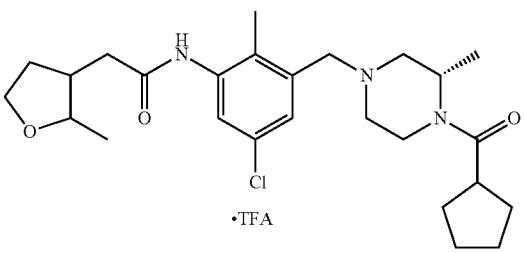 [SMILES: Cc1c(CN2CCN(C(=O)C3CCCC3)[C@@H](C)C2)cc(Cl)cc1NC(=O)CC1CCOC1C] ·TFA | DIPEA/DMF | $^1$H NMR (400 MHz, DMSO-d$_6$): 9.51 (d, J = 4.9 Hz, 1H), 7.38 (d, J = 1.7 Hz, 1H), 7.16 (brs, 1H), 4.54 (brs, 0.5H), 4.19 (d, J = 10.6 Hz, 1H), 4.03-3.91 (m, 0.5H), 3.86-3.46 (m, 3H), 3.41 (s, 2H), 3.17 (t, J = 11.9 Hz, 0.5H), 3.01-2.52 (m, 4H), 2.47-2.21 (m, 2H), 2.17 (s, 3H), 2.13-1.40 (m, 12.5H), 1.30-0.98 (m, 6H). MS (ESI): $C_{26}H_{38}ClN_3O_3$ requires 475; found 476 [M + H]$^+$. |
| E15 | 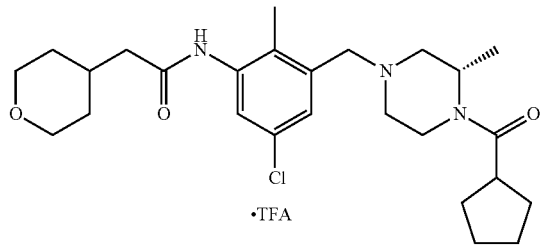 [SMILES: Cc1c(CN2CCN(C(=O)C3CCCC3)[C@@H](C)C2)cc(Cl)cc1NC(=O)CC1CCOCC1] ·TFA | DIPEA/DMF | $^1$H NMR (400 MHz, DMSO-d$_6$): 9.42 (s, 1H), 7.38 (d, J = 1.8 Hz, 1H), 7.16 (s, 1H), 4.54 (brs, 0.5H), 4.19 (d, J = 9.4 Hz, 1H), 3.91-3.65 (m, 2.5H), 3.47-3.37 (m, 2H), 3.31-3.07 (m, 2.5H), 2.99-2.82 (m, 1H), 2.81-2.55 (m, 2.5H), 2.29 (d, J = 7.1 Hz, 2H), 2.16 (s, 3H), 2.12-1.41 (m, 13H), 1.36-0.97 (m, 5H). MS (ESI): $C_{26}H_{38}ClN_3O_3$ requires 475; found 476 [M + H]$^+$. |
| E16 | 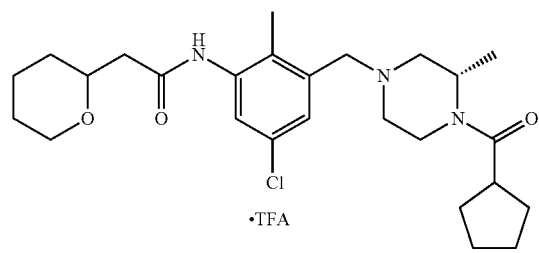 [SMILES: Cc1c(CN2CCN(C(=O)C3CCCC3)[C@@H](C)C2)cc(Cl)cc1NC(=O)CC1CCCCO1] ·TFA | DIPEA/DMF | $^1$H NMR (400 MHz, DMSO-d$_6$): 9.52-9.06 (m, 1 H), 7.78-6.95 (m, 2 H), 4.89-4.02 (m, 3 H), 3.86 (d, J = 11.0 Hz, 2 H), 3.51-3.11 (m, 5 H), 3.05-2.58 (m, 3 H), 2.46-2.07 (m, 4 H), 1.90-0.99 (m, 18 H). MS (ESI): $C_{26}H_{38}ClN_3O_3$ requires 475; found 476 [M + H]$^+$. |
| E17 | 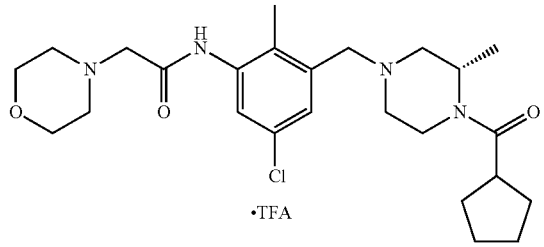 ·TFA | DIPEA/DMF | $^1$H NMR (400 MHz, MeOD-d$_4$): 7.67 (d, J = 2.3 Hz, 1H), 7.50 (d, J = 2.4 Hz, 1H), 4.58 (brs, 0.5H), 4.38-3.86 (m, 8.5H), 3.64-3.35 (m, 5H), 3.35-3.31 (m, 2H), 3.30-3.27 (m, 0.5H), 3.18-2.91 (m, 2.5H), 2.33 (s, 3H), 2.03-1.17 (m, 12H). MS (ESI): $C_{25}H_{37}ClN_4O_3$ requires 476; found 477 [M + H]$^+$. |

-continued

| | Structure | Base/Solvent | Characterization |
|---|---|---|---|
| E18 | 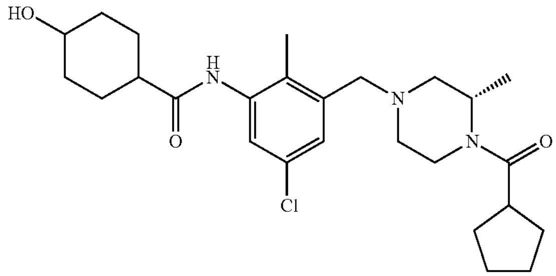 [SMILES: Cc1c(CN2CCN(C(=O)C3CCCC3)[C@@H](C)C2)cc(Cl)cc1NC(=O)C1CCC(O)CC1] | DIPEA/DMF | $^1$H NMR (400 MHz, MeOD-$d_4$): 7.27 (d, J = 1.8 Hz, 1H), 7.21 (d, J = 1.6 Hz, 1H),4.74-4.52 (m, 1H), 4.38-4.20 (m, 1H), 4.01-3.73 (m, 1H), 3.64-3.33 (m, 2.5H), 3.12-2.60 (m, 3.5H), 2.55-2.31 (m, 1H), 2.28-2.20 (m, 3H), 2.20-1.53 (m, 17H), 1.47-1.08 (m, 4H). MS (ESI): $C_{26}H_{38}ClN_3O_3$ requires 475; found 476 [M + H]$^+$. |
| E19 | 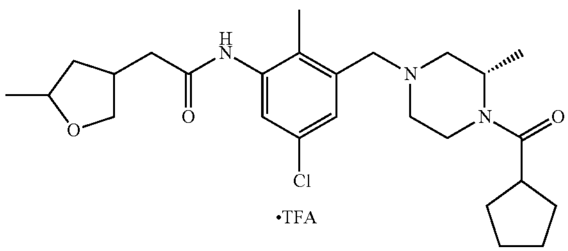 [SMILES: Cc1c(CN2CCN(C(=O)C3CCCC3)[C@@H](C)C2)cc(Cl)cc1NC(=O)CC1COC(C)C1] | DIPEA/DMF | $^1$H NMR (400 MHz, MeOD-$d_4$): 7.36 (s, 2H), 4.47 (brs, 1H), 4.24-3.75 (m, 5H), 3.56-3.30 (m, 2H), 3.20-3.12 (m, 0.5H), 3.05-2.81 (m, 2.5H), 2.75-2.60 (m, 1.5H), 2.53-2.36 (m, 2H), 2.28-2.12 (m, 3.5H), 1.91-1.42 (m, 10H), 1.40-1.03 (m, 7H). MS (ESI): $C_{26}H_{38}ClN_3O_3$ requires 475; found 476 [M + H]$^+$. |
| E20 | 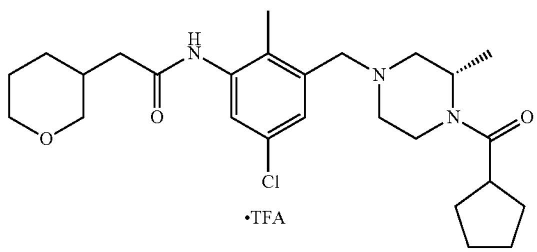 [SMILES: Cc1c(CN2CCN(C(=O)C3CCCC3)[C@@H](C)C2)cc(Cl)cc1NC(=O)CC1CCCOC1] | DIPEA/DMF | $^1$H NMR (400 MHz, MeOD-$d_4$): 7.50 (s, 1H), 7.48 (s, 1H), 4.62 (brs, 0.5H), 4.36 (brs, 2H), 4.17 (d, J = 11.9 Hz, 0.5H), 3.98-3.78 (m, 2H), 3.65-3.34 (m, 3.5H), 3.29-2.86 (m, 4.5H), 2.41-2.31 (m, 2H), 2.29 (s, 3H), 2.22-1.56 (m, 13H), 1.49-1.16 (m, 4H). MS (ESI): $C_{26}H_{38}ClN_3O_3$ requires 475; found 476 [M + H]$^+$. |
| E21 | 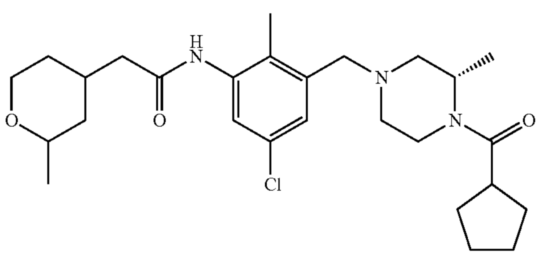 [SMILES: Cc1c(CN2CCN(C(=O)C3CCCC3)[C@@H](C)C2)cc(Cl)cc1NC(=O)CC1CCOC(C)C1] | DIPEA/DMF | $^1$H NMR (400 MHz, MeOD-$d_4$): 7.32 (d, J = 2.0 Hz, 1H), 7.21 (d, J = 1.7 Hz, 1H), 4.65 (brs, 0.5H), 4.40-4.18 (m, 1H), 3.97 (dd, J = 11.5, 3.7 Hz, 1H), 3.89-3.66 (m, 1H), 3.55-3.32 (m, 4H), 3.07-2.41 (m, 4H), 2.34 (d, J = 7.2 Hz, 1.5H), 2.25 (s, 3H), 2.22-1.50 (m, 13H), 1.50-0.94 (m, 8H). MS (ESI): $C_{27}H_{40}ClN_3O_3$ requires 489; found 488 [M + H]$^+$. |
| E22 | 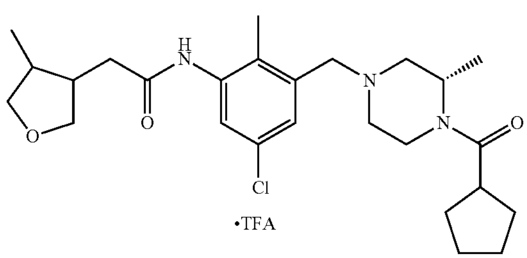 [SMILES: Cc1c(CN2CCN(C(=O)C3CCCC3)[C@@H](C)C2)cc(Cl)cc1NC(=O)CC1COCC1C] | DIPEA/DMF | $^1$H NMR (400 MHz, MeOD-$d_4$): 7.46-7.35 (m, 2H), 4.54 (brs, 1H), 4.38-4.25 (m, 2H), 4.17-3.80 (m, 2.5H), 3.58-3.23 (m, 5H), 3.18-2.83 (m, 3.5H), 2.70-2.49 (m, 2H), 2.44-2.25 (m, 2H), 2.19 (s, 3H), 1.88-1.06 (m, 11H), 1.05-0.88 (m, 3H). MS (ESI): $C_{26}H_{38}ClN_3O_3$ requires 475; found 476 [M + H]$^+$. |
| E23 | 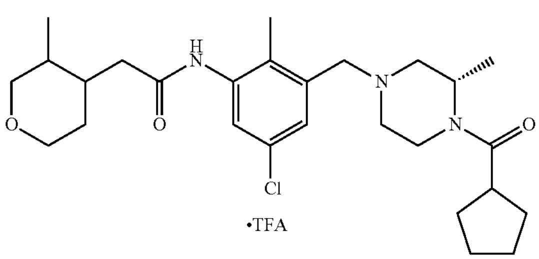 [SMILES: Cc1c(CN2CCN(C(=O)C3CCCC3)[C@@H](C)C2)cc(Cl)cc1NC(=O)CC1CCOCC1C] | DIPEA/DMF | $^1$H NMR (400 MHz, MeOD-$d_4$): 7.51 (d, J = 1.7 Hz, 1H), 7.48 (d, J = 1.7 Hz, 1H), 5.04-4.93 (m, 0.5H), 4.63 (brs, 1H), 4.49-4.28 (m, 2H), 4.18 (d, J = 13.2 Hz, 0.5H), 3.98-3.77 (m, 1H), 3.74-3.53 (m, 2H), 3.52-3.35 (m, 3H), 3.26-2.67 (m, 4H), 2.51-2.16 (m, 6H), 2.01-1.17 (m, 15H), 1.12-0.86 (m, 3H). MS (ESI): $C_{27}H_{40}ClN_3O_3$ requires 489; found 490 [M + H]$^+$. |

-continued

| | Structure | Base/Solvent | Characterization |
|---|---|---|---|
| E24 | 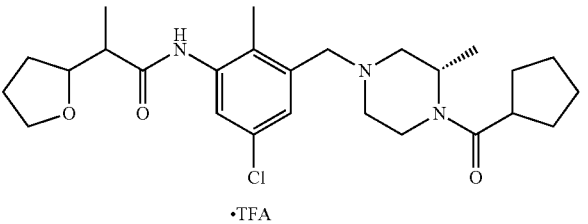 [SMILES: Cc1c(CN2CCN(C(=O)C3CCCC3)[C@@H](C)C2)cc(Cl)cc1NC(=O)C(C)C1CCCO1] •TFA | DIPEA/DMF | ¹H NMR (400 MHz, CDCl₃): 8.81 (s, 1H), 8.15 (s, 1H), 7.16 (d, J = 1.6 Hz, 1H), 5.02-4.98 (m, 2H), 4.66-4.62 (m, 1.5H), 4.28-4.17 (m, 2.5H), 4.12-4.01 (m, 2H), 3.93-3.84 (m, 0.5H), 3.60-3.54 (m, 1.5H), 2.26-2.20 (m, 1H), 2.82-2.71 (m, 2H), 2.51-2.38 (m, 2H), 2.27 (s, 3H), 2.05-1.96 (m, 4H), 1.83-1.60 (m, 7H), 1 38-134 (in, 3H), 1.02-0.97 (m, 3H). MS (ESI): C₂₆H₃₈ClN₃O₃ requires 475; found 476 [M + H]⁺. |
| E25 | 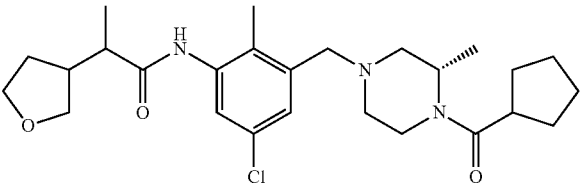 [SMILES: Cc1c(CN2CCN(C(=O)C3CCCC3)[C@@H](C)C2)cc(Cl)cc1NC(=O)C(C)C1CCOC1] | DIPEA/DMF | ¹H NMR (400 MHz, DMSO-d₆): 9.46 (d, J = 4.8 Hz, 1H), 7.33 (dd, J = 6.8, 2.0 Hz, 1H), 3.75 (m, 2.5H), 3.65-3.62 (m, 1H), 3.50-3.42 (m, 3H), 3.25-3.20 (m, 0.5H), 2.94-2.90 (m, 1H), 2.80-2.61(m, 2.5H), 2.50-2.30 (m, 2H). 2.19-2.16 (m, 3H), 2.15-1.80 (m, 3H), 1.80-1.45 (m, 9H), 1.30-1.00 (m, 6H). MS (ESI): C₂₆H₃₈ClN₃O₃ requires 475; found 476 [M + H]⁺. |
| E26 | 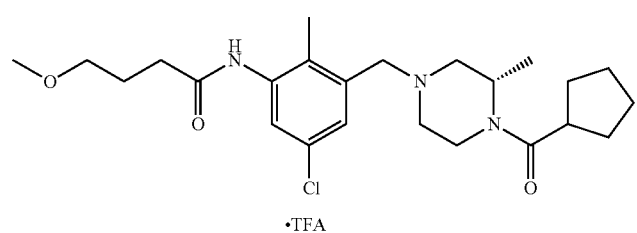 [SMILES: COCCCC(=O)Nc1cc(Cl)cc(CN2CCN(C(=O)C3CCCC3)[C@@H](C)C2)c1C] •TFA | DIPEA/DMF | ¹H NMR (400 MHz, MeOD-d₄): 7.51 (s, 2H), 4.65 (brs, 1H), 4.49-4.36 (m, 2H), 4.19 (d, J = 11.0 Hz, 0.5H), 3.65-3.38 (m, 5H), 3.35 (s, 3H), 3.29-2.97 (m, 3.5H), 2.52 (t, J = 7.3 Hz, 2H), 2.29 (s, 3H), 1.97 (quin, J = 6.7 Hz, 2H), 1.92-1.56 (m, 8H), 1.49-1.19 (m, 3H). MS (ESI): C₂₄H₃₆ClN₃O₃ requires 449; found 450 [M + H]⁺. |
| E27 | 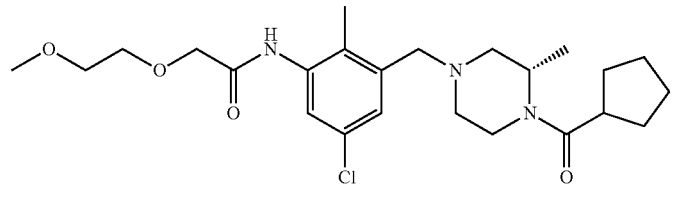 [SMILES: COCCOCC(=O)Nc1cc(Cl)cc(CN2CCN(C(=O)C3CCCC3)[C@@H](C)C2)c1C] | DIPEA/DCM | ¹H NMR (400 MHz, DMSO-d₆): 9.22 (s, 1H), 7.58 (d, J = 2.0 Hz, 1H), 7.18 (s, 1H), 4.54 (brs, 0.5H), 4.20 (d, J = 10.5 Hz, 1H), 4.11 (s, 2H), 3.75 (d, J = 13.6 Hz, 0.5H), 3.70 (dd, J = 5.5, 3.8 Hz, 2H), 3.53 (dd, J = 5.5, 3.8 Hz, 2H), 3.48-3.37 (m, 2H), 3.27 (s, 3H), 3.18 (t, J = 12.4 Hz, 0.5H), 2.95-2.85 (m, 1H), 2.83-2.68 (m, 1.5H), 2.61 (d, J = 11.0 Hz, 1H), 2.17 (s, 3H), 2.15-1.45 (m, 10H), 1.27-1.03 (m, 3H). MS (ESI): C₂₄H₃₆ClN₃O₄ requires 465; found 466 [M + H]⁺. |
| E28 | 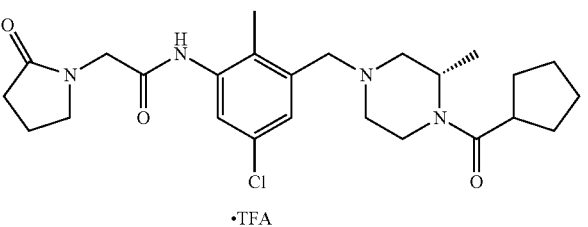 [SMILES: Cc1c(CN2CCN(C(=O)C3CCCC3)[C@@H](C)C2)cc(Cl)cc1NC(=O)CN1CCCC1=O] •TFA | DIPEA/DMF | ¹H NMR (400 MHz, MeOD-d₄): 7.57 (d, J = 2.2 Hz, 1H), 7.53 (d, J = 2.2 Hz, 1H), 4.65 (brs, 1H), 4.50-4.35 (m, 2H), 4.20 (brs, 2.5H), 3.60 (t, J = 7.1 Hz, 2H), 3.51-3.37 (m, 2.5H), 3.29-2.96 (m, 3.5H), 2.45 (t, J = 8.1 Hz, 2H), 2.30 (s, 3H), 2.13 (quin, J = 7.6 Hz, 2H), 1.97-1.57 (m, 8H), 1.49-1.20 (m, 3H). MS (ESI): C₂₅H₃₅ClN₄O₃ requires 474; found 475 [M + H]⁺. |

-continued

| | Structure | Base/Solvent | Characterization |
|---|---|---|---|
| E29 | 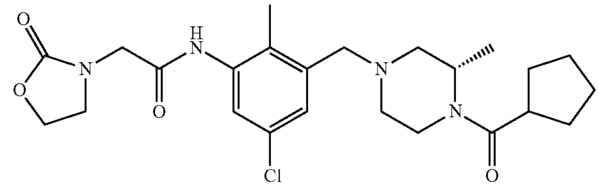 [SMILES: Cc1c(CN2CCN(C(=O)C3CCCC3)[C@@H](C)C2)cc(Cl)cc1NC(=O)CN1CCOC1=O] | DIPEA/DMF | ¹H NMR (400 MHz, MeOD-d$_4$): 7.37 (d, J = 2.2 Hz, 1H), 7.23 (d, J = 1.7 Hz, 1H), 4.72-4.50 (m, 0.5H), 4.43 (t, J = 8.1 Hz, 2H), 4.36-4.23 (m, 1H), 4.16 (s, 2H), 3.83 (d, J = 13.7 Hz, 0.5H), 3.77 (t, J = 8.1 Hz, 2H), 3.60-3.40 (m, 2H), 3.40-3.33 (m, 0.5H), 3.07-2.89 (m, 1.5H), 2.82 (d, J = 10.8 Hz, 1H), 2.71 (t, J = 10.4 Hz, 1H), 2.26 (s, 3H), 2.23-2.12 (m, 1H), 2.09-1.54 (m, 9H), 1.40-1.16 (m, 3H). MS (ESI): C$_{24}$H$_{33}$ClN$_4$O$_4$ requires 476; found 477 [M + H]⁺. |
| E30 | 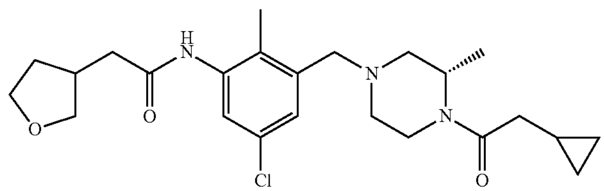 [SMILES: Cc1c(CN2CCN(C(=O)CC3CC3)[C@@H](C)C2)cc(Cl)cc1NC(=O)CC1CCOC1] | DIPEA/DMF | ¹H NMR (400 MHz, MeOD-d$_4$): 7.21 (d, J = 2.1 Hz, 1H), 7.11 (d, J = 1.8 Hz, 1H), 4.57 (brs, 0.5H), 4.22 (d, J = 13.8 Hz, 0.5H), 4.03 (brs, 0.5H), 3.89-3.76 (m, 2H), 3.68 (q, J = 7.7 Hz, 1H), 3.60 (d, J = 13.2 Hz, 0.5H), 3.45-3.22 (m, 3.5H), 2.91-2.80 (m, 0.5H), 2.72 (t, J = 8.9 Hz, 1H), 2.66-2.56 (m, 2H), 2.48-2.27 (m, 2.5H), 2.19 (d, J = 6.6 Hz, 1H), 2.15 (s, 3H), 2.13-1.84 (m, 3.5H), 1.67-1.53 (m, 1H), 1.28-1.08 (m, 3H), 0.98-0.78 (m, 1H), 0.50-0.35 (m, 2H), 0.08 (brs, 2H). MS (ESI): C$_{24}$H$_{34}$ClN$_3$O$_3$ requires 447; found 448 [M + H]⁺. |
| E31 | 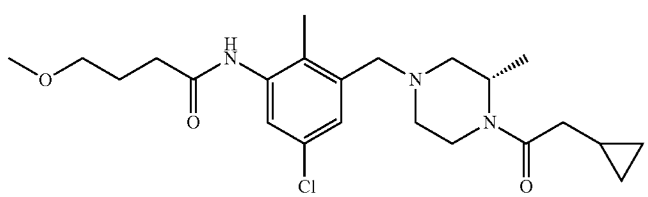 [SMILES: COCCCC(=O)Nc1cc(Cl)cc(CN2CCN(C(=O)CC3CC3)[C@@H](C)C2)c1C] | DIPEA/DMF | ¹H NMR (400 MHz, MeOD-d$_4$): 7.32 (d, J = 2.2 Hz, 1H), 7.21 (d, J = 2.0 Hz, 1H), 4.67 (brs, 0.5H), 4.32 (d, J = 13.4 Hz, 0.5H), 4.14 (brs, 0.5H), 3.70 (d, J = 12.7 Hz, 0.5H), 3.54-3.44 (m, 4H), 3.43-3.36 (m, 0.5H), 3.35 (s, 3H), 2.95 (t, J = 12.8 Hz, 0.5H), 2.82 (t, J = 9.8 Hz, 1H), 2.71 (d, J = 11.5 Hz, 1H), 2.50 (t, J = 7.3 Hz, 2H), 2.43 (dd, J = 14.9, 6.4 Hz, 0.5H), 2.30 (d, J = 6.4 Hz, 1H), 2.25 (s, 3H), 2.23-2.13 (m, 1.5H), 2.11-1.90 (m, 3H), 1.36-1.18 (m, 3H), 1.05-0.93 (m, 1H), 0.59-0.48 (m, 2H), 0.18 (brs, 2H). MS (ESI): C$_{23}$H$_{34}$ClN$_3$O$_3$ requires 435; found 436 [M + H]⁺. |
| E32 | 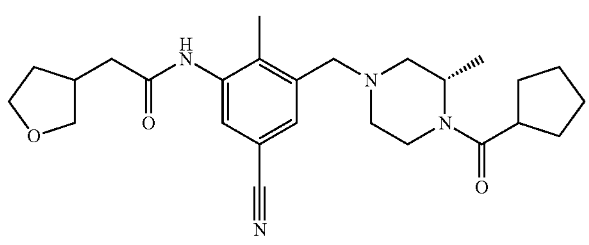 [SMILES: Cc1c(CN2CCN(C(=O)C3CCCC3)[C@@H](C)C2)cc(C#N)cc1NC(=O)CC1CCOC1] | DIPEA/DMF | ¹H NMR (400 MHz, MeOD-d$_4$): 7.68 (s, 1H), 7.54 (s, 1H), 4.67 (brs, 0.5H), 4.41-4.19 (m, 1H), 4.04-3.73 (m, 3.5H), 3.63-3.42 (m, 3H), 3.40-3.33 (m, 0.5H), 3.12-2.90 (m, 1.5H), 2.86-2.65 (m, 3H), 2.63-2.48 (m, 2H), 2.37 (s, 3H), 2.29-1.51 (m, 12H), 1.43-1.13 (m, 3H). MS (ESI): C$_{26}$H$_{36}$N$_4$O$_3$ requires 452; found 453 [M + H]⁺. |
| E33 | ·TFA | DIPEA/DMF | ¹H NMR (400 MHz, DMSO-d$_6$): 9.64 (s, 1H), 9.23 (brs, 1H), 7.64 (s, 1H), 7.52 (s, 1H), 4.78 (brs, 0.5H), 4.55-4.30 (m, 2.5H), 4.20-4.00 (m, 0.5H), 3.40-3.10 (m, 2H), 3.05-2.85 (m, 2H), 2.66-2.61 (m, 2H), 2.25 (s, 3H), 1.85-1.50 (m, 12H), 1.34-1.32 (m, 1H), 1.25- |

| | Structure | Base/Solvent | Characterization |
|---|---|---|---|
| | | | 1.10 (m, 3H), 1.00-0.85(m, 2.5H). $^{19}$F (376 MHz, DMSO-$d_6$): −69.2, −71.1. MS (ESI): $C_{26}H_{35}ClN_4O_2$ requires 470; found 471 $[M + H]^+$. |
| E34 | 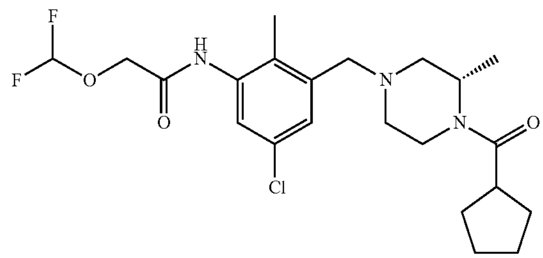 [SMILES: Cc1c(CN2CCN(C(=O)C3CCCC3)[C@@H](C)C2)cc(Cl)cc1NC(=O)COC(F)F] | DIPEA/DMF | $^1$H NMR (400 MHz, CDCl$_3$): 7.97 (brs, 1H), 7.88 (s, 1H), 7.13 (s, 1H), 6.43 (t, J = 72.8 Hz, 1H), 4.78 (brs, 0.5H), 4.54 (s, 2H), 4.44-4.40 (m, 0.5H), 4.15 (brs, 0.5H), 3.70-3.65 (m, 0.5H), 3.49-3.30 (m, 2.5H), 2.87-2.63 (m, 3.5H), 2.25 (s, 3H), 2.20-2.17(m, 1H), 2.05-1.95 (m, 1H), 1.85-1.64 (m, 5H), 1.67-1.51 (m, 3H), 1.31-1.22 (m, 3H). $^{19}$F (376 MHz, CDCl$_3$): −85.0, −85.2. MS (ESI): $C_{22}H_{30}ClF_2N_3O_3$ requires 457; found 458 $[M + H]^+$. |
| E35 | 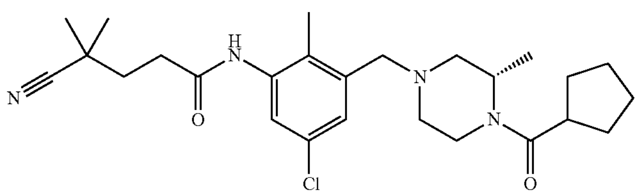 [SMILES: Cc1c(CN2CCN(C(=O)C3CCCC3)[C@@H](C)C2)cc(Cl)cc1NC(=O)CCC(C)(C)C#N] | DIPEA/DMF | $^1$H NMR (500 MHz, DMSO-$d_6$): 9.54 (s, 1H), 7.42 (brs, 1H), 7.16 (brs, 1H), 4.55 (brs, 0.5H), 4.23-4.20 (m, 1H), 3.77-3.73 (m, 0.5H), 3.42 (s, 2H), 3.22-3.15 (m, 1H), 2.93-2.90 (m, 1H), 2.78-2.71 (m, 2H), 2.56-2.53 (m, 2H), 2.20 (s, 3H), 2.12-2.03 (m, 2H), 1.90-1.81 (m, 3H), 1.72-1.51 (m, 8H), 1.34 (s, 6H), 1.23-1.10 (m, 3H), MS (ESI): $C_{26}H_{37}ClN_4O_2$ requires 472; found 473 $[M + H]^+$. |
| E36 | 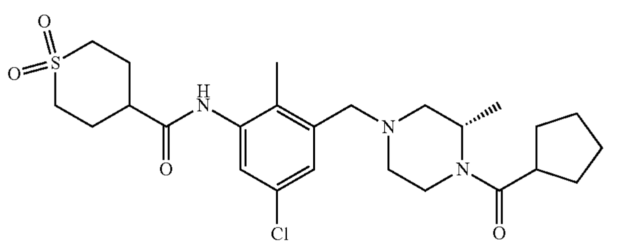 [SMILES: Cc1c(CN2CCN(C(=O)C3CCCC3)[C@@H](C)C2)cc(Cl)cc1NC(=O)C1CCS(=O)(=O)CC1] | DIPEA/DMF | $^1$H NMR (400 MHz, MeOD-$d_4$): 7.42-7.14 (m, 2H), 4.67 (brs, 1H), 4.31 (brs, 1H), 3.86 (brs, 1H), 3.49 (brs, 3H), 3.22 (brs, 3H), 3.10-2.63 (m, 5H), 2.50-1.55 (m, 16H), 1.49-1.12 (m, 3H). MS (ESI): $C_{25}H_{36}ClN_3O_4S$ requires 509, found 510 $[M + H]^+$. |
| E37 | 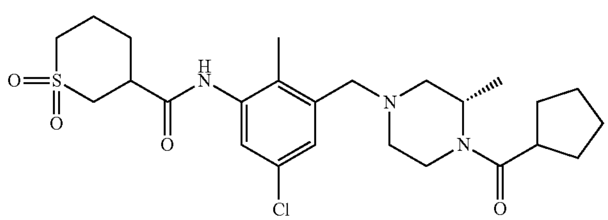 [SMILES: Cc1c(CN2CCN(C(=O)C3CCCC3)[C@@H](C)C2)cc(Cl)cc1NC(=O)C1CCCS(=O)(=O)C1] | DIPEA/DMF | $^1$H NMR (400 MHz, MeOD-$d_4$): 7.32 (s, 1H), 7.22 (brs, 1H), 4.66 (brs, 0.5H), 4.37-4.19 (m, 1H), 3.83 (d, J = 12.7 Hz, 0.5H), 3.46 (d, J = 7.0 Hz, 2H), 3.36-3.32 (m, 1H), 3.29-2.87 (m, 6H), 2.87-2.55 (m, 2H), 2.25 (s, 3H), 2.20-1.46 (m, 14H), 1.41-1.14 (m, 3H). MS (ESI): $C_{25}H_{36}ClN_3O_4S$ requires 509; found 510 $[M + H]^+$. |
| E38 | 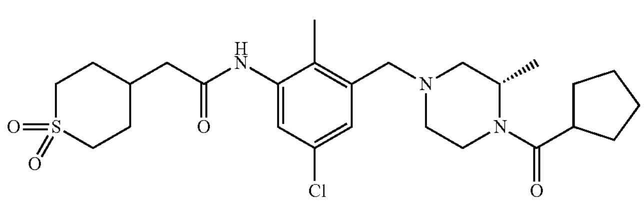 [SMILES: Cc1c(CN2CCN(C(=O)C3CCCC3)[C@@H](C)C2)cc(Cl)cc1NC(=O)CC1CCS(=O)(=O)CC1] | DIPEA/DMF | $^1$H NMR (500 MHz, DMSO-$d_6$) : 9.46 (s, 1H), 7.42 (d, J = 2.0 Hz, 1H), 7.17 (s, 1H), 4.54 (brs, 0.5H), 4.23-4.20 (m, 1H), 3.77-3.74 (m, 0.5H), 3.46-3.39 (m, 2H), 3.21-3.15 (m, 2.5H), 3.14-3.01 (m, 2H), 2.93-2.90 (m, 1H), 2.77-2.70 (m, 1.5H), 2.61-2.59 (m, 1H), 2.37 (d, J = 7.5 Hz, 2H), 2.18 (s, 3H), 2.16-2.04 (m, 5H), 2.00-1.80 (m, 1H), 1.75-1.48 (m, 9H), 1.23-1.10 (m, 3H). MS (ESI): $C_{26}H_{38}ClN_3O_4S$ requires 523; found 524 $[M + H]^+$. |

| | Structure | Base/Solvent | Characterization |
|---|---|---|---|
| E39 | (structure) ·TFA | DIPEA/DMF | ¹H NMR (400 MHz, MeOD-d₄): 7.49 (d, J = 2.8 Hz, 2H), 6.41 (t, J = 75.2 Hz, 1H), 4.61 (brs, 0.5H), 4.29-4.20 (m, 4.5H), 4.23 (t, J = 5.6 Hz, 2H), 3.57-3.50 (m, 0.5H), 3.39-3.36 (m, 1.5H), 3.14-3.01 (m, 3H), 2.78 (t, J = 5.6 Hz, 2H), 2.29 (s, 3H), 1.84-1.64 (m, 8H), 1.41-1.27 (m, 3H). 1H (376 MHz, MeOD-d₄): −85.6, −85.4. MS (ESI): $C_{23}H_{32}ClF_2N_3O_3$ requires 471; found 472 [M + H]⁺. |
| E40 | (structure) | DIPEA/DMF | ¹H NMR (400 MHz, CDCl₃): 8.48 (brs, 1H), 7.95 (s, 1H), 7.06 (s, 1H), 4.77 (brs, 1H), 4.40 (d, J = 12.2 Hz, 0.5H), 4.27 (s, 2H), 4.23-4.07 (m, 2.5H), 3.95 (t, J = 4.8 Hz, 2H), 3.72-3.54 (m, 2H), 3.51-3.23 (m, 3H), 2.98-2.68 (m, 2.5H), 2.64 (d, J = 11.5 Hz, 1H), 2.28-2.10 (m, 4H), 1.98 (t, J = 11.1 Hz, 1H), 1.92-1.46 (m, 8H), 1.38-1.15 (m, 3H). MS (ESI): $C_{25}H_{35}ClN_4O_4$ requires 490; found 491 [M + H]⁺. |
| E41 | (structure) | DIPEA/DMF | ¹H NMR (400 MHz, MeOD-d₄): 7.65 (d, J = 2.0 Hz, 1H), 7.18 (d, J = 1.5 Hz, 1H), 4.66 (brs, 0.5H), 4.59 (brs, 0.5H), 4.36-4.22 (m, 1H), 3.83 (d, J = 12.7 Hz, 0.5H), 3.56-3.40 (m, 2H), 3.40-3.34 (m, 0.5H), 3.08-2.89 (m, 1.5H), 2.82 (d, J = 10.5 Hz, 1H), 2.76-2.67 (m, 1H), 2.28 (s, 3H), 2.23-2.12 (m, 1H), 2.09-1.54 (m, 9H), 1.47 (s, 6H), 1.39-1.17 (m, 3H). MS (ESI): C23H34ClN3O3 requires 435, found 436 [M + H]⁺. |
| E42 | (structure) | DIPEA/DMF | ¹H NMR (400 MHz, MeOD-d₄): 7.59 (d, J = 1.7 Hz, 1H), 7.17 (d, J = 1.0 Hz, 1H), 4.66 (brs, 0.5H), 4.37-4.22 (m, 1H), 3.83 (d, J = 13.9 Hz, 0.5H), 3.54-3.39 (m, 2H), 3.39-3.33 (m, 0.5H), 3.08-2.89 (m, 1.5H), 2.81 (d, J = 11.2 Hz, 1H), 2.76-2.66 (m, 1H), 2.56 (s, 2H), 2.28 (s, 3H), 2.23-2.12 (m, 1H), 2.08-1.56 (m, 9H), 1.42-1.16 (m, 9H). MS (ESI): C24H36ClN3O3 requires 449, found 450 [M + H]⁺. |

Example 43

(S)—N-(5-chloro-3-((4-(cyclopentanecarbonyl)-3-methylpiperazin-1-yl)methyl)-2-methylphenyl)-3-(methylsulfonyl)propanamide (E43)

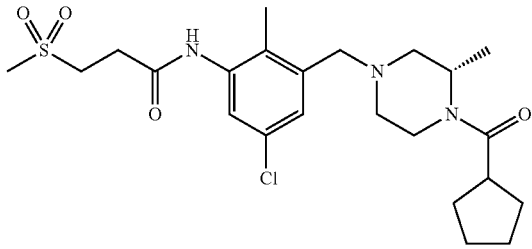 [SMILES: Cc1c(CN2CCN(C(=O)C3CCCC3)[C@@H](C)C2)cc(Cl)cc1NC(=O)CCS(C)(=O)=O]

3-(Methylsulfonyl)propanoic acid (65.2 mg) and DIPEA (0.15 mL) were dissolved in DMF (3 mL). To this solution, HATU (217 mg) was added gradually. The reaction mixture was stirred at RT for 1 hour, then (S)-(4-(3-amino-5-chloro-2-methylbenzyl-2-methylpiperazin-1-yl)(cyclopentyl)methanone (D157, 100 mg) in DMF (2 mL) was added into the mixture, which was stirred at RT for 2 days. Water (10 mL) was added, extracted with EtOAc (2×10 mL). The organic layer was dried over $Na_2SO_4$ and filtered. The filtrate was concentrated under vacuum. The residue was purified by MADP to afford the title compound (55 mg) as white solid. $^1$H NMR (400 MHz, MeOD-$d_4$): 7.27 (d, J=2.0 Hz, 1H), 7.11 (d, J=1.8 Hz, 1H), 4.56 (brs, 0.5H), 4.26-4.11 (m, 1H), 3.73 (d, J=12.8 Hz, 0.5H), 3.42 (t, J=7.3 Hz, 2H), 3.36 (d, J=7.7 Hz, 2H), 3.33-3.24 (m, 0.5H), 2.93 (s, 3H), 2.91-2.79 (m, 3.5H), 2.72 (d, J=11.2 Hz, 1H), 2.65-2.57 (m, 1H), 2.17 (s, 3H), 2.13-1.44 (m, 10H), 1.28-1.07 (m, 3H). MS (ESI): $C_{23}H_{34}ClN_3O_4S$ requires 483; found 484 [M+H]$^+$.

Example 44

(S)—N-(5-chloro-3-((4-(cyclopentanecarbonyl)-3-methylpiperazin-1-yl)methyl)-2-methylphenyl)-4-(methylsulfonyl)butanamide (E44)

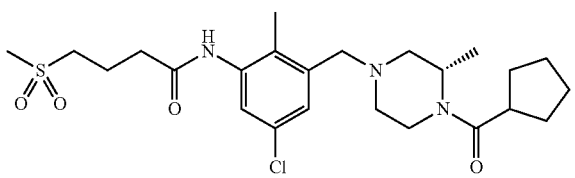 [SMILES: Cc1c(CN2CCN(C(=O)C3CCCC3)[C@@H](C)C2)cc(Cl)cc1NC(=O)CCCS(C)(=O)=O]

To a solution of 4-(methylsulfonyl)butanoic acid (D43, 73.1 mg) and (S)-(4-(3-amino-5-chloro-2-methylbenzyl)-2-methylpiperazin-1-yl)(cyclopentyl)methanone (D157, 140 mg) in DCM (100 mL) was added HATU (228 mg) at 0° C., then stirred at RT for 10 min. DIPEA (0.105 mL) was added, and the reaction mixture was stirred at RT overnight. The mixture was washed with saturated $NaHCO_3$ solution and brine, dried over $Na_2SO_4$ and filtered. The filtrate was concentrated to dryness under vacuum to get crude product, which was purified by MDAP to afford the title compound (150 mg) as white solid. $^1$H NMR (400 MHz, CDCl$_3$): 7.76 (s, 1H), 7.33 (brs, 1H), 7.10 (s, 1H), 4.75 (brs, 0.5H), 4.39 (d, J=13.3 Hz, 0.5H), 4.12 (brs, 0.5H), 3.66 (d, J=13.1 Hz, 0.5H), 3.48-3.25 (m, 2.5H), 3.18 (t, J=7.0 Hz, 2H), 2.95 (s, 3H), 2.91-2.79 (m, 1.5H), 2.78-2.66 (m, 3H), 2.62 (d, J=11.0 Hz, 1H), 2.32 (quin, J=6.9 Hz, 2H), 2.22 (s, 3H), 2.20-2.13 (m, 1H), 2.04-1.66 (m, 7H), 1.60-1.50 (m, 2H), 1.35-1.15 (m, 3H). MS (ESI): $C_{24}H_{36}ClN_3O_4S$ requires 497; found 498 [M+H]$^+$.

Example 45

(S)—N-(5-cyano-3-((4-(cyclopentanecarbonyl)-3-methylpiperazin-1-yl)methyl)-2-methylphenyl)-4-(methylsulfonyl)butanamide (E45)

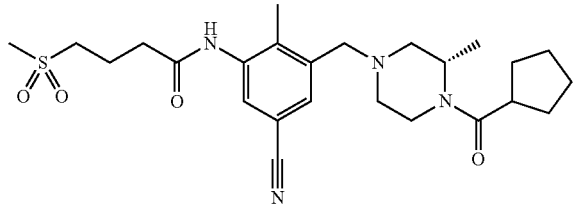 [SMILES: Cc1c(CN2CCN(C(=O)C3CCCC3)[C@@H](C)C2)cc(C#N)cc1NC(=O)CCCS(C)(=O)=O]

Example 45 was prepared using a similar procedure to that described for E44, with DIPEA/DMF as the base/solvent. $^1$H NMR (400 MHz, DMSO-$d_6$): 9.61 (s, 1H), 7.79 (d, J=1.0 Hz, 1H), 7.52 (s, 1H), 4.54 (brs, 0.5H), 4.24-4.14 (m, 1H), 3.74 (d, J=13.1 Hz, 0.5H), 3.52-3.40 (m, 2H), 3.22-3.15 (m, 2.5H), 2.99 (s, 3H), 2.96-2.86 (m, 1H), 2.82-2.66 (m, 1.5H), 2.64-2.52 (m, 3H), 2.29 (s, 3H), 2.16-1.44 (m, 12H), 1.27-1.03 (m, 3H). MS (ESI): $C_{25}H_{36}N_4O_4S$ requires 488; found 489 [M+H]$^+$.

Example 46

(S)—N-(5-chloro-3-((4-(cyclopentanecarbonyl)-3-methylpiperazin-1-yl)methyl)-2-methylphenyl)-3-(ethylsulfonyl)propanamide (E46)

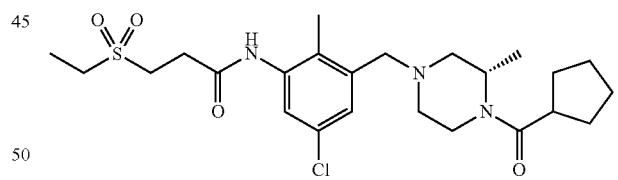

3-(Ethylsulfonyl)propanoic acid (71.2 mg) and DIPEA (0.150 mL) were dissolved in DMF (3 mL) To this solution, HATU (217 mg) was added gradually. The reaction mixture was stirred at RT for 30 min, then (S)-(4-(3-amino-5-chloro-2-methylbenzyl)-2-methylpiperazin-1-yl)(cyclopentyl)methanone (D157, 100 mg) was added into the mixture, which was stirred at RT overnight. Water (10 mL) was added, extracted with EtOAc (2×10 mL). The organic layer was dried over $Na_2SO_4$ and filtered. The filtrate was concentrated under vacuum. The residue was purified by MADP to afford the title compound (20 mg) as white solid. $^1$H NMR (400 MHz, MeOD-$d_4$): 7.39 (d, J=2.1 Hz, 1H), 7.23 (d, J=1.7 Hz, 1H), 4.68 (brs, 0.5H), 4.38-4.24 (m, 1H), 3.85 (d, J=13.3 Hz, 0.5H), 3.57-3.36 (m, 4.5H), 3.17 (q, J=7.5 Hz, 2H), 3.09-2.89 (m, 3.5H), 2.84 (d, J=11.2 Hz, 1H), 2.77-2.68

(m, 1H), 2.28 (s, 3H), 2.25-1.54 (m, 10H), 1.40 (t, J=7.5 Hz, 3H), 1.37-1.21 (m, 3H). MS (ESI): $C_{24}H_{36}ClN_3O_4S$ requires 497; found 498 $[M+H]^+$.

Example 47

(S)—N-(5-cyano-3-((4-(cyclopentanecarbonyl)-3-methylpiperazin-1-yl)methyl)-2-methylphenyl)-3-(ethylsulfonyl)propanamide, Trifluoroacetic acid salt (E47)

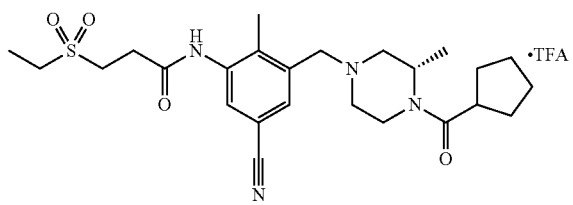 [SMILES: CCS(=O)(=O)CCC(=O)Nc1cc(C#N)cc(CN2CCN(C(=O)C3CCCC3)[C@@H](C)C2)c1C]

Example 47 was prepared using a similar procedure to that described for E46. $^1$H NMR (400 MHz, MeOD-$d_4$): 7.90 (d, J=1.1 Hz, 1H), 7.79 (s, 1H), 4.62 (brs, 1H), 4.35 (brs, 2H), 4.24-4.13 (m, 0.5H), 3.52 (t, J=7.0 Hz, 2H), 3.42-3.37 (m, 2H), 3.24-2.80 (m, 8.5H), 2.44 (s, 3H), 1.96-1.56 (m, 8H), 1.48-1.22 (m, 6H). MS (ESI): $C_{25}H_{36}N_4O_4S$ requires 488; found 489 $[M+H]^+$.

Example 48

(S)—N-(5-chloro-3-((4-(cyclopentanecarbonyl)-3-methylpiperazin-1-yl)methyl)-2-methylphenyl)-2-(1,1-dioxidothietan-3-yl)acetamide (E48)

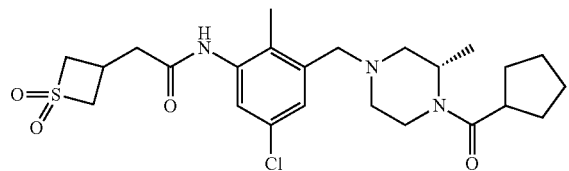 [SMILES: Cc1c(CN2CCN(C(=O)C3CCCC3)[C@@H](C)C2)cc(Cl)cc1NC(=O)CC1CS(=O)(=O)C1]

2-(1,1-Dioxidothietan-3-yl)acetic acid (D50, 40 mg) and HATU (93 mg) were added into the solution of (S)-(4-(3-amino-5-chloro-2-methylbenzyl)-2-methylpiperazin-1-yl)(cyclopentyl)methanone (D157, 85 mg) in DMF (10 mL). The reaction mixture was stirred for 6 hours at RT. Water (20 mL) was added, extracted with DCM (50 mL). The organic layer was dried over $Na_2SO_4$ and filtered. The filtrate was concentrated, and the crude product was purified by MDAP to afford the title compound (8 mg) as white solid. $^1$H NMR (500 MHz, DMSO-$d_6$): 9.57 (s, 1H), 7.43 (d, J=2.0 Hz, 1H), 7.16 (s, 1H), 4.54 (brs, 0.5H), 4.35-4.27 (m, 2H), 4.19 (d, J=11.3 Hz, 1H), 3.97-3.91 (m, 2H), 3.77-3.72 (m, 0.5H), 3.45-3.36 (m, 2H), 3.21-3.13 (m, 0.5H), 2.95-2.68 (m, 5.5H), 2.65-2.57 (m, 1H), 2.17 (s, 3H), 2.11-1.45 (m, 10H), 1.26-1.05 (m, 3H). MS (ESI): $C_{24}H_{34}ClN_3O_4S$ requires 495; found 496 $[M+H]^+$.

Example 49

(S)—N-(5-chloro-3-((4-(2-cyclopentylacetyl)-3-methylpiperazin-1-yl)methyl)-2-methylphenyl)-3-(methylsulfonyl)propanamide, Trifluoroacetic acid salt (E49)

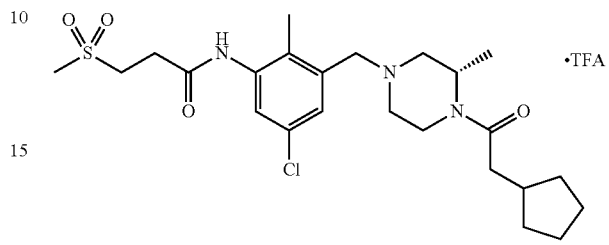

3-(Methylsulfonyl)propanoic acid (62.7 mg), DIPEA (0.144 mL) and HATU (209 mg) were dissolved in DMF (2 mL). To this solution, (S)-1-(4-(3-amino-5-chloro-2-methylbenzyl)-2-methylpiperazin-1-yl)-2-cyclopentylethanone (D170, 100 mg) was added. The reaction mixture was stirred at RT overnight. EtOAc (20 mL) and water (10 mL) were added into the reaction mixture. After 10 min stirring, the EtOAc layer was separated and condensed. The residue was purified by MDAP (acidic elution) to get the title compound (45 mg) as white solid. $^1$H NMR (400 MHz, MeOD-$d_4$): 7.57 (d, J=2.1 Hz, 1H), 7.52 (d, J=1.8 Hz, 1H), 4.62 (brs, 1H), 4.52-4.35 (m, 2H), 4.10 (d, J=7.1 Hz, 1H), 3.67-3.35 (m, 5H), 3.23-3.08 (m, 1H), 3.04 (s, 3H), 2.99 (t, J=7.1 Hz, 2H), 2.57-2.35 (m, 2H), 2.31 (s, 3H), 2.25-2.08 (m, 1H), 1.84 (brs, 2H), 1.74-1.07 (m, 10H). $^{19}$F NMR (376 MHz, MeOD-$d_4$): −78.9. MS (ESI): $C_{24}H_{36}ClN_3O_4S$ requires 497, found 498 $[M+H]^+$.

Example 50

(S)—N-(5-chloro-3-((4-(cyclohexanecarbonyl)-3-methylpiperazin-1-yl)methyl)-2-methylphenyl)-3-(methylsulfonyl)propanamide (E50)

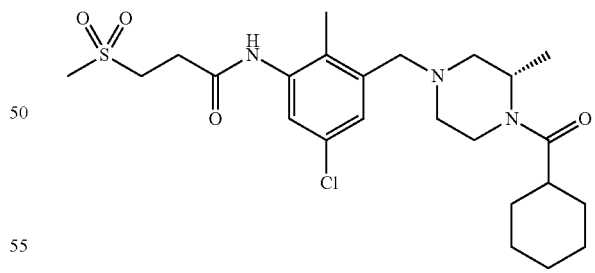

To a solution of 3-(methylsulfonyl)propanoic acid (62.7 mg), HATU (209 mg) and DIPEA (0.144 mL) in DMF (10 mL), (S)-(4-(3-amino-5-chloro-2-methylbenzyl)-2-methylpiperazin-1-yl)(cyclohexyl)methanone (D171, 100 mg) was added into the mixture, which was stirred at RT for 2 days. After extraction with EtOAc/$H_2O$, dry, and condense, the residue was purified by MDAP (basic elution) to get the required product (S)—N-(5-chloro-3-((4-(cyclohexanecarbonyl)-3-methylpiperazin-1-yl)methyl)-2-methylphenyl)-3-(methylsulfonyl)propanamide (7 mg) as white solid. $^1$H NMR (400 MHz, MeOD-d$_4$): 7.39 (s, 1H), 7.23 (brs, 1H), 4.67 (brs, 0.5H), 4.38-4.16 (m, 1H), 3.80 (d, J=12.7 Hz, 1H), 3.63-3.35 (m, 4.5H), 3.05 (s, 3H), 3.03-2.89 (m, 2.5H), 2.87-2.51 (m, 3H), 2.28 (s, 3H), 2.24-1.94 (m, 2H), 1.87-1.12 (m, 13H). MS (ESI): C$_{24}$H$_{36}$ClN$_3$O$_4$S requires 497, found 498 [M+H]$^+$.

Example 51

(S)—N-(5-chloro-3-((4-(cyclopentanecarbonyl)-3-methylpiperazin-1-yl)methyl)-2-methylphenyl)-4,4,4-trifluorobutanamide (E51)

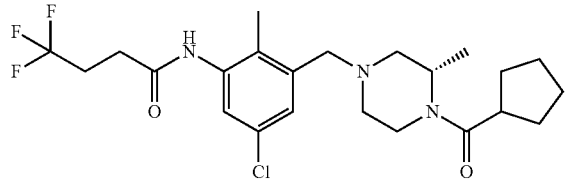 [SMILES: Cc1c(CN2CCN(C(=O)C3CCCC3)[C@@H](C)C2)cc(Cl)cc1NC(=O)CCC(F)(F)F]

To a solution of (S)-(4-(3-amino-5-chloro-2-methylbenzyl)-2-methylpiperazin-1-yl)(cyclopentyl)methanone (D157, 138.2 mg) and 4,4,4-trifluorobutanoic acid (74.5 mg) in anhydrous DMF (5 mL), HATU (302.4 mg) and DIPEA (0.207 mL) were added. The resulting reaction mixture was stirred overnight at RT. Diluted with DCM (10 mL), washed with water twice (2×20 mL), the organic layer was separated and concentrated to dryness under vacuum. The residue was purified with MDAP to afford the title compound (90.5 mg) as white solid. $^1$H NMR (400 MHz, MeOD-d$_4$): 7.33 (d, J=2.2 Hz, 1H), 7.22 (d, J=2.0 Hz, 1H), 4.72-4.53 (m, 1.5H), 4.36-4.22 (m, 1H), 3.83 (d, J=13.4 Hz, 0.5H), 3.52-3.40 (m, 2H), 3.40-3.33 (m, 0.5H), 3.07-2.90 (m, 1.5H), 2.82 (d, J=11.0 Hz, 1H), 2.75-2.66 (m, 3H), 2.66-2.52 (m, 2H), 2.25 (s, 3H), 2.23-2.12 (m, 1H), 2.10-1.53 (m, 9H), 1.39-1.16 (m, 3H). $^{19}$F NMR (376 MHz, MeOD-d$_4$): −68.2. MS (ESI): C$_{23}$H$_{31}$ClF$_3$N$_3$O$_2$ requires: 473, found 474 [M+H]$^+$.

Example 52

(S)—N-(5-chloro-3-((4-(cyclopentanecarbonyl)-3-methylpiperazin-1-yl)methyl)-2-methylphenyl)-5,5,5-trifluoropentanamide (E52)

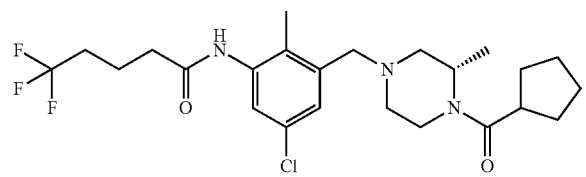 [SMILES: Cc1c(CN2CCN(C(=O)C3CCCC3)[C@@H](C)C2)cc(Cl)cc1NC(=O)CCCC(F)(F)F]

E52 was prepared using a similar procedure to that described for E51. $^1$H NMR (400 MHz, MeOD-d$_4$): 7.33 (d, J=2.0 Hz, 1H), 7.21 (d, J=1.5 Hz, 1H), 4.66 (brs, 0.5H), 4.37-4.21 (m, 1H), 3.83 (d, J=13.2 Hz, 0.5H), 3.53-3.40 (m, 2H), 3.40-3.33 (m, 0.5H), 2.90-3.07 (m, 1.5H), 2.82 (d, J=11.0 Hz, 1H), 2.75-2.66 (m, 3H), 2.54 (t, J=7.3 Hz, 2H), 2.36-2.11 (m, 6H), 2.09-1.53 (m, 11H), 1.39-1.15 (m, 3H). $^{19}$F NMR (376 MHz, MeOD-d$_4$): −67.9. MS (ESI): C$_{24}$H$_{33}$ClF$_3$N$_3$O$_2$ requires 487; found 488 [M+H]$^+$.

Example 53

(S)—N-(5-chloro-3-((4-(cyclopentanecarbonyl)-3-methylpiperazin-1-yl)methyl)-2-methylphenyl)-2-(3,3-difluorocyclobutyl)acetamide (E53)

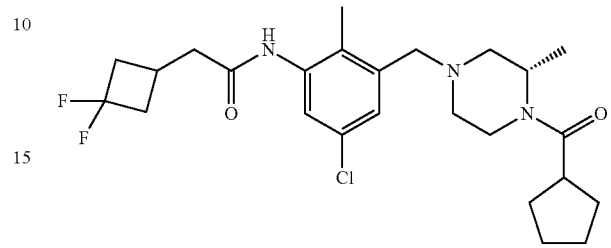

To a solution of (S)-(4-(3-amino-5-chloro-2-methylbenzyl)-2-methylpiperazin-1-yl)(cyclopentyl)methanone (D157, 117 mg) and 2-(3,3-difluorocyclobutyl)acetic acid (D16, 50 mg) in DMF (10 mL), HATU (127 mg) was added at RT. The reaction mixture was stirred for 6 hours. Water (20 mL) was added, extracted with DCM (50 mL). The organic layer was dried over Na$_2$SO$_4$ and filtered. The filtrate was concentrated and the residue was purified with MDAP to afford the title compound (20 mg) as white solid. $^1$H NMR (500 MHz, DMSO-d$_6$): 9.45 (s, 1H), 7.40 (s, 1H), 7.16 (s, 1H), 4.54 (brs, 0.5H), 4.20 (d, J=8.8 Hz, 1H), 3.75 (d, J=12.6 Hz, 0.5H), 3.45-3.36 (m, 2H), 3.21-3.13 (m, 0.5H), 2.95-2.86 (m, 1H), 2.80-2.68 (m, 3.5H), 2.65-2.55 (m, 3H), 2.44-2.31 (m, 2H), 2.17 (s, 3H), 2.13-1.45 (m, 11H), 1.27-1.04 (m, 3H). MS (ESI) C$_{25}$H$_{34}$ClF$_2$N$_3$O$_2$ requires 481; found 482 [M+H]$^+$.

Example 54

(S)—N-(3-((4-(cyclopentanecarbonyl)-3-methylpiperazin-1-yl)methyl)-5-fluoro-2-methylphenyl)-2-(3,3-difluorocyclobutyl)acetamide (E54)

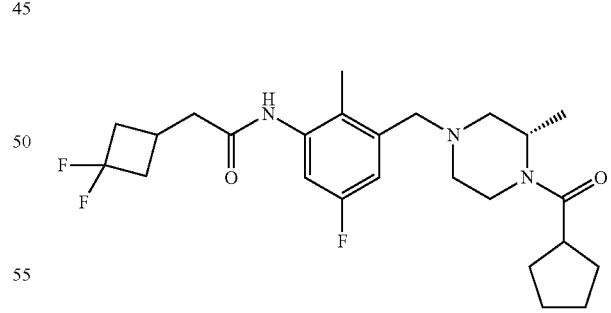

E54 was prepared using a similar procedure to that described for E53. $^1$H NMR (500 MHz, DMSO-d): 9.42 (s, 1H), 7.20 (dd, J=10.1, 2.2 Hz, 1H), 6.96 (d, J=8.5 Hz, 1H), 4.54 (brs, 0.5H), 4.19 (d, J=11.7 Hz, 1H), 3.74 (d, J=13.6 Hz, 0.5H), 3.45-3.36 (m, 2H), 3.19 (t, J=11.7 Hz, 0.5H), 2.95-2.87 (m, 1H), 2.82-2.67 (m, 3.5H), 2.66-2.56 (m, 3H), 2.44-2.30 (m, 2H), 2.15 (s, 3H), 2.10-1.45 (m, 11H), 1.30-1.05 (m, 3H). MS (ESI): C$_{25}$H$_{34}$F$_3$N$_3$O$_2$ requires 465; found 466 [M+H]$^+$.

Example 55

(S)—N-(5-chloro-3-((4-(cyclopentanecarbonyl)-3-methylpiperazin-1-yl)methyl)-2-methylphenyl)-4-cyanobutanamide, Trifluoroacetic acid salt (E55)

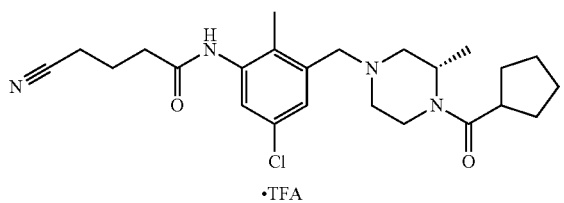 [SMILES: Cc1c(CN2CCN(C(=O)C3CCCC3)[C@@H](C)C2)cc(Cl)cc1NC(=O)CCCC#N]

·TFA

To a solution of (S)-(4-(3-amino-5-chloro-2-methylbenzyl)-2-methylpiperazin-1-yl)(cyclopentyl)methanone (D157, 99.1 mg) and 4-cyanobutanoic acid (37.1 mg) in anhydrous DMF (6 mL), HATU (162 mg) and DIPEA (0.15 mL) was added, the resulting reaction mixture was stirred overnight at rt. The mixture was sent to MDAP for purification to afford the title compound (73.5 mg) as white solid. $^1$H NMR (400 MHz, MeOD-d$_4$): 7.52 (s, 1H), 7.48 (s, 1H), 4.61 (brs, 1H), 4.30 (brs, 0.5H), 4.15 (d, J=12.5 Hz, 0.5H), 3.60-3.45 (m, 0.5H), 3.45-3.34 (m, 2H), 3.26-2.83 (m, 3.5H), 2.69-2.53 (m, 4H), 2.29 (s, 3H), 2.04 (quin, J=7.2 Hz, 2H), 1.98-1.56 (m, 8H), 1.50-1.20 (m, 3H). MS (ESI): C$_{24}$H$_{33}$ClN$_4$O$_2$ requires 444; found 445 [M+H]$^+$.

Examples 56&57

N-(5-chloro-3-(((S)-4-(cyclopentanecarbonyl)-3-methylpiperazin-1-yl)methyl)-2-methylphenyl)-2-((S)-tetrahydrofuran-3-yl)acetamide & N-(5-chloro-3-(((S)-4-(cyclopentanecarbonyl)-3-methylpiperazin-1-yl)methyl)-2-methylphenyl)-2-((R)-tetrahydrofuran-3-yl)acetamide (E56 & E57)

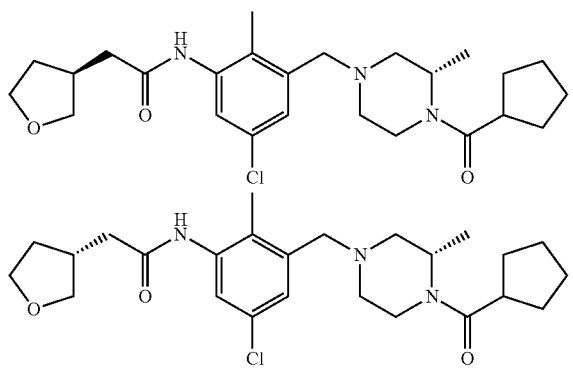

To a solution of 2-(tetrahydrofuran-3-yl)acetic acid (130 mg) and (S)-(4-(3-amino-5-chloro-2-methylbenzyl)-2-methylpiperazin-1-yl)(cyclopentyl)methanone (D157, 350 mg) in DMF (20 mL), HATU (456 mg) and DIPEA (0.349 mL) were added. The reaction mixture was stirred at 50° C. for 1 hour. Water (20 mL) was added, extracted with EtOAc (50 mL). The organic layer was dried over Na$_2$SO$_4$ and filtered. The filtrate was concentrated, and the crude product was purified by MDAP to afford N-(5-chloro-3-(((S)-4-(cyclopentanecarbonyl)-3-methylpiperazin-1-yl)methyl)-2-methylphenyl)-2-(tetrahydrofuran-3-yl)acetamide (240 mg), which was separated by preparative chiral SFC to afford the title compounds (70 mg and 78 mg) as white solid. Isomer 1: $^1$H NMR (400 MHz, DMSO-d$_6$): 9.45 (s, 1H), 7.39 (d, J=2.3 Hz, 1H), 7.16 (s, 1H), 4.54 (brs, 0.5H), 4.19 (d, J=11.0 Hz, 1H), 3.81 (dd, J=8.0, 7.0 Hz, 1H), 3.78-3.71 (m, 1.5H), 3.65 (q, J=7.4 Hz, 1H), 3.45-3.37 (m, 2H), 3.37-3.34 (m, 1H), 3.17 (t, J=13.1 Hz, 0.5H), 2.96-2.86 (m, 1H), 2.82-2.68 (m, 1.5H), 2.65-2.53 (m, 2H), 2.47-2.40 (m, 2H), 2.17 (s, 3H), 2.13-1.44 (m, 12H), 1.27-1.05 (m, 3H). MS (ESI): C$_{25}$H$_{36}$ClN$_3$O$_3$ requires 461; found 462 [M+H]$^+$. Isomer 2: $^1$H NMR (400 MHz, DMSO-d$_6$): 9.46 (s, 1H), 7.39 (d, J=2.0 Hz, 1H), 7.16 (s, 1H), 4.54 (brs, 0.5H), 4.19 (d, J=11.8 Hz, 1H), 3.81 (dd, J=8.3, 7.0 Hz, 1H), 3.78-3.71 (m, 1.5H), 3.65 (q, J=7.7 Hz, 1H), 3.45-3.38 (m, 2H), 3.17 (t, J=11.9 Hz, 0.5H), 2.96-2.86 (m, 1H), 2.81-2.68 (m, 1.5H), 2.65-2.53 (m, 2H), 2.47-2.40 (m, 2H), 2.17 (s, 3H), 2.13-1.45 (m, 12H), 1.27-1.05 (m, 3H). MS (ESI): C$_{25}$H$_{36}$ClN$_3$O$_3$ requires 461; found 462 [M+H]$^+$.

Example 58

N-(2,5-dichloro-3-(((S)-4-(cyclopentanecarbonyl)-3-methylpiperazin-1-yl)methyl)phenyl)-2-(tetrahydrofuran-3-yl)acetamide (E58)

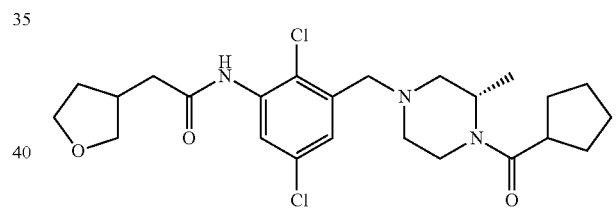

To a suspension of 2-(tetrahydrofuran-3-yl)acetic acid (39.4 mg) in DCM (10 mL), oxalyl chloride (0.030 mL) was added dropwise. The reaction mixture was stirred at 40° C. for 30 min. Solvent was removed by rotavap, then redissolved with DCM (1 mL), added to a solution of (S)-(4-(3-amino-2,5-dichlorobenzyl)-2-methylpiperazin-1-yl)(cyclopentyl)methanone (D158, 70 mg) in pyridine (2 mL). The reaction mixture was stirred at RT overnight. The reaction mixture was diluted with DCM (10 mL) then washed with brine (10 mL). DCM layer was separated and concentrated. The residue was purified by MADP to afford the title compound (7 mg) as white solid. $^1$H NMR (400 MHz, MeOD-d$_4$): 7.71 (d, J=1.5 Hz, 1H), 7.35 (d, J=2.0 Hz, 1H), 4.61 (brs, 0.5H), 4.33-4.17 (m, 1H), 3.90-3.51 (m, 5.5H), 3.45-3.27 (m, 1.5H), 3.01-2.67 (m, 3.5H), 2.67-2.41 (m, 3.5H), 2.27 (brs, 1H), 2.14-1.99 (m, 1.5H), 1.84-1.43 (m, 10H), 1.35-1.13 (m, 3H). MS (ESI): C$_{24}$H$_{33}$Cl$_2$N$_3$O$_3$ requires 481; found 482 [M+H]$^+$.

Examples 59&60

N-(2,5-dichloro-3-(((S)-4-(cyclopentanecarbonyl)-3-methylpiperazin-1-yl)methyl)phenyl)-2-((S)-tetrahydrofuran-3-yl)acetamide & N-(2,5-dichloro-3-(((S)-4-(cyclopentanecarbonyl)-3-methylpiperazin-1-yl)methyl)phenyl)-2-((R)-tetrahydrofuran-3-yl)acetamide (E59 & E60)

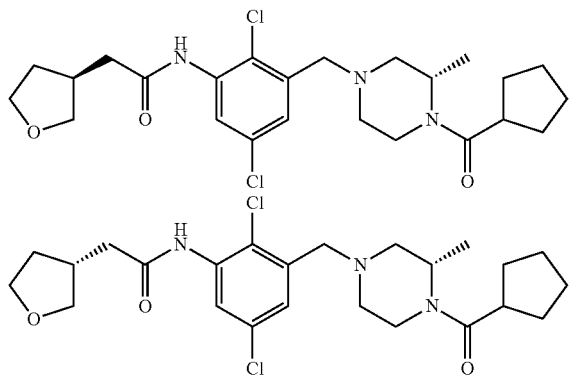

N-(2,5-dichloro-3-(((S)-4-(cyclopentanecarbonyl)-3-methylpiperazin-1-yl)methyl)phenyl)-2-(tetrahydrofuran-3-yl)acetamide (E58) (20 mg) was separated by chiral SFC to afford the title two compounds (6 mg and 7 mg). Isomer 1: $^1$H NMR (400 MHz, CDCl$_3$): 8.39 (d, J=1.0 Hz, 1H), 7.69 (s, 1H), 4.78 (brs, 0.5H), 4.44 (d, J=13.6 Hz, 0.5H), 4.14 (brs, 0.5H), 3.98 (dd, J=8.7, 6.9 Hz, 1H), 3.95-3.87 (m, 1H), 3.79 (q, J=7.5 Hz, 1H), 3.69 (d, J=13.3 Hz, 0.5H), 3.58-3.46 (m, 3H), 3.39 (t, J=12.2 Hz, 0.5H), 3.07-2.92 (m, 0.5H), 2.90-2.73 (m, 3H), 2.67 (d, J=11.0 Hz, 1H), 2.55 (d, J=8.0 Hz, 2H), 2.30-2.15 (m, 2H), 2.14-2.05 (m, 1H), 1.97-1.61 (m, 9H), 1.41-1.22 (m, 3H). MS (ESI): C$_{24}$H$_{33}$Cl$_2$N$_3$O$_3$ requires 481; found 482 [M+H]$^+$. Isomer 2: $^1$H NMR (400 MHz, CDCl$_3$): 8.39 (d, J=1.0 Hz, 1H), 7.69 (s, 1H), 4.78 (brs, 0.5H), 4.44 (d, J=13.6 Hz, 0.5H), 4.14 (brs, 0.5H), 3.98 (dd, J=8.7, 6.9 Hz, 1H), 3.95-3.86 (m, 1H), 3.79 (q, J=7.5 Hz, 1H), 3.69 (d, J=13.3 Hz, 0.5H), 3.58-3.45 (m, 3H), 3.39 (t, J=13.1 Hz, 0.5H), 3.05-2.92 (m, 0.5H), 2.90-2.73 (m, 3H), 2.67 (d, J=11.0 Hz, 1H), 2.55 (d, J=7.3 Hz, 2H), 2.28-2.15 (m, 2H), 2.10 (t, J=11.9 Hz, 1H), 1.97-1.63 (m, 9H), 1.41-1.26 (m, 3H). MS (ESI): C$_{24}$H$_{33}$Cl$_2$N$_3$O$_3$ requires 481; found 482 [M+H]$^+$.

Examples 61&62

N-(5-chloro-3-(((S)-4-(cyclopentanecarbonyl)-3-methylpiperazin-1-yl)methyl)-2-methylphenyl)-2-((1s,4R)-4-hydroxycyclohexyl)acetamide & N-(5-chloro-3-(((S)-4-(cyclopentanecarbonyl)-3-methylpiperazin-1-yl)methyl)-2-methylphenyl)-2-((1r,4S)-4-hydroxycyclohexyl)acetamide (E61 & E62)

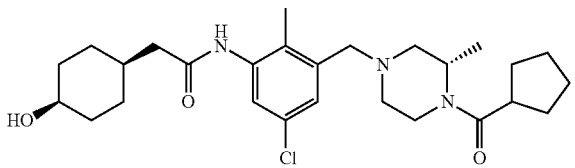

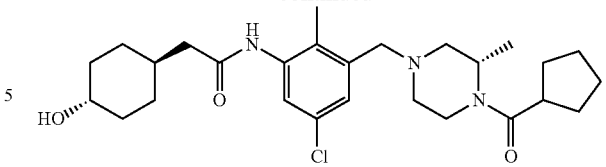

2-(4-Hydroxycyclohexyl)acetic acid (D3, 150 mg) and HATU (361 mg) were added to the (S)-(4-(3-amino-5-chloro-2-methylbenzyl)-2-methylpiperazin-1-yl)(cyclopentyl)methanone (D157, 332 mg) solution in DMF (20 mL), the reaction mixture was continued to stir for 6 hours at RT. Water (20 mL) was added and extracted with EtOAc (50 mL), the organic layer was dried over Na$_2$SO$_4$. Filtered, the filtrated was concentrated and the residue was purified by preparative HPLC to afford the two compounds (48 mg and 18 mg) as white solid. Isomer 1: $^1$H NMR (500 MHz, DMSO-d$_6$): 9.35 (s, 1H), 7.38 (s, 1H), 7.15 (s, 1H), 4.54 (brs, 0.5H), 4.47 (d, J=4.4 Hz, 1H), 4.19 (d, J=10.1 Hz, 1H), 3.75 (d, J=12.9 Hz, 0.5H), 3.45-3.36 (m, 2H), 3.36-3.33 (m, 1H), 3.17 (t, J=12.1 Hz, 0.5H), 2.97-2.86 (m, 1H), 2.81-2.68 (m, 1.5H), 2.60 (d, J=9.5 Hz, 1H), 2.21 (d, J=6.9 Hz, 2H), 2.16 (s, 3H), 2.14-1.45 (m, 15H), 1.29-0.95 (m, 7H). MS (ESI): C$_{27}$H$_{40}$ClN$_3$O$_3$ requires 489; found 490 [M+H]$^+$. Isomer 2: $^1$H NMR (500 MHz, DMSO-d$_6$): 9.37 (s, 1H), 7.38 (d, J=1.6 Hz, 1H), 7.15 (s, 1H), 4.54 (brs, 0.5H), 4.30 (d, J=3.2 Hz, 1H), 4.20 (d, J=8.5 Hz, 1H), 3.79-3.70 (m, 1.5H), 3.46-3.36 (m, 2H), 3.18 (t, J=11.7 Hz, 0.5H), 2.91 (quin, J=7.4 Hz, 1H), 2.81-2.68 (m, 1.5H), 2.65-2.57 (m, 1H), 2.26 (d, J=7.3 Hz, 2H), 2.17 (s, 3H), 2.13-1.38 (m, 19H), 1.27-1.05 (m, 3H). MS (ESI): C$_{27}$H$_{40}$ClN$_3$O$_3$ requires 489; found 490 [M+H]$^+$.

Examples 63-70

Examples 63-70 were prepared using a similar procedure to that described for E61 and E62, with the specified reaction base or solvent listed in the table.

E63: N-(3-(((S)-4-(cyclopentanecarbonyl)-3-methylpiperazin-1-yl)methyl)-5-fluoro-2-methylphenyl)-2-((1r,4S)-4-hydroxycyclohexyl)acetamide E64: N-(3-(((S)-4-(cyclopentanecarbonyl)-3-methylpiperazin-1-yl)methyl)-5-fluoro-2-methylphenyl)-2-((1s,4R)-4-hydroxycyclohexyl)acetamide E65: N-(5-chloro-3-(((S)-4-(cyclopentanecarbonyl)-3-methylpiperazin-1-yl)methyl)-2-methylphenyl)-2-((S)-1-methyl-5-oxopyrrolidin-3-yl)acetamide E66: N-(5-chloro-3-(((S)-4-(cyclopentanecarbonyl)-3-methylpiperazin-1-yl)methyl)-2-methylphenyl)-2-((R)-1-methyl-5-oxopyrrolidin-3-yl)acetamide E67: N-(5-chloro-3-(((S)-4-(cyclopentanecarbonyl)-3-methylpiperazin-1-yl)methyl)-2-methylphenyl)-2-((S)-1-ethyl-5-oxopyrrolidin-3-yl)acetamide E68: N-(5-chloro-3-(((S)-4-(cyclopentanecarbonyl)-3-methylpiperazin-1-yl)methyl)-2-methylphenyl)-2-((R)-1-ethyl-5-oxopyrrolidin-3-yl)acetamide E69: N-(5-chloro-3-(((S)-4-(cyclopentanecarbonyl)-3-methylpiperazin-1-yl)methyl)-2-methylphenyl)-2-((R)-1-methyl-2-oxopyrrolidin-3-yl)acetamide E70: N-(5-chloro-3-(((S)-4-(cyclopentanecarbonyl)-3-methylpiperazin-1-yl)methyl)-2-methylphenyl)-2-((S)-1-methyl-2-oxopyrrolidin-3-yl)acetamide

| | Structure | Base/Solvent | Characterization |
|---|---|---|---|
| E63&E64 | 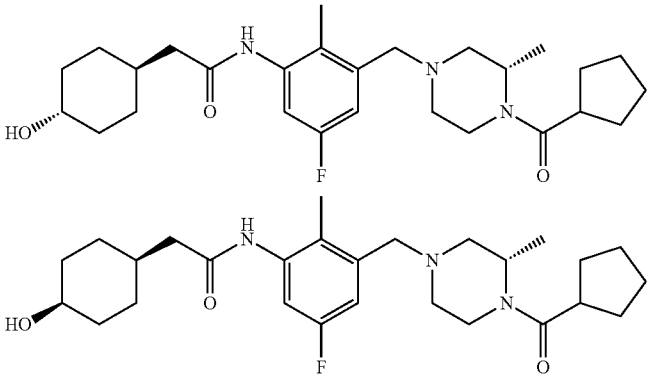 | No base/ DMF | Isomer 1: $^1$H NMR (500 MHz, DMSO-$d_6$): 9.32 (s, 1H), 7.19 (dd, J = 10.2, 2.4 Hz, 1H), 6.95 (d, J = 9.5 Hz, 1H), 4.54 (brs, 0.5H), 4.47 (d, J = 4.4 Hz, 1H), 4.19 (d, J = 11.7 Hz, 1H), 3.75 (d, J = 12.3 Hz, 0.5H), 3.45-3.36 (m, 2H), 3.36-3.33 (m, 1H), 3.19 (t, J = 11.7 Hz, 0.5H), 2.96-2.87 (m, 1H), 2.82-2.69 (m, 1.5H), 2.66-2.59 (m, 1H), 2.21 (d, J = 6.9 Hz, 2H), 2.14 (s, 3H), 2.08-1.46 (m, 15H), 1.31-0.97 (m, 7H). MS (ESI): $C_{27}H_{40}FN_3O_3$ requires 473; found 474 $[M + H]^+$.<br>Isomer 2: $^1$H NMR (500 MHz, DMSO-$d_6$): 9.34 (s, 1H), 7.20 (dd, J = 10.2, 2.7 Hz, 1H), 6.95 (d, J = 8.8 Hz, 1H), 4.54 (brs, 0.5H), 4.30 (d, J = 2.5 Hz, 1H), 4.19 (d, J = 10.7 Hz, 1H), 3.79-3.69 (m, 1.5H), 3.46-3.36 (m, 2H), 3.19 (t, J = 12.8 Hz, 0.5H), 2.97-2.86 (m, 1H), 2.83-2.68 (m, 1.5H), 2.67-2.58 (m, 1H), 2.27 (d, J = 7.6 Hz, 2H), 2.15 (s, 3H), 2.08-1.37 (m, 19H), 1.27-1.05 (m, 3H). MS (ESI): $C_{27}H_{40}FN_3O_3$ requires 473; found 474 $[M + H]^+$. |
| E65&E66 | 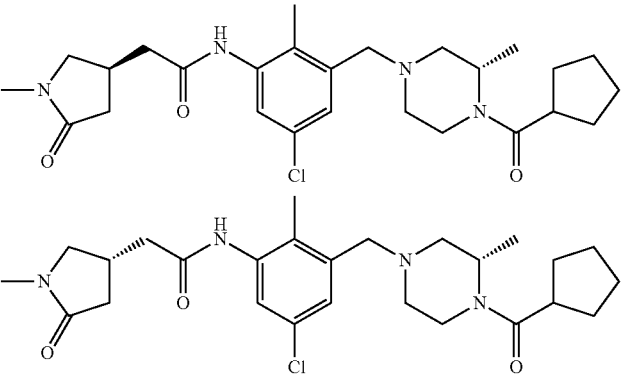 | DIPEA/ DMF | Isomer 1: $^1$H NMR (400 MHz, CDCl$_3$): 7.96-7.86 (m, 1H), 7.59 (s, 1H), 7.10 (d, J = 11.2 Hz, 1H), 4.75-4.65 (m, 0.5H), 4.36-4.25 (m, 0.5H), 4.13-4.08 (m, 0.5H), 3.71-3.61 (m, 1.5H), 3.44-3.26 (m, 2.5H), 3.22-3.15 (m, 1H), 2.99-2.50 (m, 10H), 2.26-2.09 (m, 4.5H), 2.04-1.65 (m, 8 H), 1.63-1.50 (m, 2H), 1.37-1.18 (m, 3H). MS (ESI): $C_{26}H_{37}ClN_4O_3$ requires 488; found 489 $[M + H]^+$.<br>Isomer 2: $^1$H NMR (400 MHz, CDCl$_3$): 7.71-7.63 (m, 2H), 7.10 (s, 1H), 4.76-4.67 (m, 0.5H), 4.37-4.28 (m, 0.5H), 4.16-4.08 (m, 0.5H), 3.71-3.60 (m, 1.5H), 3.45-3.25 (m, 2.5H), 3.23-3.15 (m, 1H), 2.98-2.52 (m, 10H), 2.26-2.05 (m, 4.5H), 2.04-1.65 (m, 8H), 1.63-1.50 (m, 2H), 1.34-1.18 (m, 3H). MS (ESI): $C_{26}H_{37}ClN_4O_3$ requires 488; found 489 $[M + H]^+$. |
| E67&E68 | 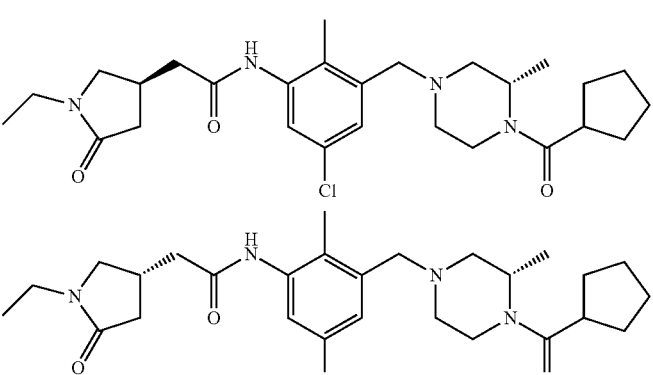 | DIPEA/ DMF | Isomer 1: $^1$H NMR (400 MHz, DMSO-$d_6$): 9.52 (s, 1H), 7.41 (d, J = 1.6 Hz, 1H), 7.17 (brs, 1H), 4.56 (brs, 0.5H), 4.30-4.22 (m, 1H), 3.77-3.71 (m, 1H), 3.55-3.50 (m, 1H), 3.41 (s, 2H), 3.25-3.05 (m, 5H), 2.92-2.84 (m, 1H), 2.75-2.55 (m, 4H), 2.46-2.42 (m, 1H), 2.17 (s, 3H), 2.06-1.75 (m, 2.5H), 1.75-1.45 (m, 8H), 1.23-1.10 (m, 6H). MS (ESI): $C_{27}H_{39}ClN_4O_3$ requires 502; found 503 $[M + H]^+$.<br>Isomer 2: $^1$H NMR (400 MHz, DMSO-$d_6$): 9.53 (s, 1H), 7.41 (d, J = 1.6 Hz, 1H), 7.17 (brs, 1H), 4.56 (brs, 0.5H), 4.29-4.22 (m, 1H), 3.77-3.71 (m, 1H), 3.55-3.50 (m, 1H), 3.41 (s, 2H), 3.25-3.07 (m, 5H), 2.93-2.84 (m, 1H), 2.80-2.57 (m, 4H), |

| Structure | Base/Solvent | Characterization |
|---|---|---|
| 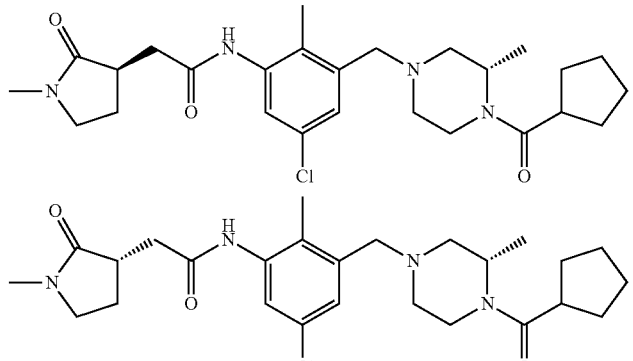 E69&E70 | DIPEA/DMF | 2.48-2.45 (m, 1H), 2.17 (s, 3H), 2.10-1.75 (m, 2.5H), 1.77-1.50 (m, 8H), 1.23-1.10 (m, 3H), 1.02-0.96 (m, 3H). MS (ESI): $C_{27}H_{39}ClN_4O_3$ requires 502; found 503 $[M + H]^+$.<br>Isomer 1: $^1H$ NMR (400 MHz, CDCl$_3$): 9.44-9.39 (brs, 1H), 7.81 (s, 1H), 7.07 d, J = 2.0 Hz, 1H), 4.80 (brs, 0.5H), 4.45-4.40 (m, 0.5H), 4.15 (brs, 0.5H), 3.68-3.61 (m, 0.5H), 3.45-3.37 (m, 4.5H), 2.93-2.88 (m, 4.5H), 2.88-2.82 (m, 2H), 2.80-2.70 (m, 1H), 2.70-2.60 (m, 2H), 2.42-2.38 (m, 1H), 2.28 (s, 3H), 2.20-2.18 (m, 1H), 2.00-1.55 (m, 10H), 1.33-1.23 (m, 3H). MS (ESI): $C_{26}H_{37}ClN_4O_3$ requires 488; found 489 $[M + H]^+$.<br>Isomer 2: $^1H$ NMR (400 MHz, CDCl$_3$): 9.41-9.40 (brs, 1H), 7.82 (s, 1H), 7.07 (s, 1H), 4.82 (brs, 0.5H), 4.45-4.40 (m, 0.5H), 4.13 (brs, 0.5H), 3.68-3.61 (m, 0.5H), 3.45-3.37 (m, 4.5H), 3.00-2.88 (m, 4.5H), 2.85-2.82 (m, 2H), 2.80-2.70 (m, 1H), 2.70-2.60 (m, 2H), 2.42-2.37 (m, 1H), 2.28 (s, 3H), 2.19-2.18 (m, 1H), 2.00-1.55 (m, 10H), 1.33 (d, J = 6.4 Hz, 1.5H), 1.23 (d, J = 6.8 Hz, 1.5H). MS (ESI): $C_{26}H_{37}ClN_4O_3$ requires 488; found 489 $[M + H]^+$. |

Example 71

(S)—N-(5-chloro-3-((4-(cyclopentanecarbonyl)-3-methylpiperazin-1-yl)methyl)-2-methylphenyl)-2-cyanoisonicotinamide, Trifluoroacetic acid salt (E71)

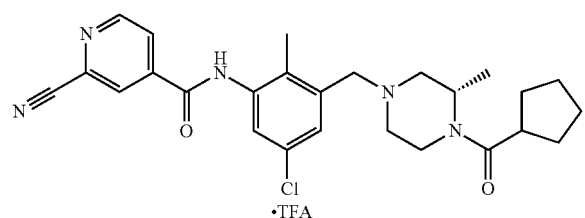 [SMILES: Cc1c(CN2CCN(C(=O)C3CCCC3)[C@@H](C)C2)cc(Cl)cc1NC(=O)c1ccnc(C#N)c1]
·TFA

To a solution of (S)-(4-(3-amino-5-chloro-2-methylbenzyl)-2-methylpiperazin-1-yl)(cyclopentyl)methanone (D157, 115.5 mg) and 2-cyanoisonicotinic acid (56.6 mg) in anhydrous DMF (5 mL), HATU (194.0 mg) and DIPEA (0.173 mL were added at RT. The resulting reaction mixture was stirred overnight. Diluted with DCM (15 mL), washed with water (10 mL), the organic layer was separated and solvent was removed under vacuum. The residue was purified with MDAP to afford the title compound (73.9 mg) as white solid. $^1H$ NMR (400 MHz, MeOD-d$_4$): 8.93 (d, J=4.9 Hz, 1H), 8.36 (s, 1H), 8.15 (dd, J=5.1, 1.7 Hz, 1H), 7.58 (s, 2H), 4.63 (brs, 1H), 4.35 (brs, 2H), 4.18 (d, J=14.9 Hz, 0.5H), 3.65-3.48 (m, 0.5H), 3.47-3.33 (m, 2H), 3.25-2.84 (m, 3.5H), 2.35 (s, 3H), 1.99-1.55 (m, 8H), 1.52-1.21 (m, 3H). MS (ESI): $C_{26}H_{30}ClN_5O_2$ requires 479; found 480 $[M+H]^+$.

Examples 72-76

Examples 72 to 76 were prepared using a similar procedure to that described for E71, with the specified reaction base or solvent listed in the table.

E72 (S)—N-(5-chloro-3-((4-(2-cyclopropylacetyl)-3-methylpiperazin-1-yl)methyl)-2-methylphenyl)-2-cyanoisonicotinamide, Trifluoroacetic acid salt E73 (S)—N-(5-chloro-3-((4-(cyclopentanecarbonyl)-3-methylpiperazin-1-yl)methyl)-2-methylphenyl)-5-cyano-6-methylnicotinamide, Trifluoroacetic acid salt E74 (S)—N-(5-cyano-3-((4-(cyclopentanecarbonyl)-3-methylpiperazin-1-yl)methyl)-2-methylphenyl)-6-methylnicotinamide E75 (S)—N-(5-cyano-3-((4-(cyclopentanecarbonyl)-3-methylpiperazin-1-yl)methyl)-2-methylphenyl)-2-methylisonicotinamide E76 (S)-5-chloro-N-(5-chloro-3-((4-(2-cyclopropylacetyl)-3-methylpiperazin-1-yl)methyl)-2-methylphenyl)-6-methylnicotinamide

| | Structure | Base/Solvent | Characterization |
|---|---|---|---|
| E72 | (structure) ·TFA | DIPEA/DMF | ¹H NMR (400 MHz, MeOD-d₄): 8.93 (dd, J = 5.1, 0.7 Hz, 1H), 8.36 (s, 1H), 8.15 (dd, J = 5.0, 1.6 Hz, 1H), 7.58 (brs, 2H), 4.62 (brs, 0.5H), 4.55-4.43 (m, 0.5H), 4.35 (brs, 2H), 4.03 (d, J = 9.5 Hz, 0.5H), 3.66-3.50 (m, 1H), 3.46-3.37 (m, 2H), 3.26-2.85 (m, 2.5H), 2.56-2.24 (m, 5H), 1.49-1.22 (m, 3H), 1.08-0.93 (m, 1H), 0.63-0.48 (m, 2H), 0.25-0.14 (m, 2H). MS (ESI): $C_{25}H_{28}ClN_5O_2$ requires 465; found 466 $[M + H]^+$. |
| E73 | (structure) ·TFA | DIPEA/DMF | ¹H NMR (400 MHz, MeOD-d₄): 9.21 (d, J = 2.2 Hz, 1H), 8.64 (d, J = 2.2 Hz, 1H), 7.55 (s, 2H), 4.61 (brs, 0.5H), 4.30 (brs, 2H), 4.21-4.08 (m, 1H), 3.53 (t, J = 12.6 Hz, 1H), 3.38 (d, J = 14.4 Hz, 2H), 3.21-2.88 (m, 3.5H), 2.84 (s, 3H), 2.35 (s, 3H), 1.99-1.55 (m, 8H), 1.50-1.20 (m, 3H). MS (ESI): $C_{27}H_{32}ClN_5O_2$ requires 493; found 494 $[M + H]^+$. |
| E74 | (structure) | TEA/DMF | ¹H NMR (400 MHz, DMSO-d₆): 10.23 (s, 1H), 9.03 (s, 1H), 8.21 (dd, J = 8.2, 1.9 Hz, 1H), 7.78 (s, 1H), 7.63 (s, 1H), 7.44 (d, J = 8.3 Hz, 1H), 4.56 (brs, 0.5H), 4.21 (d, J = 9.5 Hz, 1H), 3.76 (d, J = 12.8 Hz, 0.5H), 3.59-3.43 (m, 2H), 3.19 (t, J = 12.4 Hz, 0.5H), 2.92 (quin, J = 7.8 Hz, 1H), 2.83-2.70 (m, 1.5H), 2.68-2.60 (m, 1H), 2.56 (s, 3H), 2.33 (s, 3H), 2.23-1.45 (m, 10H), 1.30-1.05 (m, 3H). MS (ESI): $C_{27}H_{33}N_5O_2$ requires 459; found 460 $[M + H]^+$. |
| E75 | (structure) | DIPEA/DMF | ¹H NMR (400 MHz, MeOD-d₄): 8.52 (d, J = 5.1 Hz, 1H), 7.71 (s, 1H), 7.68-7.58 (m, 2H), 7.54 (s, 1H), 4.58 (brs, 0.5H), 4.29-4.14 (m, 1H), 3.75 (d, J = 13.2 Hz, 0.5H), 3.54-3.39 (m, 2H), 3.33-3.26 (m, 0.5H), 3.00-2.83 (m, 1.5H), 2.77-2.58 (m, 2H), 2.56 (s, 3H), 2.32 (s, 3H), 2.21-1.43 (m, 10H), 1.30-1.06 (m, 3H). MS (ESI): $C_{27}H_{33}N_5O_2$ requires 459; found 460 $[M + H]^+$. |
| E76 | (structure) | DIPEA/DMF | ¹H NMR (400 MHz, MeOD-d₄): 8.95 (d, J = 0.8 Hz, 1H), 8.37 (d, J = 0.6 Hz, 1H), 7.38-7.32 (d, J = 22 Hz, 2H), 4.73-4.67 (m, 0.5H), 4.36-4.33 (d, 0.5H), 4.16-4.15 (m, 0.5H), 3.75-3.72 (d, 0.5H), 3.57-3.48 (m, 2H), 3.46-3.40 (m, 0.5H), 3.01-2.95 (m, 0.5H), 2.88-2.86 (m, 1H), 2.76-2.72 (m, 4H), 2.48-2.40 (m, 1H), 2.32 (s, 4H), 2.27-2.20 (m, 3H), 1.37-1.25 (m, 3H), 1.02-0.99 (m, 1H), 0.56-0.54 (m, 2H), 0.21-0.20 (m, 2H). MS (ESI): $C_{25}H_{30}Cl_2N_4O_2$ requires 488; found 489 $[M + H]^+$. |

Example 77

(S)—N-(5-chloro-3-((4-(2-cyclopropylacetyl)-3-methylpiperazin-1-yl)methyl)-2-methylphenyl)-6-cyanonicotinamide, Trifluoroacetic acid salt (E77)

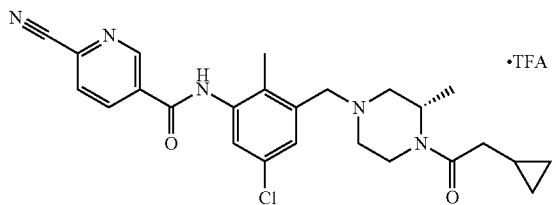 [SMILES: Cc1c(CN2CCN(C(=O)CC3CC3)[C@@H](C)C2)cc(Cl)cc1NC(=O)c1ccc(C#N)nc1]

To a solution of (S)-1-(4-(3-amino-5-chloro-2-methylbenzyl)-2-methylpiperazin-1-yl)-2-cyclopropylethanone (D169, 122.8 mg) in DCM (5 mL), 6-cyanonicotinic acid (61.9 mg), DMAP (4.9 mg) and EDC (165.5 mg) were added at RT. The resulting reaction mixture was stirred overnight. Diluted with DCM (15 mL), washed with water (10 mL). The organic layer was separated and solvent was removed under vacuum. The residue was purified with MDAP to afford the title compound (100.9 mg) as white solid. $^1$H NMR (400 MHz, MeOD-d$_4$): 9.23 (d, J=1.5 Hz, 1H), 8.52 (dd, J=8.1, 2.2 Hz, 1H), 8.06 (d, J=8.1 Hz, 1H), 7.62 (d, J=2.0 Hz, 1H), 7.59 (d, J=2.2 Hz, 1H), 4.66 (brs, 0.5H), 4.57-4.41 (m, 2.5H), 4.07 (brs, 0.5H), 3.76-3.41 (m, 3H), 3.27-2.98 (m, 2H), 2.51-2.26 (m, 5H), 1.35 (brs, 3H), 1.07-0.93 (m, 1H), 0.63-0.48 (m, 2H), 0.25-0.11 (m, 2H). MS (ESI): C$_{25}$H$_{28}$ClN$_5$O$_2$ requires 465; found 466 [M+H]$^+$.

Example 78

(S)—N-(5-chloro-3-((4-(cyclopentanecarbonyl)-3-methylpiperazin-1-yl)methyl)-2-methylphenyl)-6-cyanonicotinamide, Trifluoroacetic acid salt (E78)

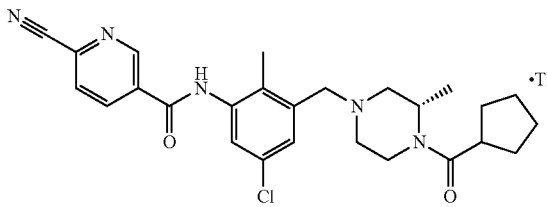

To a solution of (S)-(4-(3-amino-5-chloro-2-methylbenzyl)-2-methylpiperazin-1-yl)(cyclopentyl)methanone (D157, 115.5 mg) and 6-cyanonicotinic acid (57.2 mg) in anhydrous DMF (5 mL), HATU (255.3 mg) and DIPEA (0.173 mL) were added at RT. The resulting reaction mixture was stirred overnight. Diluted with DCM (15 mL), washed with water (10 mL). The organic layer was separated and solvent was removed under vacuum. The residue was purified with MDAP to afford the title compound (90.4 mg) as white solid. $^1$H NMR (400 MHz, MeOD-d$_4$): 9.23 (d, J=1.5 Hz, 1H), 8.52 (dd, J=8.1, 2.2 Hz, 1H), 8.06 (dd, J=8.2, 0.6 Hz, 1H), 7.65-7.57 (m, 2H), 4.67 (brs, 1H), 4.54-4.38 (m, 2H), 4.21 (d, J=14.4 Hz, 0.5H), 3.65-3.40 (m, 2.5H), 3.29-2.99 (m, 3.5H), 2.36 (s, 3H), 2.00-1.56 (m, 8H), 1.52-1.21 (m, 3H). MS (ESI): C$_{26}$H$_{30}$ClN$_5$O$_2$ requires 479; found 480 [M+H]$^+$.

Example 79

(S)—N-(5-chloro-3-((4-(2-cyclopropylacetyl)-3-methylpiperazin-1-yl)methyl)-2-methylphenyl)-5-cyano-6-methylnicotinamide, Trifluoroacetic acid salt (E79)

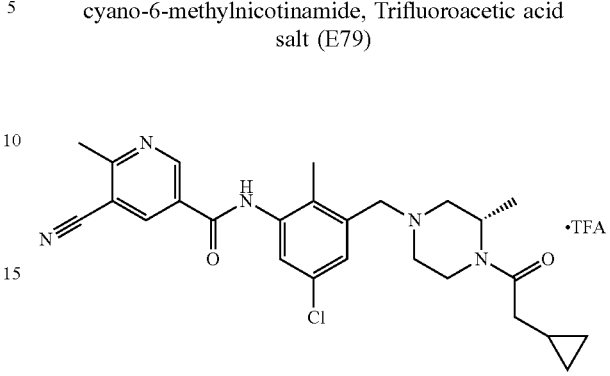

To a solution of (S)-1-(4-(3-amino-5-chloro-2-methylbenzyl)-2-methylpiperazin-1-yl)-2-cyclopropylethanone (D169, 120.9 mg) in anhydrous DMF (5 mL), 5-cyano-6-methylnicotinic acid (D117, 62.8 mg), HATU (274 mg) and DIPEA (0.126 mL) were added. The reaction mixture was stirred overnight. After the reaction, the mixture was sent to MDAP for purification (acidic condition), to give the title compound (62.5 mg) as white solid. $^1$H NMR (400 MHz, MeOD-d$_4$): 9.21 (s, 1H), 8.64 (s, 1H), 7.55 (s, 2H), 4.63 (brs, 1H), 4.46 (brs, 1H), 4.29 (brs, 2H), 4.11-3.92 (m, 1H), 3.65-3.46 (m, 1H), 3.20-2.90 (m, 3H), 2.84 (s, 3H), 2.54-2.21 (m, 5H), 1.50-1.22 (m, 3H), 1.01 (brs, 1H), 0.56 (d, J=7.6 Hz, 2H), 0.19 (d, J=4.2 Hz, 2H). $^{19}$F NMR (376 MHz, MeOD-d$_4$): −77.2. MS (ESI): C$_{26}$H$_{30}$ClN$_5$O$_2$ requires 479, found 480 [M+H]$^+$.

Example 80

(S)—N-(5-chloro-3-((4-(2-cyclopropylacetyl)-3-methylpiperazin-1-yl)methyl)-2-methylphenyl)-5-fluoro-6-methylnicotinamide (E80)

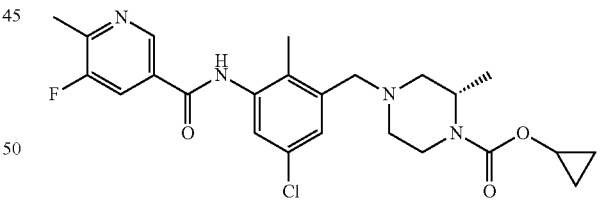

The mixture of (S)—N-(5-chloro-2-methyl-3-((3-methylpiperazin-1-yl)methyl)phenyl)-5-fluoro-6-methylnicotinamide, 2 hydrochloric acid salt (D254, 3000 mg), 2-cyclopropylacetic acid (777 mg), HATU (3689 mg) and DIPEA (3344 mg) in DCM (20 mL) was stirred overnight. After reaction completed, water (100 mL) was added, extracted with DCM twice (2×100 mL). Combined organic layer was dried over Na$_2$SO$_4$. Filtered, the filtrate was concentrated to dryness. The residue was purified by MDAP to get the title compound (1802 mg). $^1$H NMR (400 MHz, MeOD-d$_4$): 8.87 (s, 1H), 8.08 (dd, J=10.0, 1.2 Hz, 1H), 7.36 (d, J=2.0 Hz, 1H), 7.31 (d, J=2.0 Hz, 1H), 4.67-4.70 (m, 0.5H), 4.33 (d, J=12.8 Hz, 0.5H), 4.15 (m, 0.5H), 3.74 (d, J=13.2 Hz, 0.5H), 3.55-3.47 (m, 2H), 3.42-3.36 (m, 0.5H), 3.00-2.93 (m, 0.5H), 2.83-2.86 (m, 1H), 2.75, (d, J=11.6 Hz, 1H), 2.61 (d, J=2.8 Hz, 3H), 2.47-2.42 (m, 0.5H), 2.31 (s, 3H), 2.26-2.15 (m, 2.5H), 2.09-2.00 (m, 1H), 1.35-1.24 (m, 3H), 1.04-0.96 (m, 1H), 0.53-0.55 (m, 2H), 0.17-0.20 (m, 2H). MS (ESI): $C_{25}H_{30}ClFN_4O_2$ requires 472; found 473 [M+H]$^+$.

Examples 81-90

Examples 81-90 were prepared using a similar procedure to that described for E80, with the specified reaction base or solvent listed in the table.

E81 (S)—N-(5-cyano-3-((4-(2-cyclopropylacetyl)-3-methylpiperazin-1-yl)methyl)-2-methylphenyl)-2-methylpyrimidine-5-carboxamide E82 (S)—N-(5-cyano-3-((4-(2-cyclopropylacetyl)-3-methylpiperazin-1-yl)methyl)-2-methylphenyl)-6-methylnicotinamide E83 (S)—N-(5-cyano-2-methyl-3-((3-methyl-4-(spiro[2.3]hexane-5-carbonyl)piperazin-1-yl)methyl)phenyl)-6-methylnicotinamide E84 N-(3-(((3 S)-4-(bicyclo[3.1.0]hexane-3-carbonyl)-3-methylpiperazin-1-yl)methyl)-5-cyano-2-methylphenyl)-6-methylnicotinamide E85 (S)—N-(5-cyano-3-((4-(2-cyclopropylacetyl)-3-methylpiperazin-1-yl)methyl)-2-methylphenyl)-6-methoxynicotinamide, Trifluoroacetic acid salt E86 (S)-5-chloro-N-(5-cyano-3-((4-(2-cyclopropylacetyl)-3-methylpiperazin-1-yl)methyl)-2-methylphenyl)-6-methylnicotinamide E87 (S)-5-chloro-N-(3-((4-(2,2-difluorobutanoyl)-3-methylpiperazin-1-yl)methyl)-5-fluoro-2-methylphenyl)-6-methylnicotinamide E88 (S)—N-(5-chloro-3-((4-(2-cyclopropylacetyl)-3-methylpiperazin-1-yl)methyl)-2-methylphenyl)-4-cyano-4-methylpentanamide E89 (S)—N-(5-chloro-2-methyl-3-((3-methyl-4-(spiro[2.3]hexane-5-carbonyl)piperazin-1-yl)methyl)phenyl)-3-(methylsulfonyl)propanamide E90 N-(3-(((3 S)-4-(bicyclo[3.1.0]hexane-3-carbonyl)-3-methylpiperazin-1-yl)methyl)-5-chloro-2-methylphenyl)-3-(methylsulfonyl)propanamide

| | Structure | Base/Solvent | Characterization |
|---|---|---|---|
| E81 | 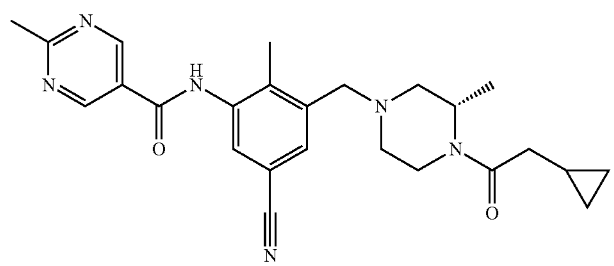 [SMILES: Cc1ncc(C(=O)Nc2cc(C#N)cc(CN3CCN(C(=O)CC4CC4)[C@@H](C)C3)c2C)cn1] | TEA/DCM | $^1$H NMR (400 MHz, DMSO-$d_6$): 10.40 (s, 1H), 9.20 (s, 2H), 7.81 (d, J = 2.0 Hz, 1H), 7.65 (d, J = 1.2 Hz, 1H), 4.52-4.50 (m, 0.5H), 4.25-4.00 (m, 1H), 3.60-3.55 (m, 0.5H), 3.52-3.48 (m, 2H), 3.30-3.10 (m, 0.5H), 3.00-2.95 (m, 0.5H), 2.73 (s, 3H), 2.64-2.61 (m, 1H), 2.35 (s, 3H), 2.23-1.91 (m, 4H), 1.23-1.05 (m, 3H), 0.95 (brs, 1H), 0.50-0.40 (m, 2H), 0.15-0.07 (m, 2H). MS (ESI): $C_{25}H_{30}N_6O_2$ requires 446; found 447 [M + H]$^+$. |
| E82 | 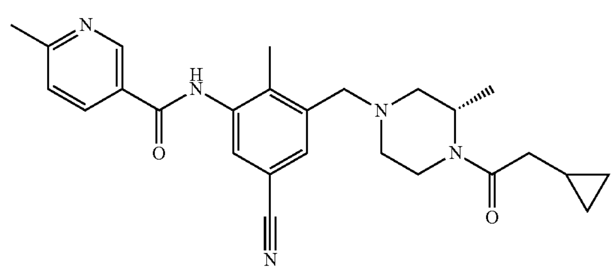 | TEA/DMF | $^1$H NMR (400 MHz, CDCl$_3$): 10.23 (s, 1H), 9.04 (d, J = 1.6 Hz, 1H), 8.22 (dd, J = 8.4, 1.6 Hz, 1H), 7.78 (s, 1H), 7.64 (s, 1H), 7.44 (d, J = 8.4 Hz, 1H), 4.55-4.49 (m, 0.5H), 4.25-4.00 (m, 1H), 3.56-3.52 (m, 0.5H), 3.52-3.47 (m, 2H), 2.80-2.64 (m, 3H), 2.57 (s, 3H), 2.34 (s, 3H), 2.25-1.92 (m, 4H), 1.23-1.18 (m, 3H), 0.95 (brs, 1H), 0.50-0.40 (m, 2H), 0.17-0.05 (m, 2H). MS (ESI): $C_{26}H_{31}N_5O_2$ requires 445; found 446 [M + H]$^+$. |
| E83 | 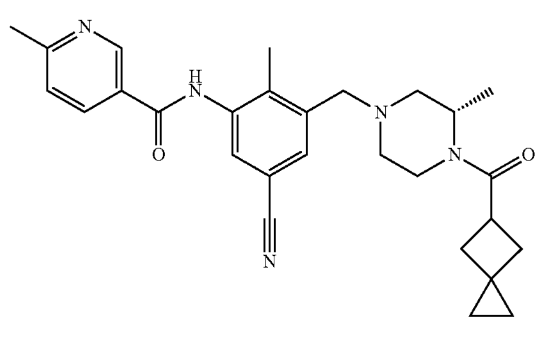 [SMILES: Cc1ccc(C(=O)Nc2cc(C#N)cc(CN3CCN(C(=O)C4CC5(CC5)C4)[C@@H](C)C3)c2C)cn1] | DIPEA/DMF | $^1$H NMR (400 MHz, CDCl$_3$): 9.02 (s, 1H), 8.17-8.14 (m, 2H), 7.97 (brs, 1H), 7.46 (brs, 1H), 7.34 (d, J = 7.6 Hz, 1H), 4.76 (brs, 0.5H), 4.41-4.38 (m, 0.5H), 3.92-3.86 (m, 0.5H), 3.51-3.37 (m, 4H), 2.92-2.90 (m, 0.5H), 2.71-2.67 (m, 0.5H), 2.67 (s, 3H), 2.58-2.53 (m, 2.5H), 2.41 (s, 3H), 2.21-2.12 (m, 3H), 2.03-1.97 (m, 1H), 1.29 (d, J = 6.4 Hz, 1.5H), 1.22 (d, J = 6.4 Hz, 1.5H), 0.47-0.38 (m, 4H). MS (ESI): $C_{28}H_{33}N_5O_2$ requires 471; found 472 [M + H]$^+$. |

-continued

| | Structure | Base/Solvent | Characterization |
|---|---|---|---|
| E84 | 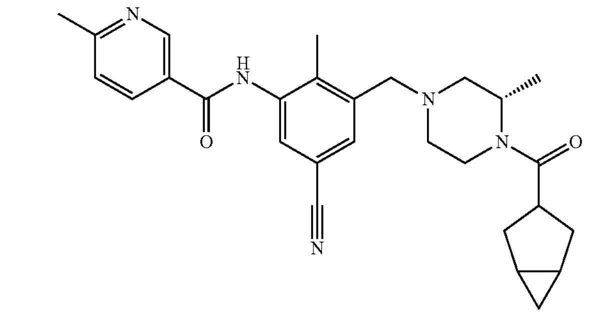 | DIPEA/DMF | ¹H NMR (500 MHz, DMSO-d₆): 10.32 (brs, 1H), 9.05 (s, 1H), 8.26 (d, J = 8.0 Hz, 1H), 7.48 (d, J = 7.5 Hz, 1H), 5.70-5.65 (m, 1H), 3.88-3.82 (m, 5H), 2.58 (s, 3H), 2.35 (brs, 4H), 2.27-1.76 (m, 8H), 1.64-1.04 (m, 6H), 0.45-0.15 (m, 2H). MS (ESI): $C_{27}H_{33}ClN_4O_2$ requires 480; found 481 [M + H]⁺. |
| E85 | 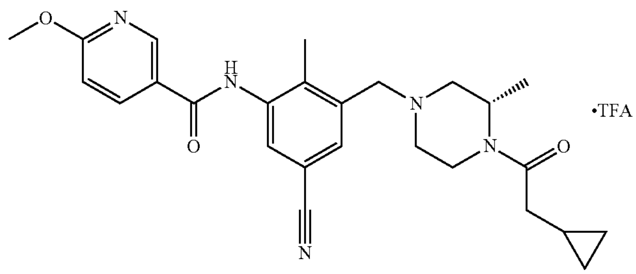 [SMILES: COc1ccc(C(=O)Nc2cc(C#N)cc(CN3CCN(C(=O)CC4CC4)[C@@H](C)C3)c2C)cn1] | DIPEA/DMF | ¹H NMR (400 MHz, MeOD-d₄): 8.82 (d, J = 2.0 Hz, 1H), 8.24 (dd, J = 8.7, 2.1 Hz, 1H), 7.89-7.71 (m, 2H), 6.93 (d, J = 8.6 Hz, 1H), 4.56 (brs, 1H), 4.41 (brs, 0.5H), 4.23 (brs, 2H), 4.01 (s, 3.5H), 3.63-3.41 (m, 1H), 3.25-2.63 (m, 4H), 2.43 (s, 3H), 2.34 (brs, 2H), 1.50-1.21 (m, 3H), 1.10-0.93 (m, 1H), 0.56 (d, J = 7.6 Hz, 2H), 0.19 (d, J = 4.6 Hz, 2H). ¹H NMR (376 MHz, MeOD-d₄): −77.4. MS (ESI): $C_{26}H_{31}N_5O_3$ requires 461; found 462 [M + H]⁺. |
| E86 | 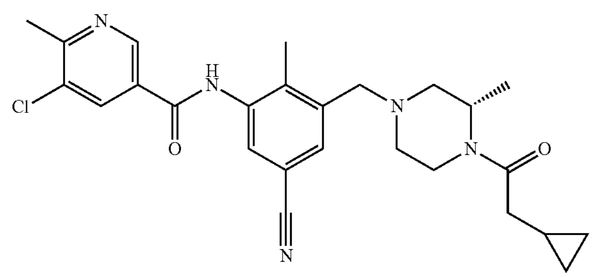 [SMILES: Cc1ncc(C(=O)Nc2cc(C#N)cc(CN3CCN(C(=O)CC4CC4)[C@@H](C)C3)c2C)cc1Cl] | DIPEA/DCM | ¹H NMR (DMSO-d₆, 400 MHz): 10.35 (brs, 1H), 8.96 (d, J = 1.6 Hz, 1H), 8.38 (d, J = 2.0 Hz, 1H), 7.78 (d, J = 1.6 Hz, 1H), 7.65 (s, 1H), 4.56 (brs, 0.5H), 4.27-4.22 (m, 0.5H), 4.10-4.01 (m, 0.5H), 3.61-3.55 (m, 0.5H), 3.55-3.49 (m, 2H), 3.30-3.22 (m, 0.5H), 2.80-2.70 (m, 1.5H), 2.67-2.60 (m, 4H), 2.33 (s, 3H), 2.25-1.82 (m, 4H), 1.21-1.11 (m, 3H), 0.93 (brs, 1H), 0.43 (d, J = 7.6 Hz, 2H), 0.11 (brs, 2H). MS (ESI): $C_{26}H_{30}ClN_5O_2$ requires 479; found 480 [M + H]⁺. |
| E87 | 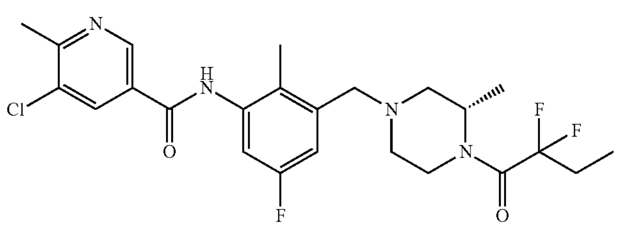 [SMILES: CCC(F)(F)C(=O)N1CCN(Cc2cc(F)cc(NC(=O)c3cnc(C)c(Cl)c3)c2C)C[C@@H]1C] | DIPEA/DMF | ¹H NMR (DMSO-d₆, 400 MHz): 8.90 (s, 1H), 8.37 (d, J = 2.0 Hz, 1H), 7.15-7.08 (m, 2H), 4.65 (brs, 0.5H), 4.49 (brs, 0.5H), 4.31-4.27 (m, 0.5H), 4.08-4.05 (m, 0.5H), 3.53 (s, 3H), 3.49-3.42 (m, 0.5H), 3.17-3.13 (m, 0.5H), 2.93-2.86 (m, 1H), 2.79-2.76 (m, 1H), 2.62-2.61 (m, 3H), 2.32 (s, 3H), 2.31-2.05 (m, 4H), 1.43-1.30 (m, 3H), 1.09-1.05 (m, 3H). MS (ESI): $C_{24}H_{28}ClF_3N_4O_2$ requires 496; found 497 [M + H]⁺. |
| E88 | 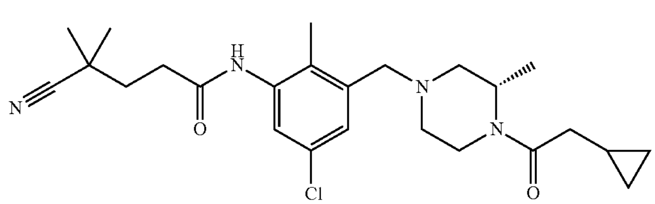 [SMILES: Cc1c(CN2CCN(C(=O)CC3CC3)[C@@H](C)C2)cc(Cl)cc1NC(=O)CCC(C)(C)C#N] | DIPEA/DMF | ¹H NMR (400 MHz, DMSO-d₆): 9.62 (s, 1H), 9.23 (brs, 1H), 7.64 (s, 1H), 7.51 (s, 1H), 4.78 (brs, 1H), 4.42 (brs, 3H), 3.98-3.91 (m, 1H), 3.27-2.95 (m, 2H), 2.60-2.55 (m, 2H), 2.30-2.22 (m, 4H), 1.88 (t, J = 7.6 Hz, 2H), 1.35-1.30 (m, 8H), 1.20-1.19 (m, 2H), 0.95 (brs, 1H), 0.45 (d, J = 7.6 Hz, 2H), 0.11-0.08 (m, 2H). ¹⁹F (376 MHz, MeOD-d₄): −73.6, −75.5. |

| Structure | Base/Solvent | Characterization |
|---|---|---|
| E89 | | MS (ESI): $C_{25}H_{35}ClN_4O_2$ requires 458; found 459 [M + H]$^+$. |
| | DIPEA/DMF | $^1$H NMR (400 MHz, CDCl$_3$): 7.66 (brs, 1H), 7.57-7.53 (m, 1H), 7.11 (brs, 1H), 4.75 (brs, 0.5H), 4.40-4.35 (m, 0.5H), 3.87(m, 0.5H), 3.51 (t, J = 75.2 Hz, 2H), 3.44-3.35 (m, 4H), 3.25-3.30 (m, 5H), 2.91-2.83 (m, 0.5H), 2.72-2.54 (m, 4H), 2.23 (s, 3H), 2.19-2.12 (m, 3H), 1.98-1.94 (m, 1H), 1.28-1.21 (m, 3H), 0.49-0.38 (m, 4H). MS (ESI): $C_{24}H_{34}ClN_3O_4S$ requires 495; found 496 [M + H]$^+$. |
| E90 | | |
| | DIPEA/DMF | $^1$H NMR (500 MHz, MeOD-d$_4$): 7.38 (d, J = 2.5 Hz, 1H), 7.23 (d, J = 1.5 Hz, 1H), 4.60 (brs, 0.5H), 4.23-4.15 (m, 1H), 3.72-3.68 (m, 1H), 3.55-3.44 (m, 4.5H), 3.05 (s, 3H), 2.99 (t, J = 7.0 Hz, 2H), 2.81-2.78 (m, 1H), 2.71-2.69 (m, 1H), 2.28 (s, 3H), 2.25-1.82 (m, 6.5H), 1.34-1.30 (m, 3.5H), 1.21 (d, J = 6.5 Hz, 2H), 0.45-0.40 (m, 1H), 0.40-0.24 (m, 1H). MS (ESI): $C_{24}H_{34}ClN_3O_4S$ requires 495; found 496 [M + H]$^+$. |

Examples 91&92

(S)—N-(5-chloro-3-((4-(2-cyclopropylacetyl)-3-methylpiperazin-1-yl)methyl)-2-methylphenyl)-2-(4-hydroxycyclohexyl)acetamide & (S)—N-(5-chloro-3-((4-(2-cyclopropylacetyl)-3-methylpiperazin-1-yl)methyl)-2-methylphenyl)-2-(4-hydroxycyclohexyl)acetamide (E91 & E92)

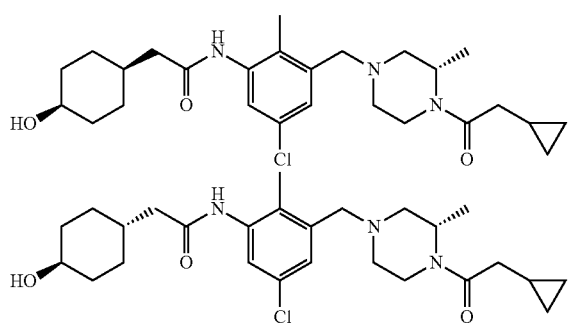

The 2-cyclopropylacetic acid (50.8 mg) and HATU (92 mg) was added into the solution of (S)—N-(5-chloro-2-methyl-3-((3-methylpiperazin-1-yl)methyl)phenyl)-2-(4-hydroxycyclohexyl)acetamide (D247, 100 mg) in DMF (10 mL). The reaction mixture was stirred for 6 hours at 40° C. The reaction mixture was added water (20 mL) and extracted with DCM (100 mL). The organic layer was separated, dried and filtered. The filtrate was concentrated and the residue was purified by column chromatography (silica gel, petroleum ether/EtOAc=1:1) then MDAP to give the title compounds (10 mg and 15 mg) as yellow solid.

Isomer 1: $^1$H NMR (500 MHz, MeOD-d$_4$): 7.31 (brs, 1H), 7.23 (s, 1H), 4.69 (brs, 0.5H), 4.39-4.32 (m, 0.5H), 4.18 (brs, 0.5H), 3.94 (brs, 1H), 3.73-3.71 (m, 0.5H), 3.52-3.26 (m, 3H), 2.97-2.90 (m, 0.5H), 2.86-2.81 (m, 1H), 2.72 (d, J=11.5 Hz, 1H), 2.45-2.43 (m, 1H), 2.38-2.18 (m, 8H), 2.10-1.95 (m, 2H), 1.80-1.76 (m, 2H), 1.62-1.55 (m, 5.5H), 1.35 (d, J=6.5 Hz, 1.5H), 1.25 (d, J=6.5 Hz, 1.5H), 1.01 (brs, 1H), 0.58-0.54 (m, 2H), 0.20 (brs, 2H). MS (ESI): $C_{26}H_{38}ClN_3O_3$ requires 475; found [M+H]$^+$. Isomer 2: $^1$H NMR (400 MHz, MeOD-d$_4$): 7.31 (d, J=2.0 Hz, 1H), 7.23 (d, J=1.5 Hz, 1H), 4.69 (brs, 1H), 4.35-4.32 (m, 0.5H), 4.15 (brs, 0.5H), 3.73-3.70 (brs, 0.5H), 3.55-3.35 (m, 4H), 3.00-2.95 (m, 0.5H), 2.88-2.80 (m, 1H), 2.72 (d, J=11.0 Hz, 1H), 2.47-2.43 (m, 0.5H), 2.32-2.17 (m, 8H), 2.09-1.97 (m, 3H), 1.89-1.80 (m, 3H), 1.35-1.13 (m, 7H), 1.00 (brs, 1H), 0.57-0.53 (m, 1.5H), 0.20 (brs, 1.5H). MS (ESI): $C_{26}H_{38}ClN_3O_3$ requires 475; found [M+H]$^+$.

Example 93

(S)—N-(5-chloro-3-((4-(2-cyclopropylacetyl)-3-methylpiperazin-1-yl)methyl)-2-methylphenyl)-6-cyano-5-methylnicotinamide (E93)

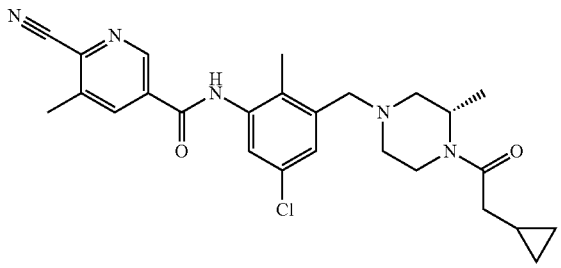 [SMILES: Cc1cc(C(=O)Nc2cc(Cl)cc(CN3CCN(C(=O)CC4CC4)[C@@H](C)C3)c2C)cnc1C#N]

To a solution of (S)—N-(5-chloro-2-methyl-3-((3-methylpiperazin-1-yl)methyl)phenyl)-6-cyano-5-methylnicotinamide (D252, 50 mg) in DCM (10 mL) was added 2-cyclopropylacetic acid (12.58 mg), HATU (57.3 mg) and DIPEA (0.066 mL). After stirred for 8 hours, the mixture was concentrated, the residue was purified by MDAP to afford the title compound (17 mg) as white solid. $^1$H NMR (400 MHz, CDCl$_3$): 9.09-9.06 (brs, 1H), 8.61 (brs, 0.5H), 8.45 (m, 0.5H), 8.27 (s, 1H), 7.61 (s, 1H), 7.18 (brs, 1H), 4.63 (brs, 0.5H), 4.23-4.14 (m, 0.5H), 3.98 (brs, 0.5H), 3.58-3.26 (m, 3H), 2.83-2.71 (m, 1H), 2.66 (s, 3H), 2.60-2.50 (m, 1H), 2.40-2.31 (m, 0.5H), 2.27 (s, 3H), 2.25-2.00 (m, 3H), 1.90-1.80 (m, 0.5H), 1.34-1.08 (m, 3.5H), 1.00 (brs, 1H), 0.55 (brs, 2H), 0.19-0.11 (d, J=4.0 Hz, 2H). MS (ESI): C$_{26}$H$_{30}$ClN$_5$O$_2$ requires 479; found 480 [M+H]$^+$.

Examples 94&95 cis N-(3-(((S)-4-(cyclopentanecarbonyl)-3-methylpiperazin-1-yl)methyl)-5-fluoro-2-methylphenyl)-2-(2-hydroxycyclopentyl)acetamide & trans N-(3-(((S)-4-(cyclopentanecarbonyl)-3-methylpiperazin-1-yl)methyl)-5-fluoro-2-methylphenyl)-2-(2-hydroxycyclopentyl)acetamide (E94 & E95)

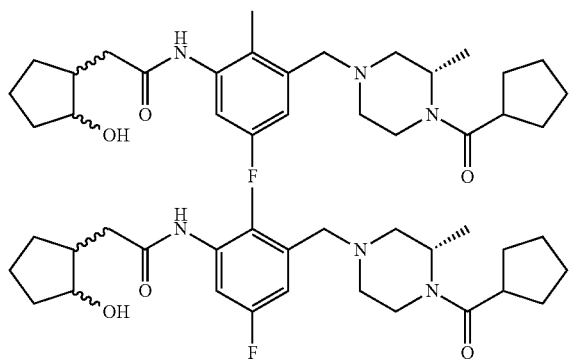

To a solution of N-(3-(((S)-4-(cyclopentanecarbonyl)-3-methyl piperazin-1-yl)methyl)-5-fluoro-2-methylphenyl)-2-(2-oxocyclopentyl)acetamide (D201, 150 mg) in ethanol (30 mL) was added NaBH$_4$ (196 mg) at 0° C. The reaction mixture was stirred at 20° C. for 6 hours. The mixture was concentrated and to the residue was added water (20 mL), extracted with EtOAc (20 mL). The organic layer was dried and concentrated to leave the crude product, which was purified by preparative HPLC and then chiral HPLC to get two isomers (10 mg and 40 mg) as yellow solid. Isomer 1: $^1$H NMR (500 MHz, DMSO-d$_6$): 9.34 (s, 1H), 7.23 (d, J=10.0 Hz, 1H), 6.95 (d, J=9.5 Hz, 1H), 4.54 (brs, 0.5H), 4.47-4.45 (m, 1H), 4.23-4.16 (m, 1H), 4.02 (brs, 1H), 3.78-3.72 (m, 0.5H), 3.45-3.39 (m, 2H), 3.23-3.15 (m, 0.5H), 2.95-2.88 (m, 1H), 2.77-2.70 (m, 1.5H), 2.66-2.61 (m, 1H), 2.36-2.31 (m, 1H), 2.20-1.92 (m, 6H), 1.90-1.37 (m, 13H), 1.35-1.09 (m, 5H). MS (ESI): C$_{26}$H$_{38}$FN$_3$O$_3$ requires 459; found 460 [M+H]$^+$. Isomer 2: $^1$H NMR (500 MHz, DMSO-d$_6$): 9.37 (s, 1H), 7.19 (d, J=10.0 Hz, 1H), 6.96 (d, J=9.0 Hz, 1H), 4.65 (d, J=5.0 Hz, 1H), 4.55 (brs, 0.5H), 4.23-4.16 (m, 1H), 3.78-3.65 (m, 1.5H), 3.44-3.36 (m, 2H), 3.22-3.15 (m, 0.5H), 2.95-2.88 (m, 1H), 2.80-2.70 (m, 1.5H), 2.66-2.60 (m, 1H), 2.22-1.39 (m, 20H), 1.30-1.07 (m, 5H). MS (ESI): C$_{26}$H$_{38}$FN$_3$O$_3$ requires 459; found 460 [M+H]$^+$.

Examples 96&97

Cis (S)—N-(5-chloro-3-((4-(cyclopentanecarbonyl)-3-methylpiperazin-1-yl)methyl)-2-methylphenyl)-2-(3-hydroxycyclobutyl)acetamide & trans (S)—N-(5-chloro-3-((4-(cyclopentanecarbonyl)-3-methylpiperazin-1-yl)methyl)-2-methylphenyl)-2-(3-hydroxycyclobutyl)acetamide (E96&E97)

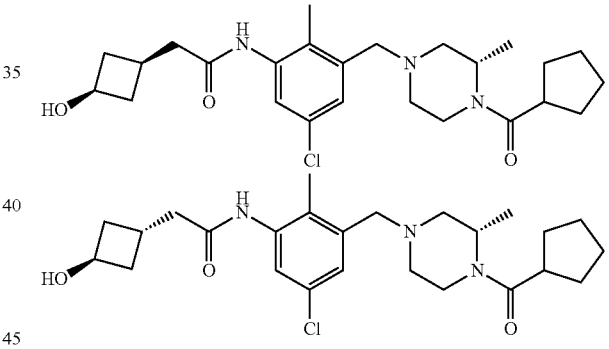

To an ice-cooled solution of (S)—N-(5-chloro-3-((4-(cyclopentanecarbonyl)-3-methylpiperazin-1-yl)methyl)-2-methylphenyl)-2-(3-oxocyclobutyl)acetamide (D202, 320 mg) in MeOH (2 mL) was added NaBH$_4$ (26.3 mg). The reaction mixture was stirred at 0° C. overnight. The mixture was evaporated under vacuum to leave the crude product, which was purified by preparative HPLC and chiral HPLC to afford the title compounds (10 mg and 10 mg) as white solids. Isomer 1: $^1$H NMR (400 MHz, CDCl$_3$): 7.70 (s, 1H), 7.01 (s, 1H), 6.92 (s, 1H), 4.69 (brs, 1H), 4.33 (d, J=12.8 Hz, 0.5H), 4.19-4.11 (m, 1H), 4.08-4.03 (m, 0.5H), 3.59 (d, J=12.8 Hz, 1H), 3.39-3.20 (m, 3H), 2.86-2.64 (m, 2H), 2.56 (d, J=10.8 Hz, 2H), 2.47 (d, J=7.2 Hz, 2H), 2.14 (s, 3H), 2.12-2.07 (m, 2H), 1.93-1.67 (m, 8H), 1.50 (brs, 2H), 1.25-1.05 (m, 5H). MS (ESI): C$_{25}$H$_{36}$ClN$_3$O$_3$ requires 461; found 462 [M+H]$^+$. Isomer 2: $^1$H NMR (400 MHz, DMSO-d$_6$): 9.38 (brs, 1H), 7.37 (d, J=2.0 Hz, 1H), 7.15 (s, 1H), 4.95 (d, J=6.0 Hz, 1H), 4.54 (brs, 0.5H), 4.28-4.18 (m, 1.5H), 3.76-3.73 (m, 0.5H), 3.30 (brs, 3H), 3.21-3.15 (m, 1H), 2.95-2.87 (m, 1H), 2.80-2.67 (m, 1.5H), 2.65-2.57 (m, 1H), 2.48-2.43 (m, 2H), 2.16 (s, 3H), 2.13-1.94 (m, 5H), 1.90-

1.45 (m, 7H), 1.24-1.09 (m, 5H). MS (ESI): $C_{25}H_{36}ClN_3O_3$ requires 461; found 462 $[M+H]^+$.

Example 98

N-(3-(((S)-4-(cyclopentanecarbonyl)-3-methylpiperazin-1-yl)methyl)-5-fluoro-2-methylphenyl)-2-(2-hydroxycyclohexyl)acetamide (E98)

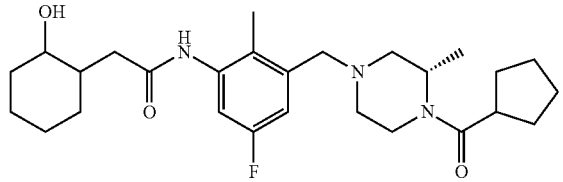 [SMILES: Cc1c(CN2CCN(C(=O)C3CCCC3)[C@@H](C)C2)cc(F)cc1NC(=O)CC1CCCCC1O]

To a solution of N-(3-(((S)-4-(cyclopentanecarbonyl)-3-methyl piperazin-1-yl)methyl)-5-fluoro-2-methylphenyl)-2-(2-oxocyclohexyl)acetamide (D200, 100 mg) in ethanol (30 mL) was added $NaBH_4$ (127 mg). The reaction mixture was stirred at 20° C. for 6 hours. The mixture was concentrated and to the residue was added water (20 mL), then extracted with EtOAc (10 mL). The organic layer was dried and concentrated to leave the crude product, which was purified by MDAP to afford the title compound (8 mg) as white solid. $^1$H NMR (400 MHz, DMSO-$d_6$): 9.33 (s, 1H), 7.21 (d, J=11.0 Hz, 1H), 6.95 (d, J=8.0 Hz, 1H), 4.56 (brs, 0.5H), 4.42-4.19 (m, 1.5H), 3.90-3.80 (m, 1H), 3.76-3.72 (m, 0.5H), 3.45-3.37 (m, 2H), 3.19-3.15 (m, 0.5H), 3.00-2.90 (m, 1H), 2.89-2.71 (m, 1.5H), 2.70-2.55 (m, 1H), 2.35-2.08 (m, 6H), 2.06-1.75 (m, 2.5H), 1.75-1.30 (m, 14H), 1.28-1.00 (m, 5H). MS (ESI): $C_{27}H_{40}FN_3O_3$ requires 473; found 474 $[M+H]^+$.

Example 99

(S)—N-(5-chloro-3-((4-(cyclopentanecarbonyl)-3-methylpiperazin-1-yl)methyl)-2-methylphenyl)-2-((1-cyanocyclopropyl)methoxy)acetamide, Trifluoroacetic acid salt (E99)

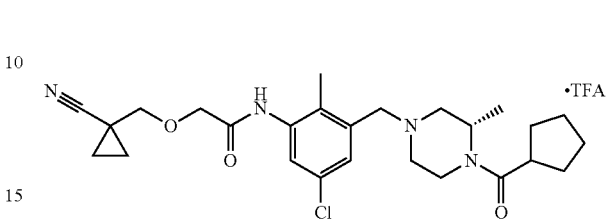

To a solution of 1-(hydroxymethyl)cyclopropanecarbonitrile (D86, 47.8 mg) in anhydrous THF (3 mL) was added sodium iodide (59.1 mg). The mixture was stirred for 0.5 hour at 0° C., followed by adding (S)-2-chloro-N-(5-chloro-3-((4-(cyclopentanecarbonyl)-3-methylpiperazin-1-yl)methyl)-2-methylphenyl)acetamide (D257, 140 mg) and sodium iodide (59.1 mg). The reaction mixture was stirred for 2 hours at 18° C. The mixture was concentrated, and the residue was purified by column chromatography (silica gel, petroleum ether/EtOAc=3/1) and MDAP to afford the title compound (20 mg) as white solid. $^1$H NMR (400 MHz, MeOD-$d_4$): 7.68 (s, 1H), 7.35 (s, 1H), 4.45 (brs, 1H), 4.18 (s, 3H), 4.14-4.10 (m, 1H), 3.58 (s, 2H), 3.45-3.36 (m, 1H), 3.21 (brs, 2H), 3.00-2.92 (m, 2H), 2.24 (s, 3H), 1.80-1.53 (m, 9.5H), 1.26 (brs, 1.5H), 1.24 (m, 2H), 1.16 (d, J=4.8 Hz, 2H), 1.05-1.02 (m, 2H); $^{19}$F NMR (376 MHz, DMSO-$d_6$): −74.0. MS (ESI): $C_{26}H_{35}ClN_4O_3$ requires 486; found 487 $[M+H]^+$.

Examples 100-101

Examples 100-101 were prepared using a similar procedure to that described for E99.

E100 (S)—N-(5-chloro-3-((4-(cyclopentanecarbonyl)-3-methylpiperazin-1-yl)methyl)-2-methylphenyl)-2-(2,2-difluoroethoxy)acetamide, trifluoroacetic acid salt E101 (S)—N-(5-chloro-3-((4-(cyclopentanecarbonyl)-3-methylpiperazin-1-yl)methyl)-2-methylphenyl)-2-(2-cyano-2-methylpropoxy)acetamide

| | Structure | Characterization |
|---|---|---|
| E100 | 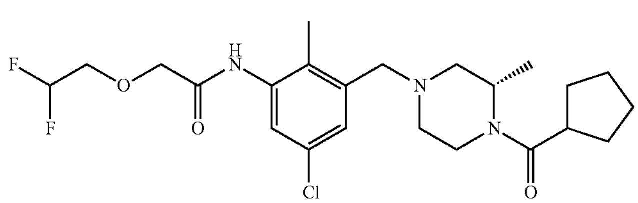 [SMILES: Cc1c(CN2CCN(C(=O)C3CCCC3)[C@@H](C)C2)cc(Cl)cc1NC(=O)COCC(F)F] | $^1$H NMR (400 MHz, CDCl$_3$): 8.34 (s, 1H), 8.14 (brs, 1H), 7.21 (d, J = 2.4 Hz, 1H), 5.99 (dt, J = 54.8, 3.2 Hz, 1H), 5.01 (brs, 0.5H), 4.67 (brs, 0.5H), 4.40-4.20 (m, 4H), 3.90 (dt, J = 14, 3.6 Hz, 2.5H), 3.80-3.60 (m, 1.5H), 3.31 (brs, 1H), 2.82-2.70 (m, 2H), 2.60-2.54 (m, 1H), 2.27 (s, 3H), 1.86-1.72 (m, 6H), 1.61-1.58 (m, 2H), 1.25-1.15 (m, 3H). $^{19}$F (376 MHz, CDCl$_3$): −125.9, −126.1. MS (ESI): $C_{23}H_{32}ClF_2N_3O_3$ requires 471; found 472 $[M + H]^+$. |

| | Structure | Characterization |
|---|---|---|
| E101 | 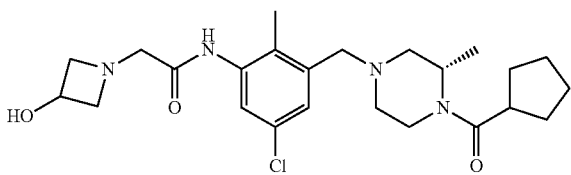 | $^{1}$H NMR (500 MHz, DMSO-$d_6$): 9.25 (s, 1H), 7.57 (s, 1H), 7.20 (s, 1H), 4.55 (brs, 0.5H), 4.225-4.20 (m, 3H), 3.76-3.74 (m, 0.5H), 3.59 (s, 2H), 3.45-3.42 (m, 2H), 3.25-3.15 (m, 0.5H), 2.92-2.90 (m, 1H), 2.76-2.60 (m, 2H), 2.20 (s, 3H), 2.10-1.50 (m, 10.5H), 1.34 (s, 6H), 1.22-1.09 (m, 3H), MS (ESI): $C_{26}H_{37}ClN_4O_3$ requires 488; found 489 [M + H]$^+$. |

Example 102

(S)—N-(5-chloro-3-((4-(cyclopentanecarbonyl)-3-methylpiperazin-1-yl)methyl)-2-methylphenyl)-2-(3-hydroxyazetidin-1-yl)acetamide (E102)

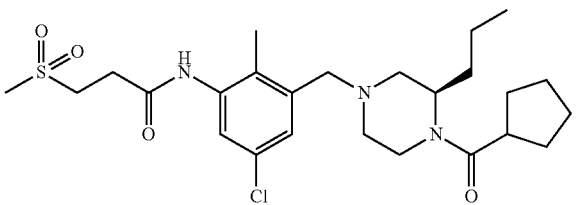 [SMILES: CCC[C@@H]1CN(Cc2cc(Cl)cc(NC(=O)CCS(C)(=O)=O)c2C)CCN1C(=O)C1CCCC1]

The solution of (S)-2-chloro-N-(5-chloro-3-((4-(cyclopentanecarbonyl)-3-methylpiperazin-1-yl)methyl)-2-methylphenyl)acetamide (D257, 50 mg), $K_2CO_3$ (32.4 mg) and azetidin-3-ol (17.14 mg) in DMF (5 mL) was stirred under nitrogen at RT overnight. Water (10 mL) was added, extracted with EtOAc (20 mL). The organic layer was concentrated and the residue was purified by MDAP to afford the title compound (28.0 mg) as white solid. $^{1}$H NMR (400 MHz, CDCl$_3$): 9.07 (s, 1H), 8.00 (d, J=2.0 Hz, 1H), 7.05 (s, 1H), 4.80 (brs, 0.5H), 4.60-4.52 (m, 1H), 4.44-4.41 (brs, 0.5H), 4.13 (brs, 0.5H), 3.85 (dd, J=8.0, 6.0 Hz, 2H), 3.68-3.62 (m, 0.5H), 3.50-3.40 (m, 1H), 3.36-3.16 (m, 3.5H), 3.24-3.20 (m, 2H), 2.92-2.60 (m, 3.5H), 2.26 (s, 3H), 2.22-2.18 (m, 2H), 2.01-1.90 (m, 1H), 1.85-1.70 (m, 8H), 1.32 (d, J=6.4 Hz, 1.5H), 1.23 (d, J=6.8 Hz, 1.5H). MS (ESI): $C_{24}H_{35}ClN_4O_3$ requires 460; found 461 [M+H]$^+$.

Example 103

(R)—N-(5-chloro-3-((4-(cyclopentanecarbonyl)-3-propylpiperazin-1-yl)methyl)-2-methylphenyl)-3-(methylsulfonyl)propanamide (E103)

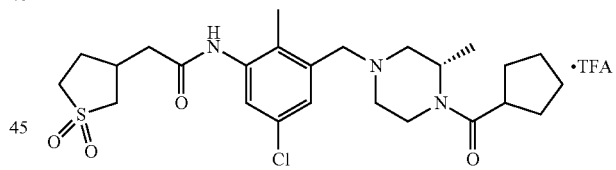

The mixture of 3-(methylsulfonyl)propanoic acid (72.5 mg) in SOCl$_2$ (2 mL) was refluxed for 2 hours. The mixture was then concentrated to dryness under reduced pressure to afford the crude acyl chloride. The above acyl chloride was dissolved in DCM (4 mL) and added slowly to the mixture of (R)-(4-(3-amino-5-chloro-2-methylbenzyl)-2-propylpiperazin-1-yl)(cyclopentyl)methanone (D177, 90 mg) and TEA (0.033 mL) in DCM (12 mL) at 0° C. The mixture was stirred at RT for 1 hour, diluted with water (10 mL) and extracted with EtOAc (10 mL). The organic phase was dried over Na$_2$SO$_4$, filtered and concentrated to leave the crude as brown oil, which was purified by MDAP to afford the title compound (90 mg) as white solid. $^{1}$H NMR (400 MHz, CDCl$_3$): 7.66-7.59 (m, 2H), 7.15 (brs, 1H), 4.63 (brs, 0.5H), 4.46-4.42 (m, 0.5H), 3.88 (brs, 0.5H), 3.71-3.67 (m, 0.5H), 3.52 (t, J=6.8 Hz, 2H), 3.42-3.31 (m, 3H), 3.04-3.00 (m, 5H), 2.88-2.73 (m, 4H), 2.23 (s, 3H), 2.16-1.98 (m, 3H), 1.86-1.58 (m, 8H), 1.23-1.21 (m, 2H), 0.96-0.90 (m, 3H). MS (ESI): $C_{25}H_{38}ClN_3O_4S$ requires 511; found 512 [M+H]$^+$.

Example 104

N-(5-chloro-3-(((S)-4-(cyclopentanecarbonyl)-3-methylpiperazin-1-yl)methyl)-2-methylphenyl)-2-(1,1-dioxidotetrahydrothiophen-3-yl)acetamide, Trifluoroacetic acid salt (E104)

To a solution of N-(5-chloro-3-(((S)-4-(cyclopentanecarbonyl)-3-methylpiperazin-1-yl)methyl)-2-methylphenyl)-2-(tetrahydrothiophen-3-yl)acetamide (D256, 32 mg) in TFA (1 mL) was added 30% hydrogen peroxide (9.11 mg). The mixture was stirred for 10 min, which was diluted with methanol (2 mL) and purified by MDAP to afford the title compound (34 mg) as white solid. $^{1}$H NMR (400 MHz, MeOD-$d_4$): 7.50 (s, 1H), 7.46 (s, 1H), 4.62 (brs, 1H), 4.30-4.10 (m, 3H), 3.67-3.65 (m, 0.5H), 3.55-3.45 (m, 1H), 3.20-3.15 (m, 1H), 3.15-3.00 (m, 4H), 3.00-2.80 (m, 3H), 2.75-2.60 (m, 2.5H), 2.50-2.40 (m, 1H), 2.28 (s, 3H), 1.97-1.55 (m, 10H), 1.38-1.26 (m, 3H). $^{19}$F (376 MHz, MeOD-$d_4$): −77.2. MS (ESI): $C_{25}H_{36}ClN_3O_4S$ requires 509; found 510 [M+H]$^+$.

Examples 105-108

Examples 105-108 were prepared using a similar procedure to that described for E104.

| | | |
|---|---|---|
| E105 | N-(5-chloro-3-(((S)-4-(cyclopentanecarbonyl)-3-methylpiperazin-1-yl)methyl)-2-methylphenyl)-2-(1,1-dioxidotetrahydrothiophen-2-yl)acetamide | |
| E106 | N-(5-chloro-3-(((S)-4-(cyclopentanecarbonyl)-3-methylpiperazin-1-yl)methyl)-2-methylphenyl)-2-(1,1-dioxidotetrahydro-2H-thiopyran-3-yl)acetamide, trifluoroacetic acid salt | |
| E107 | N-(5-chloro-3-(((S)-4-(cyclopentanecarbonyl)-3-methylpiperazin-1-yl)methyl)-2-methylphenyl)-2-(methylsulfonyl)cyclobutanecarboxamide | |
| E108 | (S)—N-(5-chloro-3-((4-(cyclopentanecarbonyl)-3-methylpiperazin-1-yl)methyl)-2-methylphenyl)-3-(methylsulfonyl)cyclobutanecarboxamide | |

| | Structure | Characterization |
|---|---|---|
| E105 | 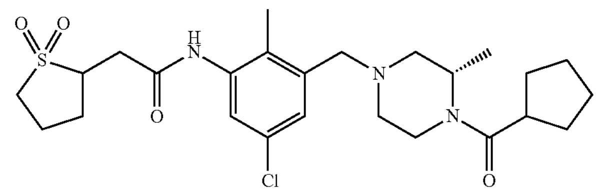 [SMILES: Cc1c(CN2CCN(C(=O)C3CCCC3)[C@@H](C)C2)cc(Cl)cc1NC(=O)CC1CCCS1(=O)=O] | $^1$H NMR (500 MHz, DMSO-d$_6$): 9.63 (s, 1H), 7.41 (d, J = 2.0 Hz, 1H), 7.18 (s, 1H), 4.55 (brs, 0.5H), 4.25-4.20 (m, 1H), 3.76-3.74 (m, 0.5H), 3.44-3.40 (m, 3H), 3.19-3.14 (m, 1.5H), 3.05-2.96 (m, 1H), 2.93-2.84 (m, 2H), 2.73-2.71 (m, 1H), 2.64-2.60 (m, 2H), 2.42-2.36 (m, 1H), 2.19 (s, 3H), 2.10-1.96 (m, 3.5H), 1.69-1.49 (m, 10H), 1.24-1.10 (m, 3H). MS (ESI): C$_{25}$H$_{36}$ClN$_3$O$_4$S requires 509; found 510 [M + H]$^+$. |
| E106 | 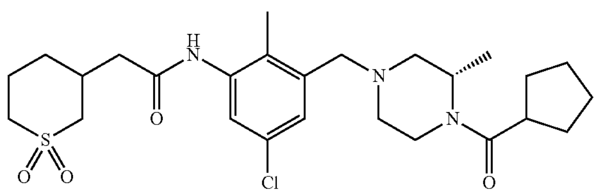 | $^1$H NMR (400 MHz, MeOD-d$_4$): 7.47 (m, 2H), 4.62 (brs, 0.5H), 4.32 (brs, 2H), 4.18-4.14 (m, 0.5H), 3.2-3.46 (m, 0.5H), 3.38-3.32 (m, 2H), 3.14-3.10 (m, 2.5H), 3.02-2.93 (m, 5H), 2.60-2.45 (m, 3H), 2.25 (s, 3H), 2.15-2.11 (m, 1H), 2.00-1.55 (m, 11H), 1.43-1.30 (m, 2H), 1.24-1.21 (m, 2H). $^{19}$F (376 MHz, MeOD-d$_4$): −77.2. MS (ESI): C$_{26}$H$_{38}$ClN$_3$O$_4$S requires 523; found 524 [M + H]$^+$. |
| E107 | 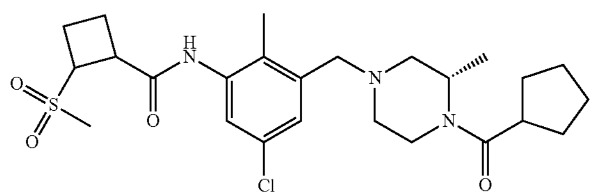 [SMILES: Cc1c(CN2CCN(C(=O)C3CCCC3)[C@@H](C)C2)cc(Cl)cc1NC(=O)C1CCC1S(C)(=O)=O] | $^1$H NMR (400 MHz, CDCl$_3$): 7.91-7.87 (m, 2H), 7.08 (s, 1H), 4.79 (brs, 0.5H), 4.45-4.41 (brs, 0.5H), 4.11-4.03 (m, 1.5H), 3.82-3.78 (q, J = 8.4 Hz, 1H), 3.65 (brs, 0.5H), 3.43-3.27 (m, 2.5H), 2.92 (s, 3H), 2.90-2.68 (m, 2H), 2.65-2.42 (m, 3H), 2.30-2.22 (t, J = 8.8 Hz, 2H), 2.23 (s, 3H), 2.20-2.18 (m, 1.5H), 2.00-1.85 (m, 1H), 1.80-1.62 (m, 8H), 1.31-1.21 (m, 3H). MS (ESI): C$_{25}$H$_{36}$ClN$_3$O$_4$S requires 509; found 510 [M + H]$^+$. |
| E108 | 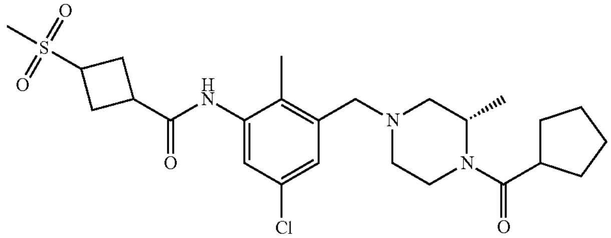 [SMILES: Cc1c(CN2CCN(C(=O)C3CCCC3)[C@@H](C)C2)cc(Cl)cc1NC(=O)C1CC(S(C)(=O)=O)C1] | $^1$H NMR (400 MHz, CDCl$_3$): 7.80 (s, 1H), 7.11 (s, 1H), 7.00 (s, 1H), 4.78 (brs, 1H), 4.74-4.50 (m, 1H), 4.48-4.35 (m, 0.5H), 4.20-4.09 (m, 0.5H), 3.94-3.82 (m, 1H), 3.73-3.62 (m, 0.5H), 3.54-3.28 (m, 3.5H), 3.02-2.91 (m, 1H), 2.86 (s, 3H), 2.84-2.73 (m, 5H), 2.65 (d, J = 8.8 Hz, 1H), 2.31-2.15 (m, 4H), 2.10-1.96 (m, 1H), 1.95-1.52 (m, 7H), 1.37-1.15 (m, 3H). MS (ESI): C$_{25}$H$_{36}$ClN$_3$O$_4$S requires 509; found 510 [M + H]$^+$. |

Example 109

2-(1-acetylpyrrolidin-3-yl)-N-(3-(((S)-4-(cyclopentanecarbonyl)-3-methylpiperazin-1-yl)methyl)-5-fluoro-2-methylphenyl)acetamide (E109)

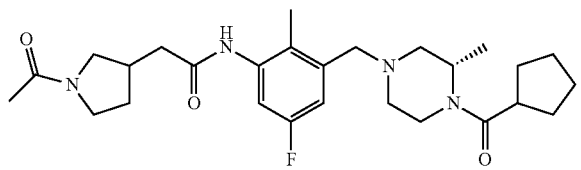 [SMILES: CC(=O)N1CCC(CC(=O)Nc2cc(F)cc(CN3CCN(C(=O)C4CCCC4)[C@@H](C)C3)c2C)C1]

N-(3-(((S)-4-(cyclopentanecarbonyl)-3-methylpiperazin-1-yl)methyl)-5-fluoro-2-methylphenyl)-2-(pyrrolidin-3-yl)acetamide, 2 hydrochloride acid salt (D238, 100 mg) and TEA (0.054 mL) were dissolved in DCM (10 mL). To this solution, acetyl chloride (0.017 mL) was added gradually. The reaction mixture was stirred at RT for 2 hours. Water (10 mL) was added, the DCM layer was separated and the aqueous layer was extracted with DCM (10 mL) again. Combined DCM layers were dried over $Na_2SO_4$. Filtered, the filtrate was concentrated under vacuum. The residue was purified by MADP to afford the title compound (27 mg) as white solid. $^1$H NMR (400 MHz, DMSO-$d_6$): 9.52 (d, J=7.9 Hz, 1H), 7.28 (td, J=10.6, 2.3 Hz, 1H), 7.03 (d, J=8.4 Hz, 1H), 4.61 (brs, 0.5H), 4.26 (d, J=9.5 Hz, 1H), 3.81 (d, J=13.0 Hz, 0.5H), 3.70 (dd, J=10.0, 7.2 Hz, 0.5H), 3.64-3.55 (m, 1H), 3.54-3.43 (m, 3H), 3.32-3.13 (m, 1.5H), 3.05-2.93 (m, 1.5H), 2.89-2.76 (m, 1.5H), 2.74-2.62 (m, 1.5H), 2.55-2.48 (m, 2H), 2.22 (d, J=2.8 Hz, 3H), 2.19-2.02 (m, 2H), 1.99 (s, 3H), 1.96-1.50 (m, 10H), 1.37-1.13 (m, 3H). $^{19}$F NMR (376 MHz, DMSO-$d_6$): −117.9. MS (ESI): $C_{27}H_{39}FN_4O_3$ requires 486; found 487 [M+H]$^+$.

Examples 110-126

Examples 110-126 were prepared using a similar procedure to that described for E109, with the specified reaction base or solvent listed in the table.

E110 (1r,3S)-3-acetamido-N-(3-(((S)-4-(cyclopentanecarbonyl)-3-methylpiperazin-1-yl)methyl)-5-fluoro-2-methylphenyl)cyclobutanecarboxamide, Trifluoroacetic acid salt E111 (1s,3R)-3-acetamido-N-(3-(((S)-4-(cyclopentanecarbonyl)-3-methylpiperazin-1-yl)methyl)-5-fluoro-2-methylphenyl)cyclobutanecarboxamide, Trifluoroacetic acid salt E112 (S)-1-acetyl-N-(3-((4-(cyclopentanecarbonyl)-3-methylpiperazin-1-yl)methyl)-5-fluoro-2-methylphenyl)azetidine-3-carboxamide E113 (S)—N-(5-chloro-3-((4-(cyclopentanecarbonyl)-3-methylpiperazin-1-yl)methyl)-2-methylphenyl)-2-(1-propionylazetidin-3-yl)acetamide E114 (R)-1-acetyl-N-(5-chloro-3-(((S)-4-(cyclopentanecarbonyl)-3-methylpiperazin-1-yl)methyl)-2-methylphenyl)pyrrolidine-3-carboxamide E115 (S)-1-acetyl-N-(5-chloro-3-(((S)-4-(cyclopentanecarbonyl)-3-methylpiperazin-1-yl)methyl)-2-methylphenyl)pyrrolidine-3-carboxamide E116 (R)-1-acetyl-N-(5-chloro-3-(((S)-4-(cyclopentanecarbonyl)-3-methylpiperazin-1-yl)methyl)-2-methylphenyl)pyrrolidine-2-carboxamide E117 (S)-1-acetyl-N-(5-chloro-3-((4-(cyclopentanecarbonyl)-3-methylpiperazin-1-yl)methyl)-2-methylphenyl)piperidine-4-carboxamide E118 (S)-1-acetyl-N-(5-chloro-3-(((S)-4-(cyclopentanecarbonyl)-3-methylpiperazin-1-yl)methyl)-2-methylphenyl)piperidine-3-carboxamide E119 (R)-1-acetyl-N-(5-chloro-3-(((S)-4-(cyclopentanecarbonyl)-3-methylpiperazin-1-yl)methyl)-2-methylphenyl)piperidine-3-carboxamide E120 (S)-1-acetyl-N-(5-chloro-3-(((S)-4-(cyclopentanecarbonyl)-3-methylpiperazin-1-yl)methyl)-2-methylphenyl)pyrrolidine-2-carboxamide E121 (S)—N-(5-chloro-3-(((S)-4-(cyclopentanecarbonyl)-3-methylpiperazin-1-yl)methyl)-2-methylphenyl)-1-propionylpyrrolidine-2-carboxamide E122 (S)—N-(5-chloro-3-(((S)-4-(cyclopentanecarbonyl)-3-methylpiperazin-1-yl)methyl)-2-methylphenyl)-1-isobutyrylpyrrolidine-2-carboxamide E123 (S)-2-(1-acetylpiperidin-4-yl)-N-(5-chloro-3-((4-(cyclopentanecarbonyl)-3-methylpiperazin-1-yl)methyl)-2-methylphenyl)acetamide E124 (S)—N-(5-chloro-3-((4-(cyclopentanecarbonyl)-3-methylpiperazin-1-yl)methyl)-2-methylphenyl)-3-(N-methylacetamido) Propanamide E125 (S)—N-(5-chloro-3-((4-(cyclopentanecarbonyl)-3-methylpiperazin-1-yl)methyl)-2-methylphenyl)-4-(N-methylacetamido) butanamide E126 4-Acetyl-N-(5-chloro-3-(((S)-4-(cyclopentanecarbonyl)-3-methylpiperazin-1-yl)methyl)-2-methylphenyl)morpholine-2-carboxamide, Trifluoroacetic acid salt

| | Structure | Base/Solvent | Characterization |
|---|---|---|---|
| E110 | • TFA | Pyridine/THF | $^1$H NMR (400 MHz, MeOD-$d_4$): 7.29 (dd, J = 9.6, 2.5 Hz, 1H), 7.24 (dd, J = 8.9, 2.5 Hz, 1H), 5.10-4.91 (m, 1.5H), 4.63 (brs, 1H), 4.50 (quin, J = 15.7 Hz, 1H), 4.39 (brs, 2H), 4.19 (d, J = 13.0 Hz, 0.5H), 3.64-3.34 (m, 3.5H), 3.29-2.94 (m, 4.5H), 2.71-2.57 (m, 2H), 2.44-2.30 (m, 2H), 2.30-2.25 (m, 3H), 1.93 (s, 3H), 1.90-1.56 (m, 8H), 1.46-1.20 (m, 3H). MS (ESI): $C_{26}H_{37}FN_4O_3$ requires 472; found 473 [M + H]$^+$. |

| | Structure | Base/Solvent | Characterization |
|---|---|---|---|
| E111 | 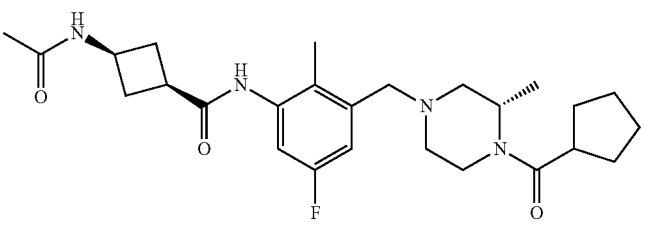 · TFA | Pyridine/THF | $^1$H NMR (400 MHz, MeOD-d$_4$): 7.31 (dd, J = 9.3, 2.4 Hz, 1H), 7.25 (dd, J = 9.0, 2.4 Hz, 1H), 5.08-4.90 (m, 1.5H), 4.64 (brs, 1H), 4.40 (brs, 2H), 4.34-4.10 (m, 1.5H), 3.63-3.34 (m, 2.5H), 3.27-2.95 (m, 4.5H), 2.58 (qd, J = 8.1, 2.7 Hz, 2H), 2.31-2.16 (m, 5H), 1.92 (s, 3H), 1.90-1.55 (m, 8H), 1.51-1.19 (m, 3H). MS (ESI): C$_{26}$H$_{37}$FN$_4$O$_3$ requires 472; found 473 [M + H]$^+$. |
| E112 | 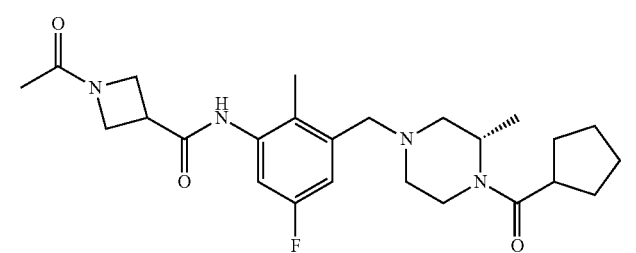 [SMILES: CC(=O)N1CC(C(=O)Nc2cc(F)cc(CN3CCN(C(=O)C4CCCC4)[C@@H](C)C3)c2C)C1] | TEA/DCM | $^1$H NMR (400 MHz, DMSO-d$_6$): 9.50 (s, 1H), 7.19 (dd, J = 10.3, 2.4 Hz, 1H), 6.92 (d, J = 8.1 Hz, 1H), 4.47 (brs, 0.5H), 4.29-4.04 (m, 3H), 4.00-3.79 (m, 2H), 3.68 (d, J = 13.2 Hz, 0.5H), 3.59-3.46 (m, 1H), 3.41-3.30 (m, 2H), 3.19-3.05 (m, 0.5H), 2.91-2.79 (m, 1H), 2.76-2.62 (m, 1.5H), 2.60-2.49 (m, 1H), 2.08 (s, 3H), 2.04-1.72 (m, 2H), 1.69 (s, 3H), 1.67-1.37 (m, 8H), 1.23-0.98 (m, 3H). MS (ESI): C$_{25}$H$_{35}$FN$_4$O$_3$ requires 458; found 459 [M + H]$^+$. |
| E113 | 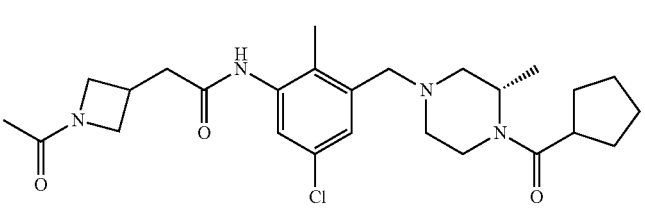 [SMILES: CC(=O)N1CC(CC(=O)Nc2cc(Cl)cc(CN3CCN(C(=O)C4CCCC4)[C@@H](C)C3)c2C)C1] | TEA/DCM | $^1$H NMR (400 MHz, MeOD-d$_4$): 7.35 (d, J = 2.0 Hz, 1H), 7.23 (d, J = 1.8 Hz, 1H), 4.67 (brs, 0.5H), 4.46-4.37 (m, 1H), 4.37-4.25 (m, 1H), 4.18 (t, J = 9.2 Hz, 1H), 4.02 (dd, J = 8.9, 5.7 Hz, 1H), 3.87 (d, J = 13.1 Hz, 0.5H), 3.77 (dd, J = 10.0, 5.7 Hz, 1H), 3.54-3.42 (m, 2H), 3.42-3.31 (m, 0.5H), 3.14-2.91 (m, 2.5H), 2.88-2.66 (m, 4H), 2.27 (s, 3H), 2.23-1.91 (m, 2H), 1.88 (s, 3H), 1.84-1.53 (m, 8H), 1.40-1.16 (m, 3H). MS (ESI): C$_{26}$H$_{37}$ClN$_4$O$_3$ requires 488; found 489 [M + H]$^+$. |
| E114 | 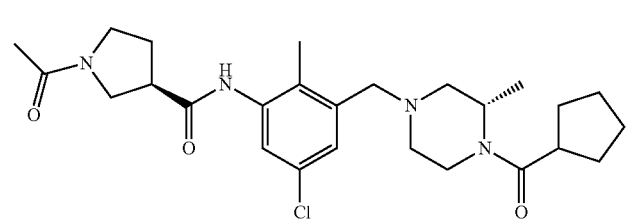 [SMILES: CC(=O)N1CC[C@@H](C(=O)Nc2cc(Cl)cc(CN3CCN(C(=O)C4CCCC4)[C@@H](C)C3)c2C)C1] | TEA/DCM | $^1$H NMR (400 MHz, CDCl$_3$): 7.73 (brs, 1H), 7.24-7.18 (m, 1H), 7.14-7.08 (m, 1H), 4.76 (brs, 0.5H), 4.43-4.37 (m, 0.5H), 4.12 (brs, 0.5H), 3.94-3.61 (m, 3.5H), 3.60-3.26 (m, 4H), 3.22-3.05 (m, 1H), 2.90-2.80 (m, 1.5H), 2.78-2.70 (brs, 1H), 2.65-2.60 (d, J = 9.8 Hz, 1H), 2.47-2.40 (m, 0.5H), 2.31-2.25 (m, 1H), 2.22 (d, J = 6.0 Hz, 3H), 2.20-2.14 (m, 1H), 2.09 (d, J = 6.0 Hz, 3H), 2.03-1.80 (m, 2.5H), 1.80-1.68 (m, 5H), 1.31-1.17 (m, 3H). MS (ESI): C$_{26}$H$_{37}$ClN$_4$O$_3$ requires 488, found 489 [M + H]$^+$. |
| E115 | 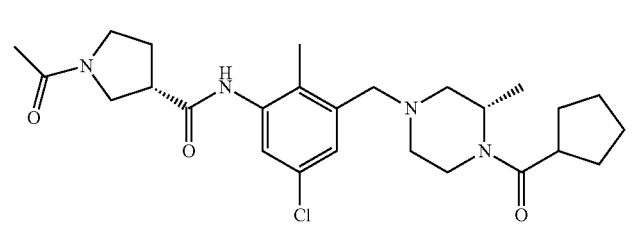 [SMILES: CC(=O)N1CC[C@H](C(=O)Nc2cc(Cl)cc(CN3CCN(C(=O)C4CCCC4)[C@@H](C)C3)c2C)C1] | TEA/DCM | $^1$H NMR (400 MHz, CDCl$_3$): 7.71 (brs, 1H), 7.30-7.26 (m, 1H), 7.12 (brs, 1H), 4.75 (brs, 0.5H), 4.40-4.37 (m, 0.5H), 4.12 (brs, 0.5H), 3.96-3.60 (m, 4H), 3.58-3.28 (m, 4H), 3.22-3.18 (m, 0.5H), 3.12-3.07 (m, 0.5H), 2.90-2.80 (m, 1.5H), 2.75-2.71 (m, 1H), 2.64-2.60 (m, 1H), 2.48-2.41 (m, 0.5H), 2.35-2.25 (m, 1H), 2.22 (d, J = 6.0 Hz, 3H), 2.21-2.17 (m, 1H), 2.08 (d, J = 6.0 Hz, 3H), 2.02-1.96 (m, |

| | Structure | Base/Solvent | Characterization |
|---|---|---|---|
| | | | 1H), 1.96-1.65 (m, 5.5H), 1.57-1.50 (m, 3H), 1.32-1.20 (m, 3H). MS (ESI): $C_{26}H_{37}ClN_4O_3$ requires 488; found 489 [M + H]$^+$. |
| E116 | 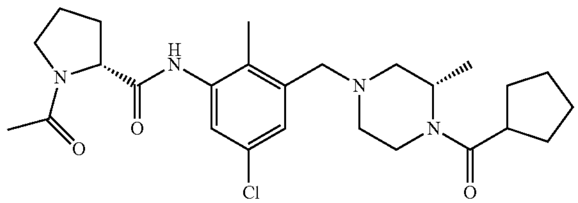 [SMILES: CC(=O)N1CCC[C@@H]1C(=O)Nc1cc(Cl)cc(CN2CCN(C(=O)C3CCCC3)[C@@H](C)C2)c1C] | TEA/DCM | $^1$H NMR (400 MHz, CDCl$_3$): 9.46 (s, 1H), 8.02 (d, J = 2.0 Hz, 1H), 7.03 (s, 1H), 4.84 (d, J = 8.0 Hz, 1H), 4.77 (brs, 0.5H), 4.42-4.38 (m, 0.5H), 4.12 (brs, 0.5H), 3.62-3.50 (m, 1.5H), 3.49-3.45 (m, 1.5H), 3.45-3.30 (m, 2H), 2.91-2.63 (m, 4.5H), 2.25 (s, 3H), 2.19-2.17 (m, 5H), 2.10-1.81 (m, 6H), 1.79-1.76 (m, 5H), 1.31-1.22 (m, 3H). MS (ESI): $C_{26}H_{37}ClN_4O_3$ requires 488; found 489 [M + H]$^+$. |
| E117 | 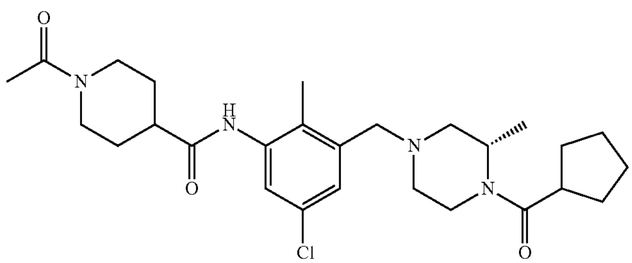 [SMILES: CC(=O)N1CCC(C(=O)Nc2cc(Cl)cc(CN3CCN(C(=O)C4CCCC4)[C@@H](C)C3)c2C)CC1] | No base/THF | $^1$H NMR (400 MHz, CDCl$_3$): 7.75 (brs, 1H), 7.18-7.10 (m, 2H), 4.80-4.64 (m, 1.5H), 4.45-4.38 (m, 0.5H), 4.13 (brs, 0.5H), 3.98-3.88 (m, 1H), 3.70-3.63 (m, 0.5H), 3.43-3.30 (m, 2.5H), 3.20-3.15 (m, 1H), 2.95-2.80 (m, 1.5H), 2.80-2.70 (m, 2H), 2.65-2.56 (m, 2H), 2.30 (s, 3H), 2.20-12.17 (m, 1H), 2.13 (s, 3H), 2.07-1.97 (m, 3H), 1.90-1.61 (m, 8H), 1.60-1.56 (m, 2H), 1.31-1.20 (m, 3H). MS (ESI): $C_{27}H_{39}ClN_4O_3$ requires 502; found 503 [M + H]$^+$. |
| E118 | 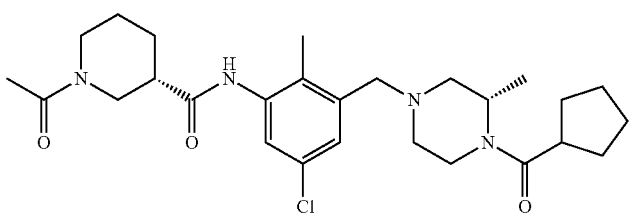 [SMILES: CC(=O)N1CCC[C@H](C(=O)Nc2cc(Cl)cc(CN3CCN(C(=O)C4CCCC4)[C@@H](C)C3)c2C)C1] | No base/THF | $^1$H NMR (400 MHz, CDCl$_3$): 7.98-7.96 (m, 1H), 7.77 (brs, 0.2H), 7.61 (brs, 0.8H), 7.13 (s, 1H), 4.83 (brs, 0.5H), 4.46-4.41 (m, 0.5H), 4.20-4.08 (m, 1.5H), 3.68-3.60 (m, 2H), 3.50-3.25 (m, 3.5H), 2.96-2.77 (m, 3H), 2.70-2.58 (m, 2H), 2.24 (s, 3H), 2.22-2.15 (m, 4H), 2.01-1.95 (m, 2H), 1.87-1.70 (m, 8H), 1.60-1.58 (m, 3H), 1.30-1.20 (m, 3H). MS (ESI): $C_{27}H_{39}ClN_4O_3$ requires 502; found 503 [M + H]$^+$. |
| E119 | 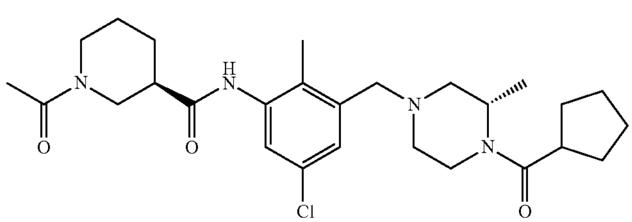 [SMILES: CC(=O)N1CCC[C@@H](C(=O)Nc2cc(Cl)cc(CN3CCN(C(=O)C4CCCC4)[C@@H](C)C3)c2C)C1] | No base/THF | $^1$H NMR (400 MHz, CDCl$_3$): 7.96 (brs, 0.6H), 7.77 (brs, 0.3H), 7.61 (s, 1H), 7.13 (brs, 1.5H), 4.78 (brs, 0.5H), 4.50-4.42 (m, 0.5H), 4.20-4.10 (m, 1H), 3.72-3.58 (m, 2H), 3.50-3.30 (m, 3.5H), 2.90-2.58 (m, 4.5H), 2.25 (brs, 3H), 2.20-2.16 (m, 4H), 2.02-1.96 (m, 2H), 1.87-1.70 (m, 8H), 1.30-1.20 (m, 3H). MS (ESI): $C_{27}H_{39}ClN_4O_3$ requires 502; found 503 [M + H]$^+$. |
| E120 | 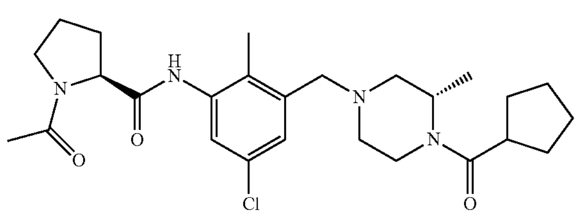 [SMILES: CC(=O)N1CCC[C@H]1C(=O)Nc1cc(Cl)cc(CN2CCN(C(=O)C3CCCC3)[C@@H](C)C2)c1C] | TEA/DCM | $^1$H NMR (400 MHz, CDCl$_3$): 9.46 (s, 1H), 8.02 (brs, 1H), 7.02 (d, J = 6.0 Hz 1H), 4.82 (d, J = 7.6 Hz, 1H), 4.76 (brs, 0.5H), 4.38-4.12 (m, 0.5H), 4.11 (brs, 0.5H), 3.62-3.57 (m, 1.5H), 3.51-3.46 (m, 1.5H), 3.37-3.30 (m, 2H), 2.90-2.64 (m, 4.5H), 2.25 (s, 3H), 2.15-2.13 (m, 5H), 2.09-2.00 (m, 1H), 1.97-1.74 (m, 8.5H), 1.66-1.50 (m, 2.5H), 1.31-1.22 (m, 3H). MS(ESI): $C_{26}H_{37}ClN_4O_3$ requires 488; found 489 [M + H]$^+$. |

-continued

| | Structure | Base/Solvent | Characterization |
|---|---|---|---|
| E121 | 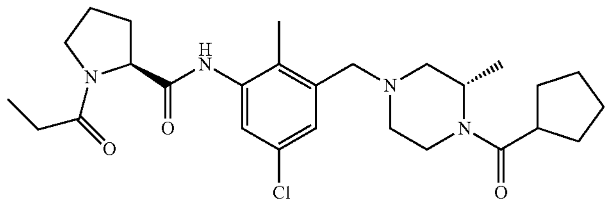 [SMILES: CCC(=O)N1CCC[C@H]1C(=O)Nc1cc(Cl)cc(CN2CCN(C(=O)C3CCCC3)[C@@H](C)C2)c1C] | TEA/DCM | $^1$H NMR (400 MHz, CDCl$_3$): 9.48 (d, J = 3.2 Hz, 1H), 8.02 (d, J = 4.8 Hz, 1H), 7.03 (d, J = 7.6 Hz, 1H), 4.87 (d, J = 8.0 Hz, 1H), 4.76 (brs, 0.5H), 4.42-4.38 (m, 0.5H), 4.11 (brs, 0.5H), 3.66-3.32 (m, 5H), 2.92-2.75 (m, 2.5H), 2.65-2.63 (m, 2H), 2.42-2.39 (m, 2H), 2.24 (s, 3H), 2.19-1.96 (m, 4H), 1.85-1.75 (m, 7H), 1.57-1.50 (m, 2H), 1.30 (d, J = 6.4 Hz, 1.5H), 1.22-1.18 (m, 4.5H). MS (ESI): C$_{27}$H$_{39}$ClN$_4$O$_3$ requires 502; found 503 [M + H]$^+$. |
| E122 | 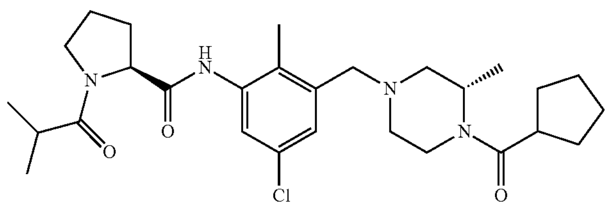 [SMILES: Cc1c(CN2CCN(C(=O)C3CCCC3)[C@@H](C)C2)cc(Cl)cc1NC(=O)[C@@H]1CCCN1C(=O)C(C)C] | TEA/DCM | $^1$H NMR (400 MHz, CDCl$_3$): 9.48 (d, J = 32 Hz, 1H), 7.99 (d, J = 6.4 Hz, 1H), 7.03 (d, J = 6.4 Hz, 1H), 4.87 (d, J = 7.2 Hz, 1H), 4.76 (brs, 0.5H), 4.42-4.38 (m, 0.5H), 4.10 (brs, 0.5H), 3.63-3.60 (m, 1.5H), 3.57-3.53 (m, 1H), 3.43-3.30 (m, 2.5H), 2.91-2.72 (m, 3.5H), 2.65-2.60 (m, 2H), 2.23 (s, 3H), 2.16-2.09 (m, 3H), 1.98-1.62 (m, 8H), 1.56-1.50 (m, 2H), 1.28 (d, J = 6.4 Hz, 1.5H), 1.21-1.15 (m, 7.5H). MS (ESI): C$_{28}$H$_{41}$ClN$_4$O$_3$ requires 516; found 517 [M + H]$^+$. |
| E123 | 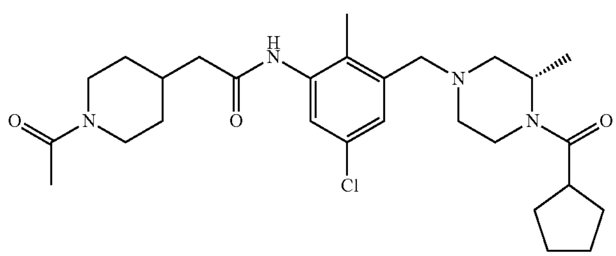 [SMILES: CC(=O)N1CCC(CC(=O)Nc2cc(Cl)cc(CN3CCN(C(=O)C4CCCC4)[C@@H](C)C3)c2C)CC1] | TEA/DCM | $^1$H NMR (400 MHz, MeOD-d$_4$): 7.35 (brs, 1H), 7.25 (brs, H), 4.69 (brs, 0.5H), 4.55 (d, J = 13.0 Hz, 1H), 4.41-4.24 (m, 1H), 4.03-3.76 (m, 1.5H), 3.50 (brs, 2H), 3.39 (d, J = 12.3 Hz, 0.5H), 3.16 (t, J = 12.1 Hz, 1H), 3.10-2.58 (m, 4.5H), 2.48-2.35 (m, 2H), 2.31-2.24 (m, 3H), 2.23-2.00 (m, 6H), 1.98-1.50 (m, 10H), 1.43-1.12 (m, 5H). MS (ESI): C$_{28}$H$_{41}$ClN$_4$O$_3$ requires 516; found 517 [M + H]$^+$. |
| E124 | 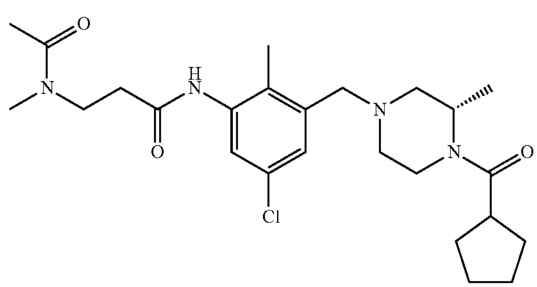 [SMILES: CC(=O)N(C)CCC(=O)Nc1cc(Cl)cc(CN2CCN(C(=O)C3CCCC3)[C@@H](C)C2)c1C] | TEA/DCM | $^1$H NMR (400 MHz, MeOD-d$_4$): 7.32 (d, J = 12.0 Hz, 1H), 7.21 (brs, 1H), 4.66 (brs, 1H), 4.31 (d, J = 14.3 Hz, 1H), 3.89-3.63 (m, 2.5H), 3.56-3.36 (m, 2H), 3.12 (s, 2H), 3.05-2.88 (m, 2.5H), 2.86-2.54 (m, 4H), 2.36-1.98 (m, 8H), 1.96-1.47 (m, 8H), 1.43-1.12 (m, 3H). MS (ESI): C$_{25}$H$_{37}$ClN$_4$O$_3$ requires 476; found 477 [M + H]$^+$. |
| E125 | 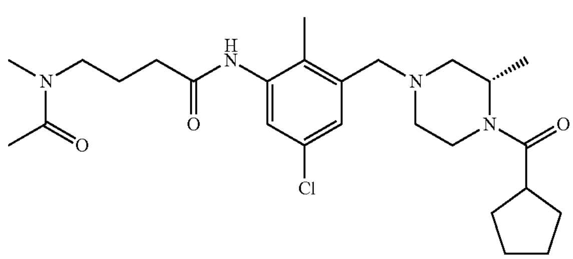 [SMILES: CC(=O)N(C)CCCC(=O)Nc1cc(Cl)cc(CN2CCN(C(=O)C3CCCC3)[C@@H](C)C2)c1C] | TEA/DCM | $^1$H NMR (400 MHz, MeOD-d$_4$): 7.36 (d, J = 3.4 Hz, 1H), 7.21 (brs, 1H), 4.66 (brs, 0.5H), 4.41-4.18 (m, 1H), 3.83 (d, J = 12.5 Hz, 0.5H), 3.52-3.34 (m, 4.5H), 3.15-2.85 (m, 4.5H), 2.82 (d, J = 11.0 Hz, 1H), 2.71 (t, J = 9.4 Hz, 1H), 2.53-2.35 (m, 2H), 2.26 (s, 3H), 2.22-1.50 (m, 15H), 1.43-1.08 (m, 3H). MS (ESI): C$_{26}$H$_{39}$ClN$_4$O$_3$ requires 490; found 491 [M + H]$^+$. |

| | Structure | Base/Solvent | Characterization |
|---|---|---|---|
| E126 | 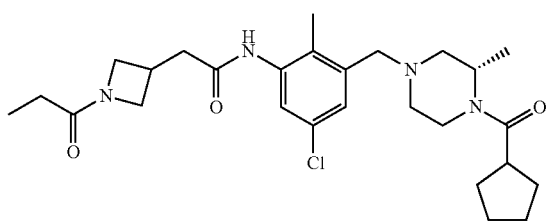 [SMILES: CCC(=O)N1CC(CC(=O)Nc2cc(Cl)cc(CN3CCN(C(=O)C4CCCC4)[C@@H](C)C3)c2C)C1] | TEA/THF | $^1$H NMR (400 MHz, MeOD-d$_4$): 7.66 (brs, 1H), 7.57 (brs, 1H), 4.81-4.59 (m, 1.5H), 4.52-4.42 (m, 2H), 4.38-3.99 (m, 3.5H), 3.92-3.36 (m, 5H), 3.30-2.95 (m, 4H), 2.93-2.78 (m, 1H), 2.31 (brs, 3H), 2.17 (s, 3H), 1.99-1.54 (m, 8H), 1.53-1.08 (m, 3H). $^{19}$F NMR (376 MHz, MeOD-d$_4$): −77.3. MS (ESI): C$_{26}$H$_{37}$ClN$_4$O$_4$ requires 504; found 505 [M + H]$^+$. |

Example 127

(S)-2-(1-acetylazetidin-3-yl)-N-(5-chloro-3-((4-(cyclopentanecarbonyl)-3-methylpiperazin-1-yl)methyl)-2-methylphenyl)acetamide (E127)

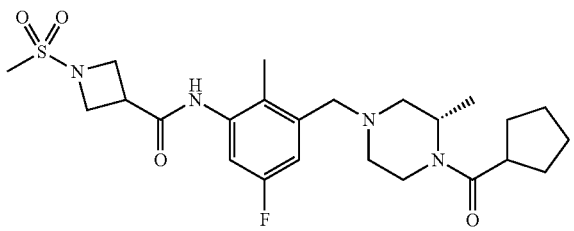 [SMILES: Cc1c(CN2CCN(C(=O)C3CCCC3)[C@@H](C)C2)cc(F)cc1NC(=O)C1CN(S(C)(=O)=O)C1]

To a solution of (S)-2-(azetidin-3-yl)-N-(5-chloro-3-((4-(cyclopentanecarbonyl)-3-methylpiperazin-1-yl)methyl)-2-methylphenyl)acetamide, Trifluoroacetic acid salt (D235, 54.9 mg) in acetonitrile (2 mL), Et$_3$N (41 µL) was added by pipette, followed by propionyl chloride (15 µL). The reaction mixture was stirred for 1 hour at RT. The mixture was sent to MDAP for purification (basic eluent), giving the title compound (21.6 mg) as white solid. $^1$H NMR (400 MHz, MeOD-d$_4$): 7.32 (s, 1H), 7.21 (s, 1H), 4.66 (brs, 0.5H), 4.38 (t, J=8.6 Hz, 1H), 4.34-4.24 (m, 1H), 4.16 (t, J=9.2 Hz, 1H), 3.99 (dd, J=8.6, 5.9 Hz, 1H), 3.83 (d, J=13.9 Hz, 0.5H), 3.75 (dd, J=9.8, 5.9 Hz, 1H), 3.40-3.53 (m, 2H), 3.40-3.34 (m, 0.5H), 3.14-2.90 (m, 2.5H), 2.88-2.75 (m, 3H), 2.75-2.66 (m, 1H), 2.25 (s, 3H), 2.20-1.50 (m, 12H), 1.40-1.15 (m, 3H), 1.09 (t, J=7.5 Hz, 3H). MS (ESI): C$_{27}$H$_{39}$ClN$_4$O$_3$ requires 502; found 503 [M+H]$^+$.

Example 128

(S)—N-(3-((4-(cyclopentanecarbonyl)-3-methylpiperazin-1-yl)methyl)-5-fluoro-2-methylphenyl)-1-(methylsulfonyl)azetidine-3-carboxamide (E128)

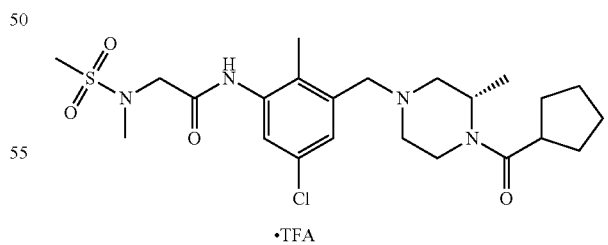

(S)—N-(3-((4-(cyclopentanecarbonyl)-3-methylpiperazin-1-yl)methyl)-5-fluoro-2-methylphenyl)azetidine-3-carboxamide (D241, 100 mg) and TEA (0.05 mL) were dissolved in DCM (10 mL). To this solution, MsCl (0.022 mL) was added gradually. The reaction mixture was stirred at RT for 1 hour. Water (10 mL) was added into the reaction mixture to quench the reaction. The DCM layer was separated and the aqueous layer was extracted with DCM (10 mL) again. Combined DCM layer was dried over Na$_2$SO$_4$ and filtered. The filtrate was concentrate under vacuum. The residue was purified by MADP to afford the title compound (53 mg) as white solid. $^1$H NMR (400 MHz, DMSO-d$_6$): 9.51 (s, 1H), 7.21 (dd, J=10.3, 2.4 Hz, 1H), 6.92 (d, J=8.4 Hz, 1H), 4.47 (brs, 0.5H), 4.20-4.07 (m, 1H), 4.03-3.91 (m, 4H), 3.68 (d, J=12.5 Hz, 0.5H), 3.56 (quin, J=7.6 Hz, 1H), 3.40-3.30 (m, 2H), 3.12 (t, J=12.0 Hz, 0.5H), 2.96 (s, 3H), 2.85 (quin, J=7.2 Hz, 1H), 2.77-2.49 (m, 2.5H), 2.09 (s, 3H), 2.05-1.37 (m, 10H), 1.23-0.99 (m, 3H). $^{19}$F NMR (376 MHz, DMSO-d$_6$): −117.8. MS (ESI): C$_{24}$H$_{35}$FN$_4$O$_4$S requires 494; found 495 [M+H]$^+$.

Example 129

(S)—N-(5-chloro-3-((4-(cyclopentanecarbonyl)-3-methylpiperazin-1-yl)methyl)-2-methylphenyl)-2-(N-methylmethylsulfonamido)acetamide, Trifluoroacetic acid salt

·TFA

E129 was prepared using a similar procedure to that described for E128. $^1$H NMR (400 MHz, MeOD-d$_4$): 7.53 (d, J=1.8 Hz, 1H), 7.41 (s, 1H), 4.88 (brs, 0.5H), 4.52 (brs, 1H), 4.26 (brs, 2H), 4.13-3.98 (m, 2.5H), 3.51-3.23 (m, 3H), 3.18-2.78 (m, 10H), 2.21 (s, 3H), 1.90-1.46 (m, 8H), 1.40-1.08 (m, 3H). MS (ESI): C$_{23}$H$_{35}$ClN$_4$O$_4$S requires 498; found 499 [M+H]$^+$.

Examples 130 & 131

2-(1-acetylpyrrolidin-3-yl)-N-(5-chloro-3-(((S)-4-(cyclopentanecarbonyl)-3-methylpiperazin-1-yl)methyl)-2-methylphenyl)acetamide & 2-(1-acetylpyrrolidin-3-yl)-N-(5-chloro-3-(((S)-4-(cyclopentanecarbonyl)-3-methylpiperazin-1-yl)methyl)-2-methylphenyl)acetamide (E130 & E131)

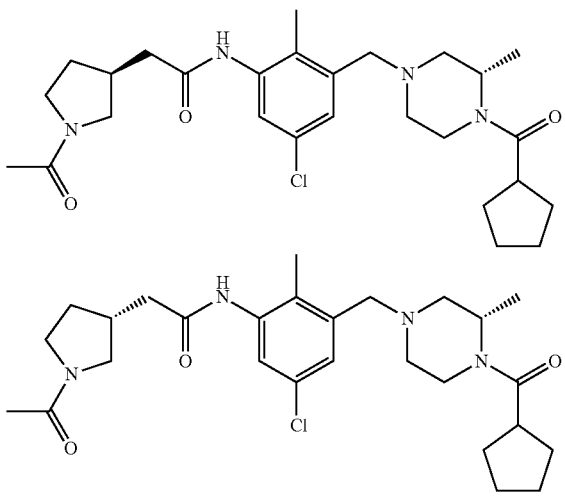

To a solution of N-(5-chloro-3-(((S)-4-(cyclopentanecarbonyl)-3-methylpiperazin-1-yl)methyl)-2-methylphenyl)-2-(pyrrolidin-3-yl)acetamide (D225, 120 mg) in DCM (10 mL) were added acetyl chloride (20.43 mg) and triethylamine (79 mg). After stirred for 2 hours, the mixture was concentrated to give a white solid, which was purified by preparative chiral HPLC (OZ-H column (5 μm, 4.6×250 mm) at a column temperature of 40° C. with 10 mM DEA buffer/n-hexane and 10 mM DEA buffer/EtOH as mobile phase with a flow rate of 60 g/min) to give the title compounds (10 mg and 12 mg). Isomer 1: $^1$H NMR (400 MHz, CDCl$_3$): 7.77-7.73 (m, 1H), 7.13-7.07 (m, 2H), 4.76 (brs, 0.5H), 4.45-4.36 (m, 0.5H), 4.12 (brs, 0.5H), 3.83-3.75 (m, 1H), 3.70-3.54 (m, 1.5H), 3.50-3.26 (m, 4H), 3.22-3.10 (m, 1H), 2.93-2.70 (m, 3.5H), 2.64-2.40 (m, 3H), 2.35-2.26 (m, 0.5H), 2.22 (s, 3H), 2.20-2.13 (m, 2H), 2.06 (s, 3H), 1.96-2.02 (m, 2H), 1.90-1.68 (m, 7H), 1.31-1.20 (m, 3H). MS (ESI): C$_{27}$H$_{39}$ClN$_4$O$_3$ requires 502, found 503 [M+H]$^+$. Isomer 2: $^1$H NMR (400 MHz, CDCl$_3$): 7.77-7.71 (m, 1H), 7.23-7.14 (brs, 1H), 7.10 (brs, 1H), 4.76 (brs, 0.5H), 4.12 (brs, 0.5H), 4.06-3.97 (m, 0.5H), 3.83-3.76 (m, 1H), 3.70-3.54 (m, 1.5H), 3.50-3.26 (m, 4H), 3.22-3.11 (m, 1H), 2.94-2.70 (m, 3.5H), 2.64-2.42 (m, 3H), 2.35-2.27 (m, 0.5H), 2.23 (s, 3H), 2.20-2.13 (m, 2H), 2.05 (s, 3H), 2.02-1.94 (m, 2H), 1.90-1.66 (m, 7H), 1.33-1.19 (m, 3H). MS (ESI): C$_{27}$H$_{39}$ClN$_4$O$_3$ requires 502, found 503 [M+H]$^+$.

Examples 132-135

Examples 132-135 were prepared using a similar procedure to that described for E130 and E131, with the specified reaction base or solvent listed in the table.

E132&E133: 2-((R)-1-acetylpyrrolidin-2-yl)-N-(5-chloro-3-(((S)-4-(cyclopentanecarbonyl)-3-methylpiperazin-1-yl)methyl)-2-methylphenyl)acetamide & 2-((S)-1-acetylpyrrolidin-2-yl)-N-(5-chloro-3-(((S)-4-(cyclopentanecarbonyl)-3-methylpiperazin-1-yl)methyl)-2-methylphenyl)acetamide E134&E135 2-((S)-1-acetylpiperidin-3-yl)-N-(5-chloro-3-(((S)-4-(cyclopentanecarbonyl)-3-methylpiperazin-1-yl)methyl)-2-methylphenyl)acetamide & 2-((R)-1-acetylpiperidin-3-yl)-N-(5-chloro-3-(((S)-4-(cyclopentanecarbonyl)-3-methylpiperazin-1-yl)methyl)-2-methylphenyl)acetamide

| | Structure | Base/Solvent | Characterization |
|---|---|---|---|
| E132 & E133 | (structure shown) | No base/THF | Isomer 1: $^1$H NMR (400 MHz, CDCl$_3$): 8.86-8.82 (m, 1H), 7.79 (s, 1H), 7.07 (s, 1H), 4.80 (brs, 0.5H), 4.45-4.34 (m, 1.5H), 4.13 (brs, 0.5H), 3.68-3.55 (m, 2H), 3.50-3.33 (m, 4H), 2.93-2.70 (m, 4H), 2.64-2.60 (m, 1H), 2.51-2.47 (m, 1H), 2.29 (s, 3H), 2.19-2.16 (m, 1.5H), 2.11-2.08 (m, 5H), 2.00-1.83 (m, 4H), 1.80-1.72 (m, 5H), 1.32-1.22 (m, 3H). MS (ESI): C$_{27}$H$_{39}$ClN$_4$O$_3$ requires 502; found 503 [M + H]$^+$. Isomer 2: $^1$H NMR (400 MHz, CDCl$_3$): 8.80 (brs, 1H), 7.81 (brs, 1H), 7.07 (brs, 1H), 4.87 (brs, 0.5H), 4.45-4.34 (m, 1.5H), 4.17 (brs, 0.5H), 3.68-3.60 (m, 2H), 3.50-3.33 (m, 4H), 2.99-2.75 (m, 4H), 2.65-2.60 (brs, 1H), 2.51-2.45 (m, 1H), 2.30 (s, 3H), 2.30-2.25 (m, 1.5H), 2.15-2.05 (m, 5H), 2.00-1.83 (m, 4H), 1.80-1.58 (m, 5H), 1.32-1.22 (m, 3H). MS (ESI): C$_{27}$H$_{39}$ClN$_4$O$_3$ requires 502; found 503 [M + H]$^+$. |

| | Structure | Base/Solvent | Characterization |
|---|---|---|---|
| E134 & E135 | | TEA/DCM | Isomer 1: ¹H NMR (400 MHz, CDCl₃): 8.46 (brs, 1H), 7.73-7.64 (m, 1H), 7.12 (brs, 1H), 4.77 (brs, 0.5H), 4.43-4.38 (m, 0.5H), 4.26-4.13 (m, 0.5H), 3.90-3.85 (m, 1H), 3.64-3.58 (m, 1.5H), 3.46-3.32 (m, 4H), 2.91-2.75 (m, 3.5H), 2.68-2.65 (m, 1H), 2.51-2.37 (m, 1H), 2.28 (s, 3H), 2.18 (s, 3H), 2.21-2.17 (m, 3.5H), 1.99-1.58 (m, 12H), 1.34-1.21 (m, 3H). MS (ESI): C₂₈H₄₁ClN₄O₃ requires 516; found 517 [M + H]⁺. Isomer 2: ¹H NMR (400 MHz, CDCl₃): 846 (brs, 1H), 7.72-7.65 (m, 1H), 7.11 (brs, 1H), 4.78 (brs, 0.5H), 4.43-4.38 (m, 0.5H), 4.25-4.14 (m, 0.5H), 3.90-3.83 (m, 1H), 3.69-3.60 (m, 1.5H), 3.47-3.30 (m, 4H), 2.98-2.85 (m, 3.5H), 2.67-2.60 (m, 1H), 2.47-2.37 (m, 1H), 2.28 (s, 3H), 2.18 (s, 3H), 2.21-2.18 (m, 3.5H), 2.00-1.48 (m, 12H), 1.34-1.23 (m, 3H). MS (ESI): C₂₈H₄₁ClN₄O₃ requires 516; found 517 [M + H]⁺. |

Example 136

(S)—N⁵-(5-chloro-3-((4-(cyclopentanecarbonyl)-3-methylpiperazin-1-yl)methyl)-2-methylphenyl)pyridine-2,5-dicarboxamide (E136)

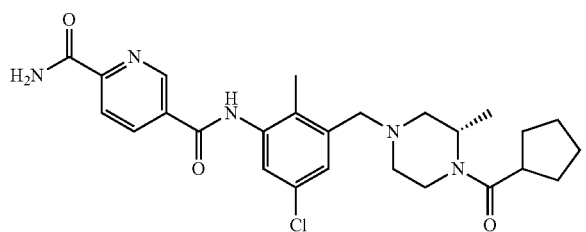 [SMILES: Cc1c(CN2CCN(C(=O)C3CCCC3)[C@@H](C)C2)cc(Cl)cc1NC(=O)c1ccc(C(N)=O)nc1]

6-Carbamoylnicotinic acid (D122, 100 mg) and DIPEA (0.150 mL) were dissolved in DMF (3 mL). To this solution, HATU (217 mg) was added gradually. The reaction mixture was stirred at RT for 1 hour, then (S)-(4-(3-amino-5-chloro-2-methylbenzyl)-2-methylpiperazin-1-yl)(cyclopentyl)methanone (D157, 100 mg) was added into the mixture, which was stirred at RT for 2 days. Water (10 mL) was added, extracted with EtOAc (2×10 mL), the organic layer was dried over Na₂SO₄. Filtered, the filtrate was concentrated under vacuum. The residue was purified by MADP to afford the title compound (30 mg) as white solid. ¹H NMR (400 MHz, DMSO-d₆): 10.32 (s, 1H), 9.14 (d, J=0.9 Hz, 1H), 8.48 (dd, J=8.1, 1.8 Hz, 1H), 8.27 (brs, 1H), 8.18 (d, J=8.1 Hz, 1H), 7.81 (brs, 1H), 7.43 (d, J=2.0 Hz, 1H), 7.29 (s, 1H), 4.56 (brs, 0.5H), 4.21 (d, J=8.6 Hz, 1H), 3.77 (d, J=12.5 Hz, 0.5H), 3.53-3.41 (m, 2H), 3.19 (t, J=11.6 Hz, 0.5H), 2.92 (quin, J=7.4 Hz, 1H), 2.84-2.70 (m, 1.5H), 2.64 (d, J=9.0 Hz, 1H), 2.24 (s, 3H), 2.18-1.42 (m, 10H), 1.30-1.04 (m, 3H). MS (ESI): C₂₆H₃₂ClN₅O₃ requires 497; found 496 [M–H]⁻.

Examples 137-138

Examples 137-138 were prepared using a similar procedure to that described for E136.

E137 (S)—N-(3-((4-(cyclopentanecarbonyl)-3-methylpiperazin-1-yl)methyl)-5-fluoro-2-methylphenyl)pyridine-2,5-dicarboxamide E138 (S)—N⁵-(5-chloro-3-((4-(2-cyclopropylacetyl)-3-methylpiperazin-1-yl)methyl)-2-methylphenyl)pyridine-2,5-dicarboxamide

| | Structure | Base/Solvent | Characterization |
|---|---|---|---|
| E137 | 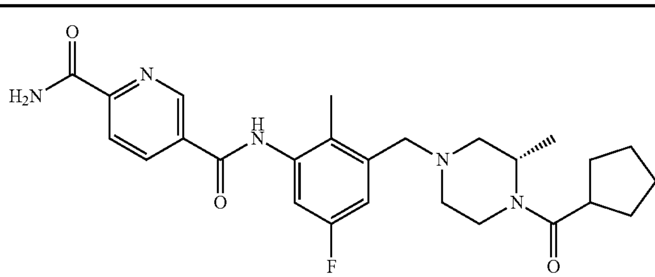 | DIPEA/DMF | ¹H NMR (400 MHz, DMSO-d₆): 10.58 (s, 1H), 9.20 (s, 1H), 8.54 (d, J = 6.4 Hz, 1H), 8.27 (s, 1H), 8.16 (d, J = 8.4 Hz, 1H), 7.82 (s, 1H), 7.19 (dd, J = 10.0 Hz, 3.2 Hz, 1H), 7.09 (d, J = 8.8 Hz, 1H), 4.56 (brs, 0.5H), 4.23-4.19 (m, 1H), 3.78-3.74 (m, 0.5H), 3.50-3.45 (m, 2H), 2.95-2.90 (m, 1H), 2.77-2.74 (m, 1H), 2.69-2.63 (m, 1H), 2.21 (s, 3H), 2.17-1.49 (m, 11H), 1.26-1.04 (m, 3H). MS (ESI): C₂₆H₃₂FN₅O₃ requires 481; found 482 [M + H]⁺. |

| Structure | Base/Solvent | Characterization |
|---|---|---|
| E138 | DIPEA/DMF | $^1$H NMR (400 MHz, DMSO-$d_6$): 10.33 (s, 1H), 9.14 (s, 1H), 8.48 (dd, J = 8.0, 1.8 Hz, 1H), 8.29 (brs, 1H), 8.18 (d, J = 8.3 Hz, 1H), 7.82 (brs, 1H), 7.43 (d, J = 1.8 Hz, 1H), 7.29 (s, 1H), 4.56 (brs, 0.5H), 4.20 (d, J = 12.5 Hz, 0.5H), 4.06 (brs, 0.5H), 3.63 (d, J = 13.6 Hz, 0.5H), 3.53-3.41 (m, 2H), 3.19 (t, J = 11.8 Hz, 0.5H), 2.83-2.69 (m, 1.5H), 2.63 (d, J = 11.0 Hz, 1H), 2.41-1.83 (m, 7H), 1.29-1.06 (m, 3H), 1.01-0.87 (m, 1H), 0.49-0.37 (m, 2H), 0.16-0.03 (m, 2H). MS (ESI): $C_{25}H_{30}ClN_5O_3$ requires 483; found 484 [M + H]$^+$. |

Example 139

(S)—N$^5$-(3-((4-(cyclopentanecarbonyl)-3-methylpiperazin-1-yl)methyl)-5-fluoro-2-methylphenyl)-N$^2$-methylpyridine-2,5-dicarboxamide, Trifluoroacetic acid salt (E139)

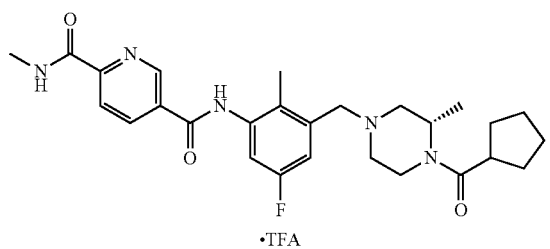 [SMILES: CNC(=O)c1ccc(C(=O)Nc2cc(F)cc(CN3CCN(C(=O)C4CCCC4)[C@@H](C)C3)c2C)cn1 ; "·TFA"]

(S)-5-((3-((4-(cyclopentanecarbonyl)-3-methylpiperazin-1-yl)methyl)-5-fluoro-2-methylphenyl)carbamoyl)picolinic acid, Trifluoroacetic acid salt (D258, 80 mg) and DIPEA (0.070 mL) were dissolved in DMF (3 mL). To this solution, HATU (82 mg) was added gradually. The reaction mixture was stirred at RT for 10 min. Then methanamine, hydrochloride acid salt (14.49 mg) was added into the mixture, which was stirred at RT overnight. Water (1 mL) was added, extracted with EtOAc (2×10 mL), the organic layer was dried over $Na_2SO_4$. Filtered, the filtrate was concentrated under vacuum. The residue was purified by MADP to afford the title compound (27 mg) as white solid. $^1$H NMR (400 MHz, MeOD-$d_4$): 9.17 (d, J=1.6 Hz, 1H), 8.49 (dd, J=8.1, 2.2 Hz, 1H), 8.28-8.17 (m, 1H), 7.41-7.33 (m, 2H), 4.98 (brs, 0.5H), 4.67 (brs, 1H), 4.45 (brs, 2H), 4.20 (d, J=13.1 Hz, 0.5H), 3.66-3.37 (m, 2.5H), 3.29-3.01 (m, 3.5H), 3.00 (s, 3H), 2.35 (s, 3H), 2.03-1.55 (m, 8H), 1.50-1.20 (m, 3H). $^{19}$F NMR (376 MHz, MeOD-$d_4$): −77.2, −116.9. MS (ESI): $C_{27}H_{34}FN_5O_3$ requires 495; found 496 [M+H]$^+$.

Example 140

(S)—N-(5-cyano-3-((4-(cyclobutanecarbonyl)-3-methylpiperazin-1-yl)methyl)-2-methylphenyl)-6-methylnicotinamide (E140)

To a solution of (S)-4-(5-cyano-2-methyl-3-(6-methylnicotinamido)benzyl)-2-methylpiperazin-1-ium, 2 hydrochloride acid salt (D245, 50 mg) and triethylamine (55.5 mg) in DCM (4 mL), cyclobutanecarbonyl chloride (32.5 mg) was added at RT. The reaction mixture was stirred for 1 hour at RT. Solvent was removed under vacuum, the crude product was purified by MDAP to afford the title compound (26.3 mg). $^1$H NMR (400 MHz, DMSO-$d_6$): 10.22 (s, 1H), 9.03 (s, 1H), 8.21 (d, J=8.3 Hz, 1H), 7.77 (s, 1H), 7.63 (s, 1H), 7.44 (d, J=7.8 Hz, 1H), 4.51 (brs, 0.5H), 4.16 (d, J=12.3 Hz, 0.5H), 3.91 (brs, 0.5H), 3.56-3.40 (m, 2.5H), 3.11 (t, J=12.8 Hz, 0.5H), 2.84-2.58 (m, 3.5H), 2.56 (s, 3H), 2.32 (s, 3H), 2.25-1.65 (m, 8H), 1.24-1.07 (m, 3H). MS (ESI): $C_{26}H_{31}N_5O_2$ requires 445; found 446 [M+H]$^+$.

Examples 141-145

Examples 141-145 were prepared using a similar procedure to that described for E140, with the specified reaction base or solvent listed in the table.

E141 (S)—N-(5-cyano-3-((4-(cyclopentanecarbonyl)-3-methylpiperazin-1-yl)methyl)-2-methylphenyl)-2-methylpyrimidine-5-carboxamide E142 (S)-3-cyano-N-(5-cyano-3-((4-(cyclopentanecarbonyl)-3-methylpiperazin-1-yl)methyl)-2-methylphenyl)benzamide E143 (S)-5-chloro-N-(5-fluoro-3-((4-isobutyryl-3-methylpiperazin-1-yl)methyl)-2-methylphenyl)-6-methylnicotinamide E144 (S)—N-(3-((4-butyryl-3-methylpiperazin-1-yl)methyl)-5-fluoro-2-methylphenyl)-5-chloro-6-methylnicotinamide E145 (S)-5-chloro-N-(5-chloro-3-((4-(cyclopropanecarbonyl)-3-methylpiperazin-1-yl)methyl)-2-methylphenyl)-6-methylnicotinamide

| | Structure | Base/Solvent | Characterization |
|---|---|---|---|
| E141 | 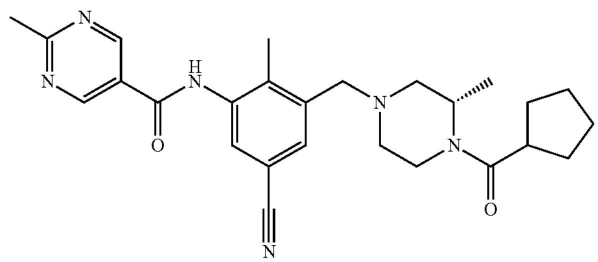 [SMILES: Cc1ncc(C(=O)Nc2cc(C#N)cc(CN3CCN(C(=O)C4CCCC4)[C@@H](C)C3)c2C)cn1] | TEA/DCM | $^1$H NMR (400 MHz, DMSO-d$_6$): 10.39 (s, 1H), 9.20 (s, 2H), 7.81 [d, J = 1.6 Hz, 1H), 7.66 (s, 1H), 4.56 (brs, 0.5H), 4.23-4.20 (m, 1H), 3.80-3.70 (m, 0.5H), 3.56-3.48 (m, 2H), 3.25-3.15 (m, 0.5H), 2.95-2.91 (m, 1H), 2.85-2.62 (m, 5.5H), 2.35 (s, 3H), 2.25-1.45 (m, 10H), 1.25-1.15 (m, 3H). MS (ESI): C$_{26}$H$_{32}$N$_6$O$_2$ requires 460; found 461 [M + H]+. |
| E142 | 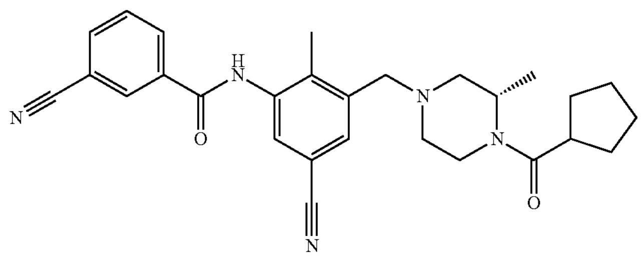 [SMILES: Cc1c(CN2CCN(C(=O)C3CCCC3)[C@@H](C)C2)cc(C#N)cc1NC(=O)c1cccc(C#N)c1] | TEA/DCM | $^1$H NMR (400 MHz, MeOD-d$_4$): 8.25 (s, 1H), 8.18 (d, J = 7.9 Hz, 1H), 7.88 (d, J = 7.8 Hz, 1H), 7.71-7.57 (m, 2H), 7.54 (s, 1H), 4.64-4.52 (m, 0.5H), 4.30-4.09 (m, 1H), 3.76 (d, J = 13.2 Hz, 0.5H), 3.59-3.38 (m, 2H), 3.33-3.24 (brs, 0.5H), 3.02-2.50 (m, 3.5H), 2.32 (s, 3H), 2.21-1.41 (m, 10H), 1.31-1.09 (m, 3H). MS (ESI): C$_{28}$H$_{31}$N$_5$O$_2$ requires 469; found 470 [M + H]$^+$. |
| E143 | 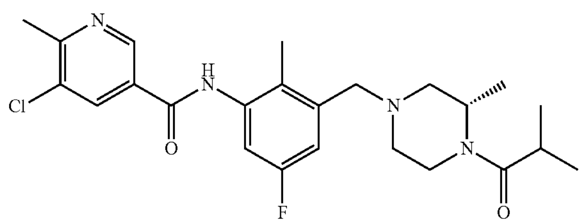 [SMILES: Cc1ncc(C(=O)Nc2cc(F)cc(CN3CCN(C(=O)C(C)C)[C@@H](C)C3)c2C)cc1Cl] | DIPEA/DCM | $^1$H NMR (400 MHz, MeOD-d$_4$): 8.94 (d, J = 2 Hz, 1H), 8.37 (d, J = 1.6 Hz, 1H), 7.15-7.09 (m, 2H), 4.69 (s, 0.5H), 4.36-4.26 (m, 1H), 3.85-3.81 (m, 0.5H), 3.56-3.50 (m, 2H), 3.44-3.39 (m, 0.5H), 3.01-2.86 (m, 2.5H), 2.80-2.71 (m, 4H), 2.30 (s, 3H), 2.28-1.99 (m, 2H), 1.39-1.24 (m, 3H), 1.19-0.91 (m, 6H). MS (ESI): C$_{24}$H$_{30}$ClFN$_4$O$_2$ requires 460; found 461 [M + H]$^+$. |
| E144 | 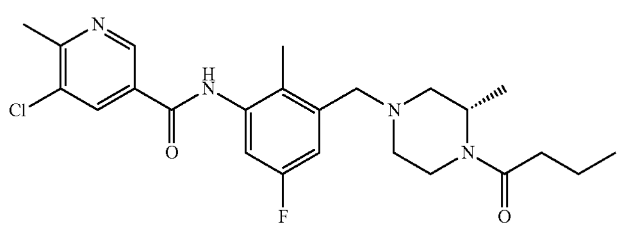 [SMILES: CCCC(=O)N1CCN(Cc2cc(F)cc(NC(=O)c3cnc(C)c(Cl)c3)c2C)C[C@@H]1C] | DIPEA/DCM | $^1$H NMR (400 MHz, MeOD-d$_4$): 8.94 (d, J = 1.2 Hz, 1H), 8.37 (d, J = 1.6 Hz, 1H), 7.15-7.09 (m, 2H), 4.69 (brs, 0.5H), 4.36-4.20 (m, 1H), 3.76-3.73 (m, 0.5H), 3.56-3.50 (m, 2H), 3.44-3.39 (m, 0.5H), 3.01-2.94 (m, 0.5H), 2.88-2.85 (m, 1H), 2.78-2.71 (m, 4H), 2.50-2.32 (m, 2H), 2.30 (s, 3H), 2.28-1.99 (m, 3H), 1.68-1.60 (m, 2H), 1.39-1.24 (m, 3H), 1.01-0.91 (m, 3H). MS (ESI): C$_{24}$H$_{30}$ClFN$_4$O$_2$ requires 460; found 461 [M + H]$^+$. |
| E145 | 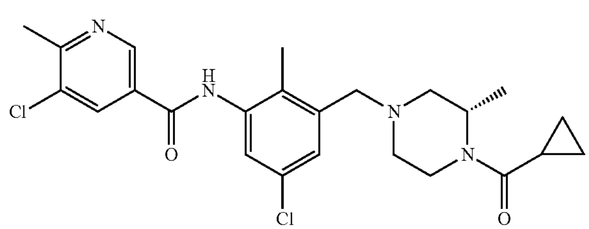 [SMILES: Cc1ncc(C(=O)Nc2cc(Cl)cc(CN3CCN(C(=O)C4CC4)[C@@H](C)C3)c2C)cc1Cl] | DIPEA/DCM | $^1$H NMR (400 MHz, MeOD-d$_4$): 8.95 (d, J = 1.6 Hz, 1H), 8.37 (d, J = 1.6 Hz, 1H), 7.38-7.32 (dd, J = 19.2, 2.0 Hz, 2H), 4.66 (brs, 0.5H), 4.54 (brs, 0.5H), 4.29-4.10 (m, 1H), 3.56-3.50 (m, 2.5H), 3.04-2.97 (m, 0.5H), 2.87 (br, 1H), 2.80-2.71 (m, 4H), 2.30 (s, 3H), 2.21-1.95 (m, 3H), 1.39-1.24 (m, 3H), 0.89-0.81 (m, 4H). MS (ESI): C$_{24}$H$_{28}$Cl$_2$N$_4$O$_2$ requires 474; found 475 [M + H]$^+$. |

Example 146

(S)—N-(5-cyano-3-((4-(2-cyclopropylacetyl)-3-methylpiperazin-1-yl)methyl)-2-methylphenyl)-5-fluoro-6-methylnicotinamide, Trifluoroacetic acid salt (E146)

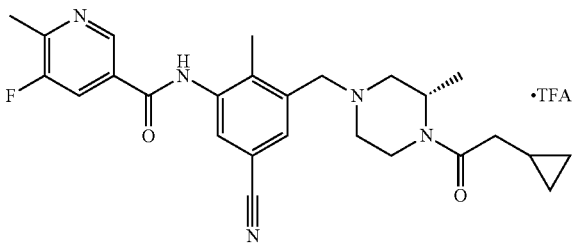 [SMILES: Cc1ncc(C(=O)Nc2cc(C#N)cc(CN3CCN(C(=O)CC4CC4)[C@@H](C)C3)c2C)cc1F]

To a suspension of 5-fluoro-6-methylnicotinic acid (D113, 57.0 mg) in DCM (10 mL), oxalyl dichloride (0.048 mL) was added dropwise. The reaction mixture was stirred at RT under nitrogen for 2 hours. Solvent was removed by rotavap, then re-dissolved with DCM (1 mL), added to a solution of (S)-3-amino-5-((4-(2-cyclopropylacetyl)-3-methylpiperazin-1-yl)methyl)-4-methylbenzonitrile (D174, 80 mg) and DIPEA (0.128 mL) in DCM (10 mL). The reaction mixture was stirred at RT overnight. Diluted with DCM (20 mL) then washed with brine (20 mL). DCM layer was separated, dried over MgSO4 and filtered. The filtrate was concentrated and purified by MADP to afford the title compound (51 mg) as white solid. $^1$H NMR (400 MHz, MeOD-d$_4$): 8.88 (s, 1H), 8.09 (dd, J=9.7, 1.7 Hz, 1H), 7.86 (s, 1H), 7.85 (s, 1H), 4.59 (brs, 1H), 4.31 (brs, 2H), 3.99 (brs, 1H), 3.71-3.32 (m, 2H), 3.23-2.68 (m, 3H), 2.61 (d, J=2.8 Hz, 3H), 2.53-2.15 (m, 5H), 1.48-1.22 (m, 3H), 1.07-0.93 (m, 1H), 0.60-0.49 (m, 2H), 0.23-0.13 (m, 2H). $^{19}$F NMR (376 MHz, MeOD-d$_4$): −77.4, −125.2. MS (ESI): $C_{26}H_{30}FN_5O_2$ requires 463; found 464 [M+H]$^+$.

Examples 147-148

Examples 147-148 were prepared using a similar procedure to that described for E146.

E147 (S)—N-(5-cyano-3-((4-(2-cyclopropylacetyl)-3-methylpiperazin-1-yl)methyl)-2-methylphenyl)-6-(fluoromethyl)nicotinamide, Trifluoroacetic acid salt E148 (S)—N-(3-((4-butyryl-3-methylpiperazin-1-yl)methyl)-5-chloro-2-methylphenyl)-5-fluoro-6-methylnicotinamide

| | Structure | Base/Solvent | Characterization |
|---|---|---|---|
| E147 | 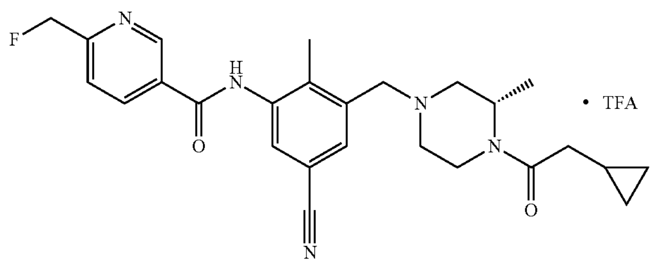 [SMILES: Cc1c(CN2CCN(C(=O)CC3CC3)[C@@H](C)C2)cc(C#N)cc1NC(=O)c1ccc(CF)nc1] | DIPEA/DCM | $^1$H NMR (400 MHz, MeOD-d$_4$): 9.13 (d, J = 1.6 Hz, 1H), 8.46 (dd, J = 8.2, 2.1 Hz, 1H), 7.88 (s, 1H), 7.85 (s, 1H), 7.72 (d, J = 8.2 Hz, 1H), 5.57 (d, J = 46.8 Hz, 2H), 5.10-4.91 (m, 0.5 H), 4.75-4.41 (m, 1H), 4.32 (brs, 2H), 3.99 (brs, 0.5H), 3.55 (brs, 0.5H), 3.36 (brs, 1H), 3.23-2.65 (m, 3H), 2.46 (s, 3H), 2.34 (brs, 2H), 1.54-1.21 (m, 3H), 1.11-0.87 (m, 1H), 0.64-0.41 (m, 2H), 0.28-0.11 (m, 2H). $^{19}$F NMR (376 MHz, MeOD-d$_4$): −78.9. MS (ESI): $C_{26}H_{30}FN_5O_2$ requires 463; found 464 [M + H]$^+$. |
| E148 | | DIPEA/DCM | $^1$H NMR (400 MHz, MeOD-d$_4$): 8.88 (s, 1H), 8.10-8.07 (dd, J = 9.6, 1.6 Hz 1H), 7.38-7.32 (dd, J = 20, 2.4 Hz, 2H), 4.69 (m, 0.5H), 4.35-4.19 (m, 1H), 3.76-3.73 (m, 0.5H), 3.56-3.48 (m, 2H), 3.42-3.36 (m, 0.5H), 2.99-2.93 (m, 0.5H), 2.87-2.85 (m, 1H), 2.77-2.72 (m, 1H), 2.62-2.61 (m, 3H), 2.49-2.34 (m, 2H), 2.32 (s, 3H), 2.29-1.99 (m, 2H), 1.70-1.64 (m, 2H), 1.36-1.24 (m, 3H), 1.00-0.96 (m, 3H). $^{19}$F NMR (376 MHz, MeOD-d$_4$): −127.2. MS (ESI): $C_{24}H_{30}ClFN_4O_2$ requires 460; found 461 [M + H]$^+$. |

Example 149

(S)—N-(5-cyano-3-((4-(cyclopentanecarbonyl)-3-methylpiperazin-1-yl)methyl)-2-methylphenyl)-3-(difluoromethyl)benzamide (E149)

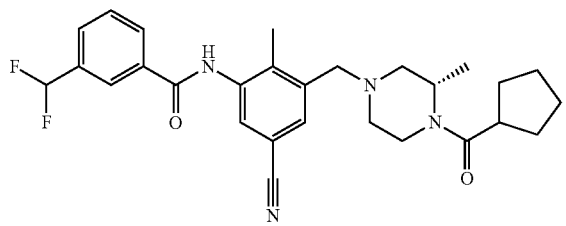 [SMILES: Cc1c(CN2CCN(C(=O)C3CCCC3)[C@@H](C)C2)cc(C#N)cc1NC(=O)c1cccc(C(F)F)c1]

To a solution of (S)-3-amino-5-((4-(cyclopentanecarbonyl)-3-methylpiperazin-1-yl)methyl)-4-methylbenzonitrile (D173, 330 mg) and triethylamine (98 mg) in anhydrous DCM (3 mL) was added the solution of 3-(difluoromethyl) benzoyl chloride (D127, 185 mg) in anhydrous DCM (3 mL) dropwise. The reaction mixture was stirred for 1 hour at RT. After the reaction completed, the mixture was washed with brine, and the organic layer was concentrated to give the crude product which was purified by MDAP to afford the title compound (260 mg) as white solid. $^1$H NMR (400 MHz, DMSO-$d_6$): 10.30 (s, 1H), 8.19-8.16 (m, 2H), 7.82 (d, J=7.6 Hz, 1H), 7.77 (d, J=1.6 Hz, 1H), 7.71 (t, J=7.6 Hz, 1H), 7.64 (s, 1H), 7.16 (t, J=55.6 Hz, 1H), 4.56 (brs, 0.5H), 4.20 (brs, 1H), 3.80-3.70 (m, 0.5H), 3.55-3.47 (m, 2H), 3.20-3.15 (m, 0.5H), 2.95-2.90 (m, 1H), 2.82-2.72 (m, 1H), 2.66-2.60 (m, 1.5H), 2.33 (s, 3H), 2.27-1.80 (m, 2H), 1.75-1.48 (m, 8H), 1.26-1.15 (m, 3H); $^{19}$F NMR (376 MHz, DMSO-$d_6$): −109.9, −110.1. MS (ESI): $C_{28}H_{32}F_2N_4O_2$ requires 494; found 495 [M+H]$^+$.

Examples 150-151

Examples 150-151 were prepared using a similar procedure to that described for E149, with the specified reaction base or solvent listed in the table.

E150 (S)—N-(5-cyano-3-((4-(cyclopentanecarbonyl)-3-methylpiperazin-1-yl)methyl)-2-methylphenyl)-2-(difluoromethyl)isonicotinamide, trifluoroacetic acid salt E151 (S)-5-chloro-N-(3-((4-(2-cyclopropylacetyl)-3-methylpiperazin-1-yl)methyl)-5-fluoro-2-methylphenyl)-6-methylnicotinamide

| | Structure | Base/Solvent | Characterization |
|---|---|---|---|
| E150 | 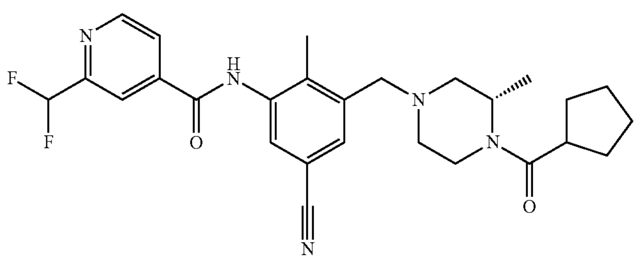 | TEA/DCM | $^1$H NMR (400 MHz, DMSO-$d_6$): 10.64 (brs, 1H), 8.94 (d, J = 4.8 Hz, 1H), 8.20 (s, 1H), 8.09 (d, J = 3.2 Hz, 1H), 8.00-7.80 (m, 2H), 7.11 (t, J = 54.8 Hz, 1H), 4.80-4.15 (brs, 1.5H), 3.60-3.10 (brs, 3H), 3.00-2.51 (m, 3.5H), 2.37 (s, 3H), 2.30-2.02 (m, 1.5H), 1.82-1.50 (m, 8.5H), 1.30-1.16 (m, 3H); $^{19}$F NMR (376 MHz, DMSO-$d_6$): −74.3, −115.8, −115.9. MS (ESI): $C_{27}H_{31}F_2N_5O_2$ requires 495; found 496 [M + H]$^+$. |
| E151 | 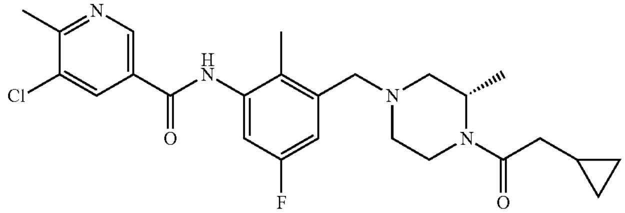 [SMILES: Cc1ncc(C(=O)Nc2cc(F)cc(CN3CCN(C(=O)CC4CC4)[C@@H](C)C3)c2C)cc1Cl] | DMAP/DCM | $^1$H NMR (400 MHz, MeOD-$d_4$): 8.94 (d, J = 1.2 Hz, 1H), 8.36 (s, 1H), 7.14-7.07 (m, 2H), 4.69 (m, 0.5H), 4.33 (d, J = 14 Hz, 0.5H), 4.15 (brs, 0.5H), 3.74 (brs, 0.5H), 3.65-3.48 (m, 2H), 3.44-3.33 (m, 0.5H), 2.96-2.98 (m, 0.5H), 2.88-2.90 (m, 0.5H), 2.75 (d, J = 11.2 Hz, 1H), 2.73-2.70 (m, 3.5H), 2.47-2.42 (m, 0.5H), 2.32-2.18 (m, 5.5H), 2.13-2.02 (m, 1H), 1.36-1.25 (m, 3H), 1.02-0.99 (m, 1H), 0.53-0.55 (m, 2H), 0.17-0.20 (m, 2H). MS (ESI): $C_{25}H_{30}ClFN_4O_2$ requires 472; found 473 [M + H]$^+$. |

Examples 152 & 153

(cis) N-(5-chloro-3-(((S)-4-(cyclopentanecarbonyl)-3-methylpiperazin-1-yl)methyl)-2-methylphenyl)-2-(2-hydroxypropan-2-yl)cyclopropanecarboxamide & (trans) N-(5-chloro-3-(((S)-4-(cyclopentanecarbonyl)-3-methylpiperazin-1-yl)methyl)-2-methylphenyl)-2-(2-hydroxypropan-2-yl)cyclopropanecarboxamide (E152&E153)

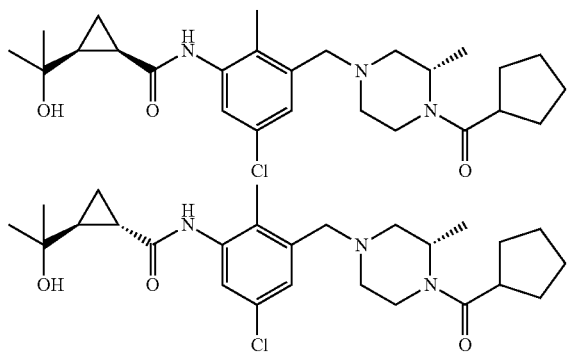

To the mixture of methyl 2-((5-chloro-3-(((S)-4-(cyclopentanecarbonyl)-3-methylpiperazin-1-yl)methyl)-2-methylphenyl)carbamoyl)cyclopropanecarboxylate (D195, 100 mg) in THF (20 mL) was added methylmagnesium chloride (3 M in ether, 0.210 mL) during 20 minutes at −50° C. The reaction mixture was warmed to 0° C. and stirred for 3 hours at 0° C. The reaction mixture was quenched with water (1 mL) and then filtered. The filtrate was concentrated to give the crude product, which was purified by chromatography on silica gel (200-300 mesh, eluting with petroleum ether/EtOAc 1:1) to afford a yellow solid, which was purified by preparative chiral to give the title compounds (10 mg and 7 mg). Isomer 1: $^1$H NMR (500 MHz, MeOD-d$_4$): 7.34 (brs, 1H), 7.21 (s, 1H), 4.68 (brs, 0.5H), 4.32-4.24 (m, 1H), 3.86-3.83 (m, 0.5H), 3.52-3.44 (m, 3H), 3.05-2.95 (m, 2H), 2.85-2.81 (m, 1H), 2.73-2.71 (m, 1H), 2.28 (s, 3H), 2.25-2.15 (m, 1H), 2.05-1.99 (m, 1H), 1.91-1.52 (m, 11H), 1.36-1.18 (m, 10H), 1.10-1.02 (m, 1H). MS (ESI): $C_{26}H_{38}ClN_3O_3$ requires 475; found 476 [M+H]$^+$. Isomer 2 $^1$H NMR (500 MHz, MeOD-d$_4$): 7.34 (d, J=1.6 Hz, 1H), 7.22 (s, 1H), 4.68 (brs, 0.5H), 4.34-4.31 (m, 1H), 3.86-3.83 (m, 0.5H), 3.52-3.44 (m, 2H), 3.04-3.00 (m, 1H), 2.85-2.80 (m, 1H), 2.75-2.70 (m, 1H), 2.28 (s, 3H), 2.21-2.15 (m, 1H), 2.05-2.00 (m, 1H), 1.92-1.61 (m, 9H), 1.55-1.53 (m, 1H), 1.28-1.18 (m, 11H), 1.10-1.02 (m, 2H). MS (ESI): $C_{26}H_{38}ClN_3O_3$ requires 475; found 476 [M+H]$^+$.

Example 154

(S)—N$^1$-(5-chloro-3-((4-(cyclopentanecarbonyl)-3-methylpiperazin-1-yl)methyl)-2-methylphenyl)-N$^4$,N$^4$-dimethylsuccinamide (E154)

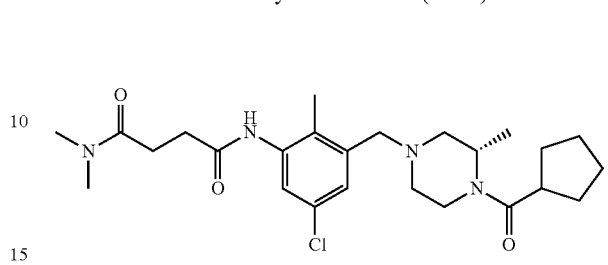

To a solution of (S)-(4-(3-amino-5-chloro-2-methylbenzyl)-2-methylpiperazin-1-yl)(cyclopentyl)methanone (D157, 400 mg) in DCM (10 mL), succinic anhydride (129.1 mg) and N,N-dimethylpyridin-4-amine (13.97 mg) were added. The reaction mixture was stirred for 6 days. The mixture was washed with water (5 mL), and the organic layer was concentrated to dryness, giving the crude (S)-4-((5-chloro-3-((4-(cyclopentanecarbonyl)-3-methylpiperazin-1-yl)methyl)-2-methylphenyl)amino)-4-oxobutanoic acid (490.3 mg). To a solution of (S)-4-((5-chloro-3-((4-(cyclopentanecarbonyl)-3-methylpiperazin-1-yl)methyl)-2-methylphenyl)amino)-4-oxobutanoic acid (153.9 mg) in anhydrous DMF (5 mL), dimethylamine, hydrochloride acid salt (84.3 mg) and HATU (227.9 mg) was added, followed by DIPEA (0.25 mL). The resulting reaction mixture was stirred overnight at RT. The mixture was sent to MDAP for purification (basic elution), giving the title compound (100.7 mg) as white solid. $^1$H NMR (500 MHz, MeOD-d$_4$): 7.38 (s, 1H), 7.19 (s, 1H), 4.66 (brs, 0.5H), 4.36-4.21 (m, 1H), 3.83 (d, J=13.2 Hz, 0.5H), 3.52-3.40 (m, 2H), 3.39-3.33 (m, 0.5H), 3.09 (s, 3H), 3.05-2.97 (m, 1.5H), 2.95 (s, 3H), 2.82 (d, J=11.0 Hz, 1H), 2.78-2.67 (m, 5H), 2.26 (s, 3H), 2.22-2.12 (m, 1H), 2.07-1.95 (m, 1H), 1.92-1.54 (m, 8H), 1.39-1.15 (m, 3H). MS (ESI): $C_{25}H_{37}ClN_4O_3$ requires 476; found 477 [M+H]$^+$.

Example 155

(S)—N-(5-chloro-3-((4-(cyclopentanecarbonyl)-3-methylpiperazin-1-yl)methyl)-2-methylphenyl)-4-oxo-4-(pyrrolidin-1-yl)butanamide (E155)

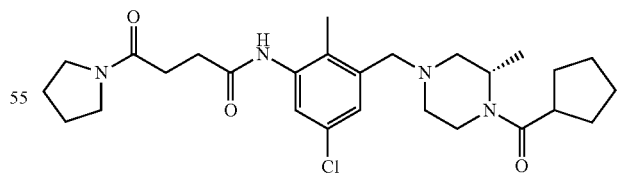

E155 was prepared using a similar procedure to that described for E154. $^1$H NMR (500 MHz, MeOD-d$_4$): 7.38 (s, 1H), 7.19 (s, 1H), 4.66 (brs, 0.5H), 4.37-4.20 (m, 1H), 3.83 (d, J=13.2 Hz, 0.5H), 3.54 (t, J=6.7 Hz, 2H), 3.50-3.36 (m, 4.5H), 3.07-2.90 (m, 1.5H), 2.82 (d, J=10.5 Hz, 1H), 2.78-2.64 (m, 5H), 2.26 (s, 3H), 2.22-2.12 (m, 1H), 2.08-1.55 (m, 13H), 1.39-1.15 (m, 3H). MS (ESI): $C_{27}H_{39}ClN_4O_3$ requires 501; found 503 [M+H]$^+$.

Example 156

(S)—N-(5-chloro-3-((4-(2,2-difluorobutanoyl)-3-methylpiperazin-1-yl)methyl)-2-methylphenyl)-5-fluoro-6-methylnicotinamide (E156)

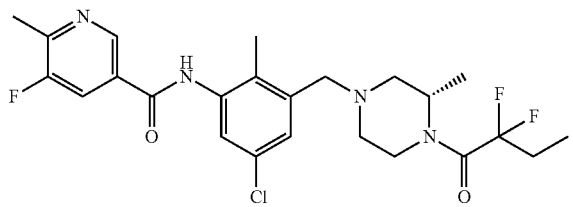 [SMILES: CCC(F)(F)C(=O)N1CCN(Cc2cc(Cl)cc(NC(=O)c3cnc(C)c(F)c3)c2C)C[C@@H]1C]

To a mixture of 2,2-difluorobutanoic acid (50 mg), HATU (229 mg), and DIPEA (104 mg) in DMF (5 mL) was added (S)—N-(5-chloro-2-methyl-3-((3-methylpiperazin-1-yl)methyl)phenyl)-5-fluoro-6-methylnicotinamide (D254, 173 mg). The mixture was stirred at 45° C. for 15 hours. The reaction was quenched with water, extracted with EtOAc (2×50 mL). The combined organic layers were dried over anhydrous sodium sulfate, filtered and concentrated. The residue was purified by MDAP to afford the title compound (14 mg). $^1$H NMR (400 MHz, MeOD-d$_4$): 8.89 (s, 1H), 8.09 (dd, J=9.9, 1.6 Hz, 1H), 7.44-7.27 (m, 2H), 4.65 (brs, 0.5H), 4.49 (brs, 0.5H), 4.29 (d, J=13.6 Hz, 0.5H), 4.07 (d, J=13.8 Hz, 0.5H), 3.53 (s, 2H), 3.51-3.41 (m, 0.5H), 3.14 (t, J=12.3 Hz, 0.5H), 2.94-2.83 (m, 1H), 2.78 (d, J=11.3 Hz, 1H), 2.59 (brs, 3H), 2.37-2.30 (m, 3H), 2.29-2.02 (m, 4H), 1.50-1.21 (m, 3H), 1.07 (td, J=7.4, 2.8 Hz, 3H). MS (ESI): $C_{24}H_{28}ClF_3N_4O_2$ requires 496; found 497 [M+H]$_+$.

Biological Data

As stated above, the compounds according to Formula I are RORγ modulators, and are useful in the treatment of diseases mediated by RORγ. The biological activities of the compounds according to Formula I can be determined using any suitable assay for determining the activity of a candidate compound as a RORγ modulator, as well as tissue and in vivo models.

Fluorescence Energy Transfer (FRET) Assay

The assays were performed in an assay buffer consisting of 50 mM NaF, 50 mM 3-(N-morpholino)propanesulfonic acid, pH 7.5, 50 µM 3-[(3-cholamidopropyl)dimethylammonio]-propanesulfonate, 0.1 mg/mL bovine serum albumin, and 10 mM dithiothreitol in 384-well plates (Greiner 784076, Longwood, Fla.). The total volume was 10 µL/well. The europium-labeled SRC1 solution was prepared by adding an appropriate amount of biotinylated SRC and europium labeled streptavidin (PerkinElmer Life and Analytical Sciences, Waltham, Mass.) into assay buffer, with final concentrations of 27 and 3.3 nM, respectively. The allophycocyanin (APC)-labeled-LBD solution was prepared by adding an appropriate amount of biotinylated RORγ-LBD and APC-labeled streptavidin (CR130-100; PerkinElmer Life and Analytical Sciences) at a final concentration of 33 nM each. After 15 min of incubation at room temperature, a 20-fold excess of biotin was added to block the remaining free streptavidin. Equal volumes of europium-labeled SRC- and APC-labeled RORγ-LBD were then mixed with 0.2 µM surrogate agonist N-(2-chloro-6-fluorobenzyl)-N-((2'-methoxy-[1,1'-biphenyl]-4-yl)methyl)benzenesulfonamide (Zhang, W., et al., Mol. Pharmacol. 2012, 82, 583-590) and dispensed into 384-well assay plates at 10 µL volume/well. The 384-well assay plates had 100 nL of test compound in DMSO predispensed into each well. The plates were incubated for 1 h at room temperature and then read on ViewLux (PerkinElmer Life and Analytical Sciences) in LANCE mode configured for europeum-APC labels. Data were collected and analyzed by Activitybase.

Dual Fluorescence Energy Transfer (FRET) Assay

This assay is based on the knowledge that nuclear receptors interact with cofactors (transcription factors) in a ligand dependent manner. RORγ is a typical nuclear receptor in that it has an AF2 domain in the ligand binding domain (LBD) which interacts with co-activators. The sites of interaction have been mapped to the LXXLL motifs in the co-activator SRC1(2) sequences. Short peptide sequences containing the LXXLL motif mimic the behavior of full-length co-activator.

The assay measures ligand-mediated interaction of the co-activator peptide with the purified bacterial-expressed RORγ ligand binding domain (RORγ-LBD) to indirectly assess ligand binding. RORγ has a basal level of interaction with the co-activator SRC1(2) in the absence of ligand, thus it is possible to find ligands that inhibit or enhance the RORγ/SRC1(2) interaction.

Materials

Generation of RORγ-LBD Bacterial Expression Plasmid

Human RORγ Ligand Binding Domain (RORγ-LBD) was expressed in E. coli strain BL21(DE3) as an amino-terminal polyhistidine tagged fusion protein. DNA encoding this recombinant protein was sub-cloned into a modified pET21a expression vector (Novagen). A modified polyhistidine tag (MKKHHHHHHLVPRGS) was fused in frame to residues 263-518 of the human RORγ sequence.

Protein Purification

Approximately 50 g E. coli cell pellet was resuspended in 300 mL of lysis buffer (30 mM imidazole pH 7.0 and 150 mM NaCl). Cells were lysed by sonication and cell debris was removed by centrifugation for 30 minutes at 20,000 g at 4° C. The cleared supernatant was filtered through a 0.45 uM cellulose acetate membrane filter. The clarified lysate was loaded onto a column (XK-26) packed with ProBond Nickel Chelating resin (Invitrogen), pre-equilibrated with 30 mM imidazole pH 7.0 and 150 mM NaCl. After washing to baseline absorbance with the equilibration buffer, the column was developed with a gradient from 30 to 500 mM imidazole pH 7.0. Column fractions containing the RORγ-LBD protein were pooled and concentrated to a volume of 5 mls. The concentrated protein was loaded onto a Superdex 200 column pre-equilibrated with 20 mM Tris-Cl pH 7.2 and 200 mM NaCl. The fractions containing the desired RORγ-LBD protein were pooled together.

Protein Biotinylation

Purified RORγ-LBD was buffer exchanged by exhaustive dialysis [3 changes of at least 20 volumes (>8000×)] against PBS [100 mM NaPhosphate, pH 8 and 150 mM NaCl]. The concentration of RORγ-LBD was approximately 30 uM in PBS. Five-fold molar excess of NHS-LC-Biotin (Pierce) was added in a minimal volume of PBS. This solution was incubated with occasional gentle mixing for 60 minutes at ambient RT. The modified RORγ-LBD was dialyzed against 2 buffer changes—TBS pH 8.0 containing 5 mM DTT, 2 mM EDTA and 2% sucrose—each at least 20 times of the volume. The modified protein was distributed into aliquots, frozen on dry ice and stored at −80° C. The biotinylated RORγ-LBD was subjected to mass spectrometric analysis to reveal the extent of modification by the biotinylation reagent. In general, approximately 95% of the protein had at least a single site of biotinylation and the overall extent of biotinylation followed a normal distribution of multiple sites ranged from one to five. A biotinylated peptide corresponding to amino acid 676 to 700 (CPSSHSSLTERH-KILHRLLQEGSPS) of the co-activator steroid receptor coactivator SRC1(2) was generated using similar method.
Assay Preparation of Europium labeled SRC1(2) peptide: biotinylated SRC1(2) solution was prepared by adding an appropriate amount of biotinylated SRC1(2) from the 100 uM stock solution to a buffer containing 10 mM of freshly added DTT from solid to give a final concentration of 40 nM. An appropriate amount of Europium labeled Streptavidin was then added to the biotinylated SRC1(2) solution in a tube to give a final concentration of 10 nM. The tube was inverted gently and incubated for 15 minutes at room temperature. Twenty-fold excess biotin from the 10 mM stock solution was added and the tube was inverted gently and incubated for 10 minutes at room temperature.

Preparation of APC labeled RORγ-LBD: biotinylated RORγ-LBD solution was prepared by adding an appropriate amount of biotinylated RORγ-LBD from the stock solution to a buffer containing 10 mM of freshly added DTT from solid to give a final concentration of 40 nM. An appropriate amount of APC labeled Streptavidin was then added to the biotinylated RORγ-LBD solution in a tube to give a final concentration of 20 nM. The tube was inverted gently and incubated for 15 minutes at room temperature. Twenty-fold excess biotin from the 10 mM stock solution was then added and the tube was inverted gently and incubated for 10 minutes at room temperature.

Equal volumes of the above-described Europium labeled SRC1(2) peptide and the APC labeled RORγ-LBD were gently mixed together to give 20 nM RORγ-LBD, 10 nM APC-Strepavidin, 20 nM SRC1(2) and 5 nM Europium-Streptavidin. The reaction mixtures were incubated for 5 minutes. Using a Thermo Combi Multidrop 384 stacker unit, 25 ul of the reaction mixtures per well was added to the 384-well assay plates containing 1 ul of test compound per well in 100% DMSO. The plates were incubated for 1 hr and then read on ViewLux in Lance mode for EU/APC.

Jurkat Cell Luciferase Assay

RORγ is known to bind to a CNS (conserved non-coding sequences) enhancer element in the IL17 promoter. In this assay, RORγ activity is indirectly assessed using a luciferase reporter construct which contains the human IL17 promoter having the RORγ-specific CNS enhancer element. Inhibition of RORγ activity by a compound will result in a decrease in luciferase activity of Jurkat cells transfected with the reporter construct.
Materials
Jurkat cell line For the luciferase reporter plasmid, the 3 Kb human IL17 promoter containing the RORγ-specific CNS enhancer element was PCR amplified from human genomic DNA and cloned into a pGL4-Luc2/hygro reporter plasmid sequentially as XhoI-HindIII (1.1 Kb) and KpnI-XhoI (1.9 Kb) fragments. For the 1.1 Kb fragment, PCR was used to amplify human IL17 proximal promoter region from genomic DNA of 293T cells using primers as follows: forward primer, 5'-CTCGAGTAGAGCAGGACAGGGAGGAA-3' (XhoI site is underlined) and reverse primer, 5'-AAGCTTGGATGGATGAGTTTGTGCCT-3' (HindIII site is underlined). The 1.1 kb DNA bands were excised, purified, and inserted into pMD19-T Simple Vector (Takara). After DNA sequencing confirmation, the 1.1 kb DNA was digested with XhoI and HindIII and inserted into XhoI/HindIII sites of pGL4.31 [luc2P/GAL4UAS/Hygro] (Promega) to generate the pIL17-1kb-luc reporter construct. For the 1.9 Kb fragment, PCR was used to amplify human IL17 promoter region from genomic DNA using primers as follows: forward primer, 5'-GGTACCTGCCCTGCTCTATCCTGAGT-3' (KpnI site is underlined) and reverse primer, 5'-CTCGAGTGGTGAGTGCTGAGAGATGG-3' (XhoI site is underlined). The resulting 1.9 kb DNA bands were excised, gel purified, and cloned into a pMD19-T Simple Vector (Takara). DNA sequencing analysis revealed that there were three point mutations but none of which affected RORγ binding. The 1.9 kb DNA fragment was released by double digestion with KpnI and XhoI and inserted into pIL17-1kb-luc to generate the luciferase reporter plasmid "pIL17-3kb-CNS-luc." To overexpress RORγt, the full-length cDNA of human RORγt identical to the published sequence NM_001001523 was cloned into pcDNA3.1 at the KpnI-NotI cloning sites to generate the RORγt overexpression plasmid "CDNA3.1DhRORγ49-8".

The luciferase reporter plasmid and the RORγt overexpression plasmid were transfected into Jurkat cell line and a stable clone was identified. The stable clone was grown in 10% dialyzed FBS in RPMI (1640) with 800 ug/ml geneticin and 400 ug/ml hygromecin.
Assay Compounds were dissolved in DMSO at three concentrations, 10 mM, 400 uM and 16 uM, and were dispensed into 384-wells assay plate at 40 nl, 12.5 nl, 5 nl respectively. The volume was adjusted with pure DMSO to a give a final uniform volume of 40 nl Jurkat cells described above were counted and centrifuged. The growth medium was discarded and the cells were resuspended with assay medium (phenol red free RPMI) at 1E-6/ml. Cells were added to each of the compounds in the assay plates. Cells were either untreated or treated with CD3 microbeads (Miltenyi Biotec) at 1 ul beads per 500,000 cells. Cells were culture overnight and luciferase assay (Promega) was performed. Data were collected by ViewLux (using luciferase greiner 384 setting).
Th17 Cell Differentiation Assay
ELISA Mouse CD4+ cells were purified using the CD4+ T Cell Isolation II Kit according to manufacturer's instructions (Miltenyi Biotec). 96 well plates were pre-coated with anti-mCD3 antibody. Un-coated wells were used as controls. CD4+ Cells were resuspended in RPMI 1640 complete medium and were added to the 96-well plates. Cytokine cocktail and the compound were then added to the wells. Antibodies and cytokines (all from R&D Systems) used in the assay were selected from the following: anti-mCD3; anti-mCD28; anti-mIFNγ; anti-mIL4; mIL-6; mIL-23; mIL-1β; hTGF-β1. The culture was incubated at 37° C. for 3 days and supernatants were collected for ELISA. The IL-17 ELISAs were performed according to manufacturer's instructions (R&D Systems). The results were analyzed using Prism software with non-linear regression to determine pIC50.
Intracellular Staining The Th17 differentiation culture described above was maintained for 5 days and cells were analyzed by IL-17 and IFN-γ intracellular staining according to manufacturer's instructions (BD Biosciences).
Assay Data The data described below represents a mean $pIC_{50}$ value of multiple test results if the test was performed more than once. It is understood that the data illustrated below may have reasonable variation depending on the specific conditions and procedures used by the person conducting the testing.

All exemplified compounds were tested in the FRET assay described above. All tested compounds were found to have a $pIC_{50}$ between 5 and 8. Example 80 was found to have a $pIC_{50}$ of about 7.3.

All exemplified compounds except Examples 4, 25, 37, 39, 47, 48, 50, 54, 58-60, 62, 64, 75, 84, 90, 94, 97-99, 104, 105, 107, 108, 130, 142, 152, and 153 were tested in the dual FRET assay described above. All tested compounds were found to have a $pIC_{50}$ between 6 and 8. Example 80 was found to have a $pIC_{50}$ of about 7.0.

All exemplified compounds except Examples 1-7, 9-22, 27-31, 33-39, 41, 45, 47-49, 51-54, 59, 60, 63-68, 71-73, 75, 78, 79, 81-85, 87, 88, 90, 91, 96-98, 100-103, 107, 108, 113, 115-121, 123, 126, 132, 133, 135-145 and 147-156 were tested in the Jurkat cell luciferase assay described above. All tested compounds were found to have a $pIC_{50}$ between 5 and 8. Example 80 was found to have a $pIC_{50}$ of about 8.2.

All exemplified compounds except Examples 3, 7, 9, 10, 18, 22-24, 30, 31, 36, 38, 39, 41, 47, 66-68, 81, 82, 84, 88, 90, 91, 97, 103, 112, 116, 126, 128, 135, 140, 147, 149 and 153 were tested in the Th17 cell differentiation assay described above. All tested compounds were found to have a $pIC_{50}$ between 5 and 9. Example 80 was found to have a $pIC_{50}$ of about 8.3.

EAE Studies

Experimental Autoimmune Encephalomyelitis (EAE) is an animal model of multiple sclerosis. The ability of a test compound to ameliorate EAE can be measured in the EAE studies. Wild-type mice of the C57BL/6 (B6) strain are maintained under pathogen-free conditions. EAE is induced by intravenous injections of 100 ng of pertussis toxin (List Biological Laboratories) and subcutaneous immunization with an emulsion composed of $MOG_{35-55}$ peptide (300 μg/mouse) in PBS and an equal volume of complete Freund's adjuvant containing 5 mg/ml heat-killed *Mycobacterium tuberculosis* H37Ra (Difco Laboratories) on day 0, followed by another intravenous injections of 100 ng of pertussis toxin on day 2 as described previously (Wang et al. (2006) *J. Clin. Invest.* 116: 2434-2441). For treatment of EAE, each compound or vehicle PBS is given orally from day 0 at various doses selected from 3, 10, 30 and 100 mg/kg twice a day. Mice are scored for disease severity daily using a EAE scoring system (Wang et al. (2006) *J. Clin. Invest.* 116: 2434-2441): 0, no overt signs of disease; 1, limp tail or hind limb weakness but not both; 2, limptail and paraparesis (weakness, incomplete paralysis of one or two hind limbs); 3, paraplegia (complete paralysis of two hind limbs); 4, paraplegia with forelimb weakness or paralysis; and 5, moribund state or death. Clinical score data can be expressed as means±S.E.M.

Human Peripheral Blood CD4+ T Cell Cultures and Cytokine Analysis

Human biological samples were cryopreserved human CD4+ T cells purchased from AllCells, LLC and Stemcell Technologies, Inc. The CD4+ T cells were differentiated to the Th17 subtype by culturing for 5 days in tissue culture plates coated with anti-CD3 antibody (2 μg/mL) in Iscove's modified Dulbecco's medium (IMDM) containing 10% HI-FBS, 55 μM 2-mercaptoethanol and soluble anti-CD28 (3 μg/mL) in the presence of a Th17 skewing cocktail, including IL-1β (10 ng/mL), IL-6 (30 ng/mL), TGFβ (0.5 ng/mL), IL-21 (10 ng/mL), IL-23 (10 ng/mL), anti-IFNγ (10 μg/mL) and anti-IL-4 (10 μg/mL). To examine compound effects on Th17 polarization, freshly thawed CD4+ cells in IMDM supplemented with all Th17 polarization cocktail constituents (above) were seeded at low cell density (20,000 cells/well) directly into anti-CD3 coated round bottom 96-well plates already containing serially diluted compounds. Cells were incubated undisturbed for 5 days at 37° C. Immediately following culture, supernatant was analyzed for secreted IL-17A and IL-22 protein by MSD electrochemiluminescent cytokine assays (Mesoscale Discovery) and ELISA (Quantikine assay, R&D Systems), respectively. Compound treatment(s) were performed in triplicate. Results are presented as the mean±SD or as mean percent inhibition (±SD) relative to the response to stimulus alone.

Example 80 as tested in this assay had an IL17A pIC50=7.54 and Inhibition Activity (ASSYM MAX)=94.

In Vitro Percutaneous Studies

The in vitro percutaneous study is aimed to predict the level of percutaneous penetration obtained for a compound in a topical formulation for psoriasis. This assay coupled with the intrinsic potency of the compound are used to predict the likelihood of success of a compound to engage the target. The higher the ratio of the percutaneous penetration to the intrinsic potency, the higher the ratio of local skin concentration to the intrinsic potency and therefore the higher the chance of a compound to engage the target in a topical formulation.

The compounds can be manufactured in a modified aqueous cream at pH=6.

| Aqueous cream composition | |
|---|---|
| Ingredients | % w/w |
| Cetostearyl alcohol | 7.2 |
| Cetomacrogol 1000 | 1.8 |
| White soft paraffin | 15.0 |
| Liquid paraffin | 6.0 |
| Water | 57.0 |
| Na2HPO4 | 0.6 |
| Citric Acid | 0.2 |
| Propylene Glycol | 10.0 |
| Methyl paraben | 0.1 |
| Caffeine | 0.1 |
| API#1 | 1.0 |
| API#2 | 1.0 |
| API#3 | 1.0 |

The study can be conducted with dermatomed abdominal human skin sourced from three skin donors using 2 cm2 Franz diffusion cells. The receiving fluid consisted of Bovine serum albumin (4% w/v) in 0.1% w/v sodium azide in Phospate Buffer Saline and can be heated at 37° C. in order to obtain 32° C. at the skin surface. The cream formulation can be applied on the donor side at a 10 mg dose, i.e. 5 mg/cm². The samples can be taken at the following time points: t=0, 3, 6, 9 and 24 h. The receiver samples can then be assayed using a method based upon protein precipitation with acetonitrile followed by LC/MS/MS analysis. The percutaneous flux (in ng/cm²/hr) can be determined using the individual API (in a multiple composition) that has permeated into the receiver compartment over 24 hrs per cm².

Imiquimod-Induced Skin Inflammation

Imiquimod is an immune modifying agent that potently activates specific Toll-like receptors (e.g., TLR7) and induces irritation/inflammation of the skin that requires the IL23R/RORγ/IL17 axis of the immune system (van der Fits et al, (2009) *J Immunol;* 182:5836-5845; Gray et al, (2013) *Nature Immunol*; June; 14(6):584-92). The imiquimod-induced skin inflammation model can be used to assess the ability of an RORγ inhibitor to reduce Th17-driven inflammation in mice. For the ear-only skin inflammation model in which ear thickness was measured with digital engineer's calipers (Mitutoyo PK-0505), female wild type C57BL/6NTac mice obtained from Taconic (Hudson, N.Y.) at 8 to 12 wk of age received a daily topical dose of 10 mg of commercially available imiquimod cream (5%) (Aldara; Medicis) distributed over both ears at approximately 11:00 h for up to 4 consecutive days. Alternatively, 72 mg of Aldara was distributed over both ears and the shaved/depiliated back skin of mice at approximately 11:00 h for 3 consecutive days to examine RORγ-dependent gene expression (RNA isolated from both ears using Qiazol followed by clean-up on with the RNeasy protocol (Qiagen, Germantown, Md.); Taqman probe/primer sets for B2M (Mm00437762_m1), IL-17A (Mm00439619_m1), IL-17F (Mm00521423_m1), or IL-22 (Mm00444241_m1) (Thermo Fisher Scientific, Inc., Waltham, Mass.) and ex vivo stimulated (anti-CD3 (2 µg/ml, clone eBio500A2, eBioscience, San Diego, Calif.), anti-CD28 (1 µg/ml, clone 37.51, BD Bioscience, San Jose, Calif.), recombinant mouse IL-13 (20 ng/ml, R&D Systems, Minneapolis, Minn.), and recombinant mouse IL-23 (20 ng/ml, R&D Systems, Minneapolis, Minn.) IL-17A protein expression from whole blood (Meso Scale Discovery, Rockville, Md.). For treatment of the skin inflammation in these models, each compound or vehicle (methylcellulose in water, 1% w/v, Sigma Aldrich, St. Louis, Mo.) was administered via oral gavage at approximately 08:00 h and 16:00 h daily at various doses selected from 1, 3, 10, and 30 mg/kg.

As shown in the table below, E43 at the 10 and 30 mg/kg doses resulted in a statistically significant reduction of imiquimod-induced ear thickening (Studies 1-4). In study B, E43 at 10 mg/kg significantly reduced IL17F and IL22 mRNA levels in the ear skin, while in study C, only the reduction in IL17A mRNA levels reached statistical significance. The ex vivo whole blood assay performed as part of study A revealed that E43 at 10 mg/kg significantly reduced the amount of IL17A protein that is expressed following ex vivo stimulation despite no significant reduction in ear mRNA levels of IL17A, IL17F, or IL22.

Methods of Use

The compounds of Formula I, Ia, Formula II, and Formulas III-IX are all modulators of RORγ and can be useful in the treatment of diseases mediated by RORγ, particularly autoimmune or inflammatory diseases. Examples of the inflammatory or autoimmune diseases of the invention include multiple sclerosis, rheumatoid arthritis, psoriasis, ankylosing spondylitis, Crohn's disease, inflammatory bowel disease, Sjorgen's syndrome, optic neuritis, chronic obstructive pulmonary disease, asthma, type I diabetes, neuromyelitis optica, Myasthenia Gavis, uveitis, Guillain-Barre syndrome, psoriatic arthritis, Gaves' disease and allergy. Accordingly, in another aspect the invention is directed to a method of treating autoimmune and inflammatory diseases mediated by RORγ with an effective amount of a compound of Formula I, Ia, Formula II, and Formulas III-IX, or a pharmaceutically acceptable salt thereof. As used herein in this section unless specially indicated to the contrary, a "compound of Formula I" also refers to compounds of Formulas Ia, II, and Formulas III-IX.

In a further aspect, the present invention provides a compound of Formula I, or a pharmaceutically acceptable salt thereof, for use in therapy.

In a further aspect, the present invention provides a compound of Formula I, or a pharmaceutically acceptable salt thereof, for use in the treatment of inflammatory and autoimmune diseases mediated by RORγ.

In a further aspect, the present invention provides a compound of Formula I, or a pharmaceutically acceptable salt thereof, for use in the treatment of multiple sclerosis.

In a further aspect, the present invention provides a compound of Formula I, or a pharmaceutically acceptable salt thereof, for use in the treatment of ankylosing spondylitis.

In a further aspect, the present invention provides a compound of Formula I, or a pharmaceutically acceptable salt thereof, for use in the treatment of psoriasis.

In a further aspect, the present invention is directed to a method of treatment of an inflammatory or autoimmune disease mediated by RORγ, which comprises administering to a mammal, particularly a human, in need thereof, an effective amount of a compound of Formula I, or a pharmaceutically acceptable salt thereof.

In yet a further aspect, the present invention is directed to a method of treating multiple sclerosis, which comprises administering to a human in need thereof, an effective amount of a compound of Formula I, or a pharmaceutically acceptable salt thereof.

In yet a further aspect, the present invention is directed to a method of treating of ankylosing spondylitis, which comprises administering to a human in need thereof, an effective amount of a compound of Formula I, or a pharmaceutically acceptable salt thereof.

In yet a further aspect, the present invention is directed to a method of treating psoriasis, which comprises administering to a human in need thereof, an effective amount of a compound of Formula I, or a pharmaceutically acceptable salt thereof.

In a further aspect, the present invention is directed to the use of a compound of Formula I, or a pharmaceutically acceptable salt thereof, in the manufacture of a medicament for use in the treatment of an inflammatory or autoimmune disease mediated by RORγ.

In a yet further aspect, the present invention is directed to the use of a compound of Formula I, or a pharmaceutically acceptable salt thereof, in the manufacture of a medicament for use in the treatment of multiple sclerosis.

In a yet further aspect, the present invention is directed to the use of a compound of Formula I, or a pharmaceutically acceptable salt thereof, in the manufacture of a medicament for use in the treatment of ankylosing spondylitis.

In a yet further aspect, the present invention is directed to the use of a compound of Formula I, or a pharmaceutically acceptable salt thereof, in the manufacture of a medicament for use in the treatment of psoriasis.

In a yet further aspect, the present invention is directed to the use of (S)—N-(5-chloro-3-((4-(2-cyclopropylacetyl)-3-methylpiperazin-1-yl)methyl)-2-methylphenyl)-5-fluoro-6-methylnicotinamide, or a pharmaceutically acceptable salt thereof, in the manufacture of a medicament for use in the treatment of psoriasis.

In yet a further aspect, the present invention is directed to a method of treating psoriasis in a human in need thereof, which comprises administering to said human an effective amount of (S)—N-(5-chloro-3-((4-(2-cyclopropylacetyl)-3-methylpiperazin-1-yl)methyl)-2-methylphenyl)-5-fluoro-6-methylnicotinamide, or a pharmaceutically acceptable salt thereof.

In yet a further aspect, the present invention is directed to a method of treatment of an inflammatory or autoimmune disease mediated by RORγ, which comprises administering to a human in need thereof, an effective amount of (S)—N-

(5-chloro-3-((4-(2-cyclopropylacetyl)-3-methylpiperazin-1-yl)methyl)-2-methylphenyl)-5-fluoro-6-methylnicotinamide, or a pharmaceutically acceptable salt thereof.

Another aspect is the use of (S)—N-(5-chloro-3-((4-(2-cyclopropylacetyl)-3-methylpiperazin-1-yl)methyl)-2-methylphenyl)-5-fluoro-6-methylnicotinamide, or a pharmaceutically acceptable salt thereof for the treatment of psoriasis.

Another aspect is the use of (S)—N-(5-chloro-3-((4-(2-cyclopropylacetyl)-3-methylpiperazin-1-yl)methyl)-2-methylphenyl)-5-fluoro-6-methylnicotinamide, or a pharmaceutically acceptable salt thereof for the treatment of an inflammatory or autoimmune disease mediated by RORγ.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As indicated above, "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the human lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the individual being treated, the medical history of the individual to be treated, the nature of concurrent therapy, the desired therapeutic effect, and like factors within the knowledge and expertise of the skilled artisan. It will be further understood by such skilled artisans that suitable dosing regimens may require adjustment given an individual's response to the dosing regimen or over time as individual needs change.

Typical daily dosages may vary depending upon the particular route of administration chosen. Typical daily dosages for oral administration range from 0.1 mg to 1000 mg. Typical daily dosages for topical administration range from about 0.001% to about 10% w/w (weight percent) and preferably from about 0.01% to about 1% w/w.

Additionally, the compounds of the invention may be administered as prodrugs. As used herein, a "prodrug" of a compound of the invention is a functional derivative of the compound which, upon administration to an individual, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

Compositions

The compounds of the invention will normally, but not necessarily, be formulated into pharmaceutical compositions prior to administration to an individual. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the individual such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 0.1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to an individual and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the individual by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the individual from one organ, or portion of the body, to another organ, or portion of the body. Certain pharmaceutically-acceptable excipients may be chosen for their ability to enhance compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of Formula IV or a pharmaceutically acceptable salt thereof:

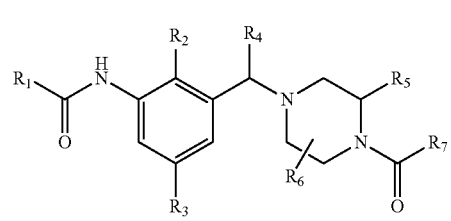

Formula IV wherein $R_1$ is a-6 membered heteroaryl substituted with two substituents selected from the group consisting of: i) F and methyl, ii) CN and methyl, and iii) Cl and methyl;
$R_2$ is $C_1$-$C_3$ alkyl or halo;
$R_3$ is halo or CN;
$R_4$ is H;
$R_5$ is $C_1$-$C_3$ alkyl;
$R_6$ is H or methyl; and
$R_7$ is selected from the group consisting of:
 $C_3$-$C_6$ cycloalkyl optionally substituted with methyl;
 methyl substituted with $C_3$-$C_5$ cycloalkyl; and
 $C_2$-$C_3$ alkyl optionally substituted with two F.

2. The compound or a pharmaceutically acceptable salt according to claim 1, wherein $R_1$ is pyridinyl substituted with i) F and methyl, or ii) CN and methyl.

3. The compound or a pharmaceutically acceptable salt according to claim 1, wherein $R_2$ is methyl.

4. The compound or a pharmaceutically acceptable salt according to claim 1, wherein $R_3$ is Cl or F.

5. The compound or a pharmaceutically acceptable salt according to claim 1, wherein $R_5$ is methyl.

6. The compound or a pharmaceutically acceptable salt according to claim 1, wherein $R_6$ is H.

7. The compound or a pharmaceutically acceptable salt according to claim 1, wherein $R_7$ is methyl substituted with cyclopropyl.

8. The compound according to claim 1, which is (S)—N-(5-chloro-3-((4-(2-cyclopropylacetyl)-3-methylpiperazin-1-yl)methyl)-2-methylphenyl)-5-fluoro-6-methylnicotinamide or a pharmaceutically acceptable salt thereof.

9. A pharmaceutical composition comprising a compound or a pharmaceutically acceptable salt thereof according to claim 1, and a pharmaceutically acceptable carrier or diluent thereof.

10. A method of treating an inflammatory or autoimmune disease mediated by RORγ, which comprises administering to a human in need thereof, an effective amount of a compound or a pharmaceutically acceptable salt thereof according to claim 1 wherein the inflammatory or autoimmune disease mediated by RORγ disease is psoriasis.

11. A pharmaceutical composition comprising a compound or a pharmaceutically acceptable salt thereof according to claim 8, and a pharmaceutically acceptable carrier or diluent thereof.

12. The compound according to claim 1, which is (S)—N-(5-chloro-3-((4-(cyclopentanecarbonyl)-3-methylpiperazin-1-yl)methyl)-2-methylphenyl)-5-cyano-6-methylnicotinamide;

(S)-5-chloro-N-(5-chloro-3-((4-(2-cyclopropylacetyl)-3-methylpiperazin-1-yl)methyl)-2-methylphenyl)-6-methylnicotinamide;

(S)—N-(5-chloro-3-((4-(2-cyclopropylacetyl)-3-methylpiperazin-1-yl)methyl)-2-methylphenyl)-5-cyano-6-methylnicotinamide;

(S)-5-chloro-N-(5-cyano-3-((4-(2-cyclopropylacetyl)-3-methylpiperazin-1-yl)methyl)-2-methylphenyl)-6-methylnicotinamide;

(S)-5-chloro-N-(3-((4-(2,2-difluorobutanoyl)-3-methylpiperazin-1-yl)methyl)-5-fluoro-2-methylphenyl)-6-methylnicotinamide;

(S)—N-(5-chloro-3-((4-(2-cyclopropylacetyl)-3-methylpiperazin-1-yl)methyl)-2-methylphenyl)-6-cyano-5-methylnicotinamide (S)-5-chloro-N-(5-fluoro-3-((4-isobutyryl-3-methylpiperazin-1-yl)methyl)-2-methylphenyl)-6-methylnicotinamide;

(S)—N-(3-((4-butyryl-3-methylpiperazin-1-yl)methyl)-5-fluoro-2-methylphenyl)-5-chloro-6-methylnicotinamide;

(S)-5-chloro-N-(5-chloro-3-((4-(cyclopropanecarbonyl)-3-methylpiperazin-1-yl)methyl)-2-methylphenyl)-6-methylnicotinamide;

(S)—N-(5-cyano-3-((4-(2-cyclopropylacetyl)-3-methylpiperazin-1-yl)methyl)-2-methylphenyl)-5-fluoro-6-methylnicotinamide;

(S)—N-(3-((4-butyryl-3-methylpiperazin-1-yl)methyl)-5-chloro-2-methylphenyl)-5-fluoro-6-methylnicotinamide;

(S)-5-chloro-N-(3-((4-(2-cyclopropylacetyl)-3-methylpiperazin-1-yl)methyl)-5-fluoro-2-methylphenyl)-6-methylnicotinamide; and (S)—N-(5-chloro-3-((4-(2,2-difluorobutanoyl)-3-methylpiperazin-1-yl)methyl)-2-methylphenyl)-5-fluoro-6-methylnicotinamide;

or a pharmaceutically acceptable salt thereof.

13. A pharmaceutical composition comprising a compound or a pharmaceutically acceptable salt thereof according to claim 12, and a pharmaceutically acceptable carrier or diluent thereof.

\* \* \* \* \*